US007557929B2

(12) United States Patent
Fang-Yen et al.

(10) Patent No.: US 7,557,929 B2
(45) Date of Patent: Jul. 7, 2009

(54) SYSTEMS AND METHODS FOR PHASE MEASUREMENTS

(75) Inventors: Christopher M. Fang-Yen, Somerville, MA (US); Gabriel Popescu, Brighton, MA (US); Changhuei Yang, Pasadena, CA (US); Adam Wax, Chapel Hill, NC (US); Ramachandra R. Dasari, Lexington, MA (US); Michael S. Feld, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 271 days.

(21) Appl. No.: 10/871,610

(22) Filed: Jun. 18, 2004

(65) Prior Publication Data

US 2005/0105097 A1 May 19, 2005

Related U.S. Application Data

(63) Continuation-in-part of application No. 10/823,389, filed on Apr. 13, 2004, now Pat. No. 7,365,858, which is a continuation-in-part of application No. 10/024,455, filed on Dec. 18, 2001, now Pat. No. 6,934,035.

(60) Provisional application No. 60/479,732, filed on Jun. 19, 2003.

(51) Int. Cl.
*G01B 9/02* (2006.01)
*G01B 11/02* (2006.01)
(52) U.S. Cl. .................................. 356/484; 356/497
(58) Field of Classification Search ................. 356/479, 356/497, 484–489
See application file for complete search history.

(56) References Cited

U.S. PATENT DOCUMENTS 3,434,787 A 3/1969 Chitayat (Continued)

FOREIGN PATENT DOCUMENTS

DE 3328773 3/1984

(Continued)

OTHER PUBLICATIONS

Xiaoli et al., "High-accuracy absolute distance measurement by means of wavelength scanning heterodyne interferometry," Meas. Sci. Technol. 9 (1998) 1031-1035. Printed in the UK.

(Continued)

*Primary Examiner*—Patrick J Connolly
(74) *Attorney, Agent, or Firm*—Weingarten, Schurgin, Gagnebin & Lebovici LLP

(57) ABSTRACT

Preferred embodiments of the present invention are directed to systems for phase measurement which address the problem of phase noise using combinations of a number of strategies including, but not limited to, common-path interferometry, phase referencing, active stabilization and differential measurement. Embodiment are directed to optical devices for imaging small biological objects with light. These embodiments can be applied to the fields of, for example, cellular physiology and neuroscience. These preferred embodiments are based on principles of phase measurements and imaging technologies. The scientific motivation for using phase measurements and imaging technologies is derived from, for example, cellular biology at the sub-micron level which can include, without limitation, imaging origins of dysplasia, cellular communication, neuronal transmission and implementation of the genetic code. The structure and dynamics of sub-cellular constituents cannot be currently studied in their native state using the existing methods and technologies including, for example, x-ray and neutron scattering. In contrast, light based techniques with nanometer resolution enable the cellular machinery to be studied in its native state. Thus, preferred embodiments of the present invention include systems based on principles of interferometry and/or phase measurements and are used to study cellular physiology. These systems include principles of low coherence interferometry (LCI) using optical interferometers to measure phase, or light scattering spectroscopy (LSS) wherein interference within the cellular components themselves is used, or in the alternative the principles of LCI and LSS can be combined to result in systems of the present invention.

25 Claims, 79 Drawing Sheets

U.S. PATENT DOCUMENTS

| | | | |
|---|---|---|---|
| 3,849,003 A | 11/1974 | Velzel | |
| 3,970,389 A | 7/1976 | Mendrin et al. | |
| 4,702,603 A | 10/1987 | Augustyn | |
| 4,834,111 A | 5/1989 | Khanna et al. | |
| 4,865,029 A | 9/1989 | Pankratov et al. | |
| 4,938,584 A | 7/1990 | Suematsu et al. | |
| 5,018,862 A | 5/1991 | Aiello | |
| 5,127,731 A | 7/1992 | DeGroot | |
| 5,153,669 A | 10/1992 | DeGroot | |
| 5,220,405 A | 6/1993 | Barbee et al. | |
| 5,263,776 A | 11/1993 | Abraham et al. | |
| 5,321,501 A | 6/1994 | Swanson et al. | |
| 5,349,440 A | 9/1994 | DeGroot | |
| 5,371,587 A | 12/1994 | DeGroot et al. | |
| 5,404,221 A | 4/1995 | DeGroot | |
| 5,412,474 A | 5/1995 | Reasenberg et al. | |
| 5,444,532 A | 8/1995 | Sueyoshi | |
| 5,459,570 A | 10/1995 | Swanson et al. | |
| 5,459,571 A | 10/1995 | Dammann et al. | |
| 5,477,323 A | 12/1995 | Andrews et al. | |
| 5,543,914 A | 8/1996 | Henshaw et al. | |
| 5,548,403 A | 8/1996 | Sommargren | |
| 5,579,109 A | 11/1996 | Suh et al. | |
| 5,589,641 A | 12/1996 | Johnson et al. | |
| 5,706,084 A | 1/1998 | Gutierrez | |
| 5,717,218 A | 2/1998 | Coufal et al. | |
| 5,781,295 A | 7/1998 | Fuchs et al. | |
| 5,867,268 A | 2/1999 | Gelikonov et al. | |
| 5,991,033 A | 11/1999 | Henshaw et al. | |
| 5,995,223 A | 11/1999 | Power | |
| 6,002,480 A * | 12/1999 | Izatt et al. | 356/479 |
| 6,020,963 A | 2/2000 | DiMarzio | |
| 6,021,223 A | 2/2000 | Toyoda et al. | |
| 6,034,774 A | 3/2000 | Marcus et al. | |
| 6,043,884 A * | 3/2000 | Curbelo | 356/502 |
| 6,102,905 A | 8/2000 | Baxter et al. | |
| 6,181,429 B1 * | 1/2001 | Barberis et al. | 356/484 |
| 6,208,415 B1 | 3/2001 | De Boer et al. | |
| 6,263,133 B1 | 7/2001 | Hamm | |
| 6,271,924 B1 | 8/2001 | Ngoi et al. | |
| 6,295,131 B1 | 9/2001 | Yamaba et al. | |
| 6,327,493 B1 | 12/2001 | Ozawa et al. | |
| 6,423,055 B1 | 7/2002 | Farr et al. | |
| 6,485,413 B1 | 11/2002 | Boppart et al. | |
| 6,501,551 B1 | 12/2002 | Tearney et al. | |
| 6,507,389 B1 | 1/2003 | Yeh | |
| 6,552,803 B1 | 4/2003 | Wang et al. | |
| 6,611,339 B1 * | 8/2003 | Yang et al. | 356/485 |
| 6,934,035 B2 | 8/2005 | Yang et al. | |
| 7,365,858 B2 | 4/2008 | Fang-Yen et al. | |
| 2002/0048025 A1 | 4/2002 | Takaoka | |
| 2002/0091321 A1 | 7/2002 | Goldstein et al. | |
| 2002/0101593 A1 | 8/2002 | Yang et al. | |
| 2002/0135775 A1 | 9/2002 | DeGroot et al. | |
| 2003/0112444 A1 | 6/2003 | Yang et al. | |
| 2004/0100636 A1 | 5/2004 | Somekn et al. | |
| 2005/0008323 A1 | 1/2005 | Han | |

FOREIGN PATENT DOCUMENTS

| | | |
|---|---|---|
| EP | 0636858 | 2/1995 |
| EP | 0840159 | 11/1997 |
| EP | 2000234914 | 8/2000 |
| EP | 2000275582 | 10/2000 |
| JP | 9061109 | 3/1997 |
| JP | 11257920 | 9/1999 |
| JP | 2000234914 | 8/2000 |
| JP | 2000275582 | 10/2000 |
| RU | 2020409 | 9/1994 |
| SU | 1357712 | 12/1987 |
| WO | WO 89/06781 | 7/1989 |
| WO | WO 99/57507 | 11/1999 |
| WO | WO 00/02339 | 1/2000 |
| WO | WO 01/01849 | 1/2001 |

OTHER PUBLICATIONS

Yang et al., "ambiguity-free optical distance measurement with subnanometer precision with a novel phase-crossing low-coherence interferometer," Optical Society of America, Optics Letters, Jan. 15, 2002, vol. 27, No. 2.

Yang et al., "Interferometric phase-dispersion microscopy," Optical Society of America, Optics Letters, vol. 25, No. 20, Oct. 15, 2000.

Yang et al., "Phase-dispersion optical tomography," Optical Society of America, Optics Letters, vol. 26, No. 10, May 15, 2001.

Yang et al., "Phase dispersion optical tomography applied to study sub-cellular motions," Conference on lasers and electro-optics, technical digest, postconference edition, vol. 56, May 6, 2001.

Yang et al., "Phase-referenced interferometer with subwavelength and subhertz sensitivity applied to the study of cell membrane dynamics," Optical Society of America, Optics Letters, vol. 25, No. 16, Aug. 15, 2001.

Hitzenberger et al., "Differential phase measurements in low-coherence interferometry without $2\pi$ ambiguity," Optical Society of America, Optics Letters, vol. 26, No. 23, Dec. 1, 2001.

Riza et al., "Submicrosecond speed optical coherence tomography system design and analysis by use of acousto-optics," Optical Society of America, Applied Optics, vol. 42, No. 16, Jun. 1, 2003.

Harada et al., "Nonlinear image self-filtering with liquid crystal spatial light modulator," Optics & Laser Tech. 30 (1998) 147-155.

Mogensen et al., "Dynamic array generation and pattern formation for optical tweezers," Optics Communications 175 (2000) 75-81.

Torii, Yasuhiro "Synthesis of deterministic phase codes for phase shifter in holography," Optics Communications, vol. 24, No. 2, Feb. 1978.

Nishchal et al., "Optical phase encryption by phase contrast using electrically addressed spatial light modulator," Optics Communications 217 (2003) 117-122.

Akkin et al., "Interferometric fiber-based optical biosensor to measure ultra-small changes in refractive index," Optical Fibers and Sensors for Medical Applications II, SPIE, vol. 4616 (2002).

Ren et al., "Phase-resolved polarization sensitive optical coherence tomography imaging of tendon muscle," Coherence Domain Optical Methods and Optical Coherence Tomography in Biomedicine VII, SPIE, vol. 4956, 2003.

Hitzenberger et al., "Imaging of cell layers by differential phase contrast optical coherence microscopy," Coherence Domain Optical Methods and Optical Coherence Tomography in Biomedicine VII, SPIE, vol. 4956, 2003.

Matthews et al., "Surface profiling by phase-locked interferometry," Applied Optics, vol. 25, No. 14, Jul. 15, 1986.

Somervell et al, "Unambiguous measurement of surface profile using a Sagnac Interferometer with phase feedback," Optics Communications 150 (1998) 61-65.

Bush et al. "Synchronous phase detection for optical fiber interferometric sensors," Optical Society of America, Applied Optics, vol. 22, No. 15, Aug. 1983.

Clivaz et al. "High-resolution reflectometry in biological tissues," Optics Letters, 17(1992) Jan. 1, No. 1, New York, NY.

* cited by examiner

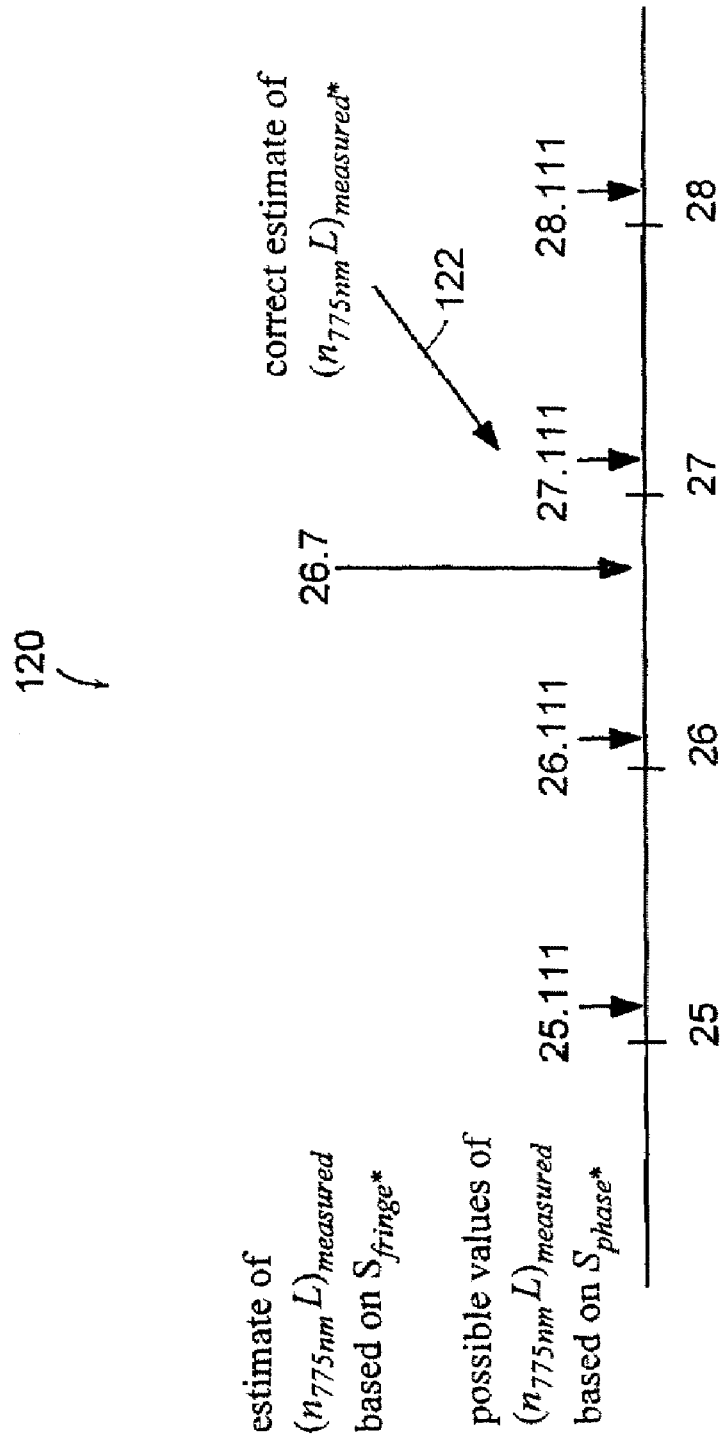

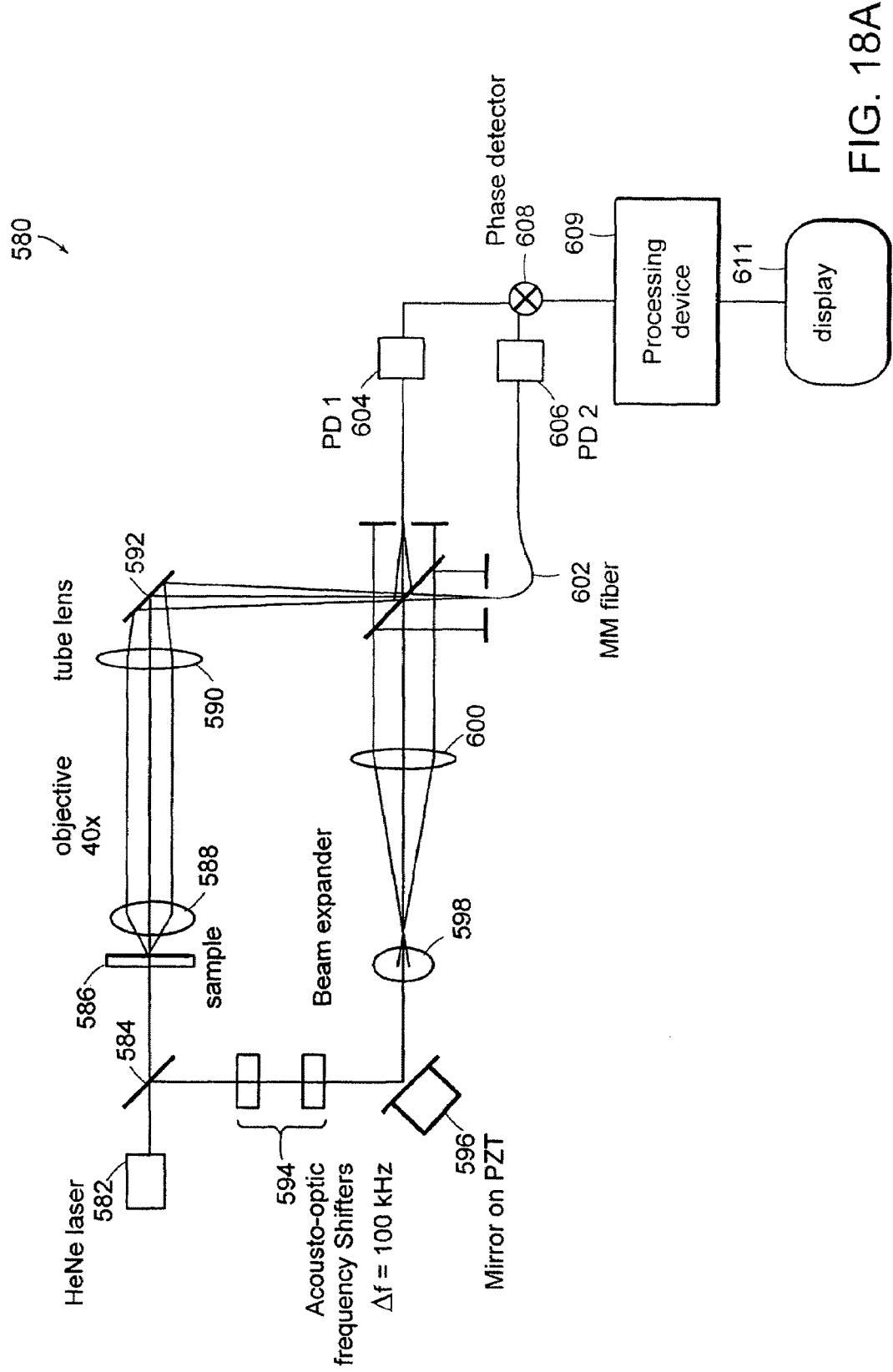

Optical design by ray tracing

```
f0 = 6.4;
f1 = 300;
f2 = 100;
f3 = 50;
delta = .1;

x0 = f0;
x1 = 2 f0 + f1;
x2 = 2 f0 + 2 f1 + f2;
x3 = 2 f0 + 2 f1 + f2;

na = 0.4;

(* TRANSFER AND LENS MATRICES *)

t[z_] := {{1, z}, {0, 1}};
lens[f_] := {{1, 0}, {-1/f, 1}};
```

```
delta = .1;
soln =
 Solve[
  (t[z0 - delta].lens[f0]  .t[a1 - z0].
    lens[f1].t[z2 - z1]     .lens[f2].
     lens[d3var] .lens [f3].
      t[d3var] .lens    {[1]] - 0,f3var]
       {.6 wmax, 0}) [[1]] - 0,f3var]

Out[246]= {{(d3var → 104.489)}}
```

Distance between f3 and f2 in order
to shift focus by 100 microns

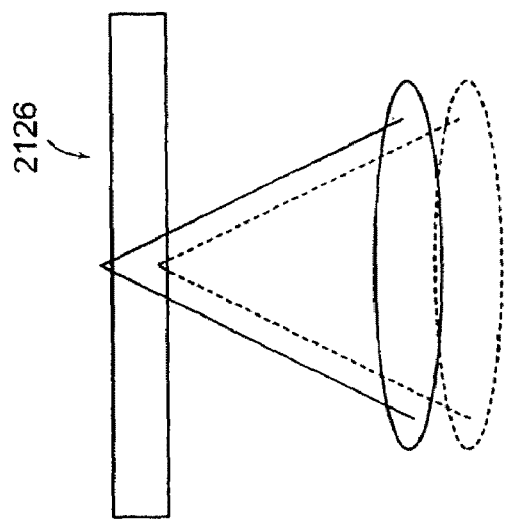
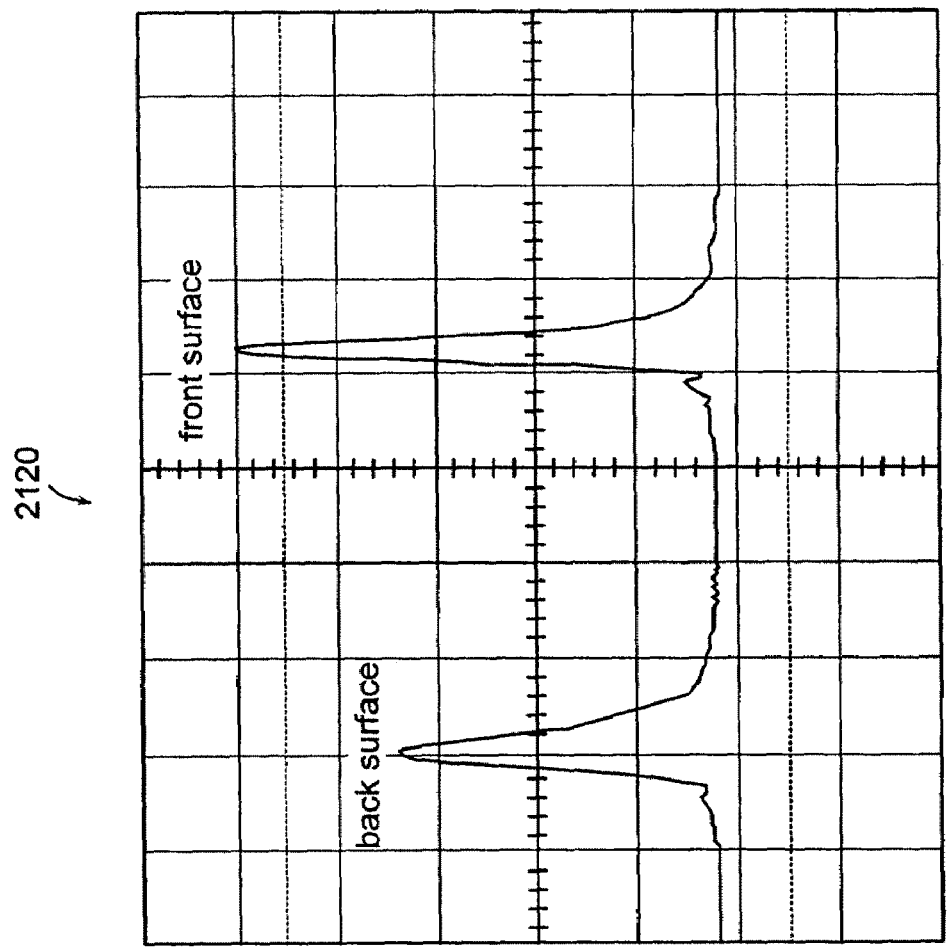
FIG. 38

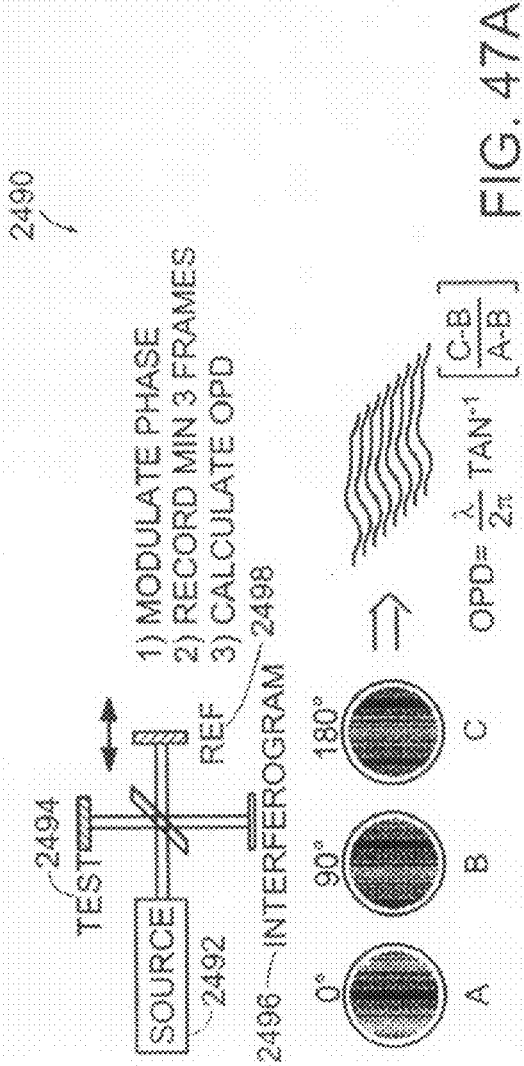
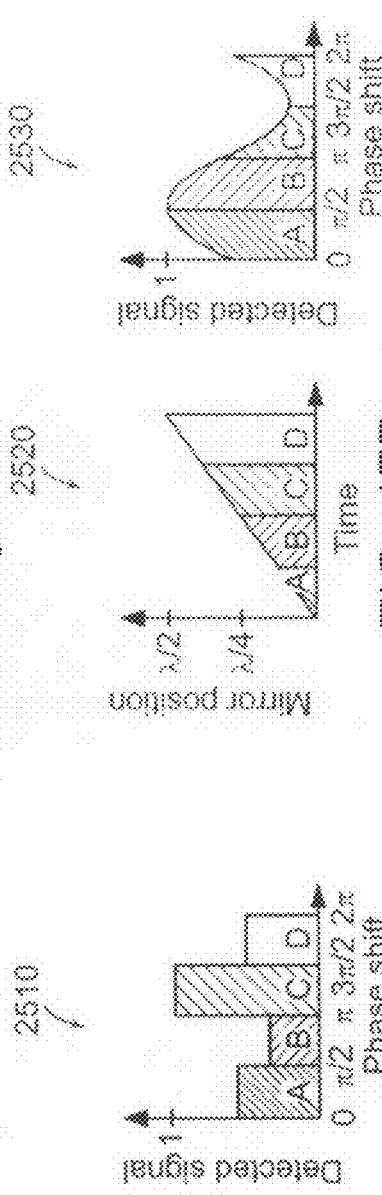
FIG. 47A
FIG. 47B
FIG. 47C
FIG. 47D
FIG. 47E

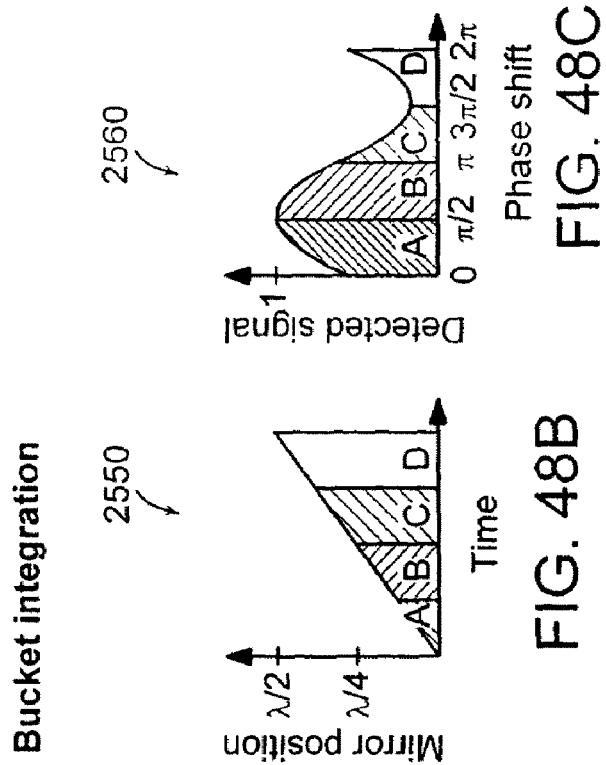
FIG. 48C
FIG. 48B
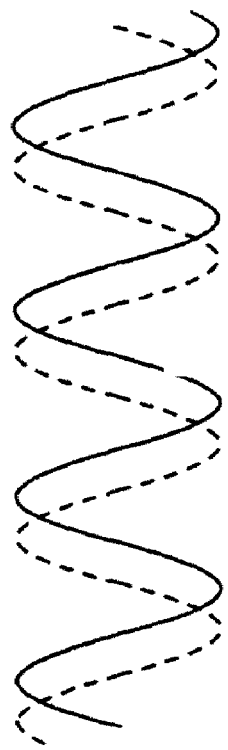
FIG. 48A

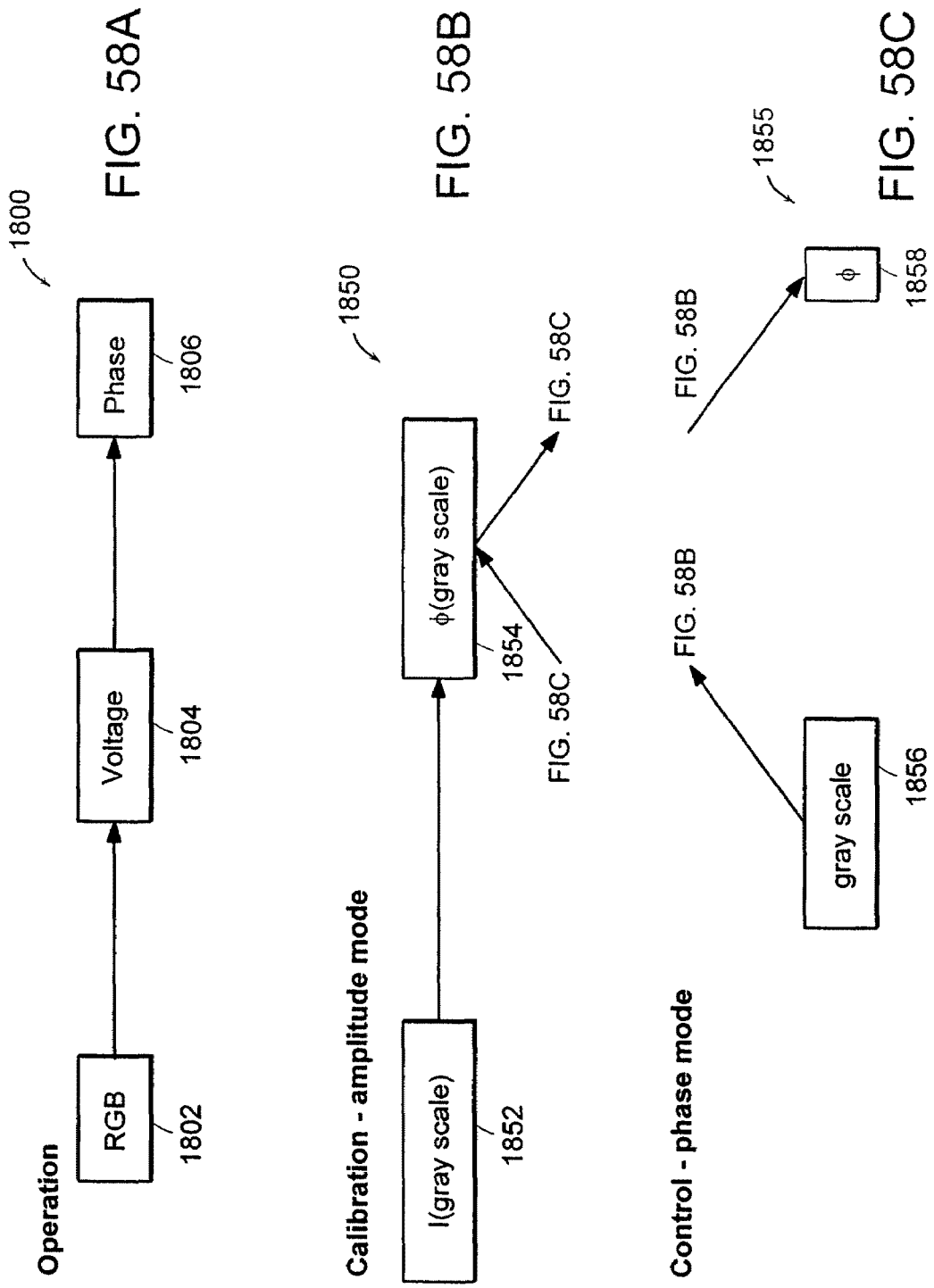

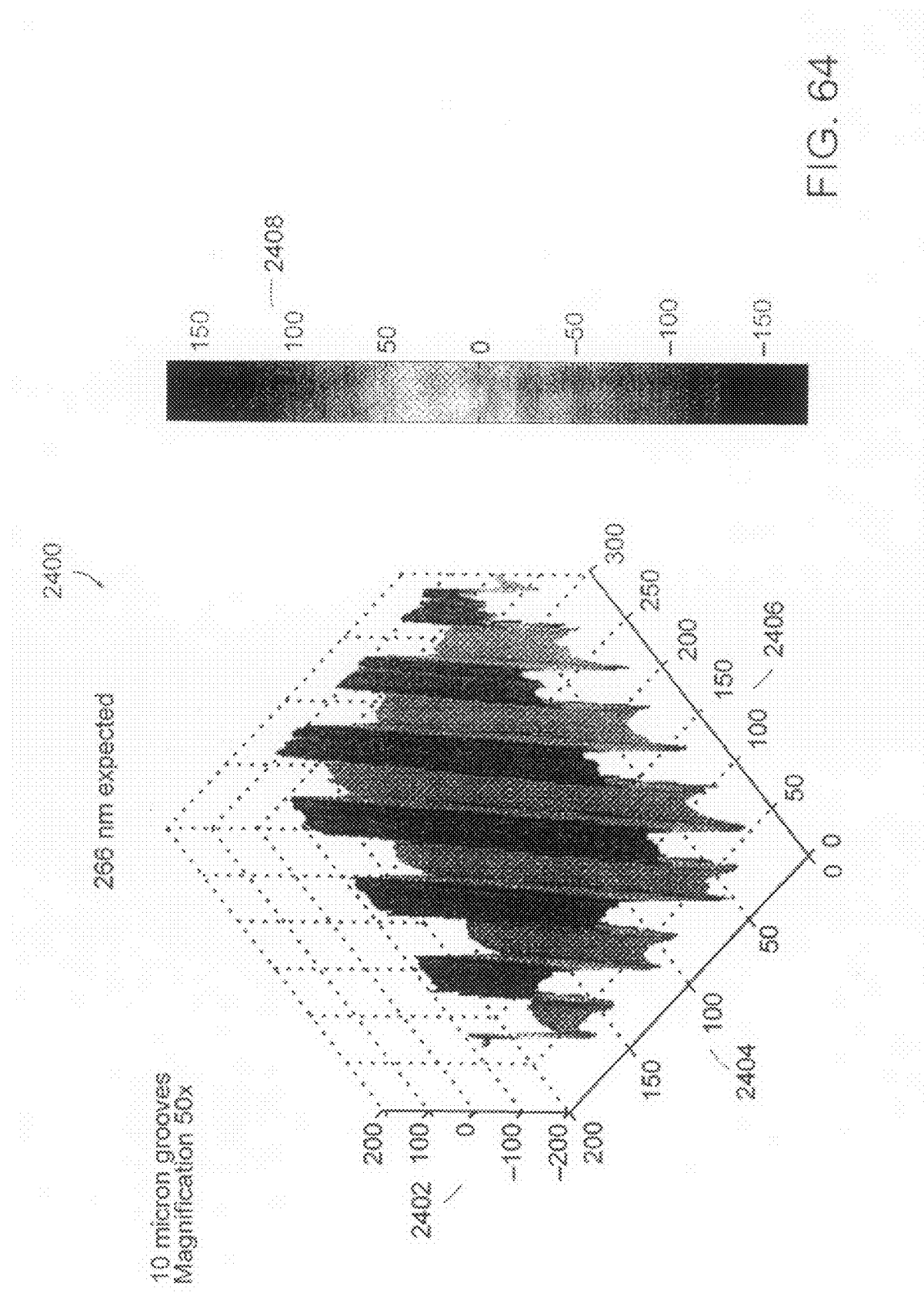

SYSTEMS AND METHODS FOR PHASE MEASUREMENTS

CROSS REFERENCES TO RELATED APPLICATIONS

The present application is a continuation-in-part of U.S. patent application Ser. No. 10/823,389, filed Apr. 13, 2004, now U.S. Pat. No. 7,365,858, which is a continuation-in-part of U.S. patent application Ser. No. 10/024,455, filed Dec. 18, 2001, now U.S. Pat. No. 6,934,035, and claims the benefit of U.S. Provisional Application No. 60/479,732, filed Jun. 19, 2003. The entire contents of the above applications are incorporated herein by reference in their entirety.

GOVERNMENT SUPPORT

The invention was supported, in whole or in part, by a Grant No. P41-RR02594 from the National Institutes for Health. The Government has certain rights in the invention.

BACKGROUND OF THE INVENTION

Phase-based optical interferometric techniques are widely employed in optical distance measurements in which sub-wavelength distance sensitivity is required. Optical distance is defined as the product of the refractive index and the length. However, most such techniques are limited by an issue which is widely known in the filed at $2\pi$ ambiguity or integer ambiguity which can be defined as the difficulty in telling the interference fringes of an axial scan apart from each other. An unmodified harmonic phase based low coherence interferometry (LCI) method can be used to determine the differential optical distance, $(n_{\lambda_2}-n\lambda_1)L$, where L is the physical distance, $n_{\lambda_1}$ and $n_{\lambda_2}$ are the refractive indices at the wavelengths $\lambda_1$ and $\lambda_2$, respectively, if the optical distance is increased gradually so that the differential phase measured by LCI can be tracked through its $2\pi$ wrap over. To determine $(n_{\lambda_2}-n_{\lambda_1})$ for DNA in solution, for example, the DNA concentration is gradually increased in the measuring cuvette. While such a measurement approach works well in a controlled environment, it can hardly be implemented in a situation where there is less manipulability in the sample. For example, the method does not work on a fixed slab of material which one is constrained to keep whole.

The problem lies in the fact that unmodified LCI is unable to tell the interference fringes of an axial scan apart from each other, described herein as the $2\pi$ ambiguity issue. It is a problem that plagues most phase-based optical interferometric techniques. As a result, these techniques are unable to determine optical distance absolutely. Therefore, most such techniques are used in applications, such as evaluating the texture of continuous surfaces or detecting time-dependent distance changes, in which phase unwrapping is possible through comparison of phases between adjacent points or over small time increments.

In many applications it is important to quantitatively measure the phase of light transmitted through or reflected from a sample. In particular, the phase of light transmitted through or reflected from biological samples can form a powerful probe of structure and function in living or nonliving cells.

Interferometry is a versatile technique for measuring the phase of light. One common problem in quantitative interferometry is the susceptibility to phase noise due to external perturbations such as vibrations, air motions, and thermal drafts. There remains a need for systems for phase measurement which solve the problem of phase noise.

Interferometry is one way to access the phase information associated with a specimen. Techniques such as phase contrast and Nomarski microscopy use optical phase just as a contrast agent and do not provide quantitative information about its magnitude. Several techniques exist for measuring the phase of light transmitted through nearly transparent samples. These include digital recorded interference microscopy (DRIMAPS) and noninterferometric detection of phase profiles via the transport of intensity equation.

Reflection interferometry is capable of sensitivity much smaller than the wavelength of light used. Measurements on the scale of fractions of nanometers or smaller are common in metrology and microstructure characterization. However, little work has been done in nanometer-scale interferometry in weakly reflecting samples such as biological cells and tissues. Optical coherence tomography (OCT), an interferometric technique used with biological samples, is primarily concerned with the amplitude rather than the phase of interference from reflected light, and is therefore limited in resolution to the coherence length of the light used, typically 2-20 microns.

Phase-referenced reflection interferometry has been used to measure the volume changes in a monolayer of cells. The harmonic phase-based interferometer used requires two sources, is relatively slow (5 Hz), and has a phase sensitivity of about 20 mrad over this bandwidth. There thus remains a need for effective systems for phase measurement which solve the problem of phase noise and assist in developing different imaging applications.

SUMMARY OF THE INVENTION

Preferred embodiments of the present invention are directed to systems for phase measurement which address the problems such as phase noise, for example, using combinations of a number of strategies including, but not limited to, common-path interferometry, phase referencing, active stabilization and differential measurement. Embodiments are directed to optical devices for imaging tissue or small biological objects with light. These embodiments can be applied to the fields of, for example, cellular physiology and neuroscience. These preferred embodiments are based on principles of phase measurements and imaging technologies. The scientific motivation for using phase measurements and imaging technologies is derived from, for example, cellular biology at the sub-micron level which can include, without limitation, imaging origins of dysplasia, cellular communication, neuronal transmission and implementation of procedures using the genetic code. The structure and dynamics of sub-cellular constituents cannot be currently studied in their native state using the existing methods and technologies including, for example, x-ray and neutron scattering. In contrast, light based techniques with nanometer resolution enable the cellular machinery to be studied in its native state. Thus, preferred embodiments of the present invention include systems based on principles of interferometry and/or phase measurements and are used to study cellular physiology. These systems include principles of low coherence interferometry (LCI) using optical interferometers to measure phase, or light scattering spectroscopy (LSS) wherein interference within the cellular components themselves is used, or in the alternative the principles of LCI and LSS can be combined to result in systems of the present invention.

The preferred embodiments for phase measurement and imaging systems include actively stabilized interferometers, isolation interferometers, common path interferometers and can include phase contrast microscopy using spatial light modulation.

In a preferred embodiment, the methods of the present invention are directed at an accurate phase-based technique for measuring arbitrarily long optical distances, preferably with sub-nanometer precision. A preferred embodiment of the present invention employs an interferometer, for example, a Michelson interferometer, with harmonically related light sources, one continuous wave (CW) and a second source having low coherence (LC). The low coherence source provides a broad spectral bandwidth, preferably a bandwidth of greater than 5 nm for a 1 micron (µm) wavelength, for example, the required bandwidth can vary as a function of wavelength and application. By slightly adjusting the center wavelength of the low coherence source between scans of the target sample, the phase relationship between the heterodyne signals of the CW and low coherence light can be used to measure the separation between reflecting interfaces with sub-nanometer precision. As this method is completely free of $2\pi$ ambiguity, an issue that plagues most phase-based techniques, it can be used to measure arbitrarily long optical distances without loss of precision. An application of a preferred embodiment of the method of the present invention is the precision determination of the refractive index of a sample at a given wavelength of a sample with a known physical thickness. Another application of a preferred embodiment of the method of the present invention is the precision determination of a sample's physical thickness with a known refractive index. A further application of a preferred embodiment of the method of the present invention is the precision determination of the refractive index ratio at two given wavelengths.

In an alternate preferred embodiment, the low coherence light source provides a sufficiently broad bandwidth light, preferably greater than 5 nm, to provide simultaneously a first low coherence wavelength and a second low coherence wavelength with the respective center wavelengths separated from each other by more than approximately 2 nm. The frequency spectrums for the low coherence wavelengths do not significantly overlap. An additional detector and filters are disposed in the interferometer to transmit and detect the two low coherence wavelengths.

The preferred embodiment methods can be used to make precise optical distance measurements. From such measurements, optical properties of target objects can be accurately measured. By measuring the dispersion profile of the target, structural and/or chemical properties of the target can be evaluated. The dispersion profile maps out the refractive index differences at various wavelengths. In the biomedical context, preferred embodiments of the present invention can be used to accurately determine the dispersion properties of biological tissues in a non-contact and non-invasive manner. Such dispersion determination can be used on the cornea or aqueous humor of the eye. The sensitivity achieved can be sufficient to detect glucose concentration dependent optical changes. In a preferred embodiment of the present invention method, the blood glucose level can be determined through non-invasive measurements of the dispersion profile of either the aqueous and/or vitreous aqueous humor or the cornea of the eye. A preferred embodiment of the present invention can be applied as a measurement technique in semiconductor fabrication to measure small features formed during the manufacturing of integrated circuits and/or optoelectronic components. As the preferred embodiment of the method is non-contact and non-destructive, it can be used to monitor the thickness of semiconductor structures or optical components as they are being fabricated.

In accordance with a preferred embodiment of the present invention that used a Mach-Zender heterodyne interferometer, a method for measuring phase of light passing through a portion of a sample includes the steps of providing a first wavelength of light, directing light of the first wavelength along a first optical path and a second optical path, the first optical path extending onto a sample medium to be measured and the second path undergoing a change in path length, and detecting light from the sample medium and light from the second optical path to measure a change in phase of light passing through two separate points on the sample medium. The medium comprises biological tissue such as, for example, a neuron. The method includes using a photodiode array or a photodiode-coupled fiber bundle to image the phase of the sample at a plurality of positions simultaneously. The method further includes the step of frequency shifting the light in the second optical path. The method includes providing a helium-neon laser light source that emits the first wavelength or a low coherence light source.

In accordance with another aspect of the invention an actively stabilized interferometer is used in a method for measuring phase of light passing through a portion of a sample, including the steps of providing a first signal and a second signal generated by a first light source and a second light source, respectively, the second light source being a low coherence source. The method includes directing the first signal and the second signal along a first optical path and a second optical path, varying a path length difference between the first optical path and the second optical path, generating an output signal indicative of the sum of the first and the second signal with an optical path delay between them, modulating the output signal at an interferometer lock modulation frequency, and determining the phase of the sample by the time evolution of the interferometer lock phase. The first and second signals are both low coherence signals. The method further includes demodulating the first signal by a mixer or a lock-in amplifier. The method includes electronically generating the interferometer lock phase.

In accordance with another aspect of the present invention, a dual beam reflection interferometer is used in a system for measuring phase of light passing through a portion of a sample. The system includes a first light source that generates a first signal, an interferometer that generates a second signal with two pulses separated by a time delay from the first signal, a first optical path from the interferometer in communication with the sample and a second optical path from the interferometer in communication with a reference, and a detector system that measures a first heterodyne signal from the first and the second signal from the sample and the reference, respectively, and the interference between the light reflected from the sample and the reference. The system includes detecting a phase of the heterodyne signal indicative of the phase of the sample reflection relative to the reference reflection. The first signal is a low coherence signal. The first light source can include, without limitation, one of a superluminescent diode or multimode laser diode. The second path of the interferometer further includes a first path and a second path, and the second path has acousto-optic modulators. The system includes an optical pathway including an optical fiber. The system includes a vibration-isolated heterodyne Michelson interferometer. The interferometer further includes a mirror attached to a translation stage to adjust an optical path length difference. The detection system comprises a first detector that detects a signal reflected from the sample and a second detector that detects a signal reflected from the reference.

In accordance with another aspect, the present invention provides a method for imaging a sample using phase contrast microscopy and spatial light modulation. In various embodiments, the method includes illuminating the sample, the light originating from the sample due to the illumination having low frequency spatial components and high frequency spatial components. The phase of the low frequency spatial component is shifted to provide at least three phase shifted low frequency spatial components. Preferably, the phase is shifted in increments of, for example, $\pi/2$ to produce phased shifted low frequency spatial components with phase shifts of $\pi/2$, $\pi$ and $3\pi/2$.

The unshifted low frequency spatial component and at least three phase shifted low frequency spatial components are separately interfered with the high frequency spatial component along a common optical path to produce an intensity signal for each separate interference. An image, or phase image, is then generated for the sample using at least four of the intensity signals, for example.

In accordance with another aspect, the present invention provides a method for non-contact optical measurement of a sample having reflecting surfaces having the steps of providing a first light source that generates a first signal generating a second signal with two pulses separated by a time delay from the first signal using a dual-beam interferometer, providing a first optical path from the interferometer in communication with the sample and a second optical path from the interferometer in communication with a reference; and measuring a first heterodyne signal from the first and the second signal from the sample and the reference, respectively, and the interference between the light reflected from the sample and the reference; and detecting a phase of the heterodyne signal indicative of the phase of the sample reflection relative to the reference reflection.

In a preferred embodiment, the first signal is a low coherence signal. The first light source can be a superluminescent diode or multimode laser diode. The interferometer further comprises a first path and a second path, the second path having acousto-optic modulators. The method further includes an optical pathway including an optical fiber. The sample can be a portion of a nerve cell.

In a preferred embodiment, the interferometer includes a vibration-isolated heterodyne Michelson interferometer. The interferometer further includes a mirror attached to a translation stage to controllably adjust an optical path length difference. Preferred embodiments include a heterodyne low coherence interferometer to perform the first non-contact and first interferometric measurements of nerve swelling. The biophysical mechanisms of nerve swelling can be imaged and analyzed using individual axons in accordance with a preferred embodiment of the present invention. The dual-beam low coherence interferometer may have many other applications in measuring nanometer-scale motions of living cells. Other embodiments can include a microscope based on the interferometer to detect mechanical changes in single neurons associated with action potentials. A related interferometric method is also used to measure cell volume changes in cultured cell monolayers.

Another aspect of the present invention includes a fiber optic probe for optically imaging a sample, having a housing with a proximal end and a distal end, a fiber collimator in the proximal end of the housing coupled to a light source; and a graded index lens in the distal end of the housing, the lens having a first and second surface wherein the first surface is the reference surface and wherein numerical aperture of the probe provides efficient light gathering from scattering surfaces of a sample. The probe further includes mounting the fiber optic probe on a translator stage to perform at least one of two-dimensional phase imaging and three-dimensional confocal phase imaging. The translator stage includes a scanning piezo translator. The numerical aperture of the probe is in a range of approximately 0.4 to 0.5.

The foregoing and other features and advantages of the system and method for phase measurements will be apparent from the following more particular description of preferred embodiments of the system and method as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

FIG. 5 illustrates a method of determining correct estimates of $(n_{755\ nm} L)$ measured by choosing the values that minimizes the error between estimates based on $S_{phase}$ and $S_{fringe}$ in accordance with a preferred embodiment of the present invention;

Figure 13:
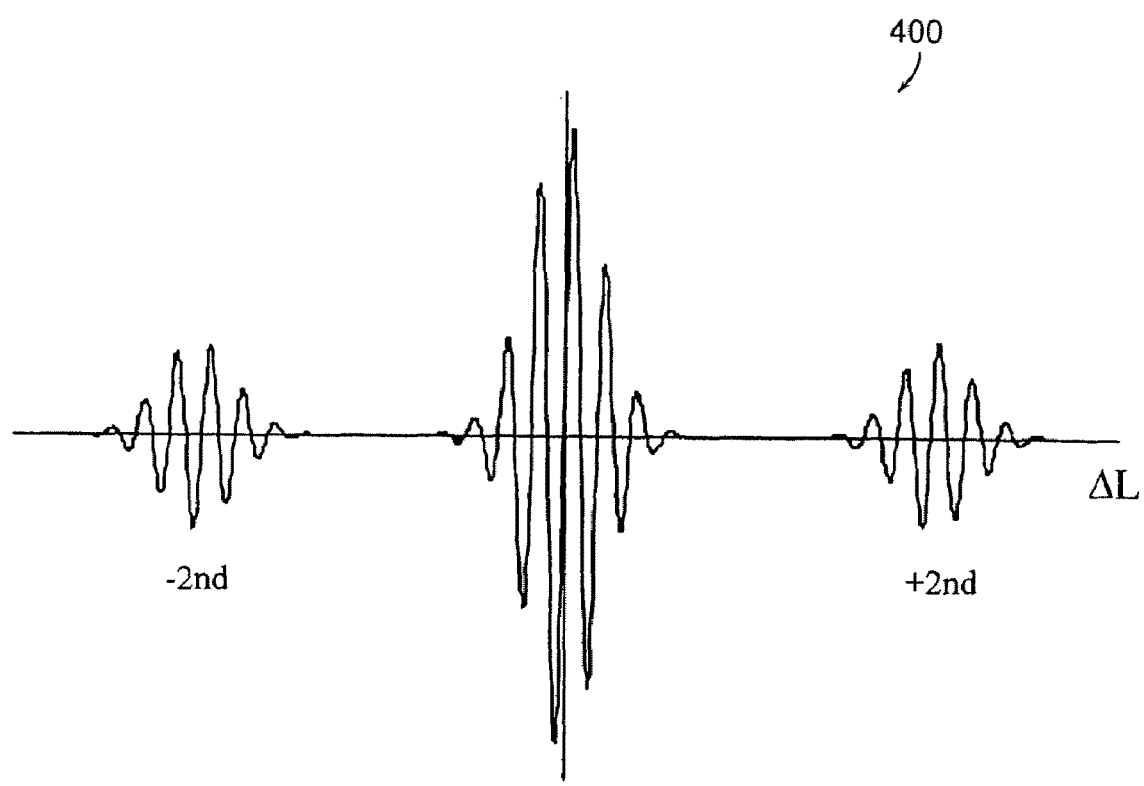
Figure 14A:
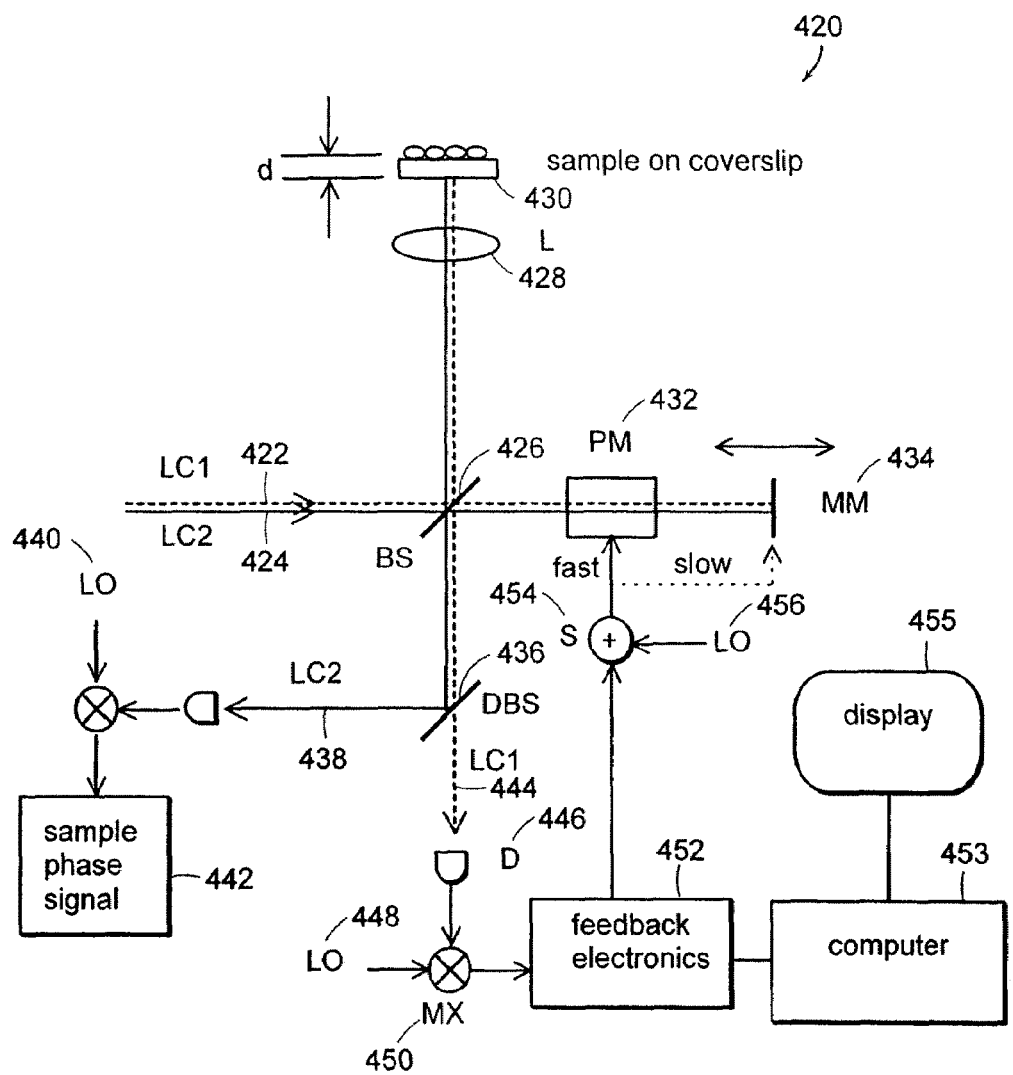
Figure 14B:
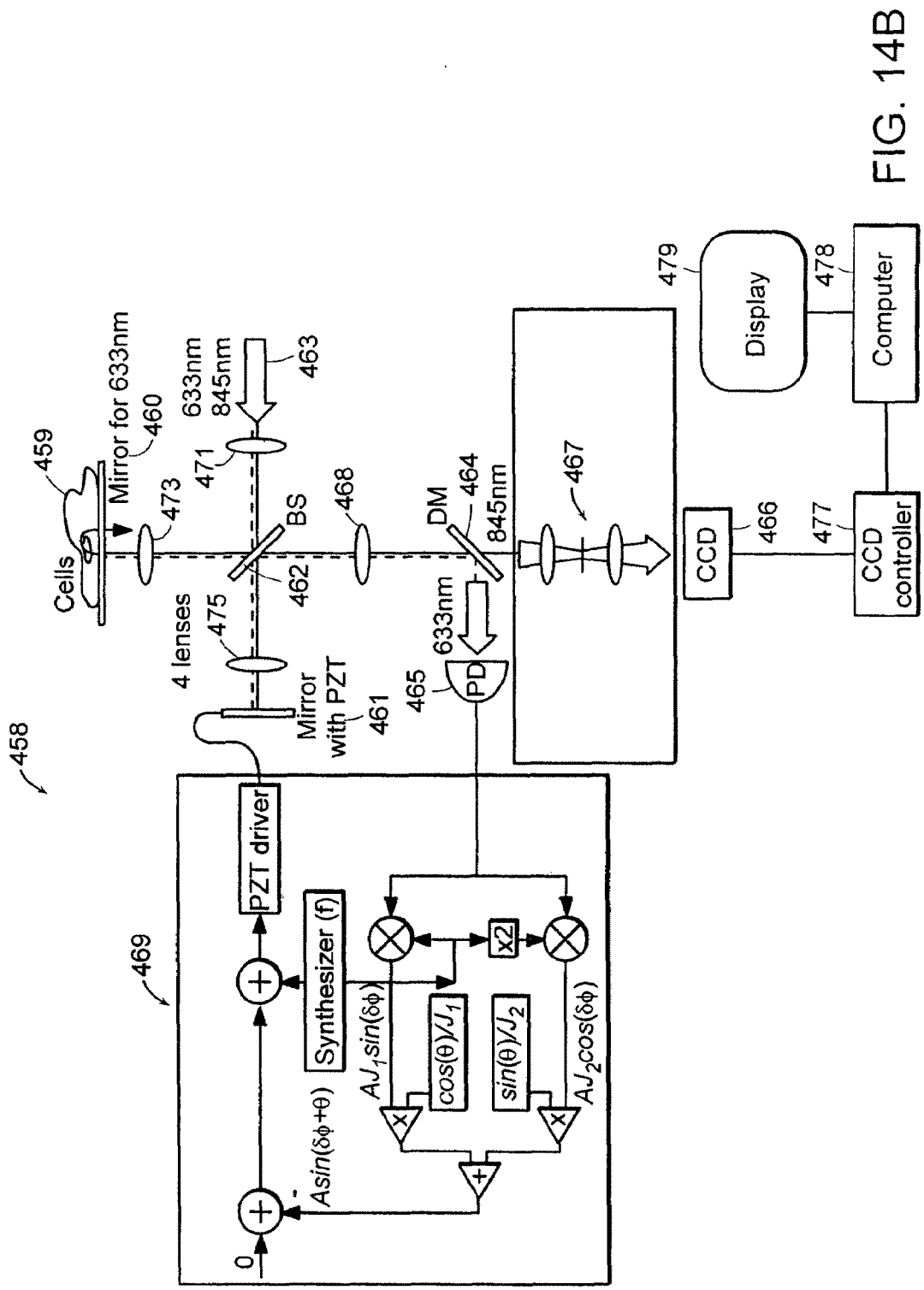
Figures 15A, 15B:
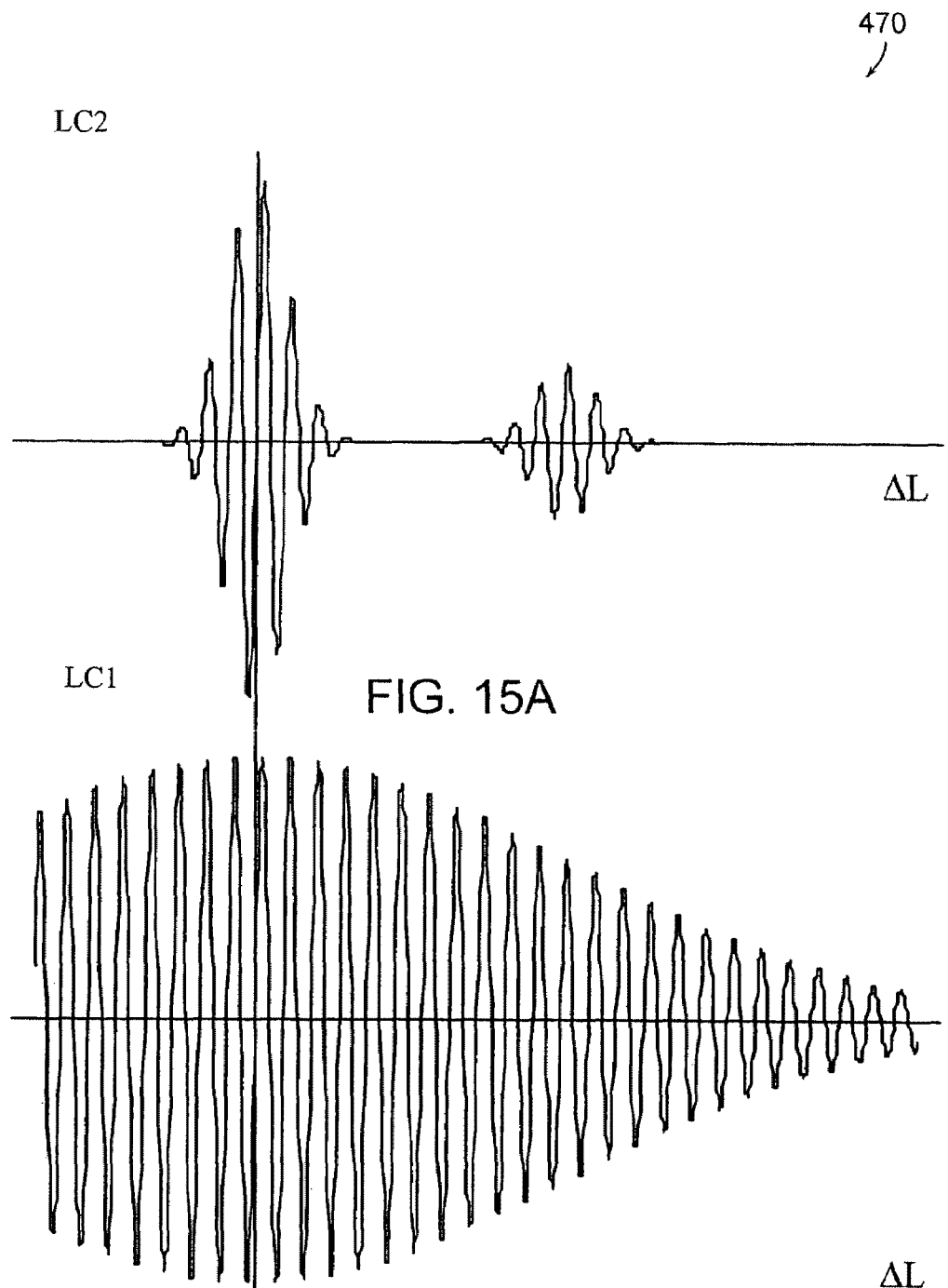
Figure 16:
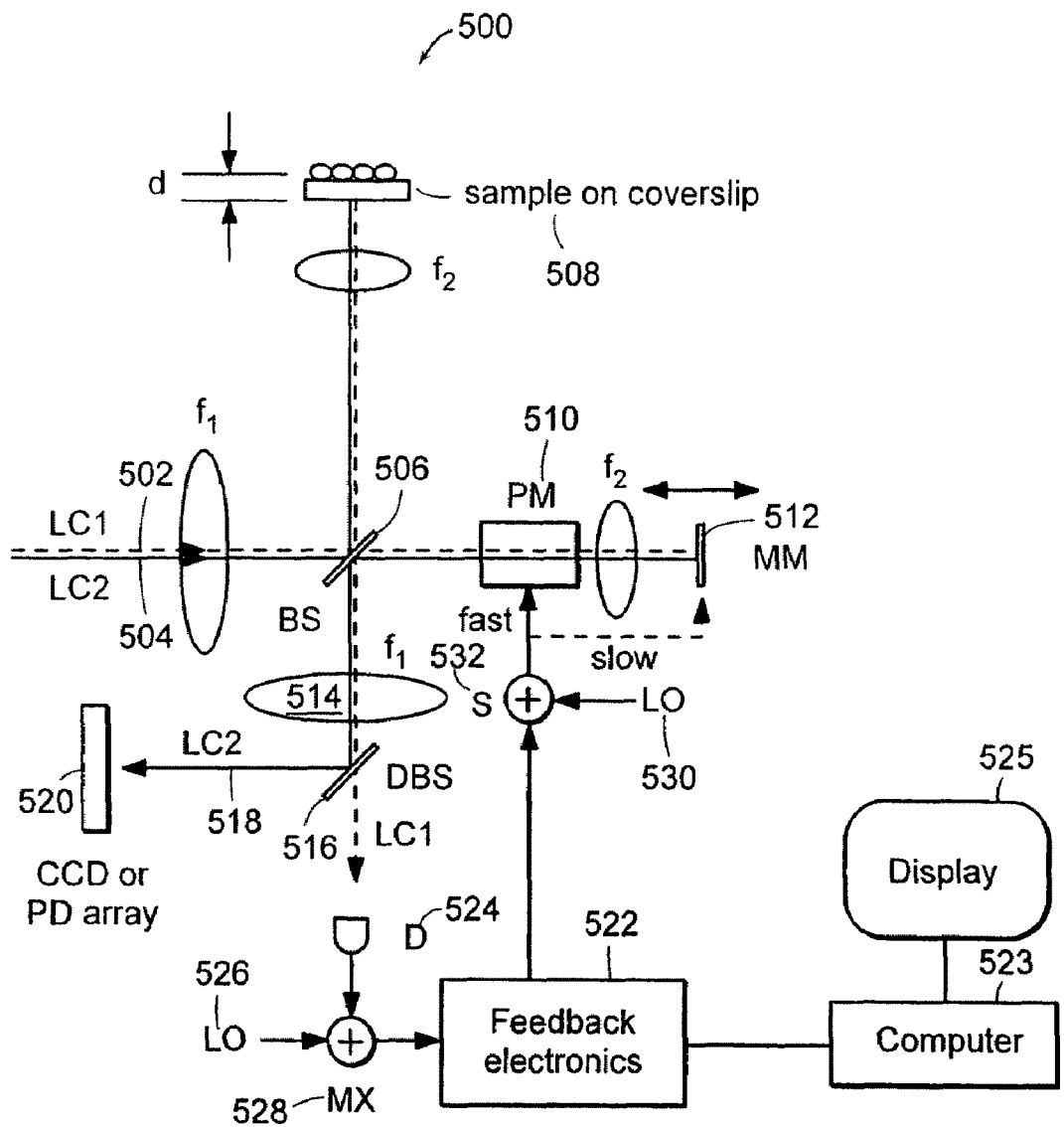
Figure 17:
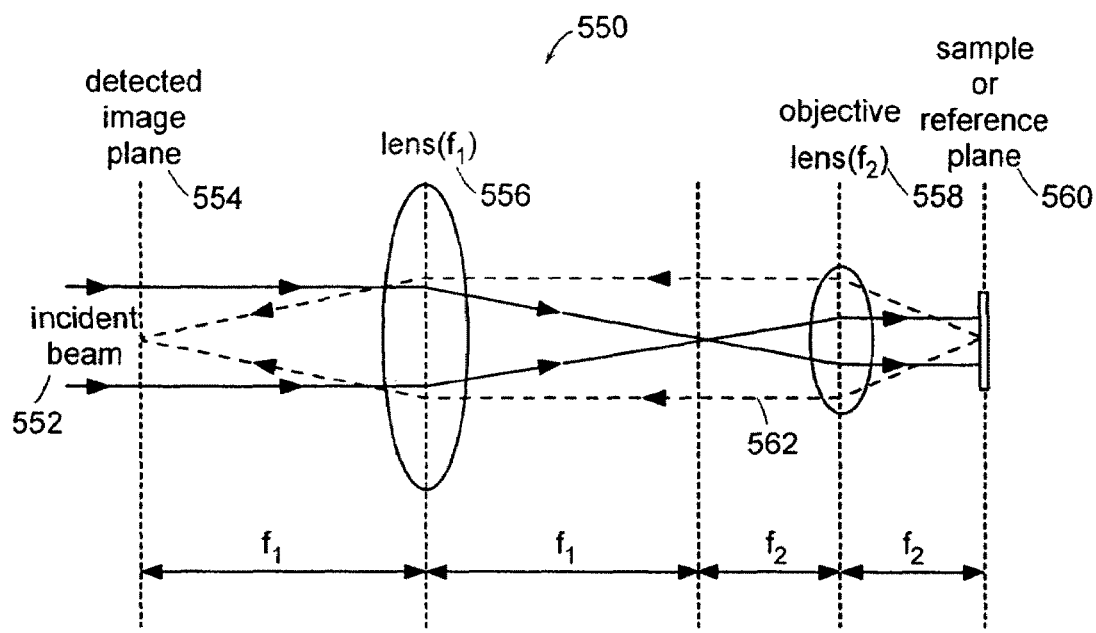
Figure 18B:
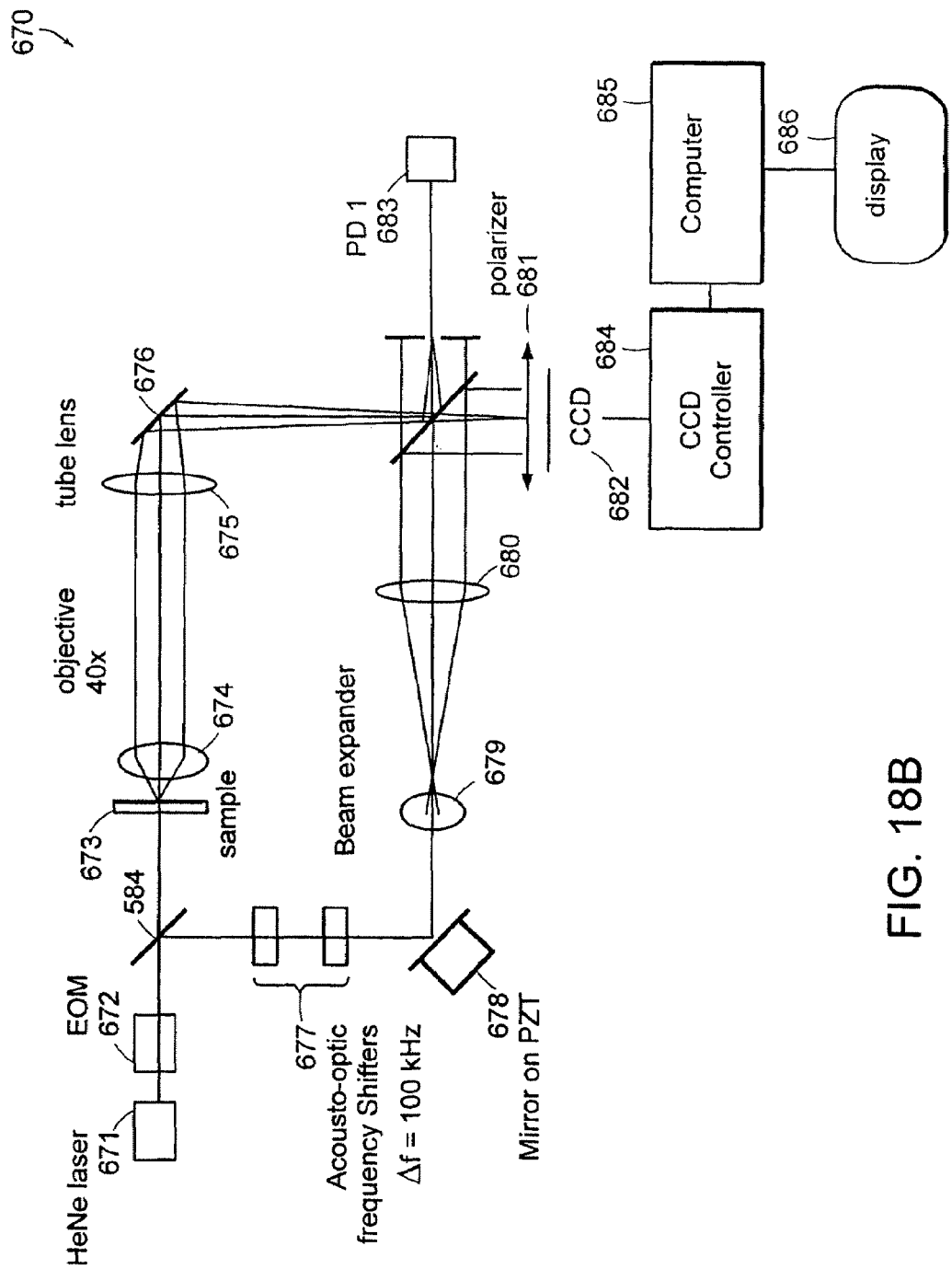
Figure 18C:
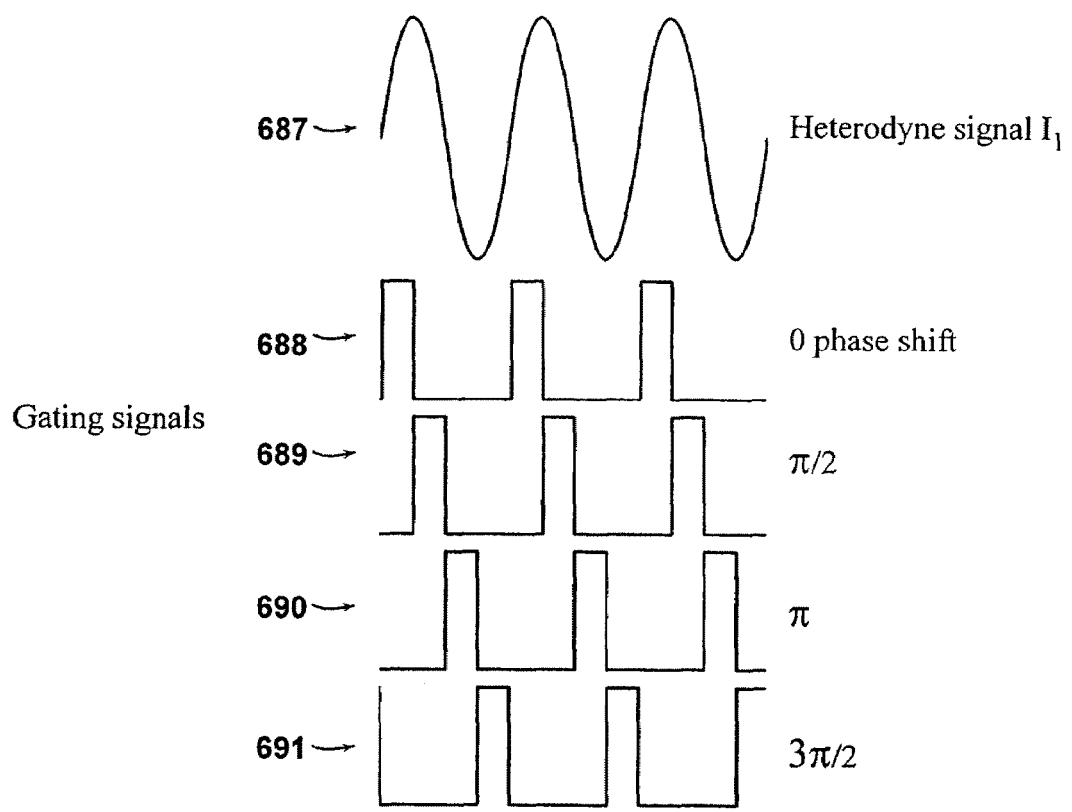
Figure 18D:
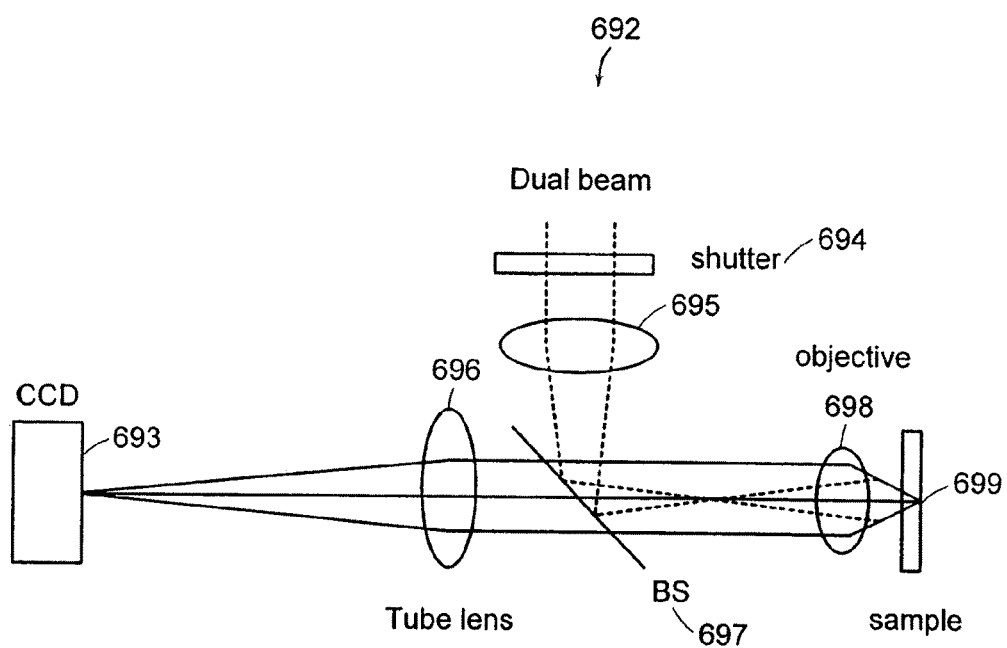
Figure 19:
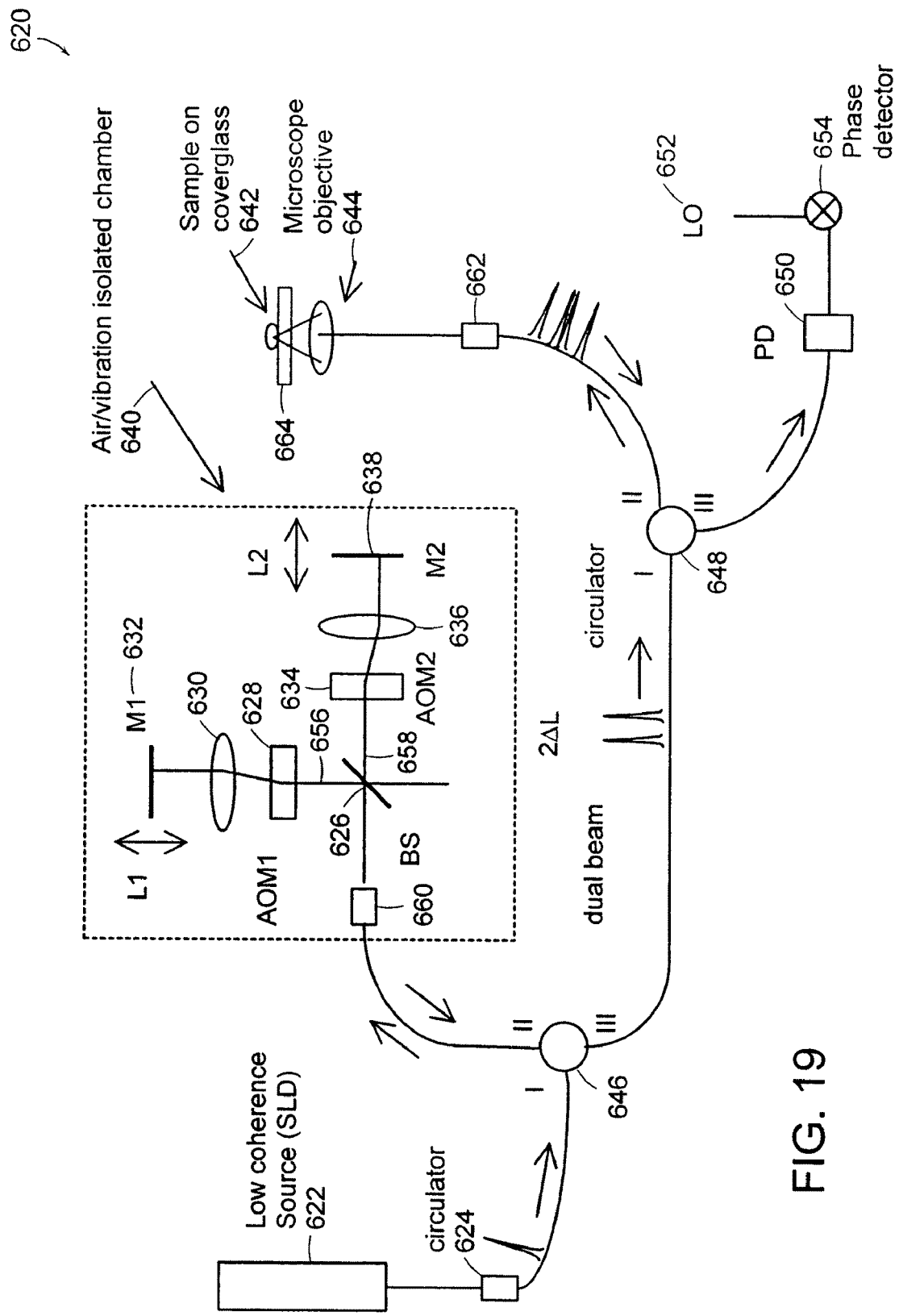
Figure 20:
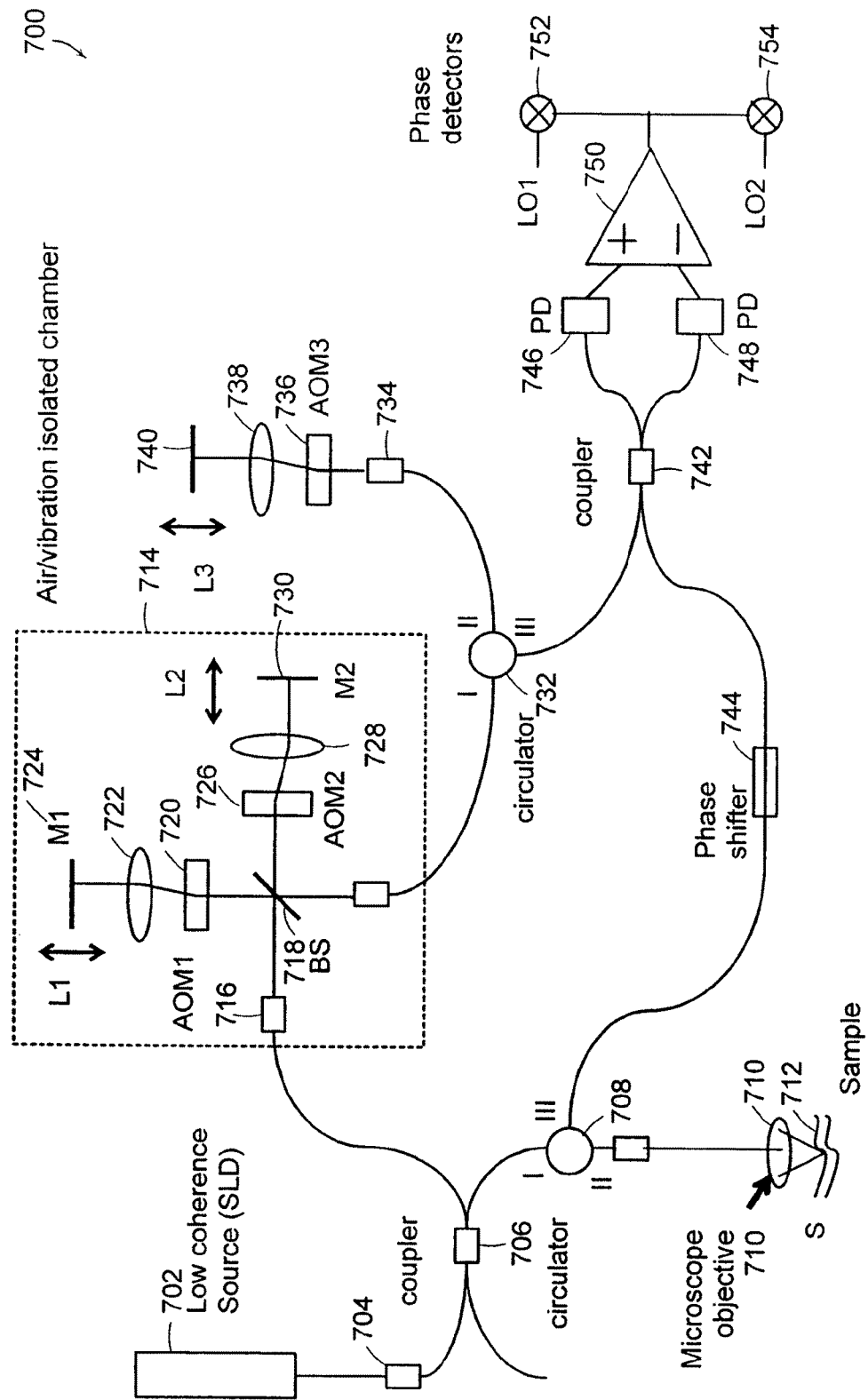
Figure 21:
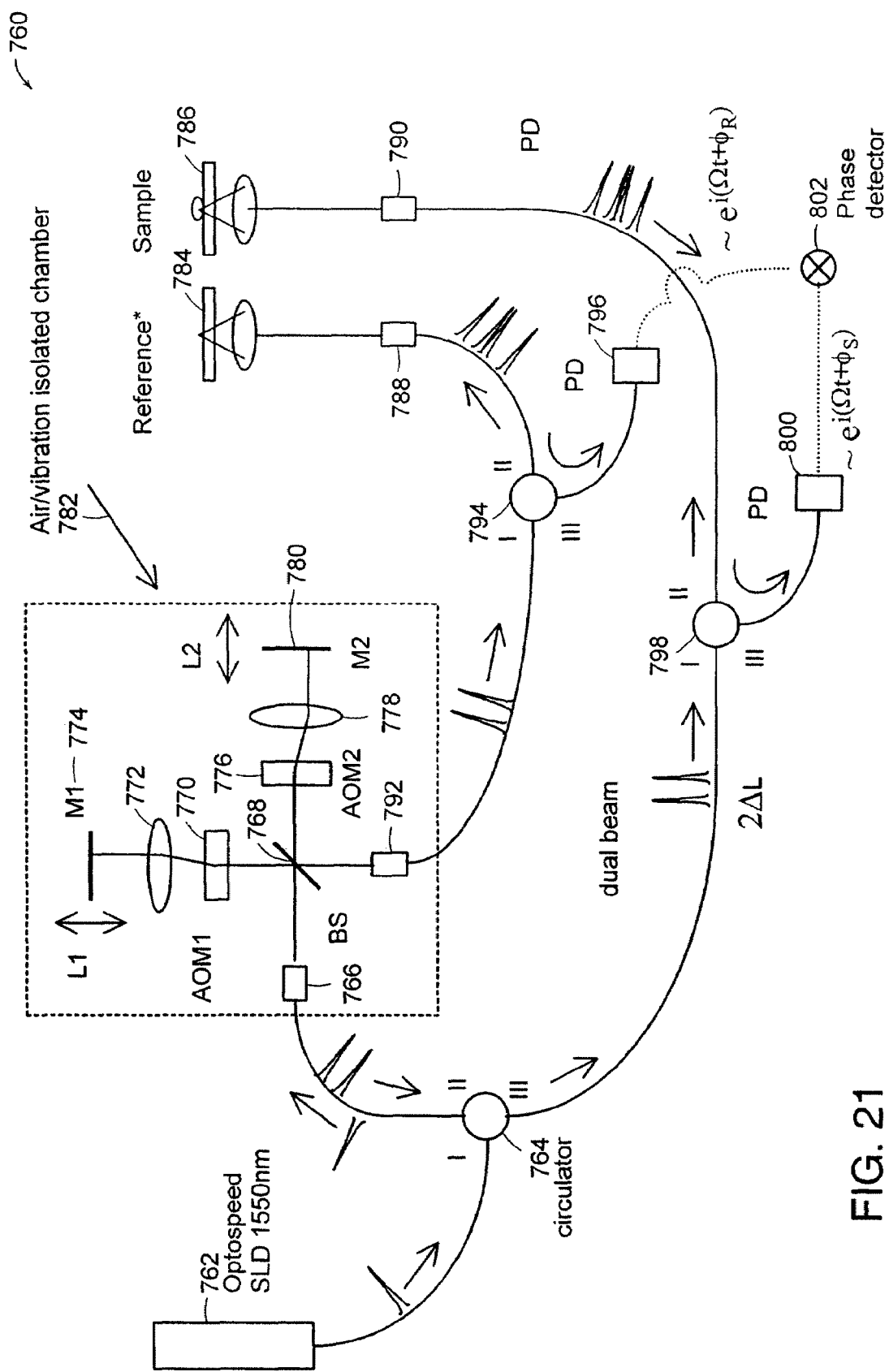
Figure 22:
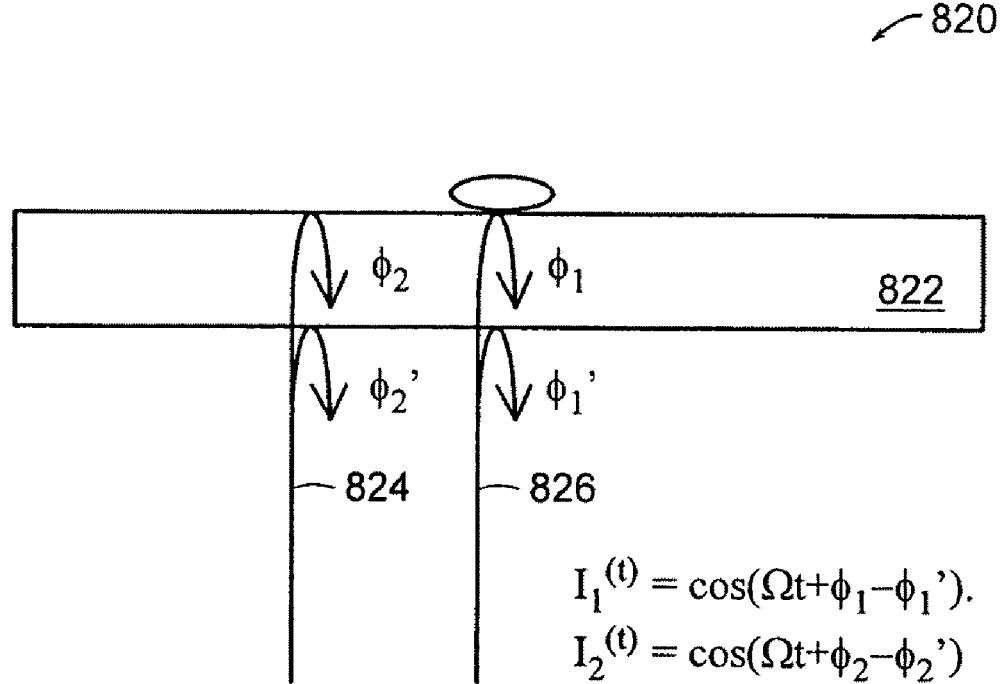
Figure 23A:
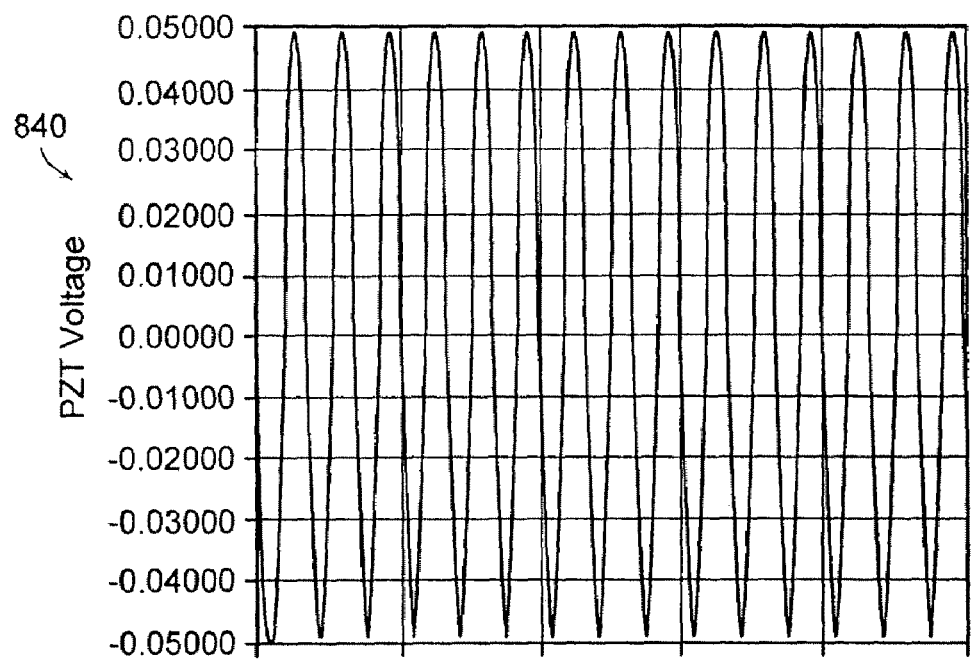
Figure 23B:
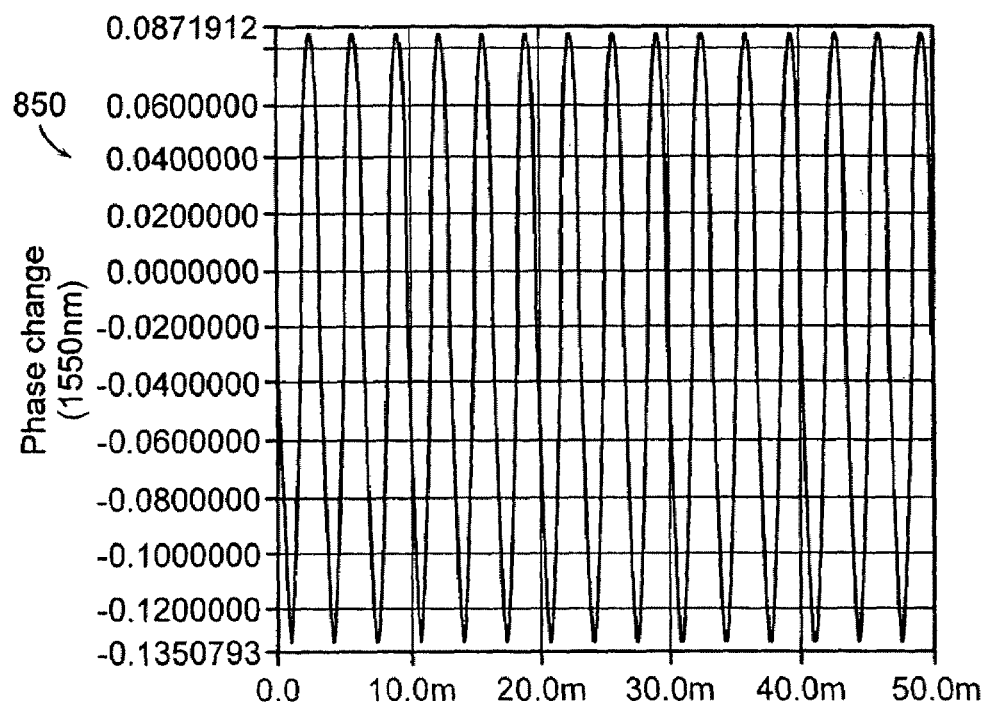
Figure 24:
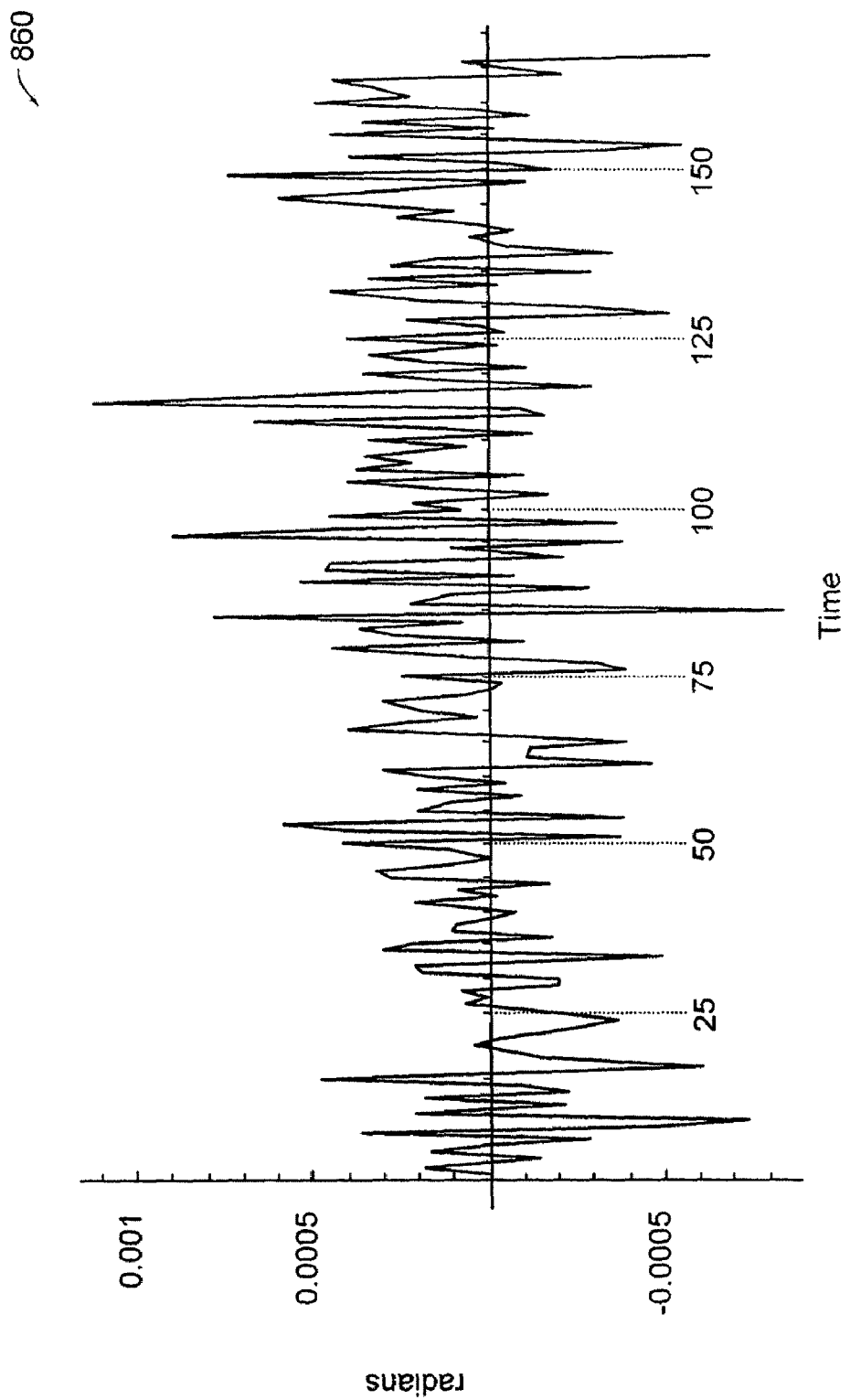
Figure 25A:
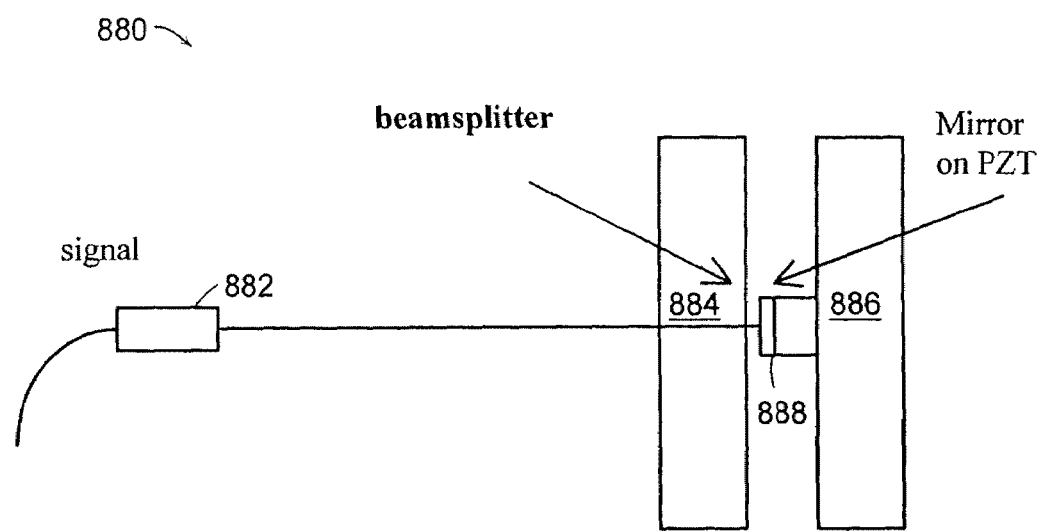
Figure 25B:
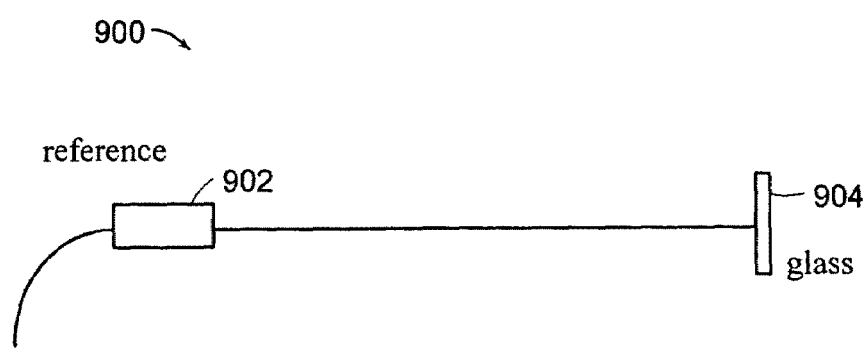
Figure 26:
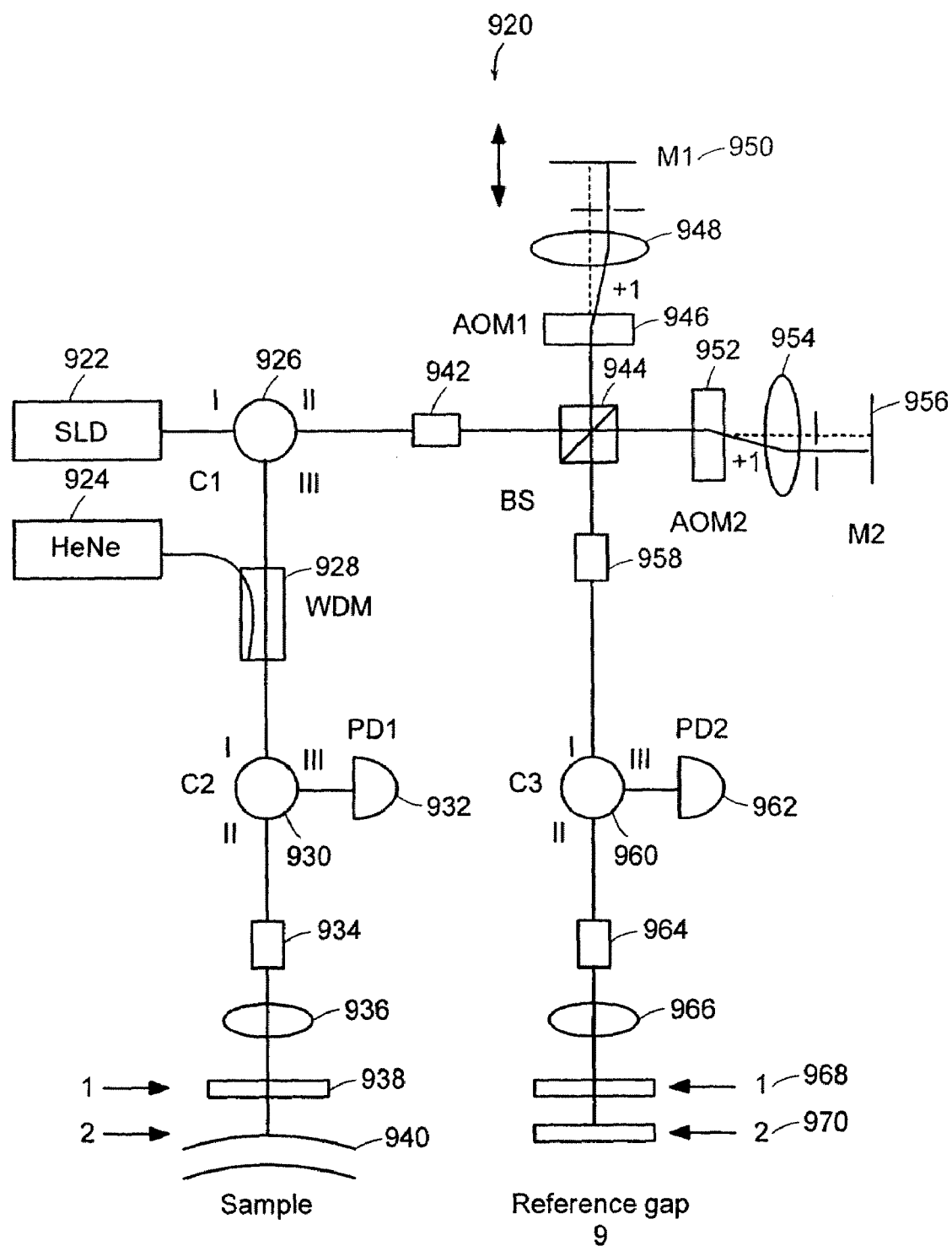
Figure 27:
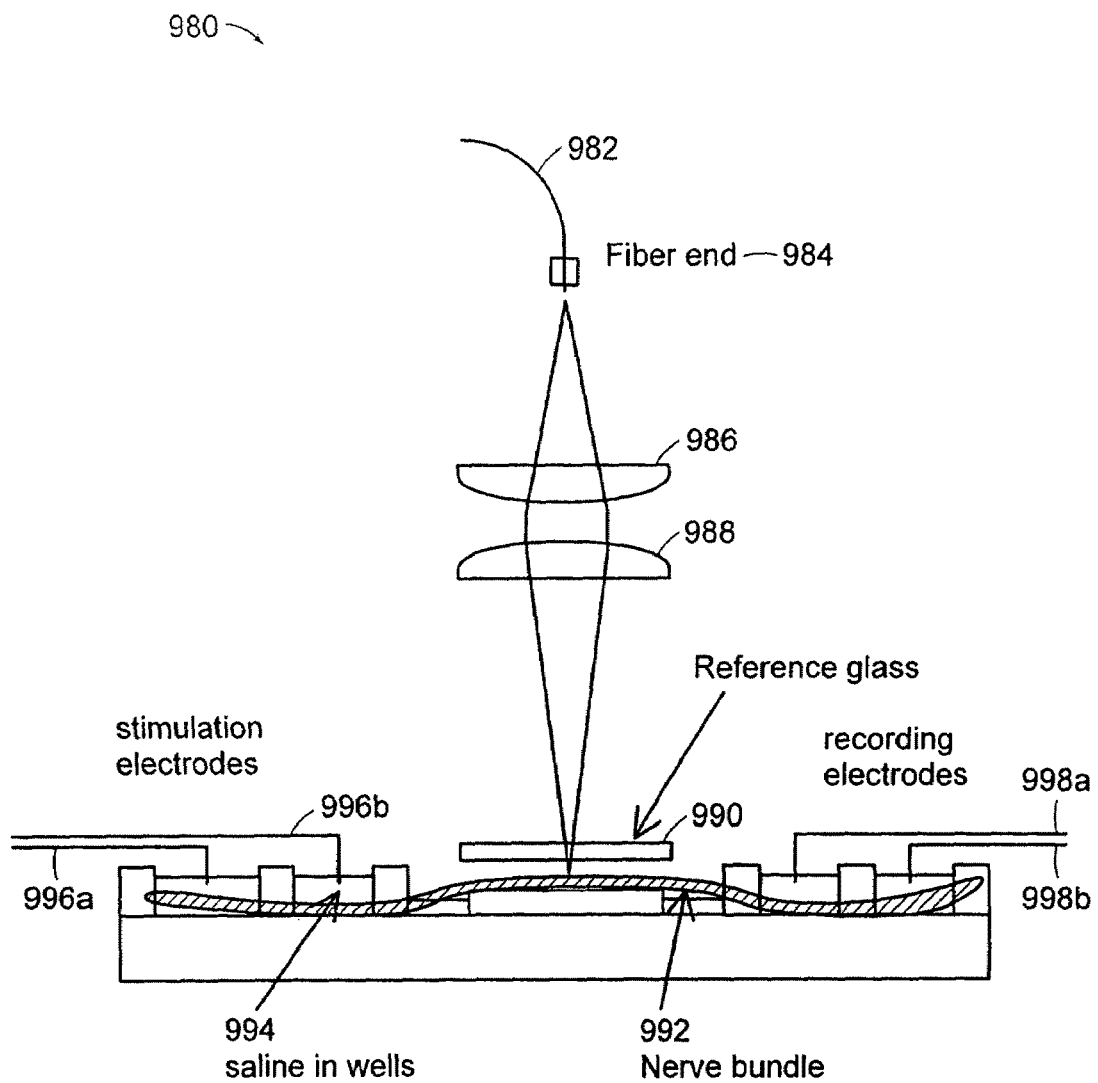
Figure 28A:
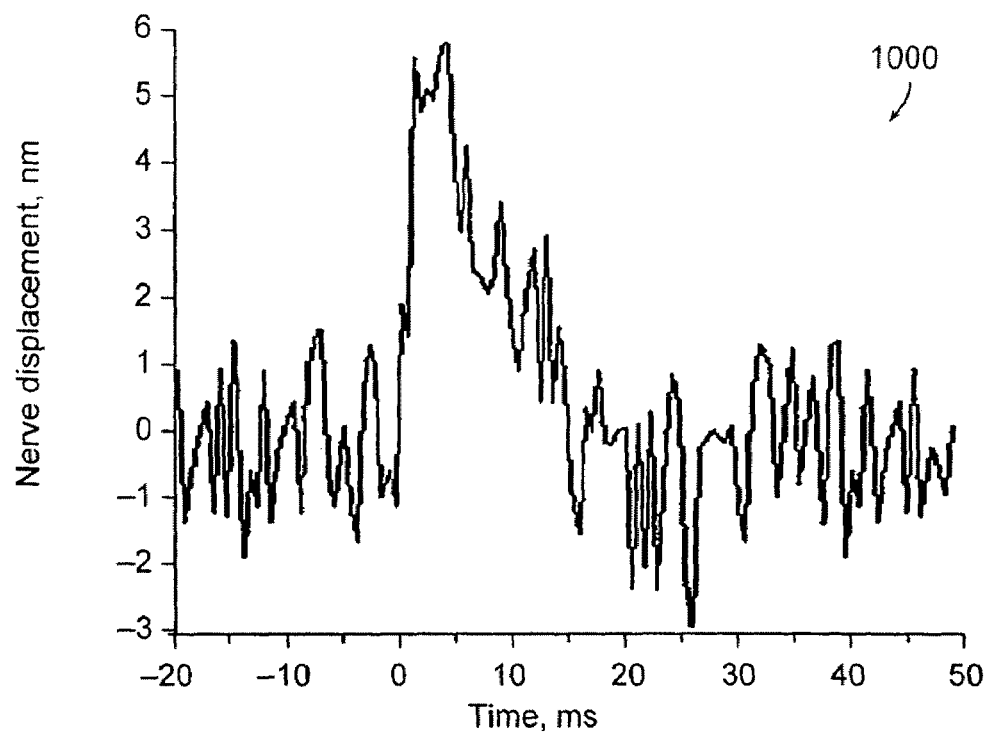
Figure 28B:
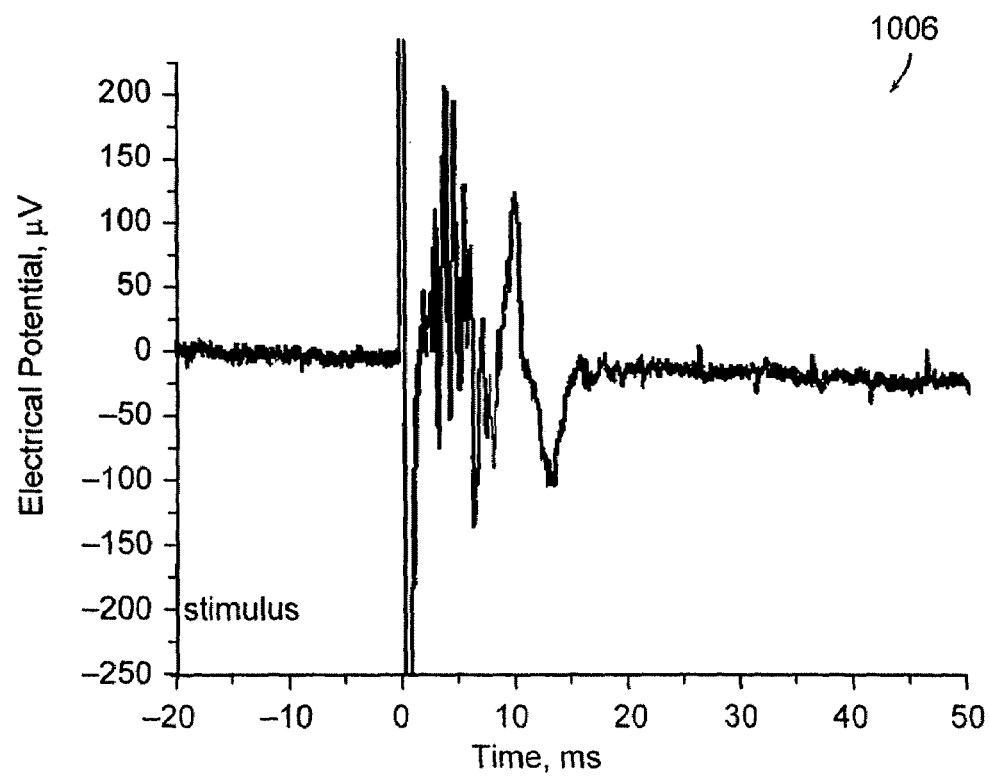
Figure 29:
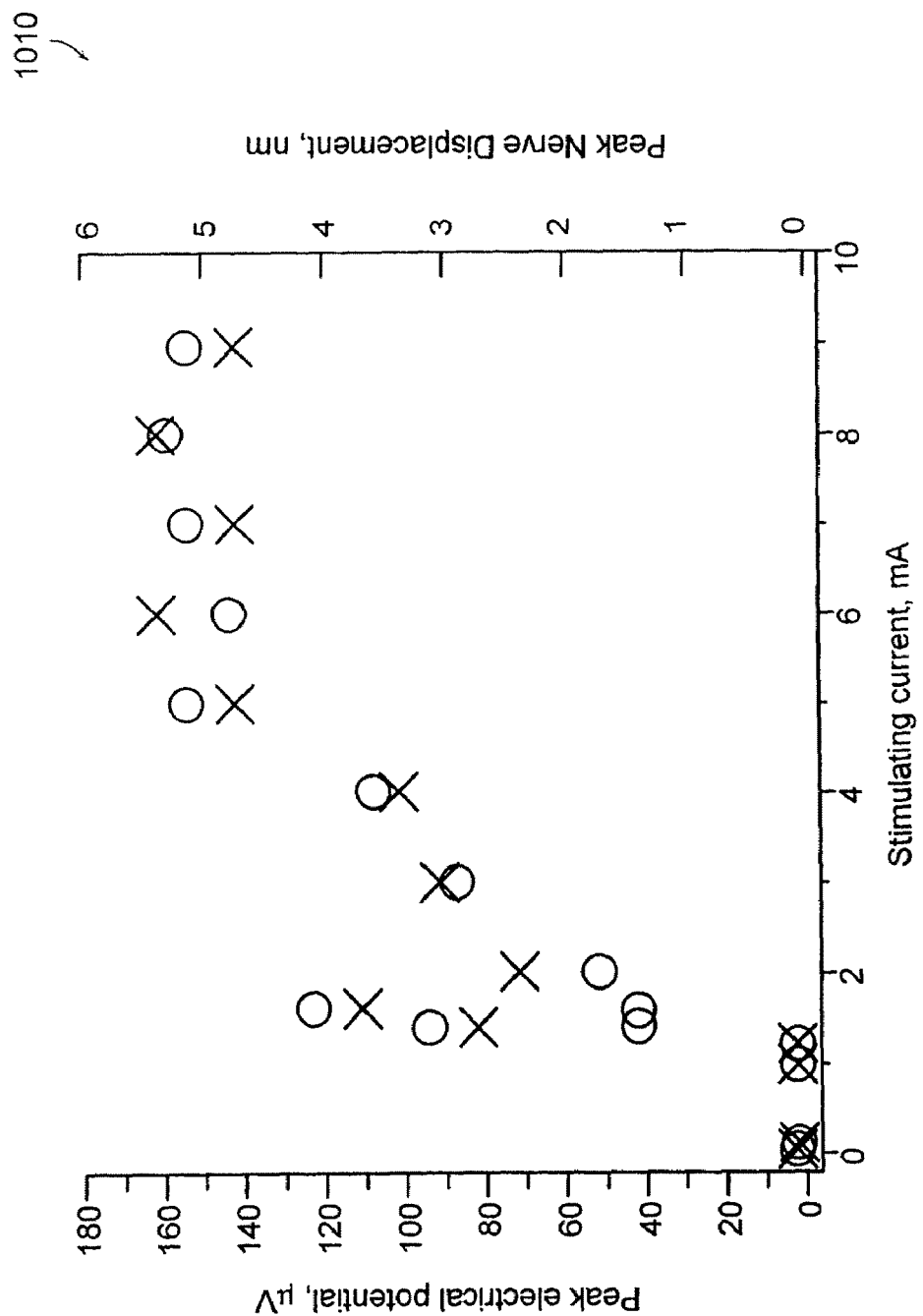
Figure 30:
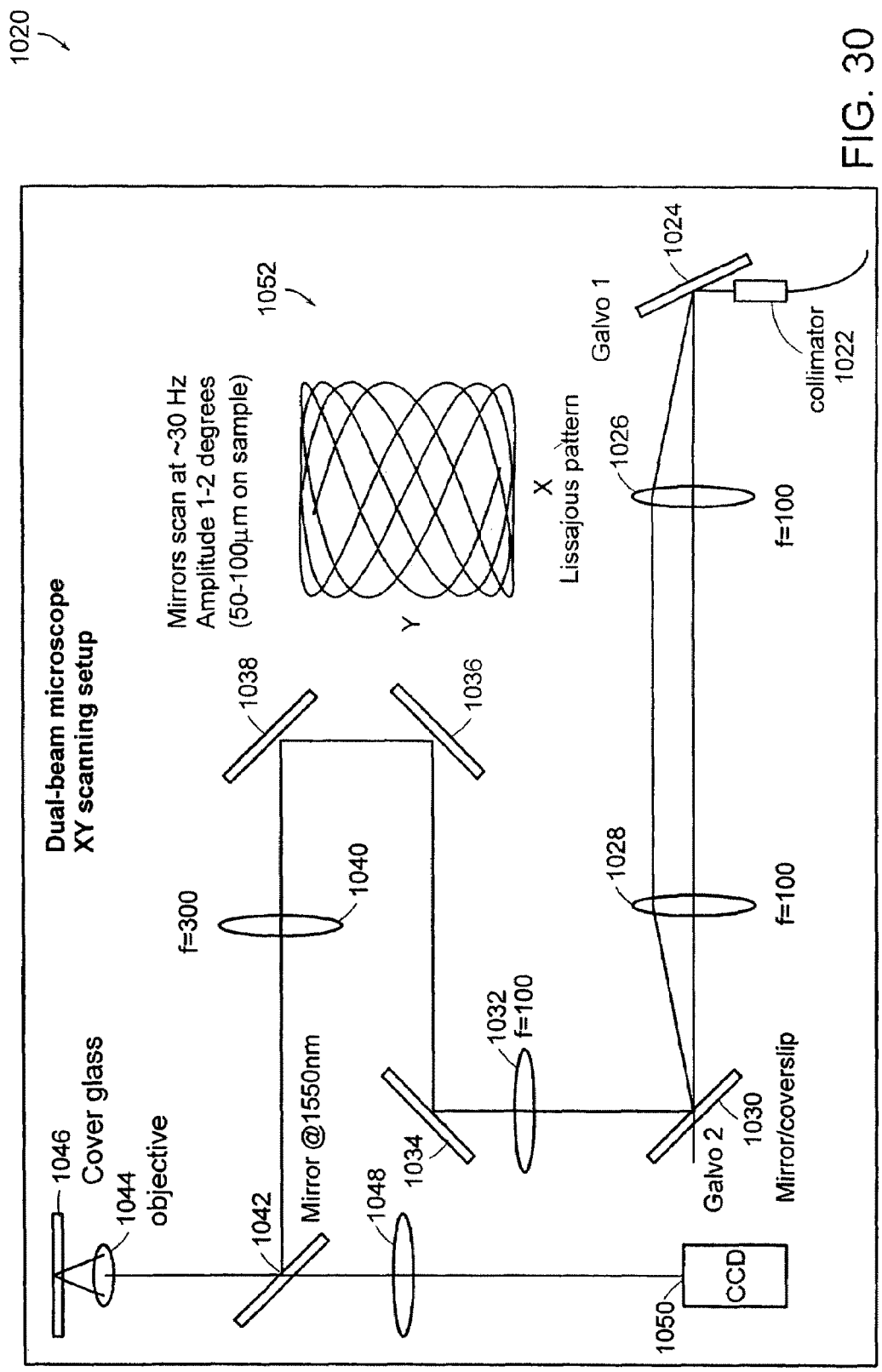
Figure 31:
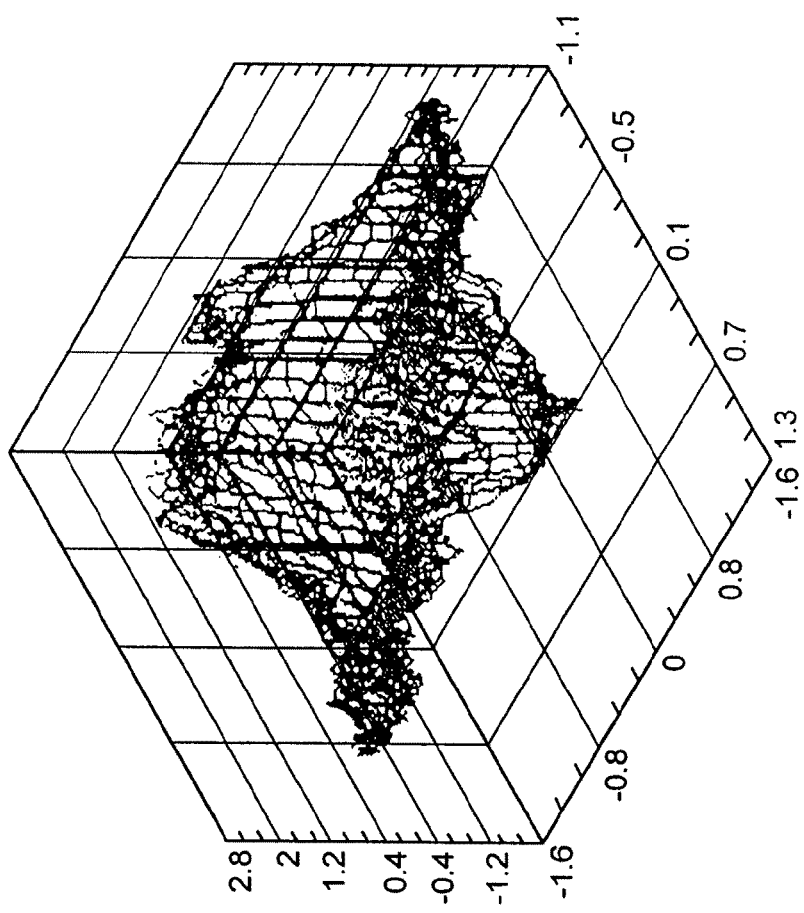
Figure 32A:
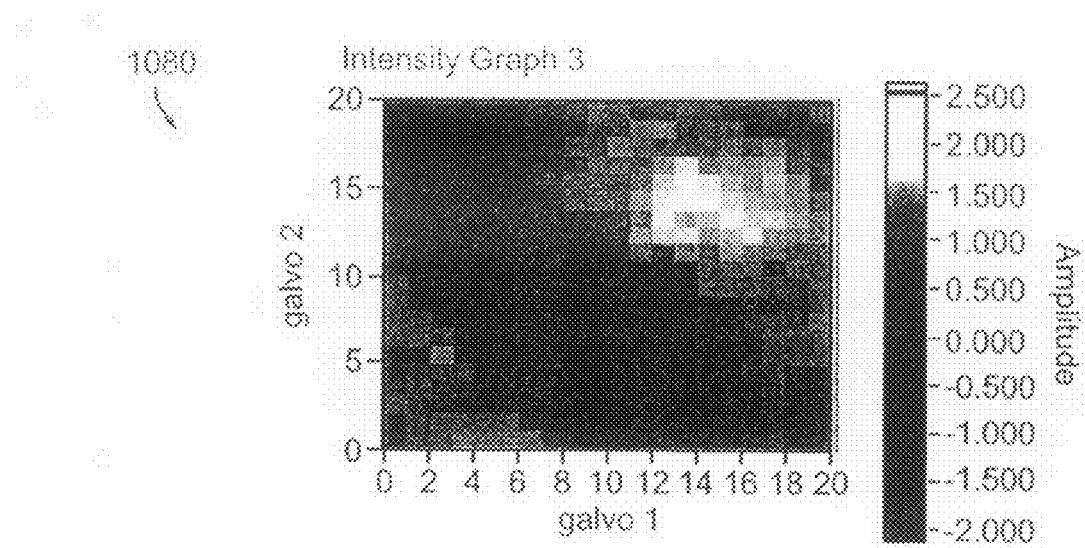
Figure 32B:
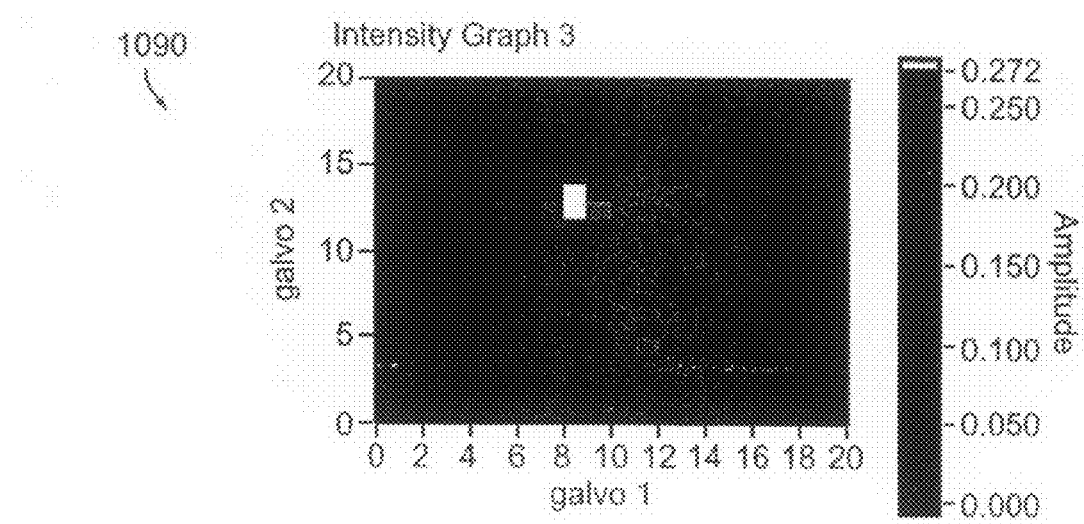
Figure 33:
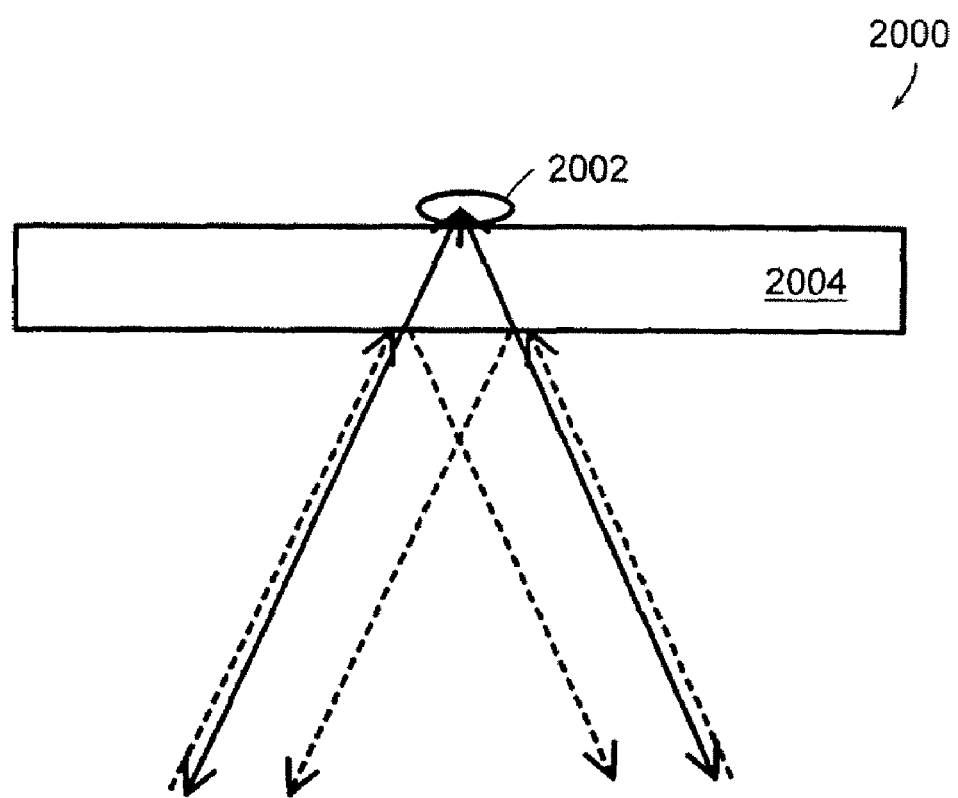
Figure 34:
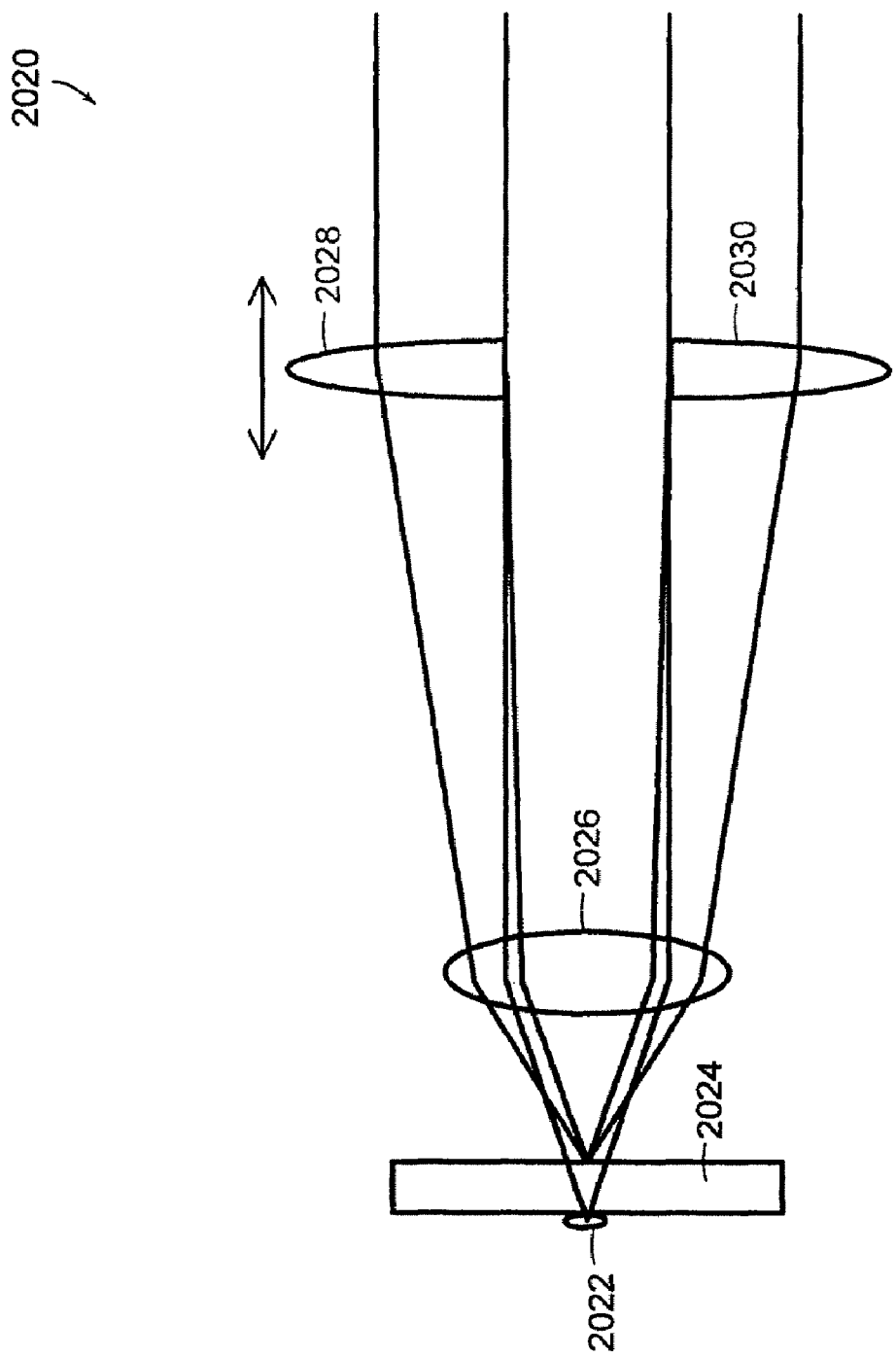
Figure 35:
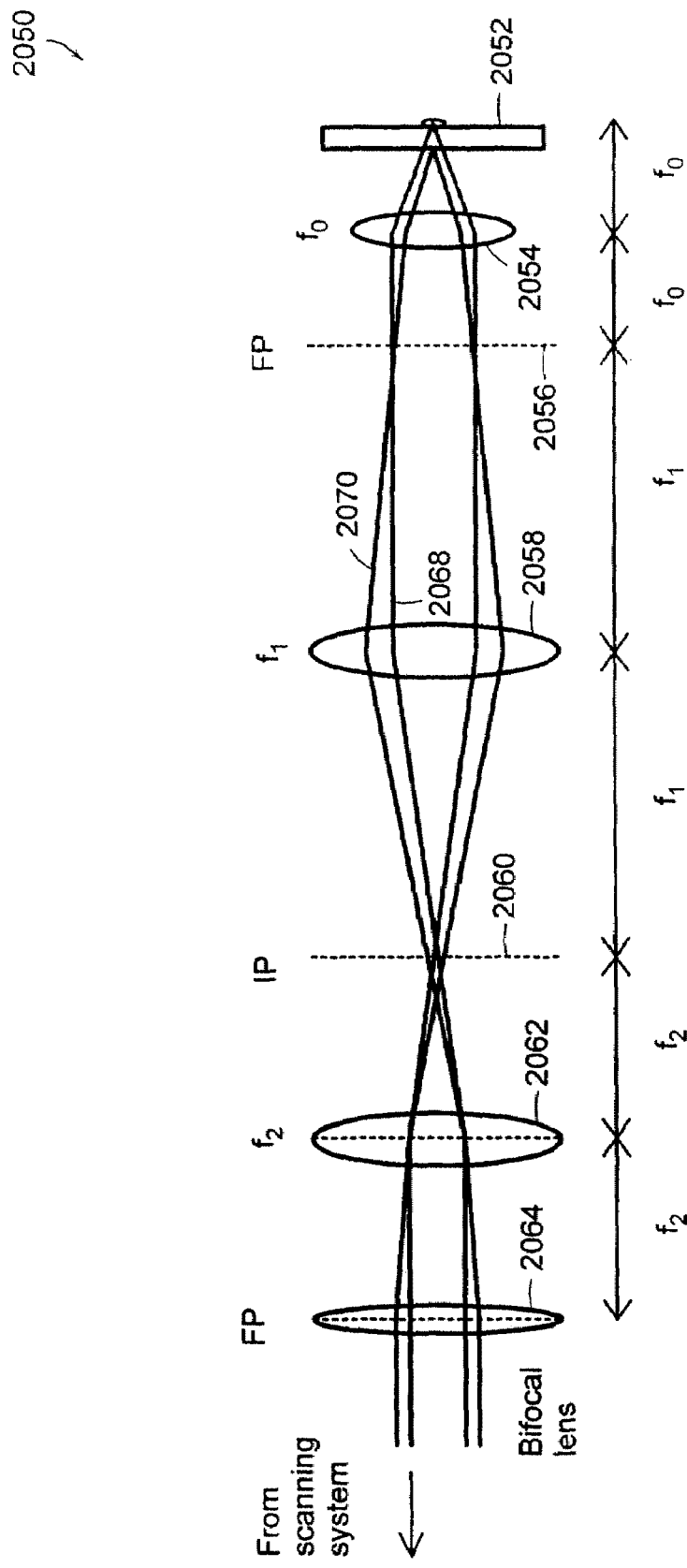
Figure 36:
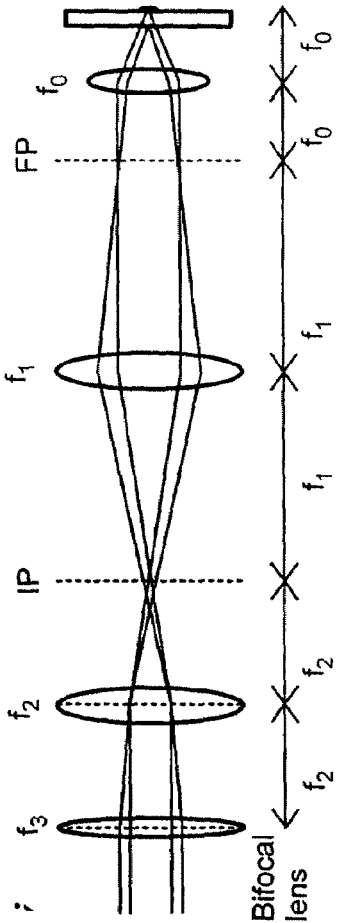
Figure 37:
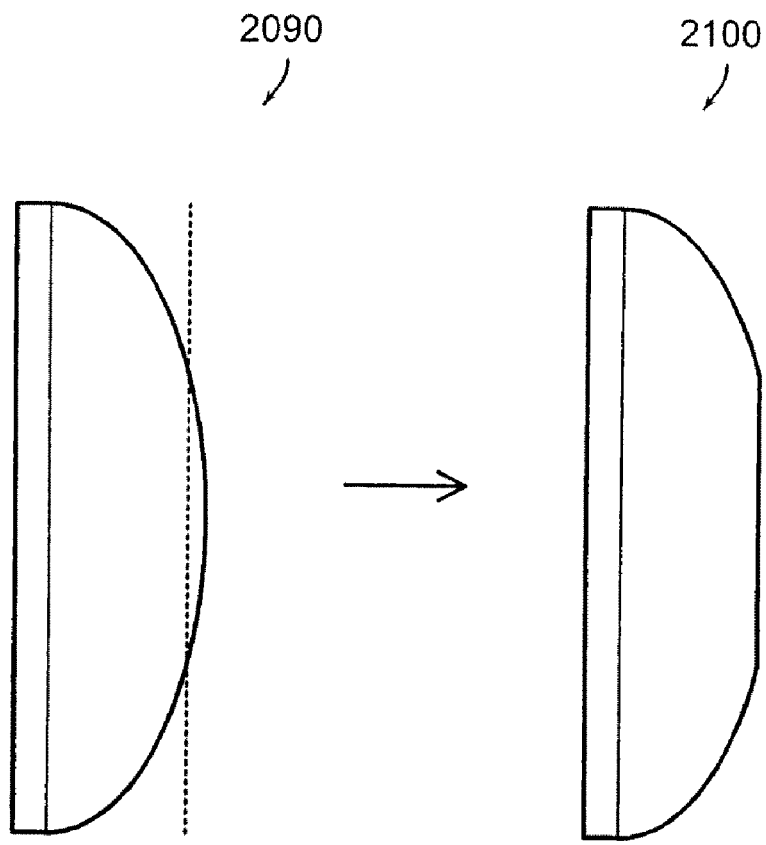
Figure 39:
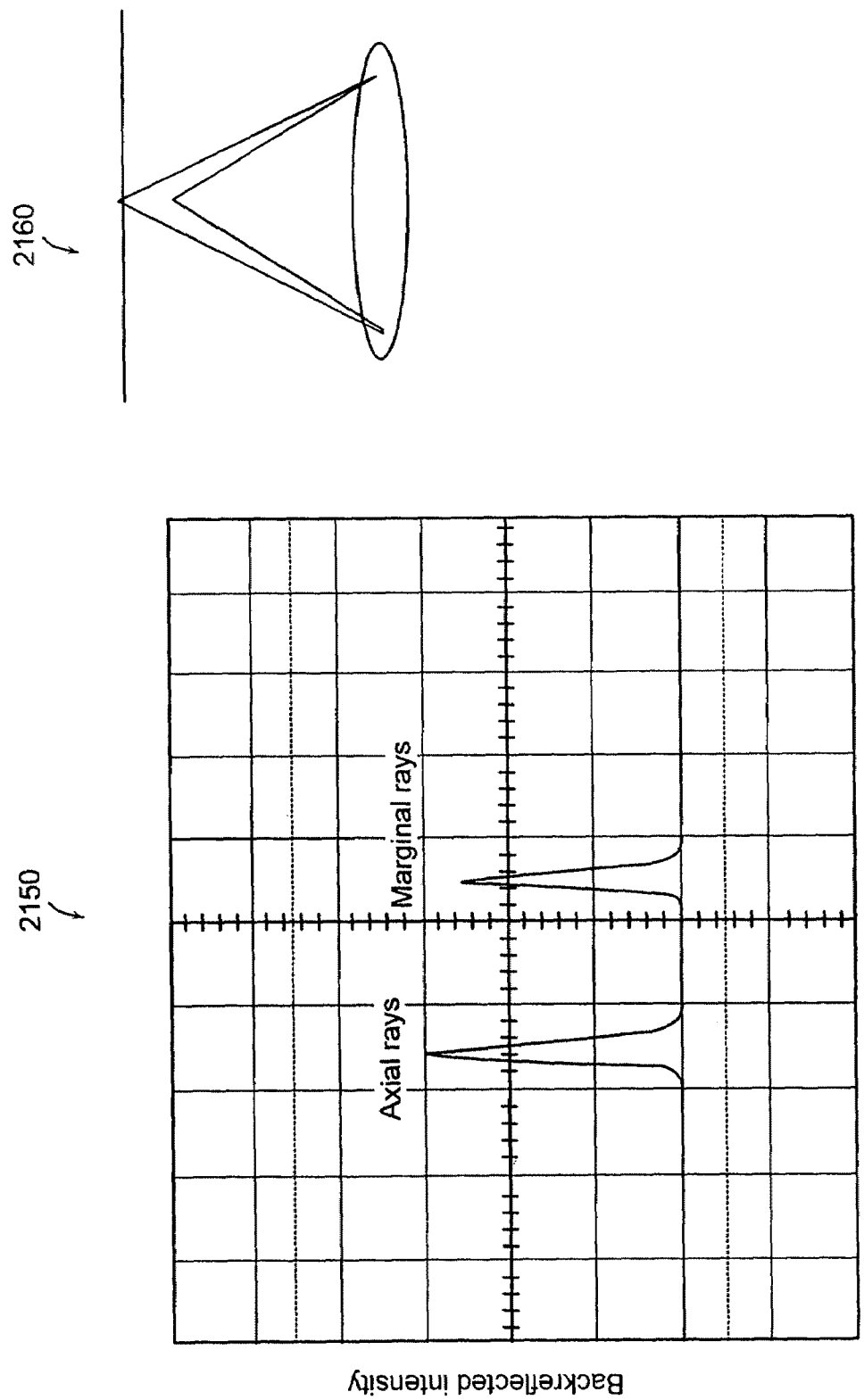
Figure 40:
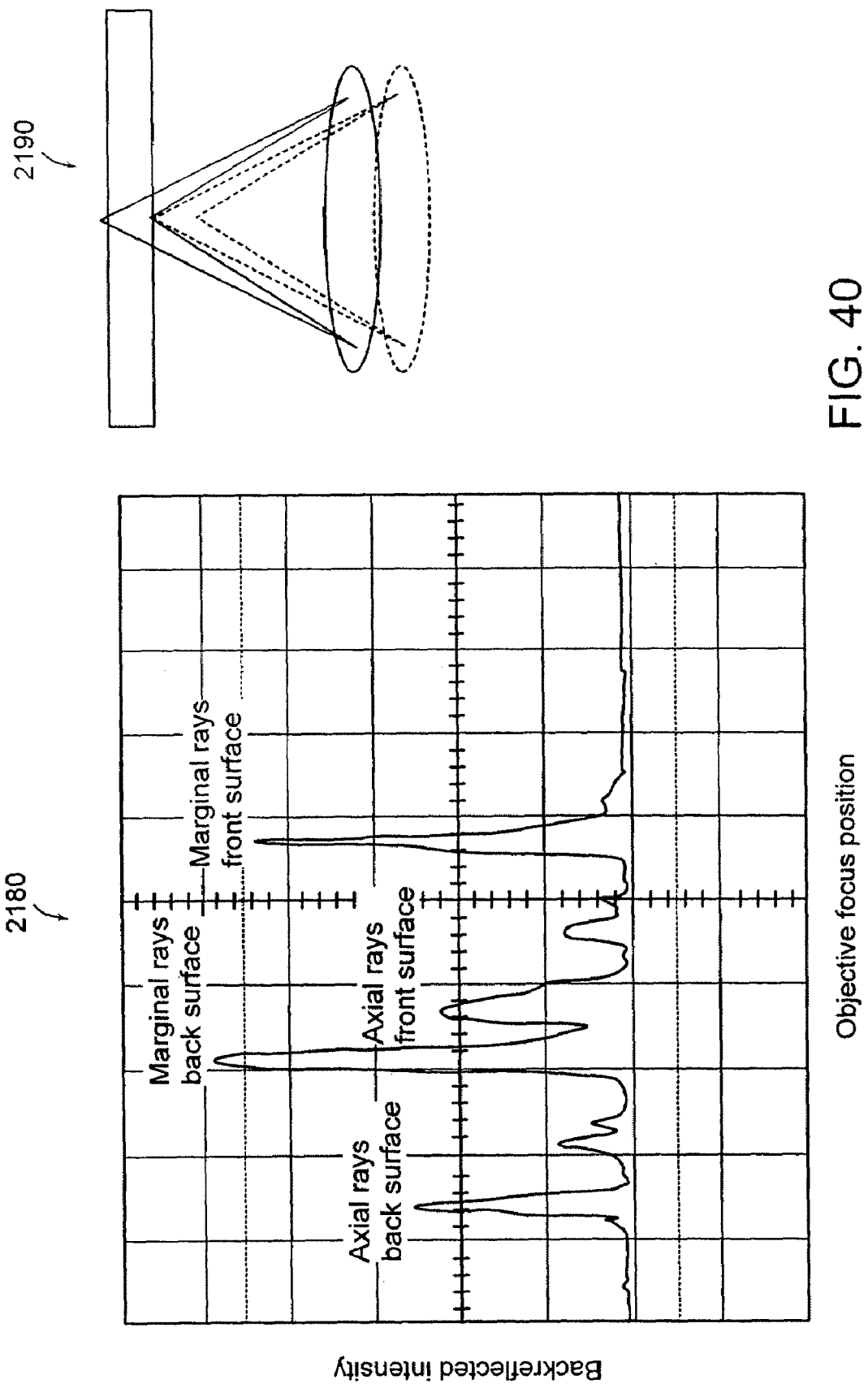
Figure 41:
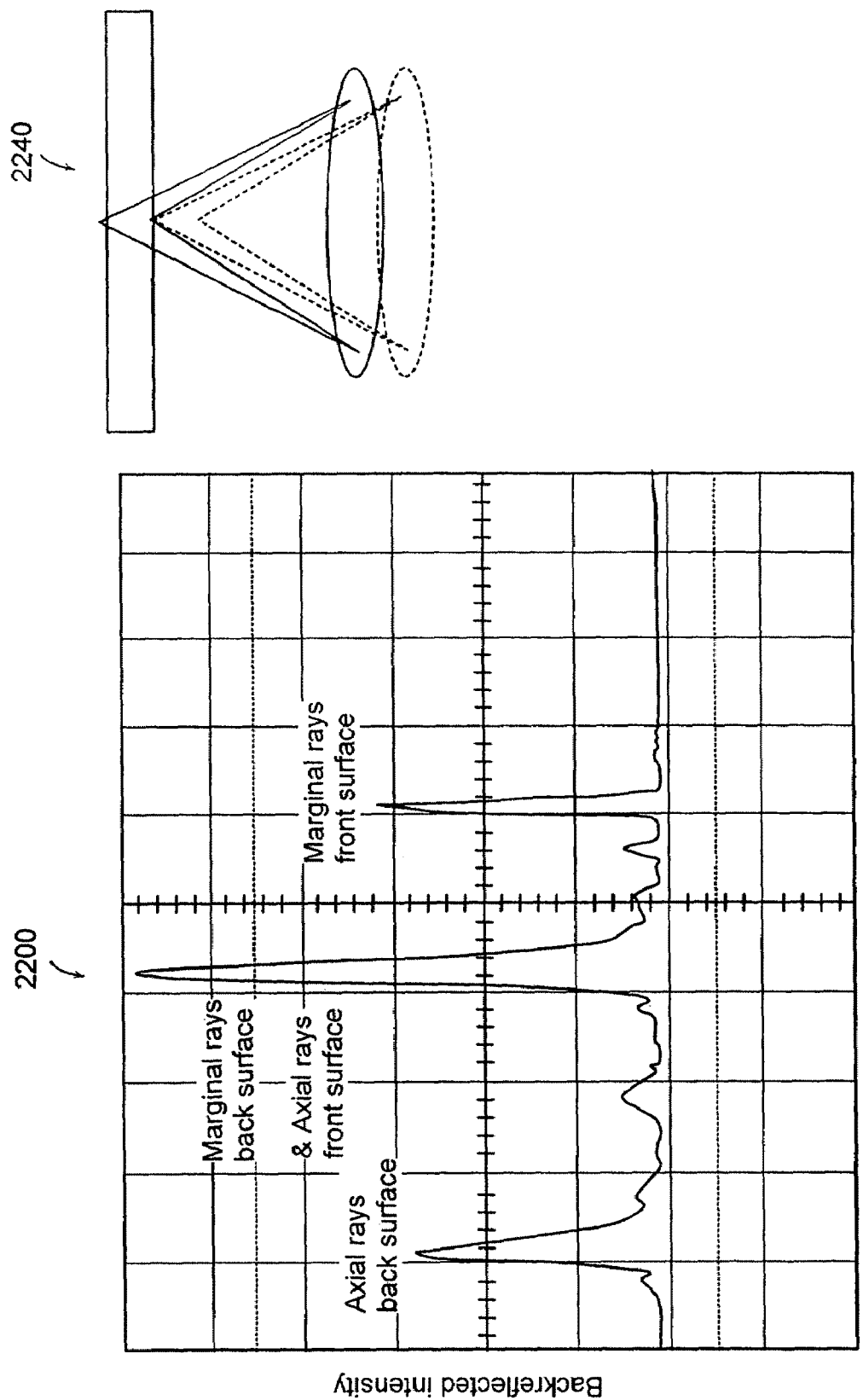
Figure 42B:
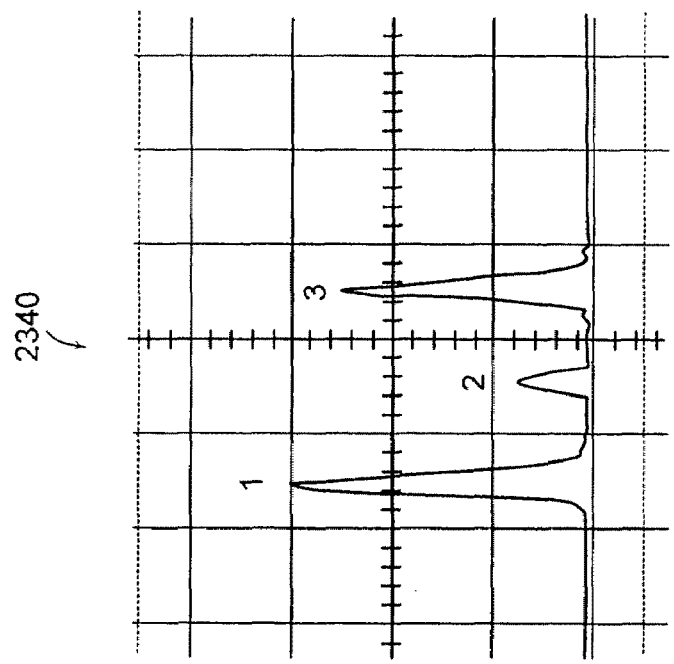
Figure 42A:
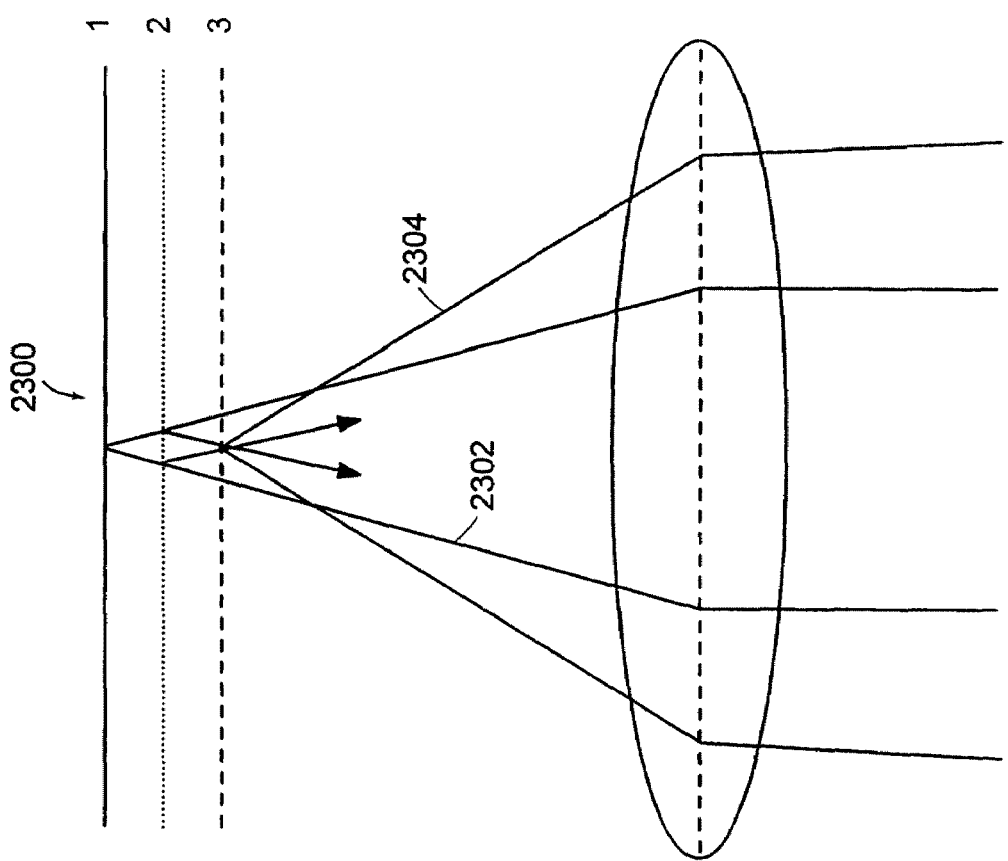
Figure 43A:
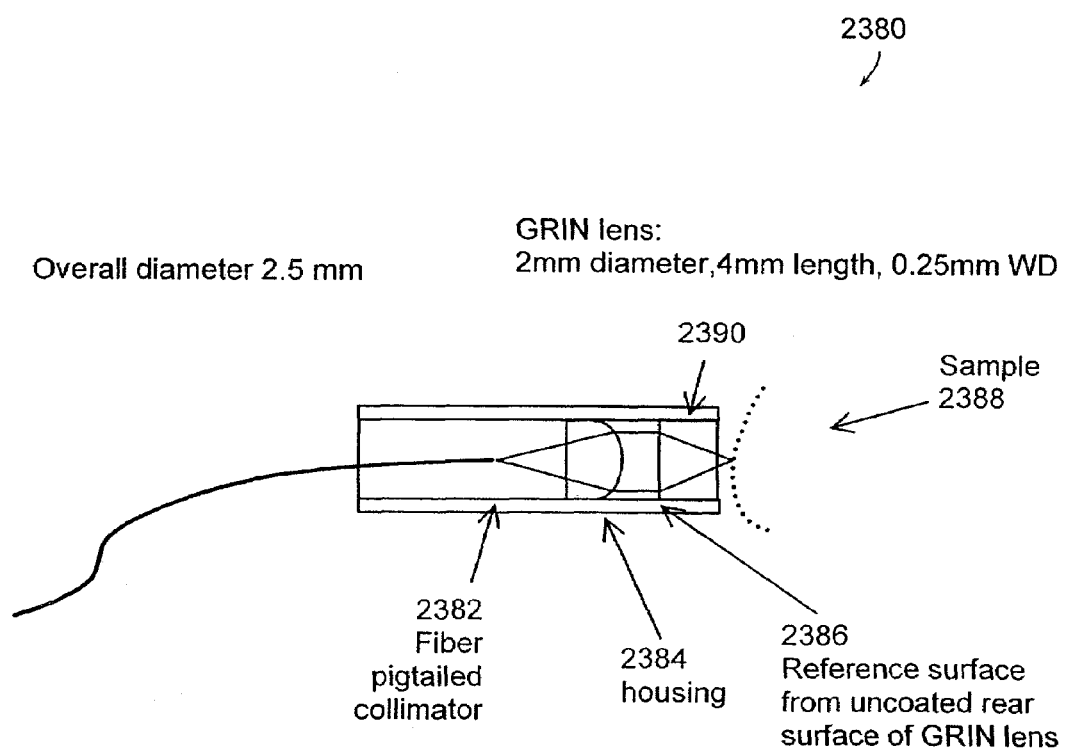
Figure 43B:
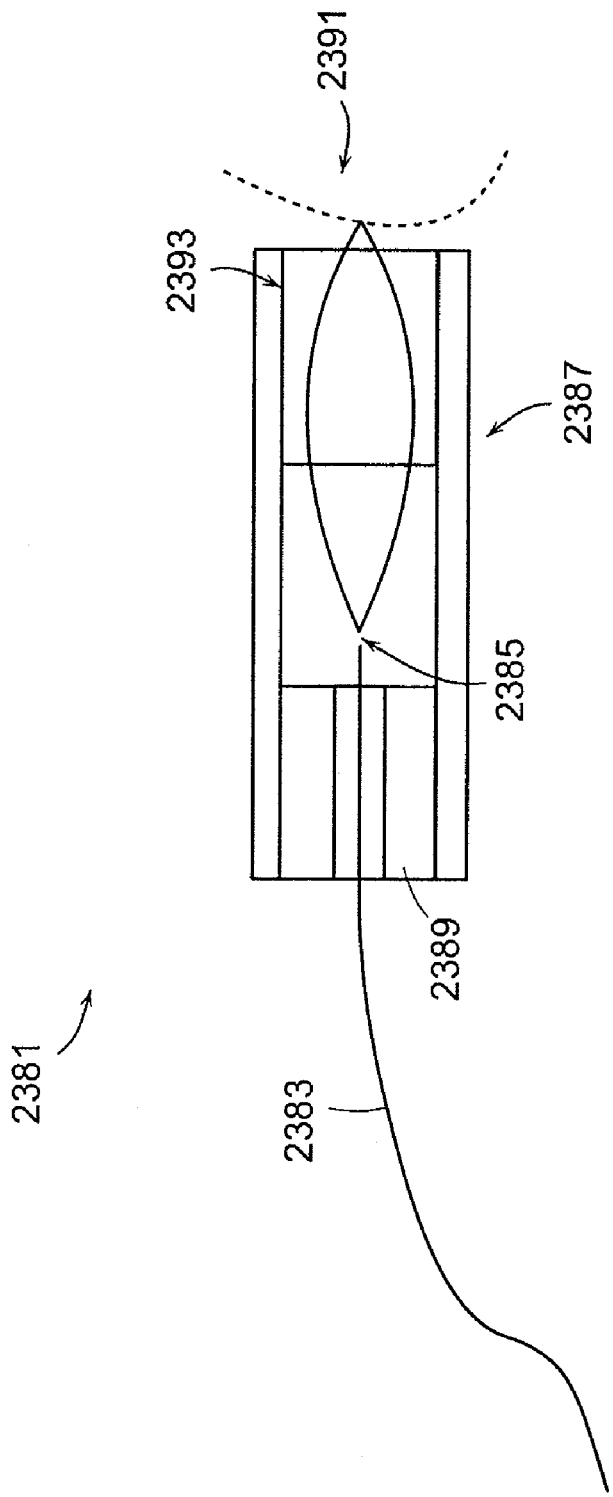
Figure 43C:
Figure 44:
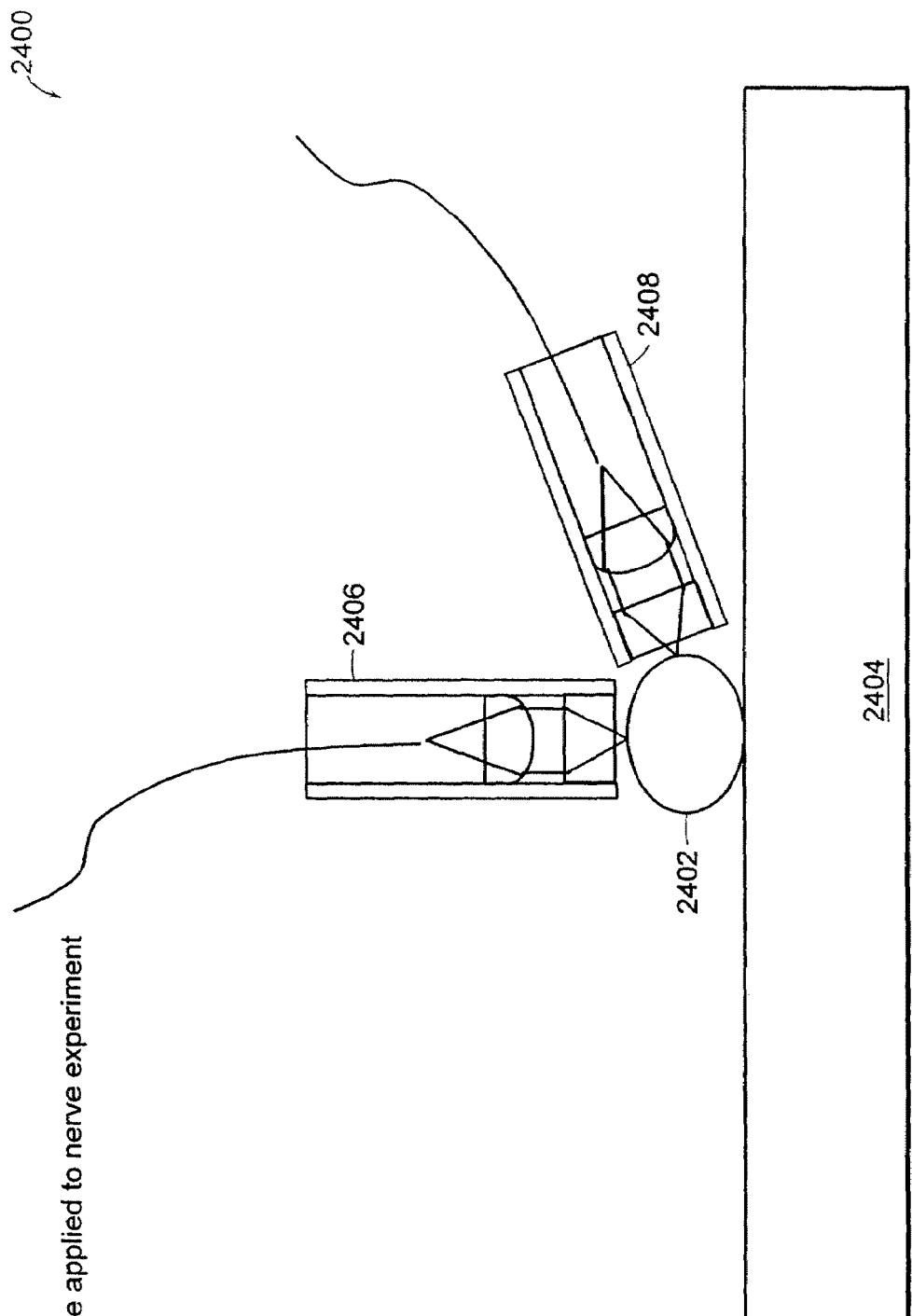
Figure 45:
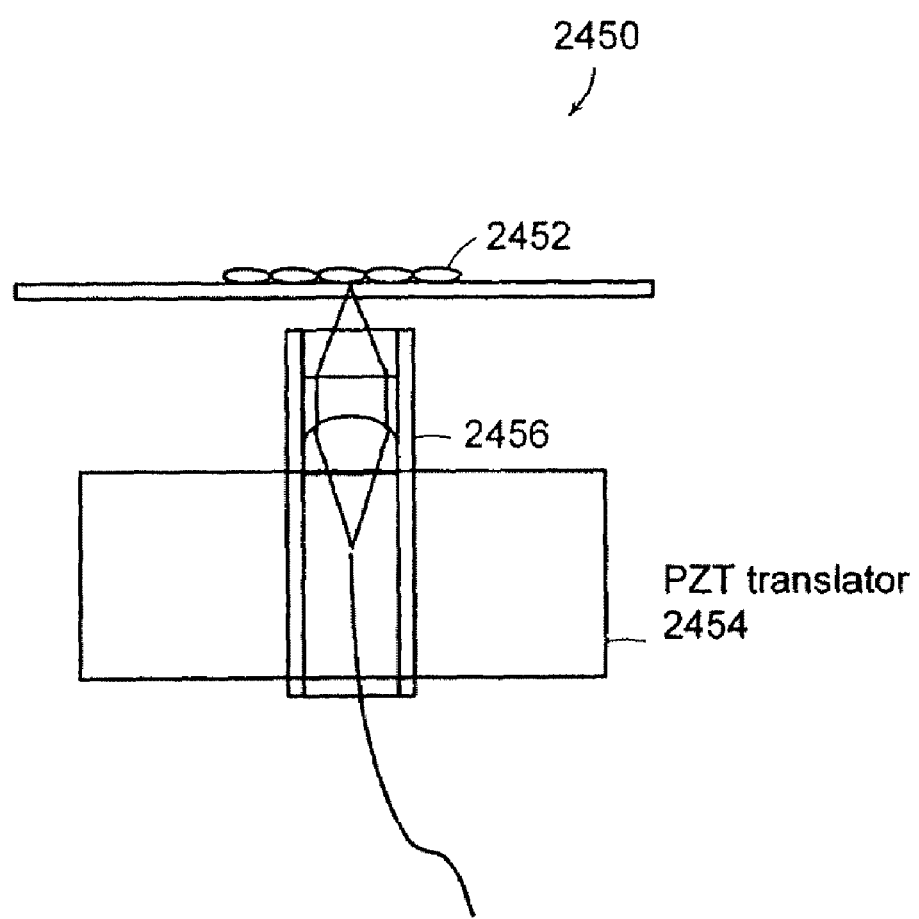
Figure 46A:
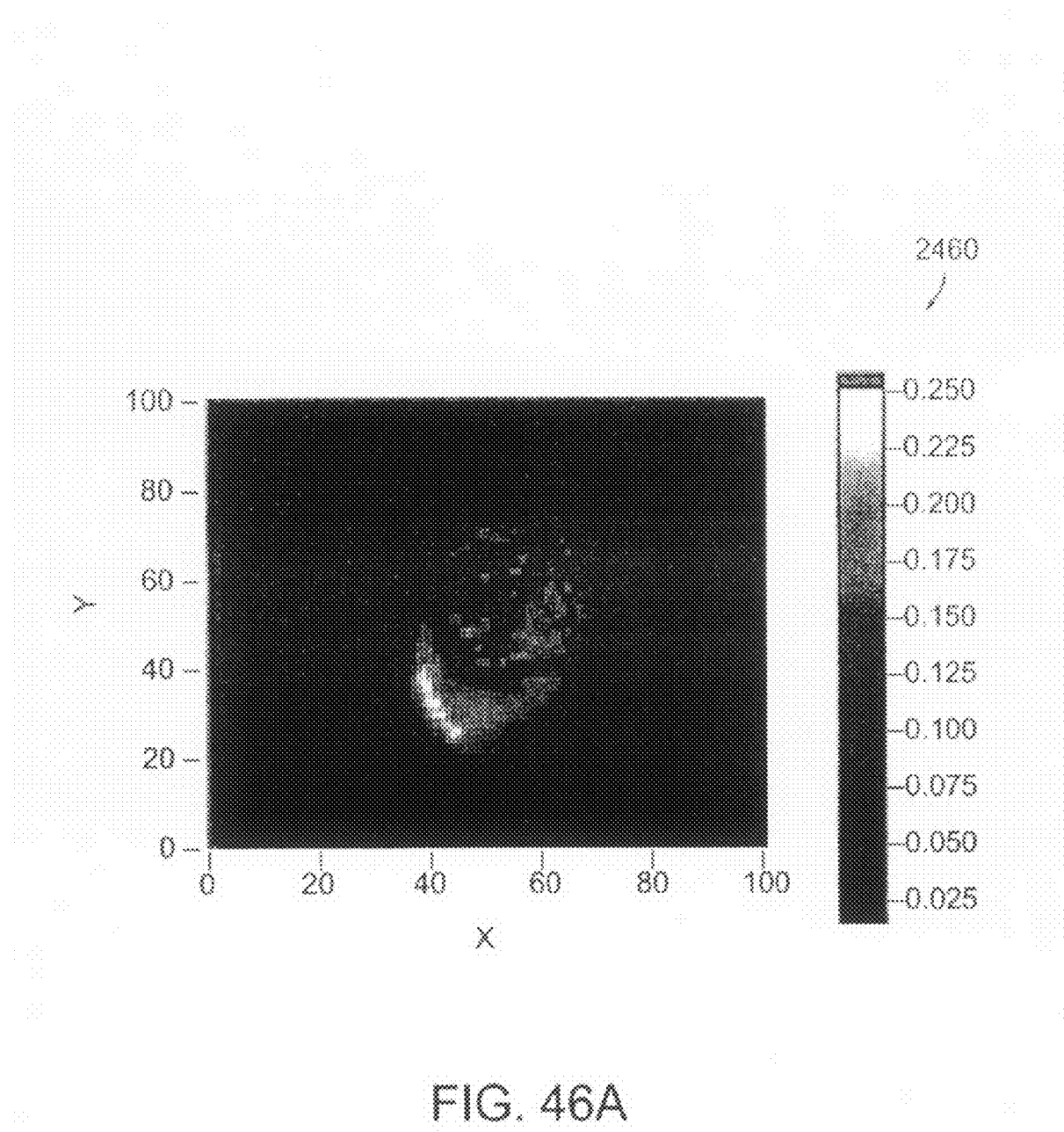
Figure 46B:
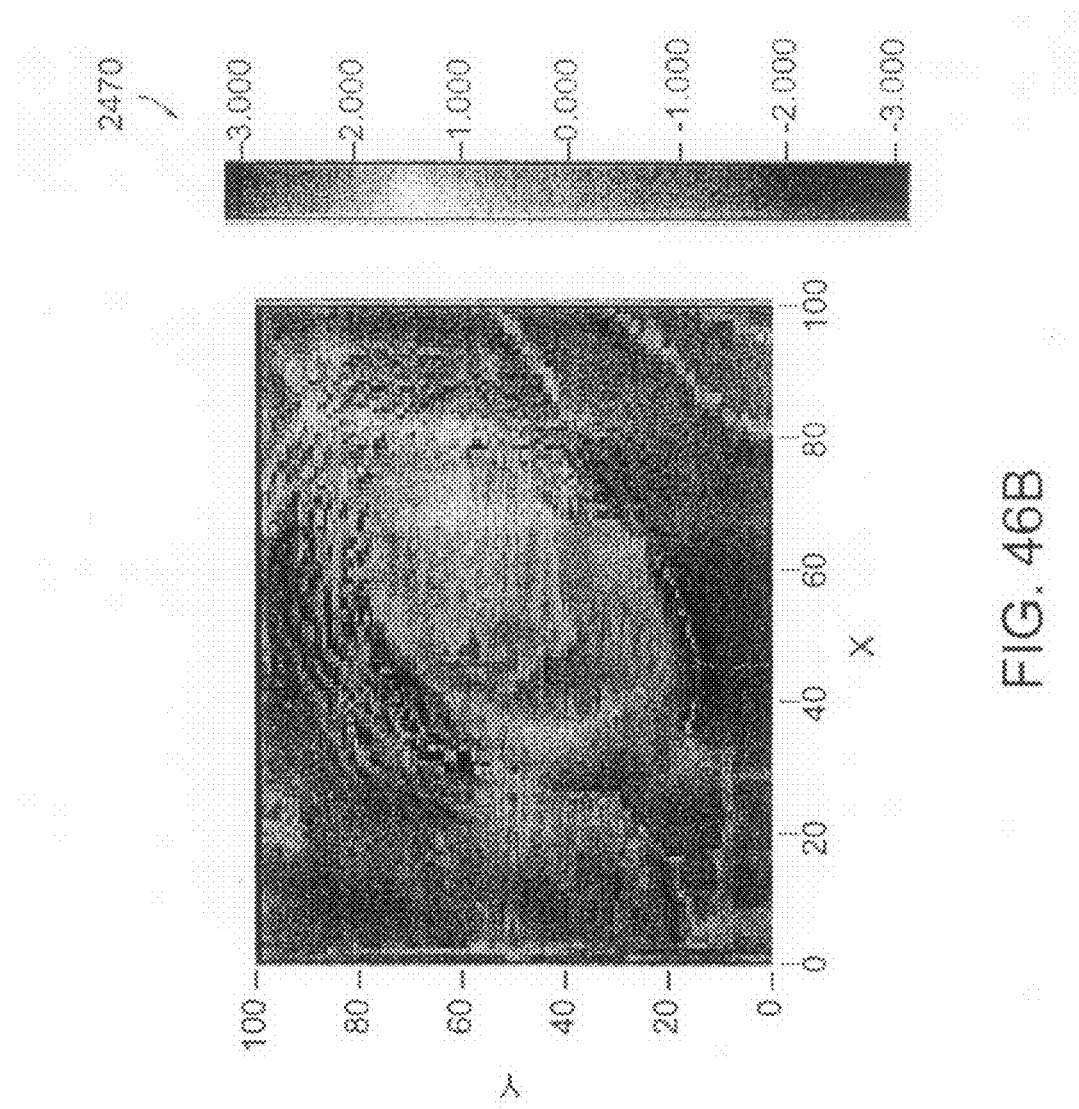
Figure 46C:
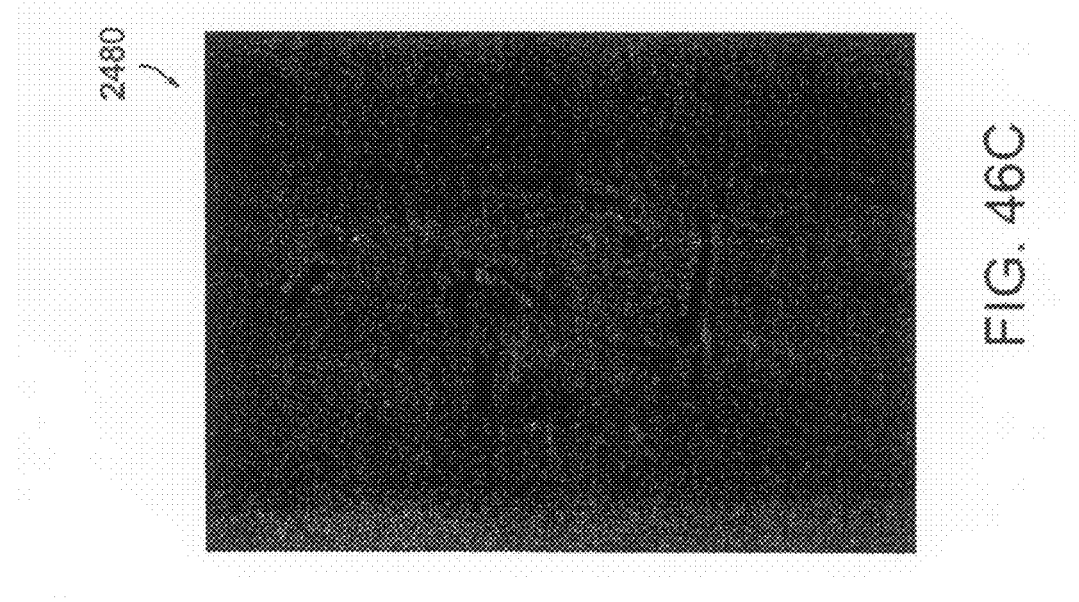
Figure 46D:
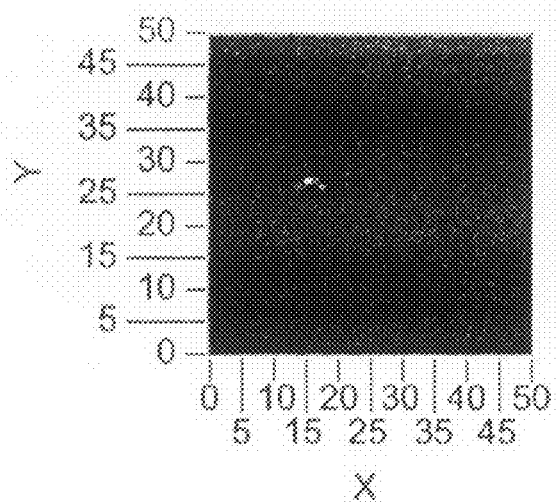
Figure 46F:
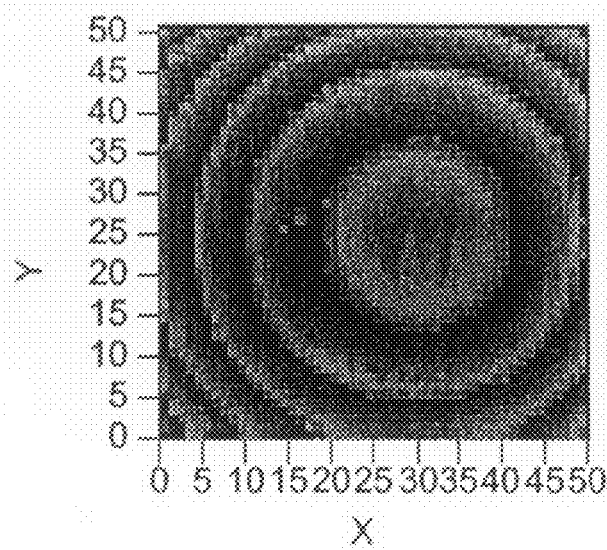
Figure 46E:
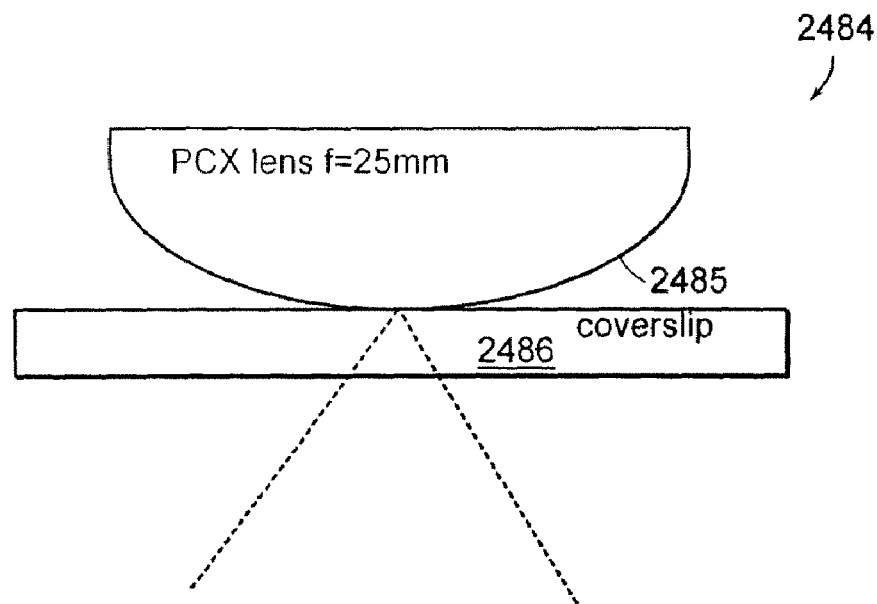
Figure 46G:
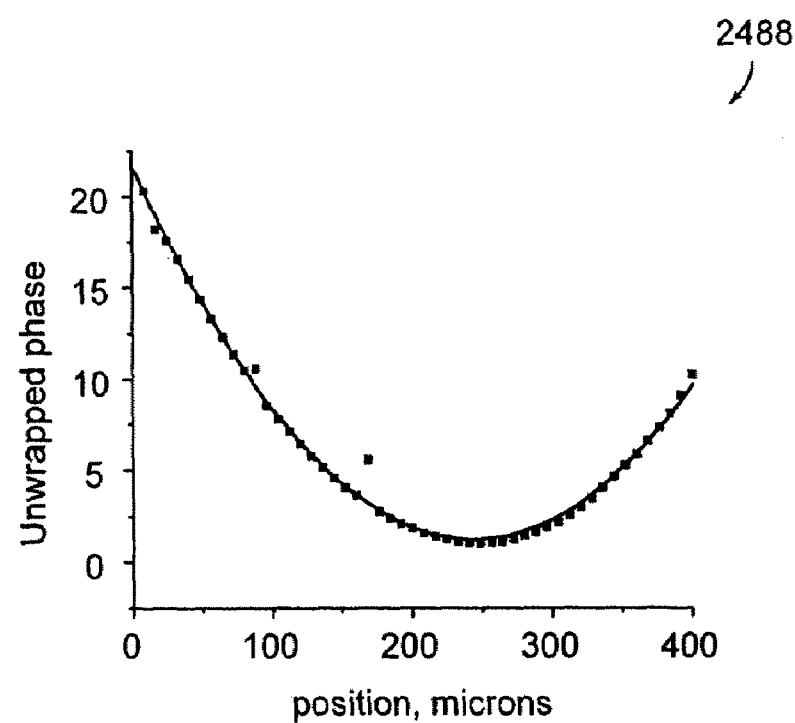

wherein DBS is a dichroic beamsplitter in accordance with a preferred embodiment of the present invention;

FIG. 13 illustrates a sample demodulated interference pattern for a pair of interfaces, as optical path length difference ΔL is varied in accordance with a preferred embodiment of the present invention;

FIG. 14A illustrates a system for stabilized phase-sensitive low coherence interferometry (LCI) wherein LC1 and LC2 are low coherence beams in accordance with a preferred embodiment of the present invention;

FIG. 14B illustrates an alternate embodiment of a system for actively stabilized phase-sensitive low coherence interferometry (LCI) using a piezoelectric transducer to generate the phase shift in accordance with the present invention;

FIGS. 15A and 15B are demodulated fringe patterns for LC1 and LC2 wherein the two peaks in the LC2 signal represent coverslip reflection (large) and reflection from a sample (small) in accordance with a preferred embodiment of the present invention;

FIG. 16 illustrates an imaging system for stabilized phase-sensitive low coherence interferometry in accordance with a preferred embodiment of the present invention;

FIG. 17 illustrates an unfolded optical design for two-dimensional phase imaging wherein the solid lines are indicative of incident rays while the dashed lines are indicative of backscattered rays in accordance with a preferred embodiment of the present invention;

FIG. 18A illustrates a two-point Mach-Zender heterodyne interferometer in accordance with a preferred embodiment of the present invention;

FIG. 18B illustrates an imaging Mach-Zender heterodyne interferometer in accordance with a preferred embodiment of the present invention;

FIG. 18C illustrates the heterodyne and gate signals associated with the embodiment described with respect to FIG. 18B;

FIG. 18D illustrates an imaging dual-beam heterodyne interferometer in accordance with a preferred embodiment of the present invention;

FIG. 19 illustrates an isolated dual-beam heterodyne low coherence interferometer in accordance with a preferred embodiment of the present invention;

FIG. 20 illustrates a dual-reference heterodyne low coherence interferometer in accordance with a preferred embodiment of the present invention;

FIG. 21 illustrates a preferred embodiment of an optical referenced interferometer in accordance with a preferred embodiment of the present invention;

FIG. 22 illustrates schematically the components of measured phase that results from locating the reference point on the same surface (glass) as the sample object in accordance with a preferred embodiment of the present invention;

FIGS. 23A and 23B graphically illustrate the piezoelectric transducer (PZT) voltage and the corresponding phase change, respectively, for the embodiment illustrated with respect to FIG. 21 in accordance with a preferred embodiment of the present invention;

FIG. 24 graphically illustrates the noise performance in radians in accordance with the interferometer illustrated in FIG. 21;

FIGS. 25A and 25B are schematic representations of the calibration setup for the sample and reference signals in accordance with a preferred embodiment of the present invention;

FIG. 26 schematically illustrates a preferred embodiment of an interferometer system in accordance with a preferred embodiment of the present invention;

FIG. 27 illustrates a schematic diagram of a system to measure nerve displacements in accordance with a preferred embodiment of the present invention;

FIGS. 28A and 28B illustrates graphically nerve displacement (nm) and electrical potential (μV) with respect to time (ms) in accordance with a preferred embodiment of the present invention;

FIG. 29 graphically illustrates the peak electrical (crosses) and displacements (circles) for a single nerve, with variable stimulus current amplitude in accordance with a preferred embodiment of the present invention;

FIG. 30 illustrates the optical layout of a scanning system for a dual-beam interferometer in accordance with a preferred embodiment of the present invention;

FIG. 31 illustrates galvanometer position and phase data collected from an empty coverglass using Lissajous scanning in accordance with a preferred embodiment of the present invention;

FIGS. 32A and 32B illustrate the color maps of phase image using the data represented and graphically illustrated in FIG. 31 and the intensity image of backrefection, respectively, in accordance with a preferred embodiment of the present invention;

FIG. 33 illustrates schematically the focusing problem that is overcome by preferred embodiments of the present invention;

FIG. 34 illustrates a design for a bifocal lens in accordance with a preferred embodiment of the present invention;

FIG. 35 illustrates an alternate design for the bifocal lens in accordance with a preferred embodiment of the present invention;

FIG. 36 illustrates the calculation of optimal distance between lenses f3 (bifocal) and f2 in accordance with a preferred embodiment of the present invention;

FIG. 37 illustrates the manufacturing of a bifocal lens in accordance with a preferred embodiment of the present invention;

FIG. 38 illustrates the backreflected intensity measured through an optical circulator, as the objective is scanned toward a glass coverslip in accordance with a preferred embodiment of the present invention;

FIG. 39 illustrates the backreflected intensity versus the objective focus position using a bifocal lens f3 in accordance with a preferred embodiment of the present invention;

FIG. 40 illustrates the backreflected intensity versus the objective focus position using a bifocal lens with both coverglass reflections in accordance with a preferred embodiment of the present invention;

FIG. 41 illustrates the backreflected intensity versus the objective focus position using a bifocal lens with both coverglass reflections in accordance with a preferred embodiment of the present invention when the distance between f2 and f3 is adjusted to match the separation between the front and back glass surfaces;

FIGS. 42A and 42B referred to collectively as FIG. 42 illustrate the extra smaller peaks that result due to coupling of the axial and the marginal beam in an optical system in accordance with a preferred embodiment of the present invention;

FIG. 43A illustrates a dual-beam probe having a reference surface as an integral element in accordance with a preferred embodiment of the present invention;

FIG. 43B is another preferred embodiment of a dual-beam interferometer probe;

FIG. 43C is an image of two nerve fibers;

FIG. 44 is a schematic illustration of the dual-beam probe being applied to investigate the geometry of the displacement effect observed in nerves during an action potential in accordance with a preferred embodiment of the present invention;

FIG. 45 is a dual-beam probe system for imaging by scanning either the probe or the sample in accordance with a preferred embodiment of the present invention;

FIGS. 46A-46C illustrate the intensity image, the phase image and brightfield image of back scattered light from a dessicated human cheek epithelial cell using a bifocal dual-beam microscope in accordance with a preferred embodiment of the present invention;

FIGS. 46D-46G illustrate the profilometry capability of the dual-beam microscope illustrated in FIG. 43 wherein FIG. 46D is the intensity image of the central portion of a lens of the plano-convex system, illustrated in FIG. 46E, FIG. 46F is the phase map of the reflected light and FIG. 46G is a cross section of the phase image, phase unwrapped, with a quadratic fit in accordance with a preferred embodiment of the present invention.

Figure 49A:
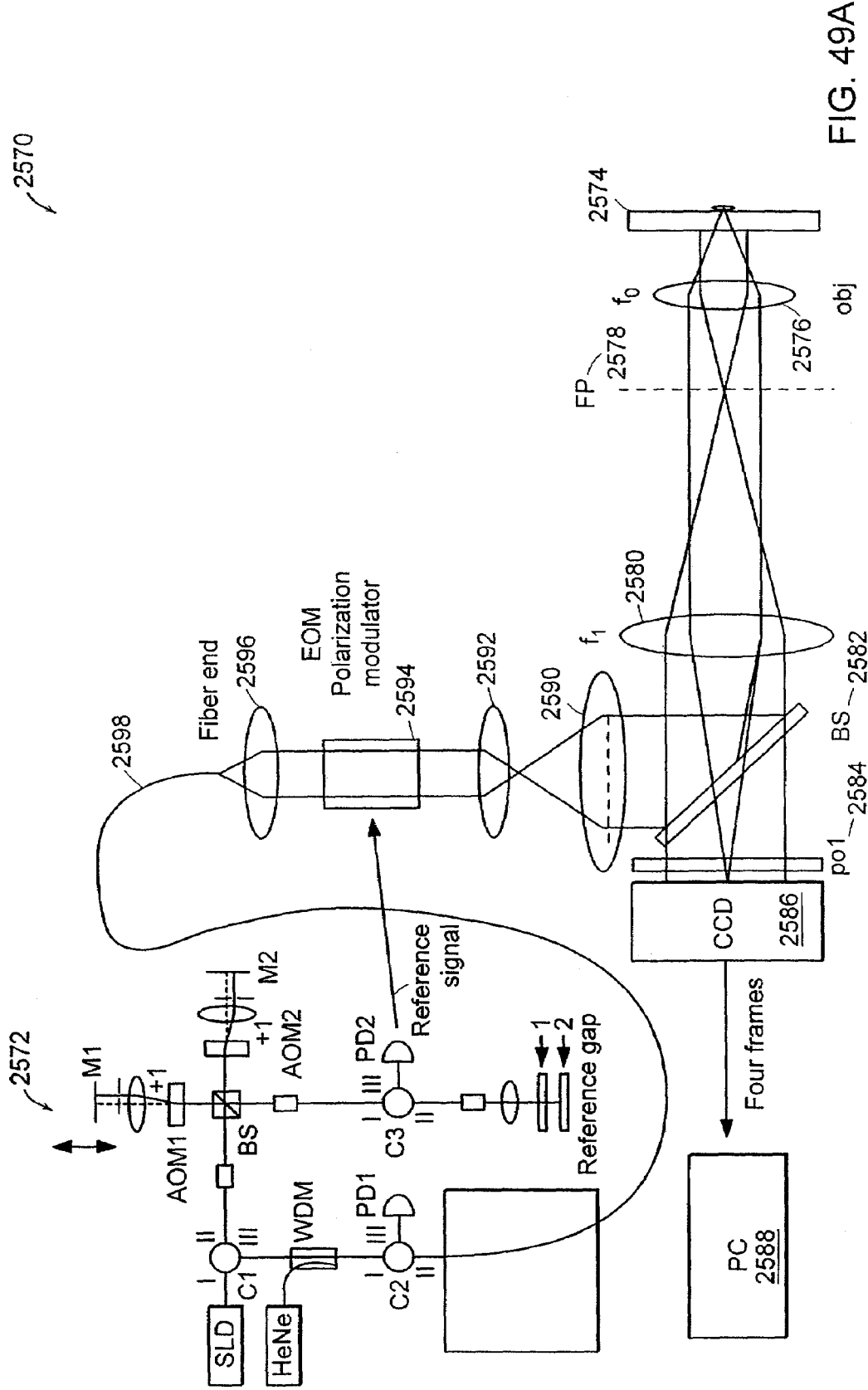
Figure 49B:
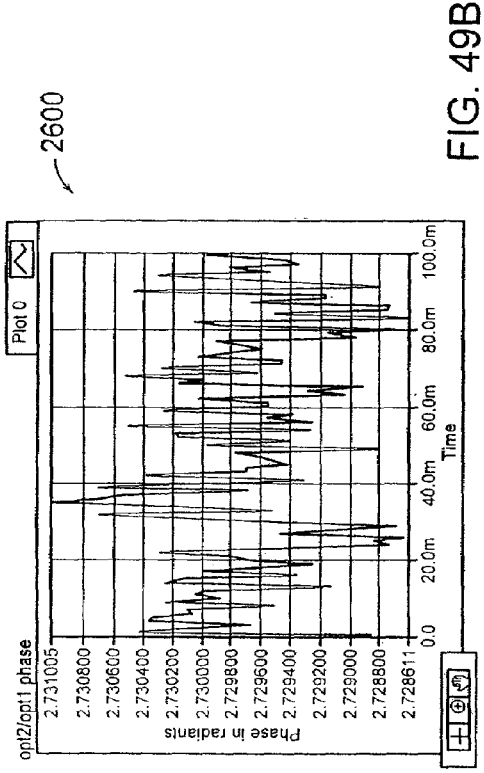
Figure 49C:
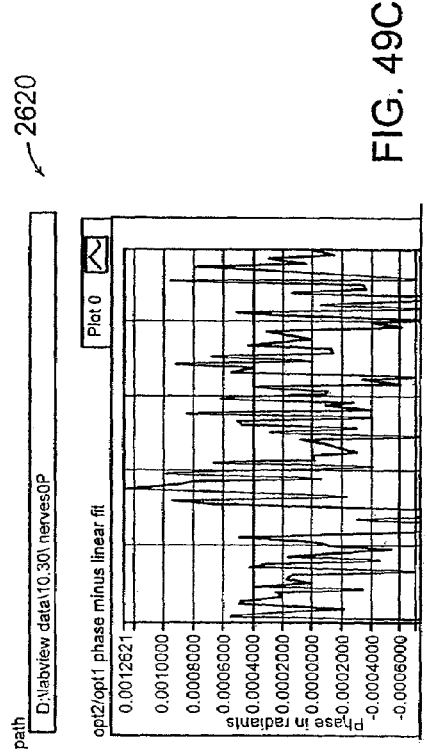
Figure 50A:
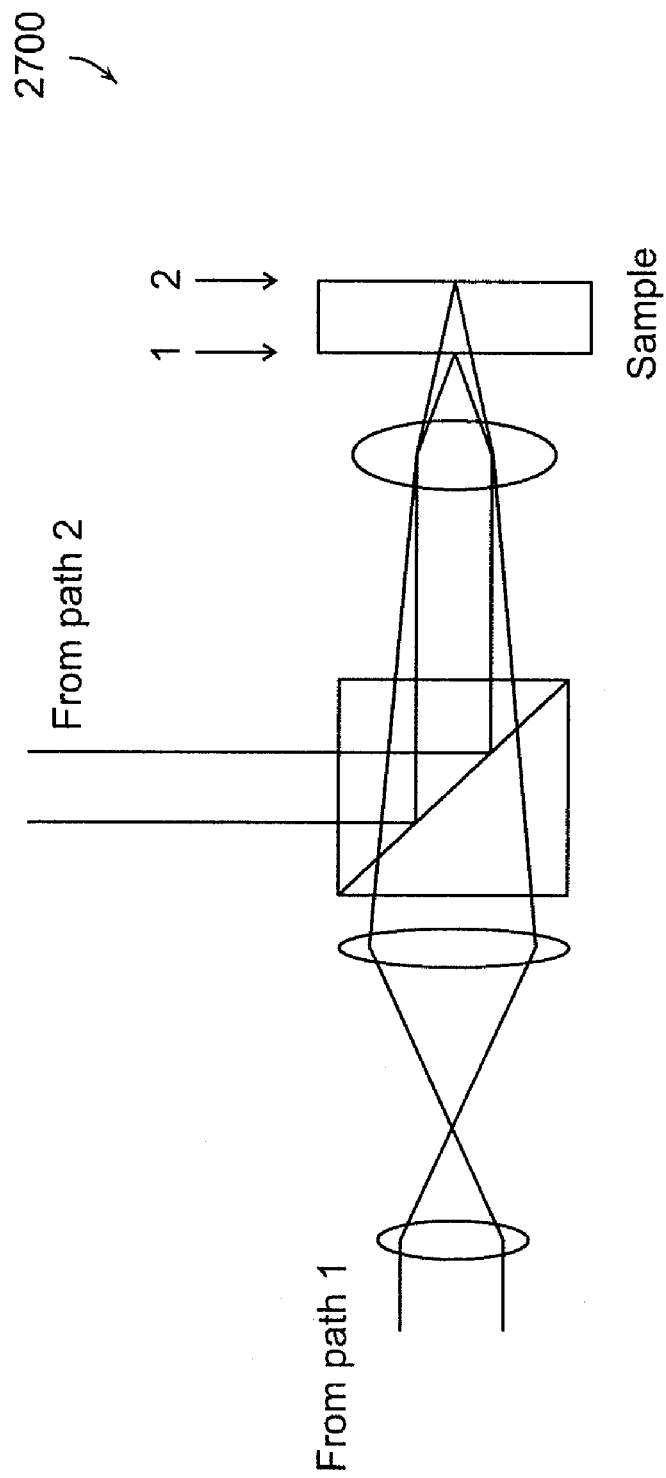
Figure 50B:
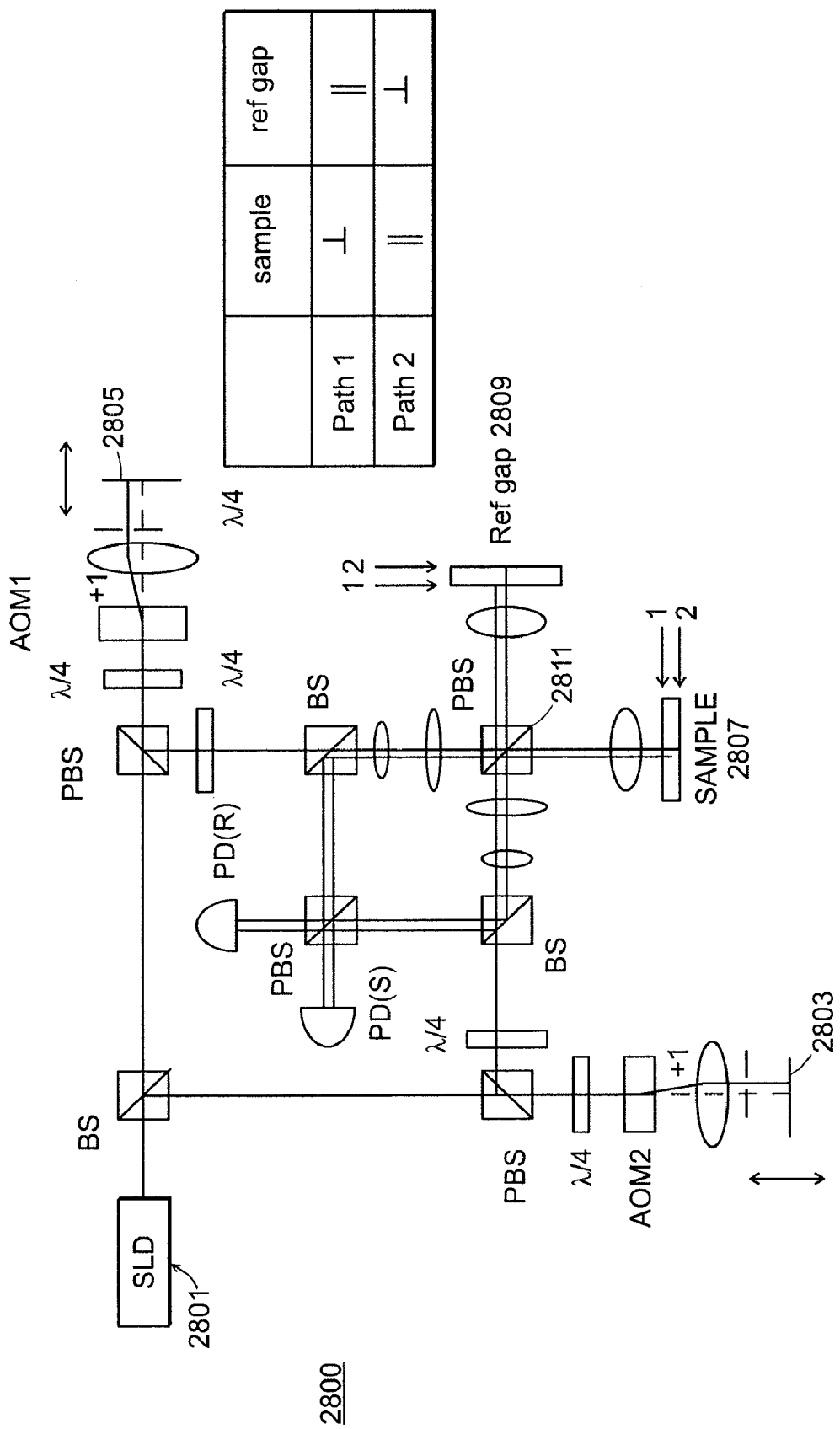
Figure 50C:
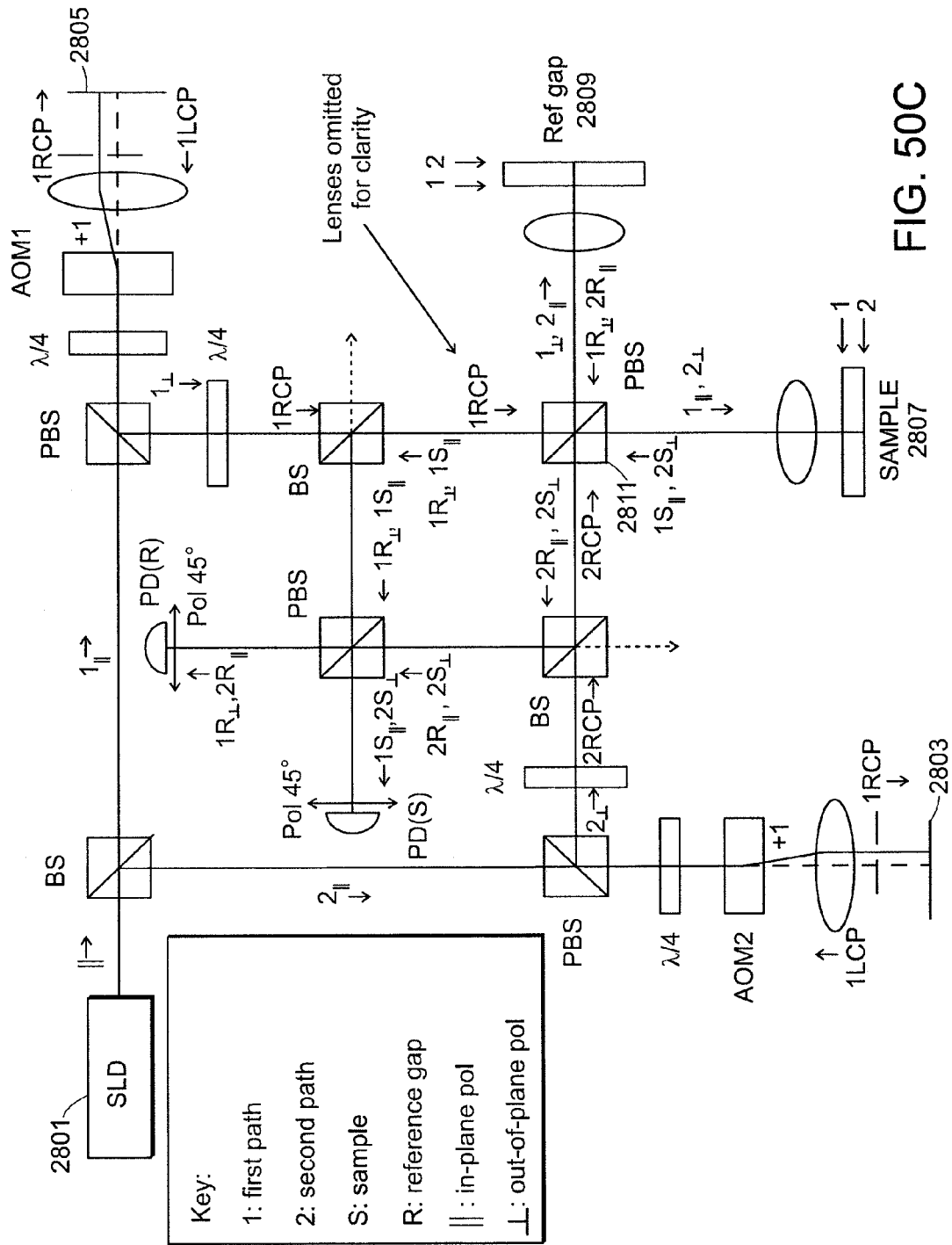
Figure 52:
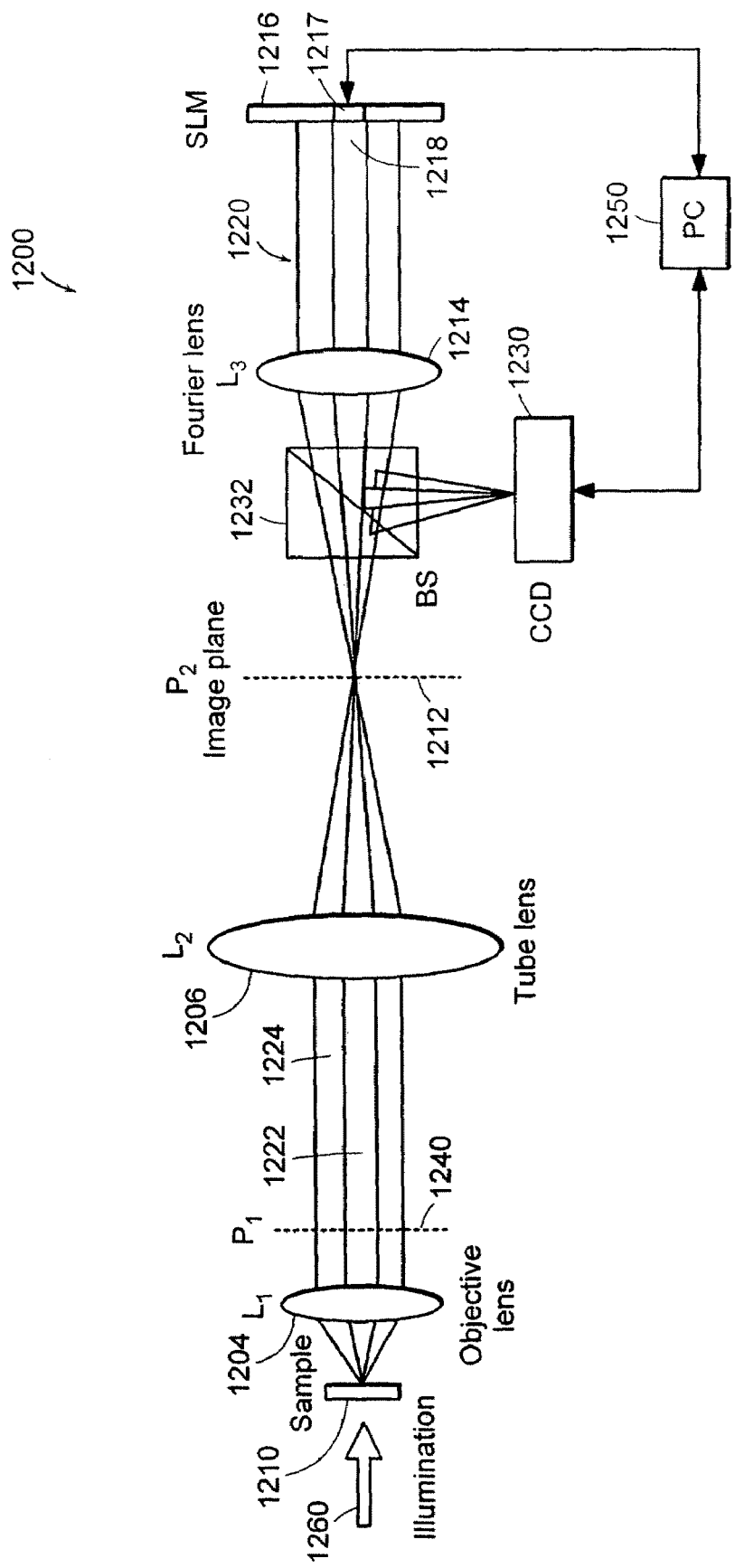
Figure 53:
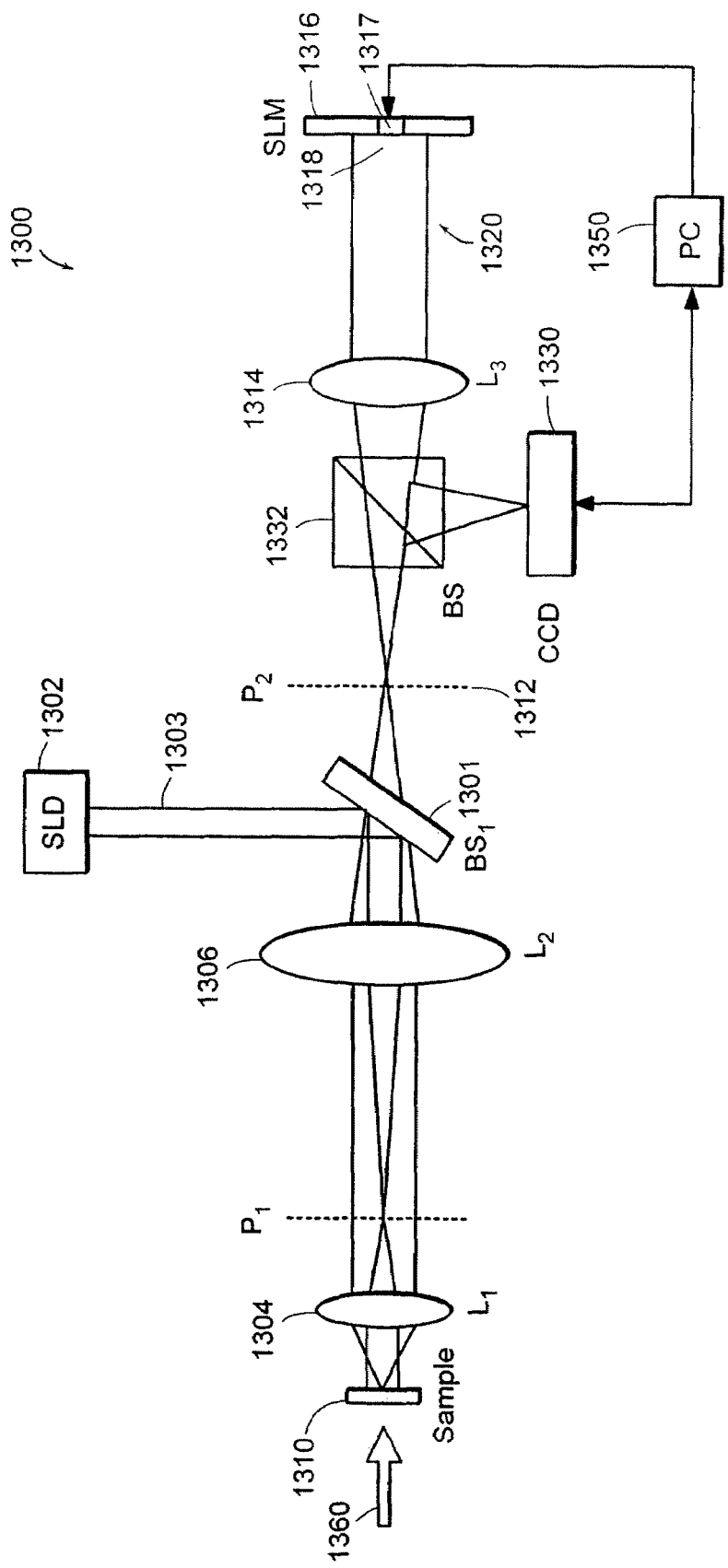
Figures 54A, 54B:
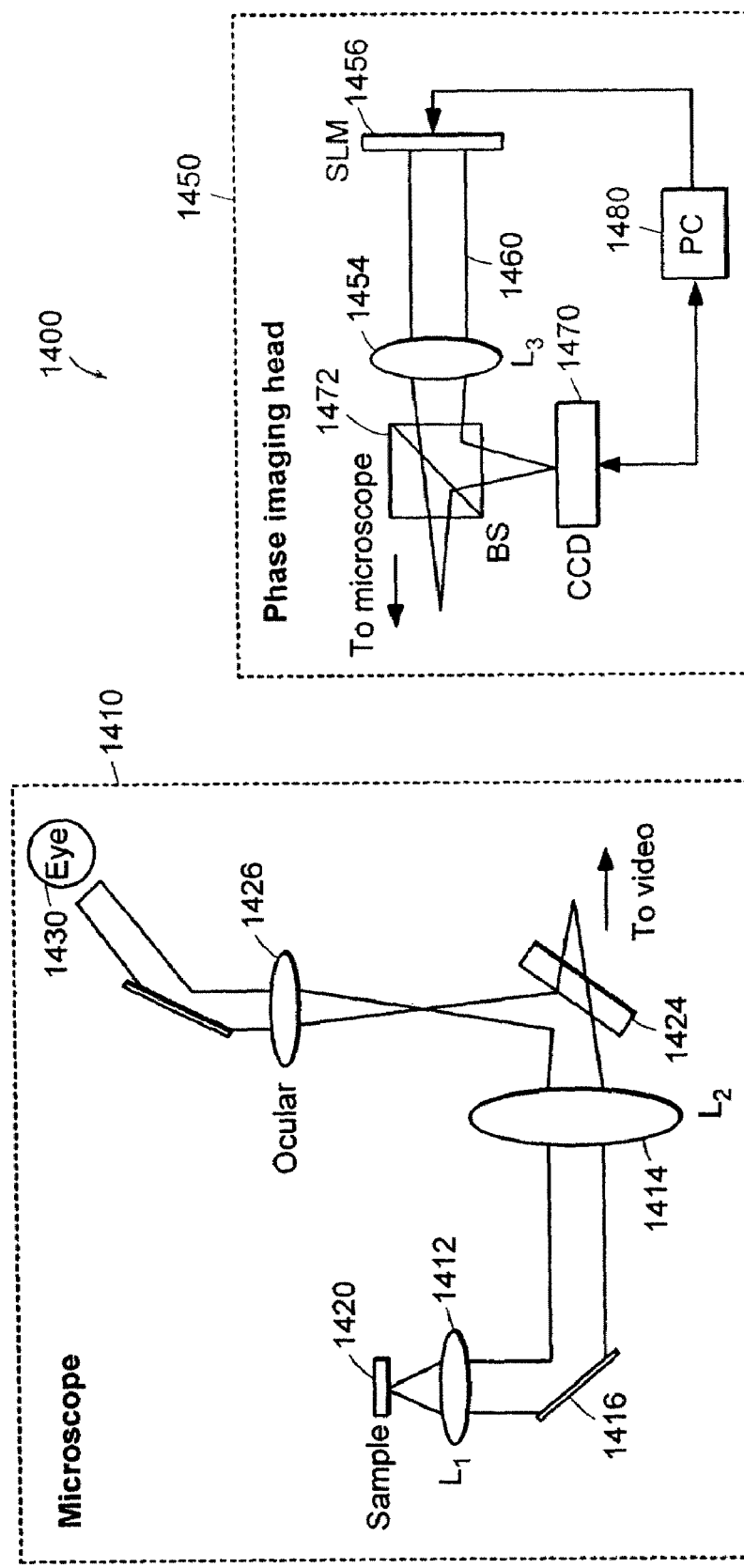
Figure 55:
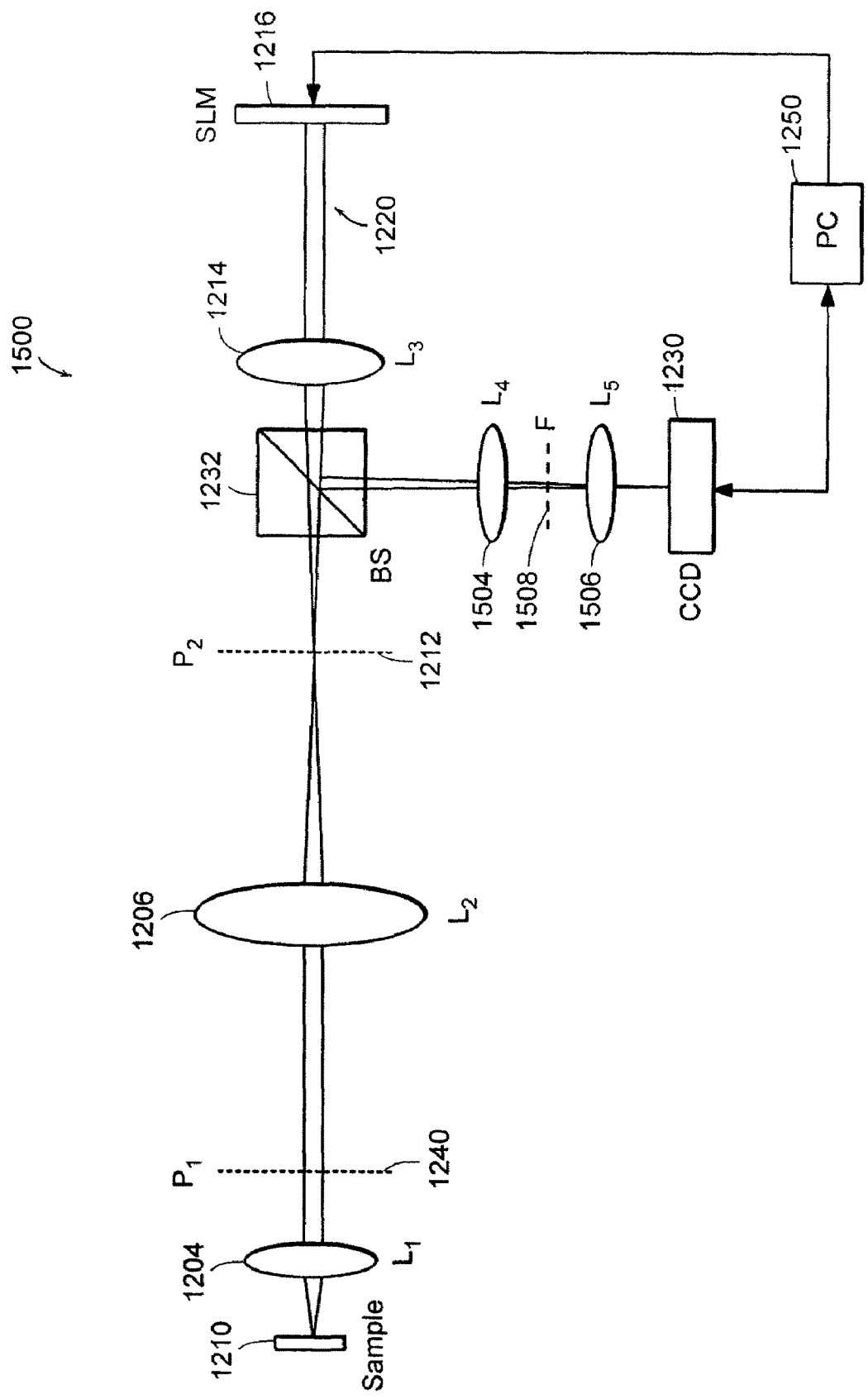
Figure 56:
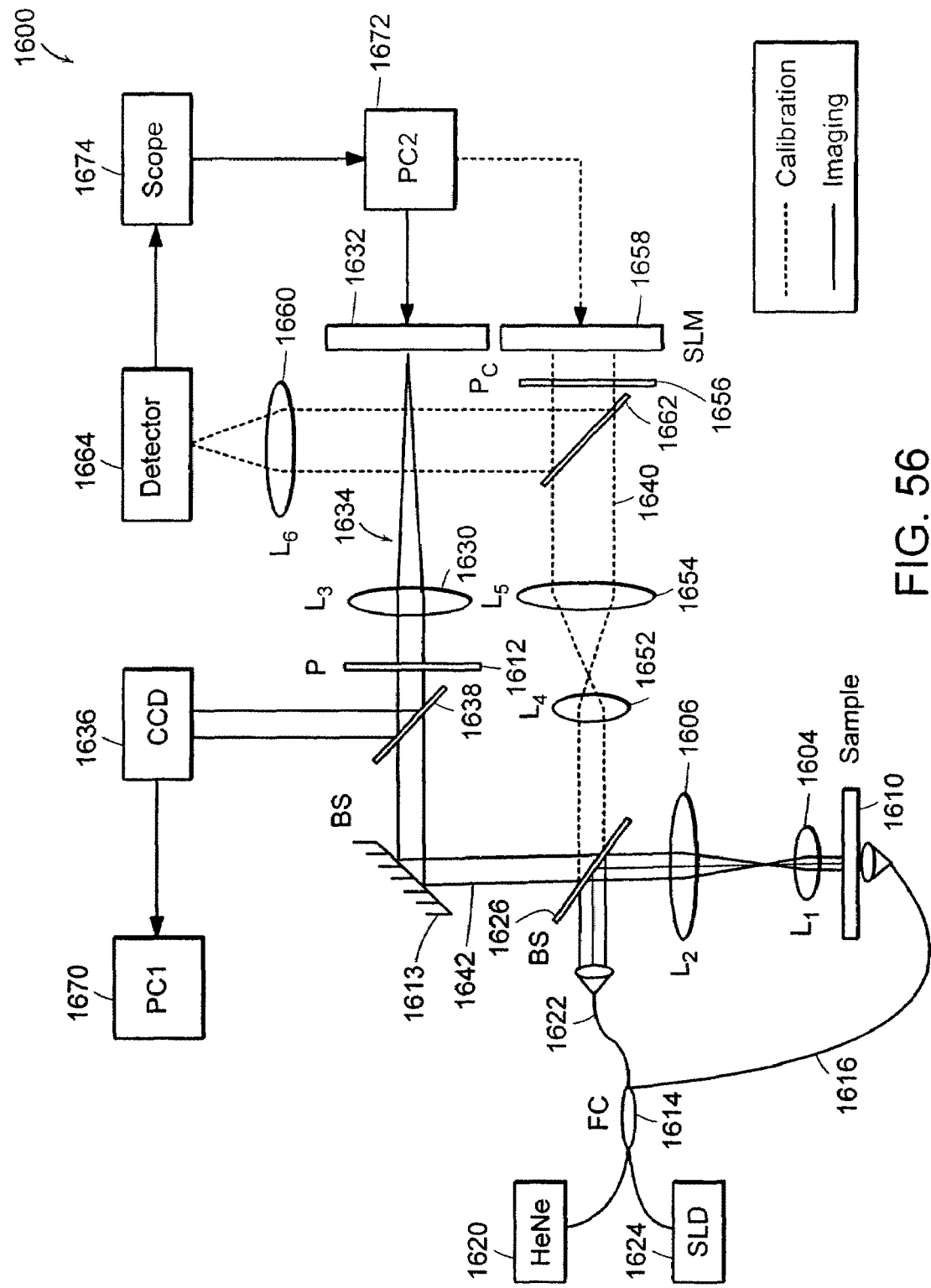
Figure 57A:
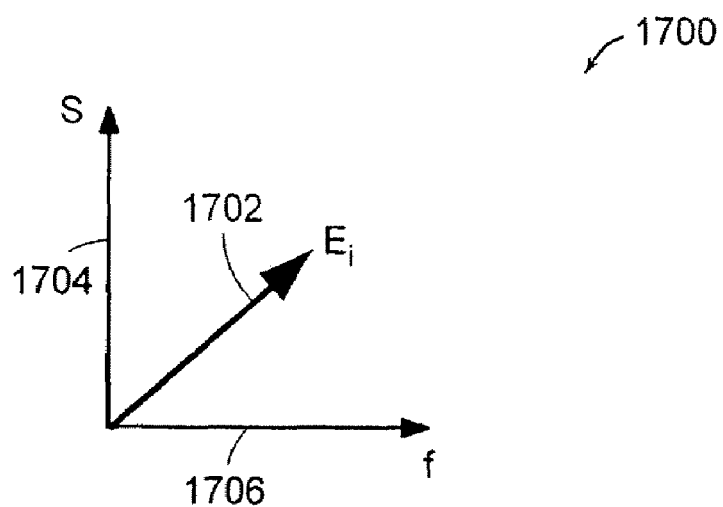
Figure 57B:
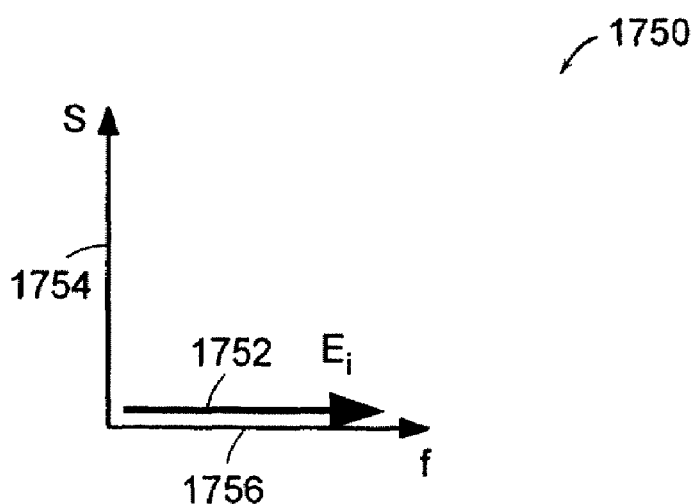
Figure 59:
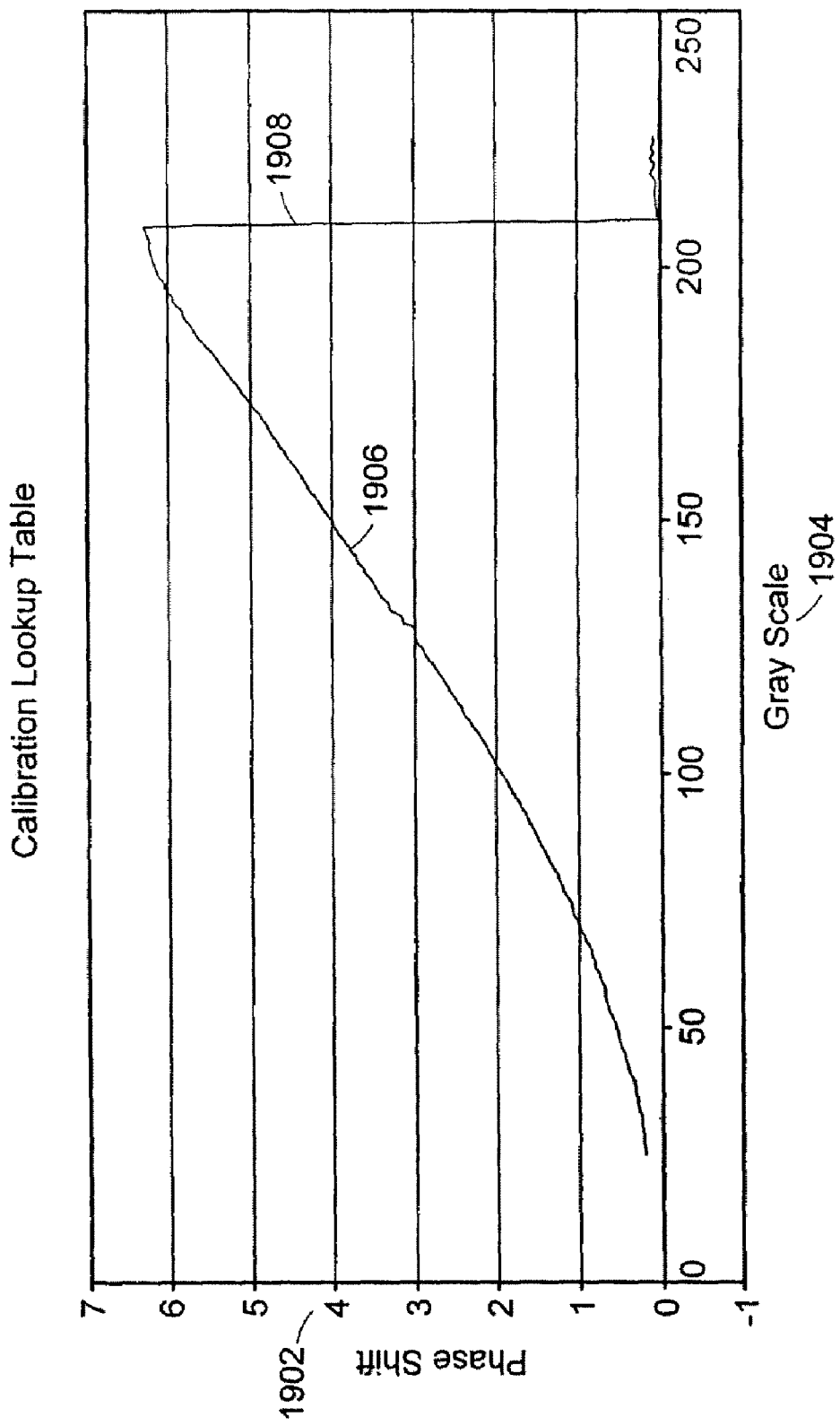
Figure 61:
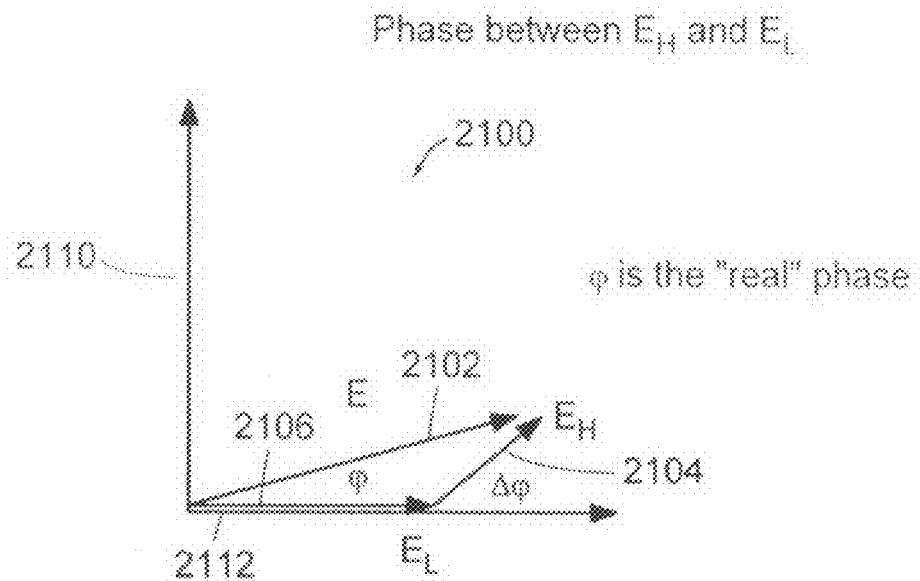
Figure 62:
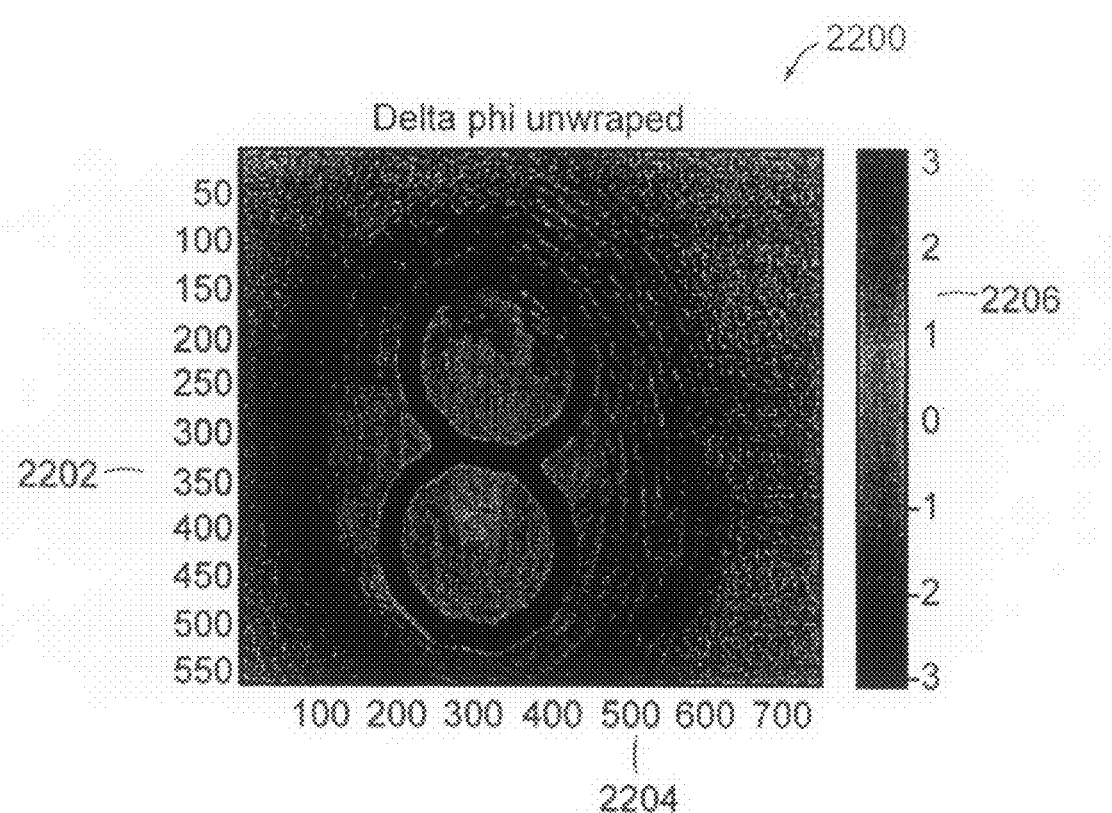
Figure 63:
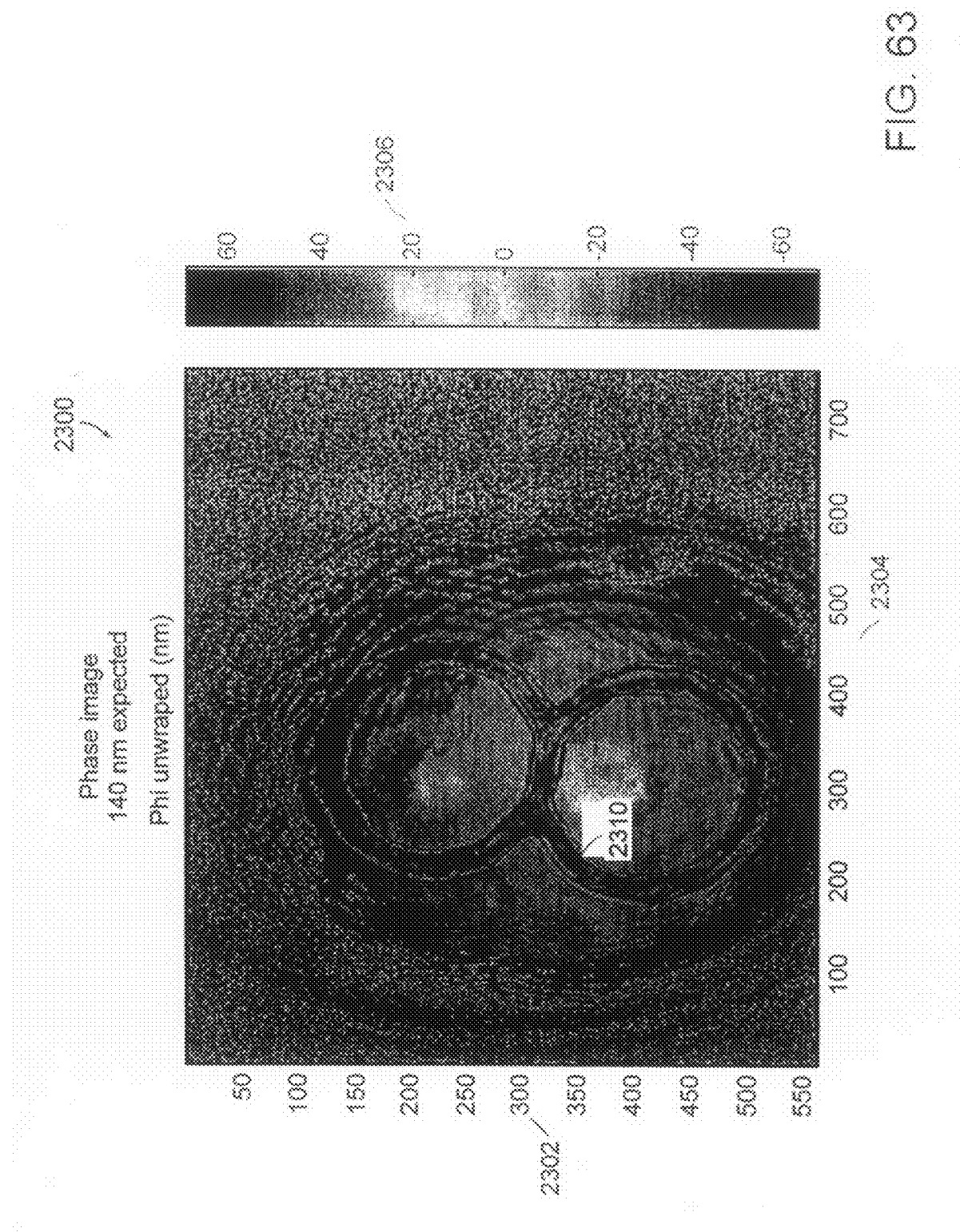
Figures 65, 66:
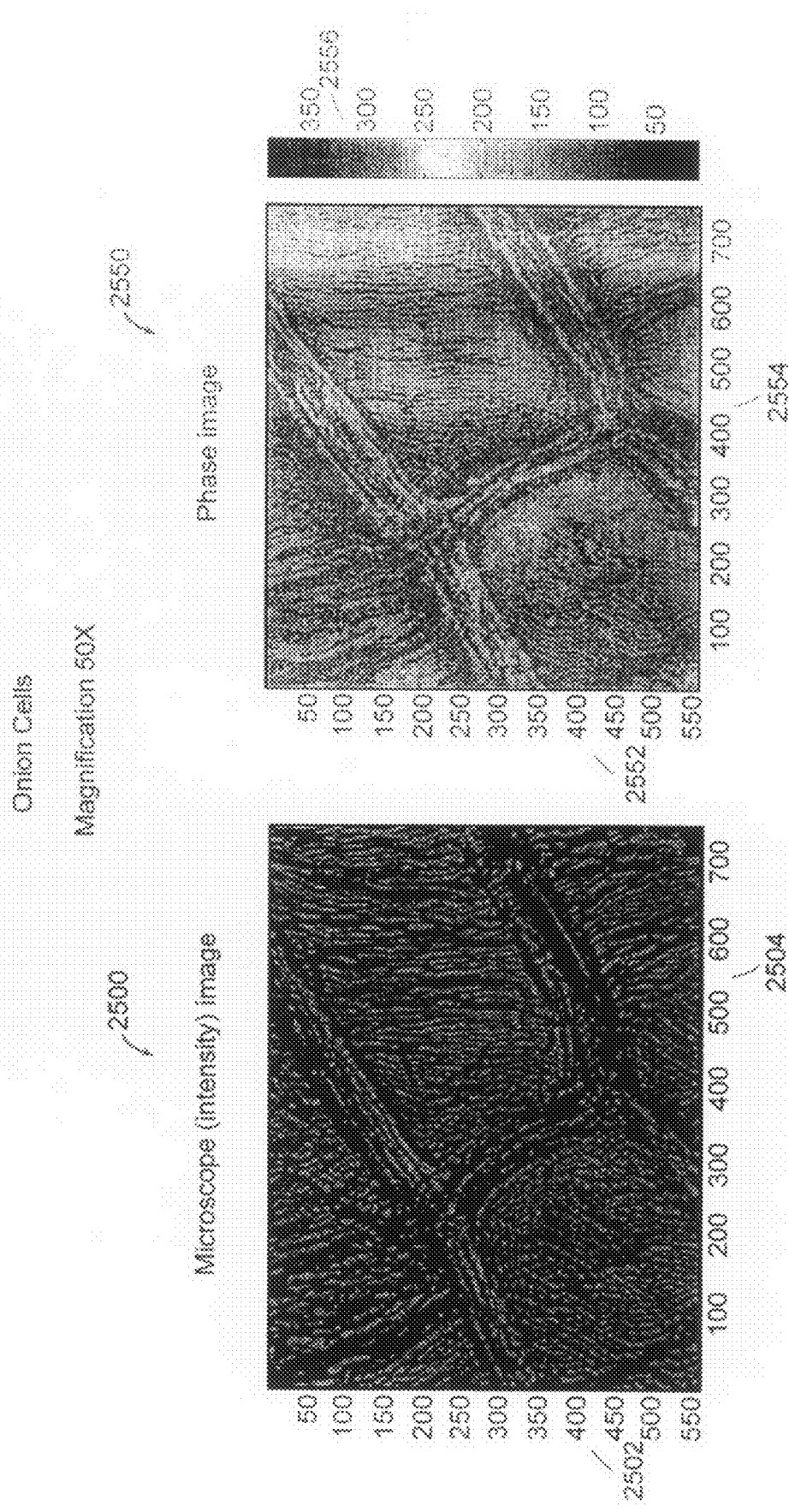
Figure 67:
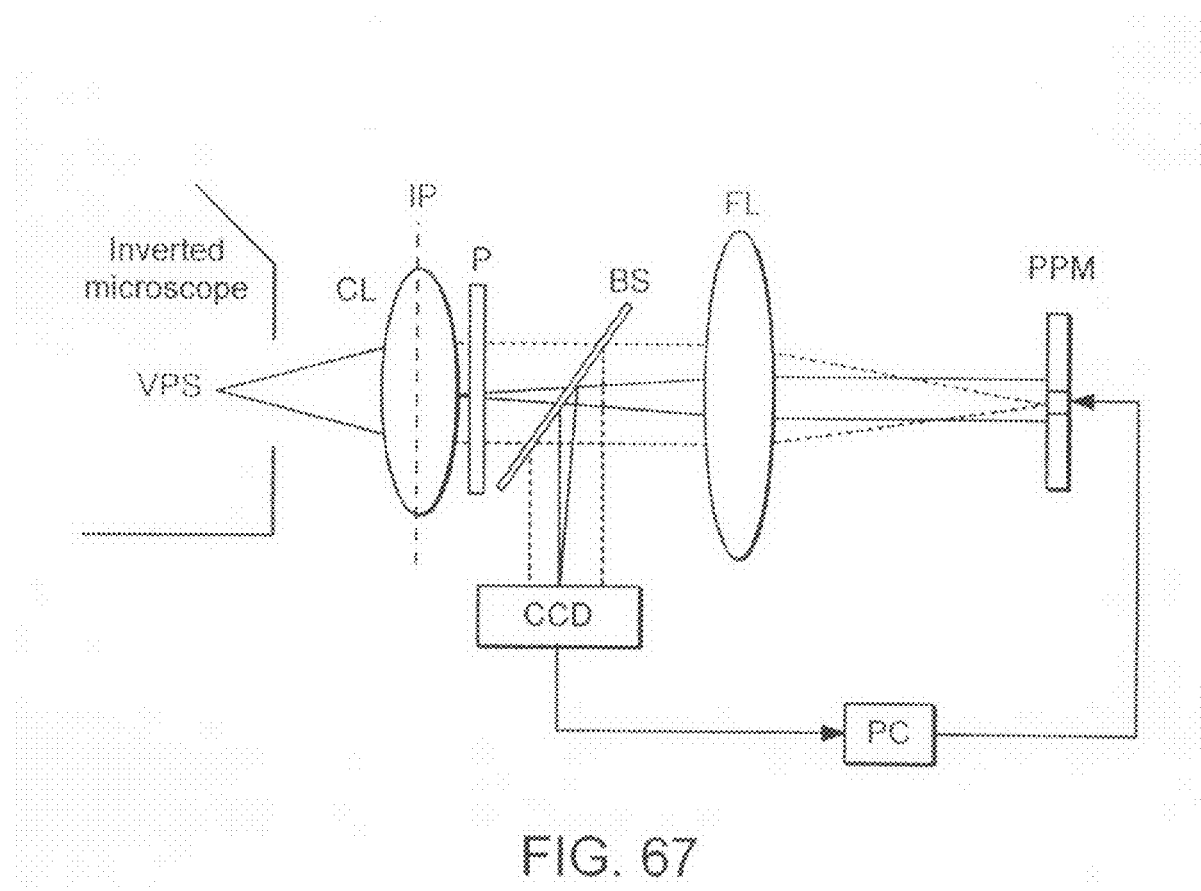
Figure 68A:
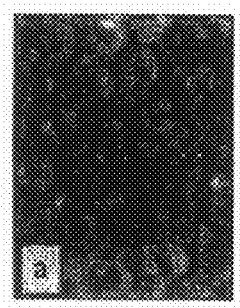
Figure 68B:
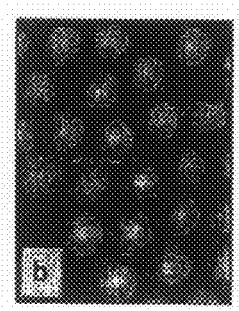
Figure 69B:
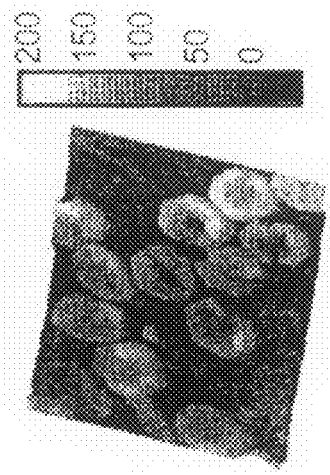
Figure 69A:
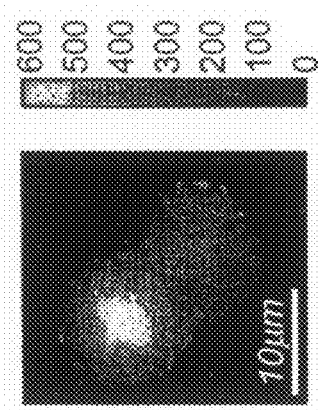
Figure 69C:
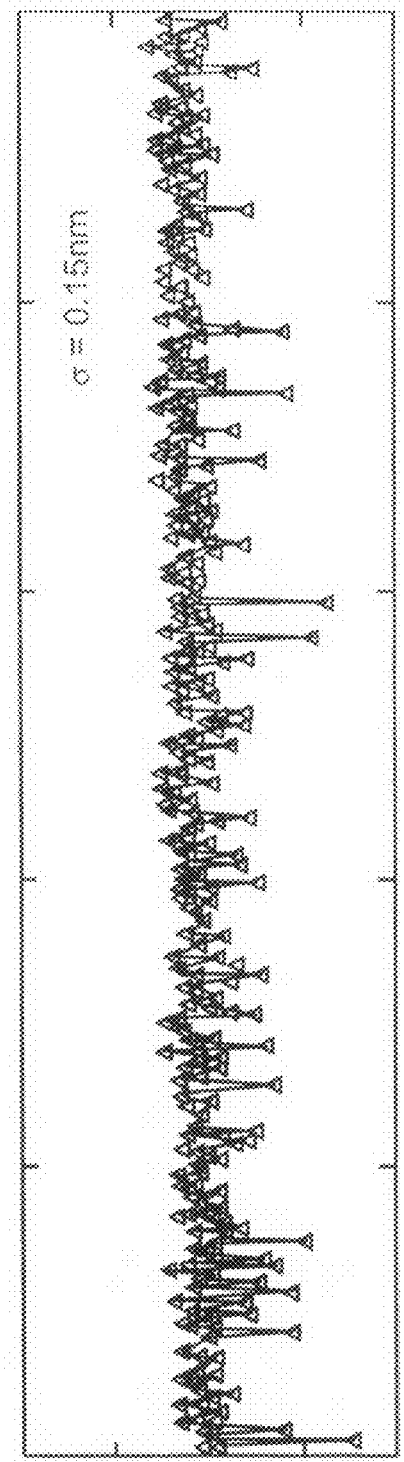

FIGS. 47A-47E illustrate a schematic diagram for a phase shifting interferometry system, phase stepping and bucket integration, respectively, in accordance with a preferred embodiment of the present invention;

FIGS. 48A-48C illustrate principles of a stroboscopic heterodyne interferometry system and bucket integration, respectively, in accordance with a preferred embodiment of the present invention;

FIG. 49A illustrates a dual-beam stroboscopic heterodyne interferometer in accordance with a preferred embodiment of the present invention;

FIGS. 49B and 49C illustrate data showing the phase noise for a dual-beam probe focused on a stationary glass surface in accordance with a preferred embodiment of the present invention;

FIG. 50A illustrates another preferred embodiment in which light from separate paths are directed along a common path and focused on different regions of material under measurement;

FIG. 50B is a preferred embodiment of a dual-beam system using the system of FIG. 50A;

FIG. 50C provides details regarding the polarization components within the system illustrated in FIG. 50B;

FIGS. 51A-51D are schematic representations of various features of such a description of an image in accordance with a preferred embodiment of the present invention;

FIG. 52 schematically illustrates various embodiments of a microscopy system in accordance with the present invention based on a transmission geometry;

FIG. 53 schematically illustrates various embodiments of a microscopy system in accordance with the present invention based on a reflection geometry;

FIGS. 54A and 54B; referred to collectively as FIG. 54 schematically illustrate one embodiment of integrating various embodiments of the present invention with an optical microscope;

FIG. 55 schematically illustrates various embodiments of a system and method of the present invention utilizing a 4-f system;

FIG. 56 schematically illustrates one embodiment of a phase contrast microscopy system utilizing spatial light modulation (SLM) in accordance with the present invention;

FIGS. 57A and 57B schematically illustrate an electro-optic effect on a pixel of an image in amplitude mode and phase mode in accordance with a preferred embodiment of the present invention;

FIGS. 58A-58C are block diagrams of various embodiments of SLM modes of operation in accordance with a preferred embodiment of the present invention;

FIG. 59 is an example of a calibration curve obtained for an instrument operated in amplitude mode in accordance with a preferred embodiment of the present invention;

FIGS. 60A-60D show images obtained at four different phase shifts δ for a system using a reflection geometry in accordance with a preferred embodiment of the present invention;

FIG. 61 schematically illustrates a relationship between the electric field vector E and the high frequency wave vector component of the field, $E_H$, and the low frequency wave vector component of the field, $E_L$, in accordance with a preferred embodiment of the present invention;

FIG. 62 is a Δϕ image of the calibrated sample generated using, for example, data such as illustrated in FIGS. 35A-35D and Equation 55 in accordance with a preferred embodiment of the present invention;

FIG. 63 is a phase image of the calibrated sample of Example 1 using a system and method in accordance with the present invention;

FIG. 64 shows a phase image obtained using a transmission geometry in accordance with a preferred embodiment of the present invention;

FIG. 65 shows an onion cell intensity image in accordance with a preferred embodiment of the present invention;

FIG. 66 shows onion cells phase imaged using a transmission geometry in accordance with the present invention;

FIG. 67 illustrates in accordance with a preferred embodiment as experimental setup wherein VPS is a virtual point source; CL is a corrective lens; IP is an image plane; P a polarizer; BS a beam splitter; FL a Fourier lens; PPM a programmable phase modulator; CCD a charge-coupled device, and PC a personal computer;

FIGS. 68A and 68B illustrate in accordance with a preferred embodiment experimental results on polystyrene microspheres immersed in 100% glycerol, using a 10× microscope objective wherein FIG. 68A is an intensity image and FIG. 68B is a quantitative phase image. The color bar represents the phase expressed in nm; and FIGS. 69A-69C illustrates in accordance with a preferred embodiment LCPM images obtained using a 40× microscope objective wherein FIG. 69A is a phase image of Hela cancer cell undergoing mitosis, FIG. 69B is a phase image of whole blood smear and FIG. 69C is a temporal phase fluctuations associated with a point in the absence of cells (the standard deviation σ is indicated). The color bars represent the phase expressed in nm.

DETAILED DESCRIPTION OF THE INVENTION

Harmonic Interferometry for Distance Measurement:

The present invention is directed at phase crossing based systems and methods for measuring optical distances that overcome the integer or 2π ambiguity problem by introducing a dispersion imbalance in an interferometer. A preferred embodiment of the method is able to measure the relative height difference of two adjacent points on a surface with precision. Further, the refractive index of a sample can be found to an accuracy that is limited only by the precision with which the physical thickness of the sample can be experimentally measured.

The substitution of one of the low coherence light sources with a continuous wave (CW) light source in harmonic phase based interferometry (HPI), allows the use of the associated CW heterodyne signal as a form of optical ruler by which the low coherence heterodyne signal can be measured. The low coherence light source provides a spectral bandwidth, for example, greater than 5 nm for 1 micron wavelength. One of the benefits of using such a modified HPI is that the measured phase is now sensitive to the length scale nL instead of $(n_{\lambda_2}-n_{\lambda_1})$, where n is the refractive index at the low coherence wavelength. The quantity n is more practically useful than the composite $(n_{\lambda_2}-n_{\lambda_1})$. By adjusting the low coherence wavelength slightly, for example, by approximately 2 nm, the quantity nL can be found without $2\pi$ ambiguity and with sub-nanometer sensitivity. This method uses the CW heterodyne interference signal as a reference optical ruler by which the optical distance is measured.

Interferometric optical distance measuring systems employing readily available low coherence light sources have achieved resolution on the order of tens of wavelengths. While this technique is relatively insensitive, it does not have to contend with the $2\pi$ ambiguity issue. A preferred embodiment includes a low coherence interferometry method that uses phase to measure arbitrarily long optical distances with sub-nanometer precision. This method uses a low coherence phase crossing technique to determine the integer number of interference fringes, and additional phase information from the measurement to accurately obtain the fractional fringe. In addition, it provides depth resolution and can be used for tomographic profiling of stratified samples. As the method can measure long optical distances with precision, it can be used to determine refractive indices of a plurality of materials accurately. As this is a phase-based method, the refractive index thus found is the phase refractive index and not the group refractive index.

Figure 1:
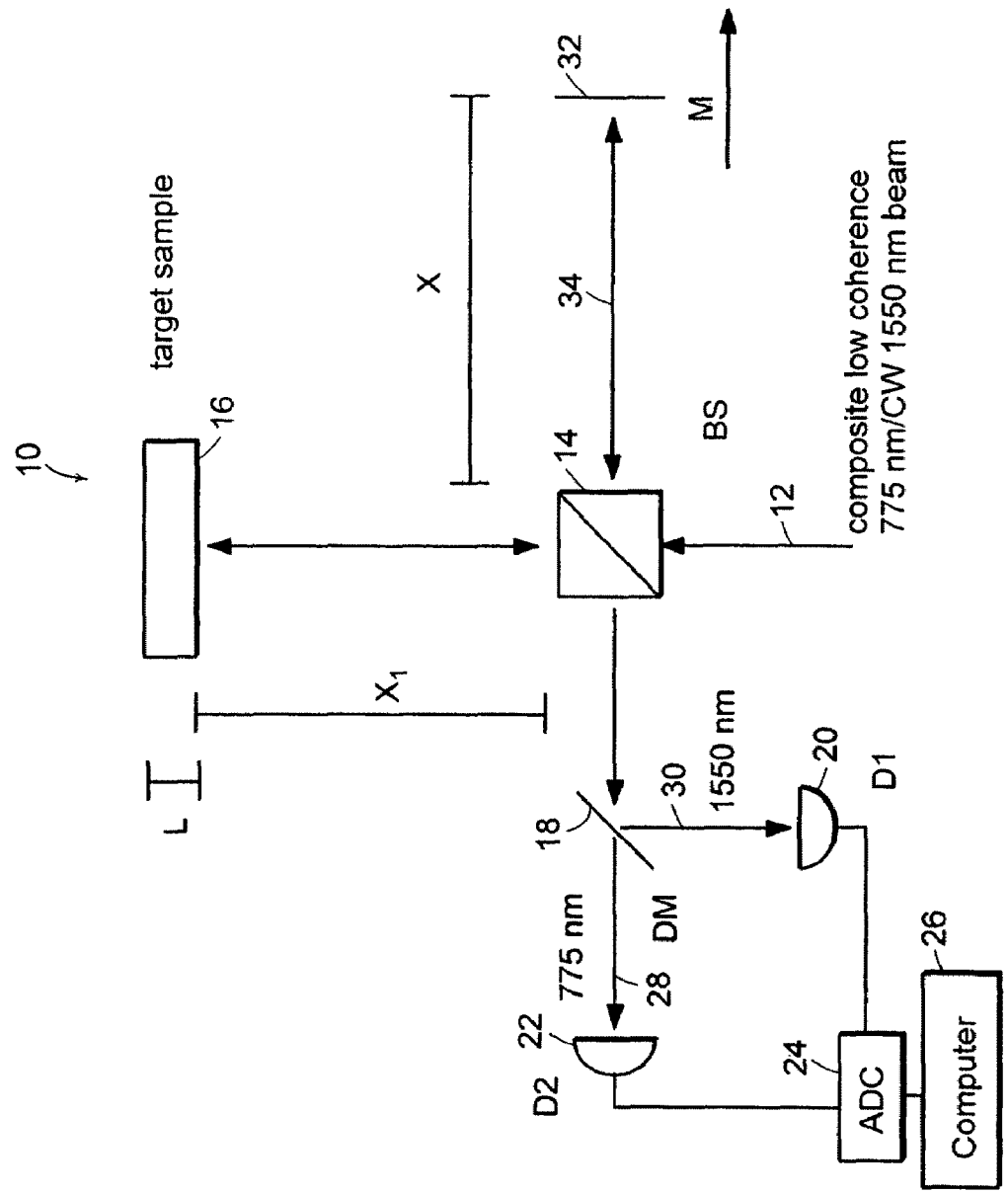
FIG. 1 is a schematic diagram of a preferred embodiment of the system to measure an optical distance in accordance with the present invention.

FIG. 1 illustrates a preferred embodiment of the system 10 of the present invention that includes a modified Michelson interferometer. The input light 12 is a two-color composite beam composed of 150-fs mode-locked light from a Ti:sapphire laser, for example, emitting at 775.0 nm and continuous wave (CW) 1550.0 nm light from, for example, a semiconductor laser. In the preferred embodiment the method evaluates optical distances in terms of the CW wavelength, (1550.0 nm exactly in this embodiment) and all optical distances are computed based on this basis. The composite beam is divided in two at the beamsplitter 14. One part signal is incident on the target sample 16, while the other is incident on a reference mirror 32 moving preferably at, for example, approximately 0.5 mm/s, which induces a Doppler shift on the reference beam 34. The Doppler shift can be induced by other means, such as, for example, through the use of an electro-optical modulator. The back-reflected beams are recombined at the beamsplitter 14, separated into their wavelength components by means of a dichroic mirror 18, and measured separately with photodetectors 20, 22. The resulting signals are digitized by an analog to digital converter (ADC) 24 such as, for example, a 16-bit 100 KHz A/D converter. A data processor such as a personal computer (PC) 26 is in communication with the ADC 24 to further process the data. The resulting heterodyne signals at their respective Doppler-shifted frequencies are bandpassed around their respective center heterodyne frequencies and Hilbert transformed to extract the corresponding phases of the heterodyne signals, $\Psi_{CW}$ and $\Psi_{LC}$. The subscripts CW and LC denote the 1550.0 nm continuous wave and 775.0 nm low coherence wavelength components, respectively.

The center wavelength of low coherence light is then adjusted by approximately 1-2 nm and a second set of $\Psi_{CW}$ and $\Psi_{LC}$ values is measured. From these two sets of readings, the various interfaces in the target sample can be localized with sub-nanometer precision. The processing of data for localization is described hereinbelow.

Consider a sample which consists of a single interface at an unknown distance $x_1$ from the beamsplitter 14. The distance from the beamsplitter 14 to the reference mirror 32, x, is a known quantity at each time point in the scan of the reference mirror.

A method to find an approximate value for $x_1$ is by scanning x and monitoring the resulting heterodyne signal in the recombined low coherence light beam. When x is approximately equal to $x_1$, a peak in the heterodyne signal amplitude is expected. The precision of such a method is limited by the coherence length, $l_c$, of the light source and the signal-to-noise quality of the heterodyne signal. Under realistic experimental conditions, the error in $x_1$ determined thus, is unlikely to be better than a fifth of the coherence length.

Given that the coherence length of a typical low coherence source is approximately 10 μm nominally, this means that the error in such a means of length determination is limited to about 2 μm.

In considering the phase of the heterodyne signal, the varying component of the heterodyne signal detected can be expressed as:

$$I_{heterodyne} = E_{ref}e^{i(2kx-\omega t)}E_{sig}e^{-i(2kx_1-\omega t)} + c.c. \quad (1)$$
$$= 2E_{ref}E_{sig}\cos(2k(x-x_1)),$$

where $E_{ref}$ and $E_{sig}$ are the electric field amplitude of the reference and signal electric field amplitude, respectively, k is the optical wavenumber, ω is the optical frequency. The factor of 2 in the exponents is due to the fact that light travels twice the path going to the mirror/sample and back to the beamsplitter.

Note that when x matches $x_1$ exactly, the heterodyne signal is expected to peak. The two returning beams are in constructive interference. This property is therefore used to localize the interface. $x_1$ is found by finding the value of x for which the two beams are in constructive interference. Since phase can be measured accurately, such an approach gives a length sensitivity of about 5 nm. Unfortunately, this method is calculation intensive because there are multiple values of x for which the heterodyne signal peaks; specifically, the heterodyne signal peaks at:

$$x = x_1 + a\frac{\lambda}{2} \quad (2)$$

where a is an integer and λ is the optical wavelength. This is a manifestation of the $2\pi$ ambiguity issue.

Figure 2:
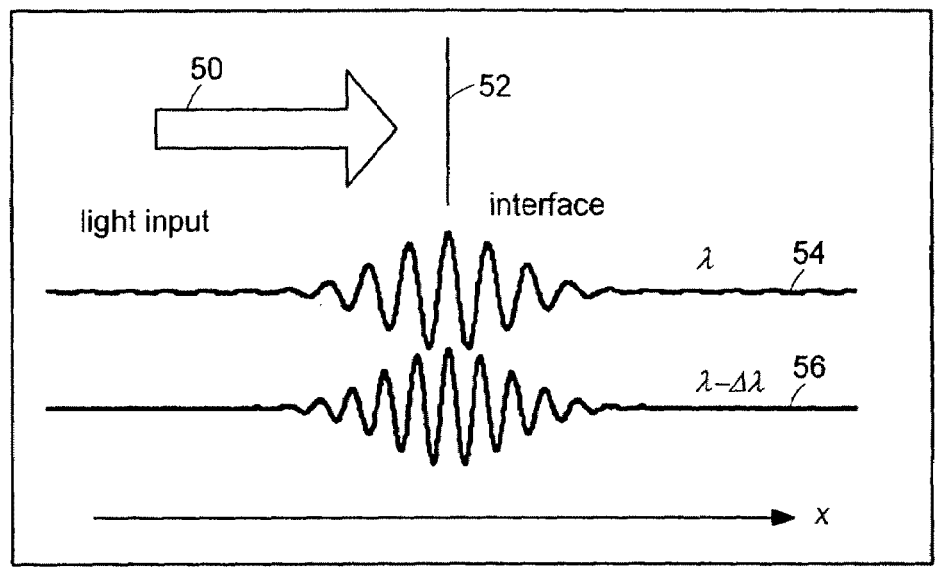
FIG. 2 illustrates the low coherence heterodyne signals associated with a reflecting interface in accordance with a preferred embodiment wherein adjusting the low coherence wavelength compresses or expands (depending on the direction of adjustment of the center wavelength of the low coherence source) the heterodyne signal around the interface.

The preferred embodiment includes a method to distinguish the correct peak. Note that when $x=x_1$ exactly, the heterodyne signal peaks regardless of the optical wavelength. On the other hand, the subsequent peaks are wavelength dependent, as illustrated in FIG. 2. FIG. 2 illustrates the low coherence heterodyne signals associated with the reflecting interface 52 in the sample. Therefore, by adjusting the low coherence wavelength, the heterodyne signal is compressed around the interface and the correct peak associated with the situation where $x=x_1$ exactly can be distinguished. It should be noted that the heterodyne signal may be compressed or expanded around the interface depending upon the direction of adjustment. An intuitive way of visualizing the localization is to picture the heterodyne signal squeezing in or expanding away from the fringe where $x=x_1$ exactly.

Figure 3:
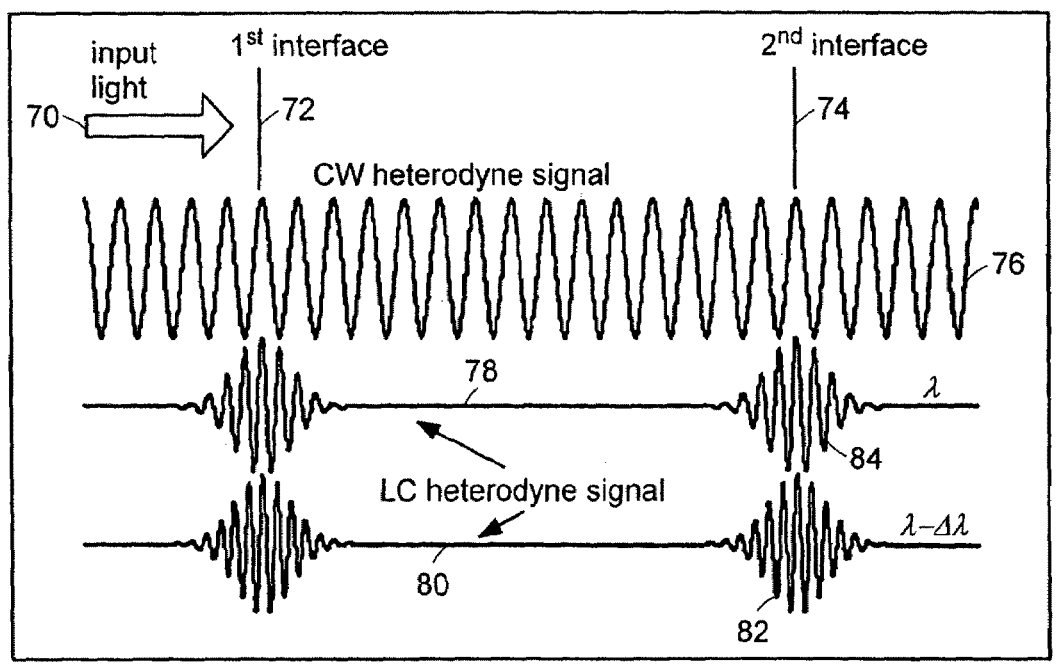
FIG. 3 illustrates heterodyne signals associated with two reflecting interfaces in a sample in accordance with a preferred embodiment wherein decreasing the low coherence wavelength compresses the heterodyne signal around the interfaces.

The CW light source is needed in such a localization method for two reasons. First, it is very difficult in practice to know the value absolutely and accurately in an interferometer. The CW component of the interferometer permits highly accurate measurements of x to be made as the reference mirror is scanned. In a specific preferred embodiment, to determine the distance between two interfaces in the sample, a count of the number of CW interference fringes that occurred between where $x_1$ is equal to the distance to the first interface as shown in FIG. 1 and where $x_2$ ($x_2=x_1+nL$ wherein n is the refractive index of the sample) is equal to the distance to the second interface is made. FIG. 3 illustrates the heterodyne signals associated with two reflecting interfaces in a sample. Adjusting the low coherence wavelength compresses 82, 84 the heterodyne signal 78, 80 around the interfaces.

Second, the prior described method for localization of the interface may partly fail if there is a phase shift associated with the reflection process. For example, if the surface is metallic, the phase shift is non-trivial and the phase of the heterodyne signal takes on some other value when $x=x_1$ exactly. While the prior method allows the correct interference fringe to be identified where $x=x_1$, however sub-wavelength sensitivity may be compromised. The presence of the CW heterodyne signal allows the difference phase via the HPI method to be found. The knowledge of this value, allows the localization of the interface with a high level of sensitivity.

The principle of the HPI method can be illustrated through the exemplary embodiment of a sample of thickness, L, and refractive index, $n_{775\,nm}$, at a wavelength of 775 nm. The two interfaces of the sample are at optical distances x1 and x2 (where $x2=x_1+n_{775\,nm}L$) from the beamsplitter, respectively. Note that the method only works if the optical distance separation is greater than the coherence length, for example, typically between 1 micron and a 100 microns of the low coherence light source. Otherwise, the heterodyne phase signals associated with the interfaces merge together and result in inaccurate interface localization. For clarity of explanation, the incorporation of the phase shifts associated with reflection are deferred until later.

Figure 4:
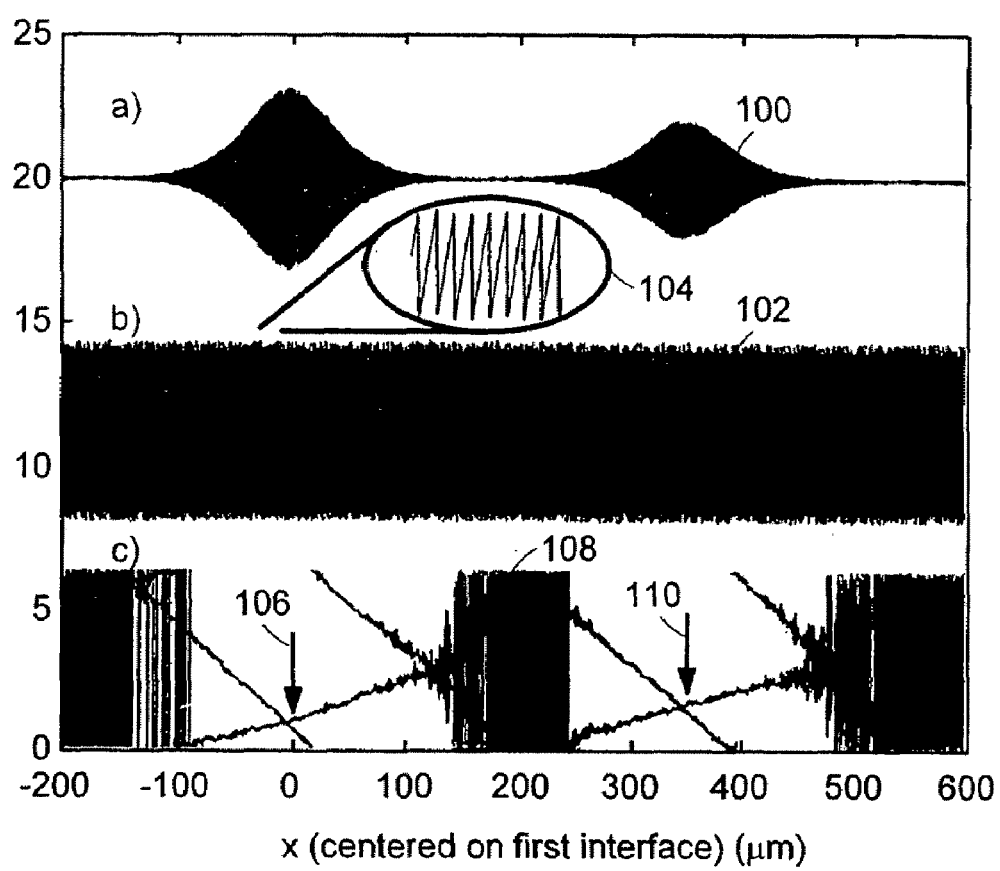
FIG. 4 illustrates a scan of a sample with two interfaces in accordance with a preferred embodiment of the present invention (a) low coherence heterodyne signal, (b) trace wherein the magnified view shows the phase fringes, each fringe corresponds to an optical distance of $\lambda_{CW}$, (c) traces at two difference values of $\Delta$, wherein the arrows indicate the phase crossing points, the vertical axis is in radians.

FIG. 4 is a scan illustrating the mathematical description. The scan is of a sample with two interfaces. The signal 100 is a low coherence heterodyne signal. The trace 102 is $\Psi_{CW}(x)$. The magnified view 104 shows the phase fringes. Each fringe corresponds to an optical distance of $\lambda_{CW}$. The lower traces of $\Psi_D(x)$ are at two different values of $\Delta$. The arrows 106, 110 indicate the phase crossing points. The vertical axis is in radians. As the reference mirror is scanned, the phase of the low coherence heterodyne signal is given by:

$$\Psi_{LC}(x) = \mathrm{mod}_{2\pi}(\arg(R_{LC,1}e^{i2k_{LC}(x-x_1)}e^{-(2a(x-x_1))^2} + R_{LC,2}e^{i2k_{LC}(x-x_2)}e^{-(2a(x-x_2))^2})) \approx h_c(x-x_1)\mathrm{mod}_{2\pi}(2k_{LC}(x-x_1)) + h_c(x-x_2)\mathrm{mod}_{2\pi}(2k_{LC}(x-x_2)), \quad (3)$$

with $R_{LC,j}$ the reflectivity of the interface j at the low coherence wavelength, k the optical wavenumber, $a=4\ln(2)/l_c$, $l_c$ the coherence length, x the distance of the reference mirror from the beamsplitter, and $h_c(x)$ a piecewise continuous function with value of 1 for $|x|<2l_c$ and 0 otherwise. The factors of 2 in the exponents are due to the effective doubling of optical paths in the backreflection geometry. Equation 3 reflects the fact that phase cannot be measured far beyond the coherence envelopes, due to noise. Although the coherence envelops modeled are Gaussian in profile, the same phase treatment is valid for profiles of any slowly varying envelope.

The phase of the CW heterodyne signal is given by:

$$\psi_{cw}(x) = \mathrm{mod}_{2\pi}(\arg(R_{cw,1}e^{i2k_{cw}(x-x_1)} + \quad (4)$$

-continued
$$R_{cw,2}e^{i2k_{cw}(x-(x_1+n_{1550nm}L)}$$
$$= \mathrm{mod}_{2\pi}(\arg(\overline{R}e^{i2k_{cw}(x-\overline{x})}))$$
$$= \mathrm{mod}_{2\pi}(2k_{cw}(x-\overline{x})),$$

with $R_{CW,j}$ the reflectivity of the interface j at the CW wavelength, $n_{1550\,nm}$ the sample's refractive index, $\overline{R}$ and $\overline{x}$ the effective average reflectivity and distance from the beamsplitter, respectively. If the center wavelengths of the two light sources are chosen such that $$k_{LC}=2k_{cw}+\Delta, \quad (5)$$

where $\Delta$ is a small intentionally added shift, then a difference phase, $\Psi_D$, of the form is obtained:

$$\psi_D(x) = \psi_{LC}(x) - 2\psi_{cw}(x) \quad (6)$$
$$= h_c(x-x_1)\mathrm{mod}_{2\pi}(4k_{cw}(\overline{x}-x_1) + 2\Delta(x-x_1)) + h_c(x-x_2)\mathrm{mod}_{2\pi}(4k_{cw}(\overline{x}-x_2) + 2\Delta(x-x_2)).$$

The above quantity provides both the approximate number of fringes in the interval ($x_2-x_1$) and the fractional fringe, which provides sub-wavelength precision.

As the parameter $\Delta$ is varied by a small amount (corresponding to a wavelength-shift of approximately 1-2 nm), the slope of $\Psi_D(x)$ pivots around the points where $x=x_1$ and $x=x_2$. In other words, the phase scans at different values of $\Delta$ crosses at those points. The optical distance from $x_1$ to $x_2$ can be found by counting the fringes that $\Psi_{CW}(x)$ goes through between the two phase crossing points. Twice the quantity thus found is denoted by $S_{fringe}$, which is not an integer value, and corresponds to the number of fringes at the low coherence wavelength. In the event where multiple phase crossing points occur for a single interface, the point that corresponds to the position of the interface can be found by making multiple scans at additional values of $\Delta$. The position of the interface is the only location where $\Psi_D(x)$ will cross for all $\Delta$ values.

The phase shift information is used to further localize the interface separation. Specifically, the difference between the phase shifts at $x=x_1$ and $x=x_2$ is:

$$S_{phase} = \frac{\mathrm{mod}_{2\pi}(\psi_D(x=x_1) - \psi_D(x=x_2))}{2\pi} \quad (7)$$
$$= \frac{\mathrm{mod}_{2\pi}(4k_{cw}(x_2-x_1))}{2\pi}.$$

This measures the fractional fringe with great sensitivity.

The absolute optical separation ($x_2-x_1$) can be determined with precision from $S_{fringe}$ and $S_{phase}$ through the following equation:

$$(x_2-x_1)_{measured} = (n_{775nm}L)_{measured} \quad (8)$$
$$= \frac{\lambda_{cw}}{4}\left(\left[int(S_{fringe}) + U\left(\Delta S - \frac{1}{2}\right) - \right.\right.$$

$$U\left(-\Delta S - \frac{1}{2}\right)\right] + S_{phase}\right)$$

where $\Delta S = \operatorname{res}(S_{fringe}) - S_{phase}$ and $U(\,)$ is a unit step function. Here, int( ) and res( ) denote the integer and fractional parts of the argument respectively. The first term localizes the optical distance to the correct integer number of fringes by minimizing the error between $S_{phase}$ and the fractional part of $S_{fringe}$. The error of an optical separation determination is limited only by the measurement error of $S_{phase}$. In an experiment such error translates to an error in $(n_{775\,nm}L)_{measured}$ of approximately 0.5 nm. The measurement error of $S_{fringe}$ needs only be smaller than half a fringe so that the correct interference fringe can be established; having satisfied this criterion, it does not enter into the error of $(n_{775\,nm}L)_{measured}$. The maximum measurable optical distance simply depends on the ability of the system to accurately count fringes between two crossing points and the frequency stability of the light sources.

The above equation is a condensed expression of the method for finding the correct fringe and the fractional fringe. The operation can be illustrated through the following example and FIG. 5 which shows the determination of the correct estimate of $(n_{775\,nm}L)_{measured}$ by choosing the value that minimizes the error between estimates based on $S_{phase}$ and $S_{fringe}$. Assume that $S_{fringe}$ and $S_{phase}$ are 26.7 and 0.111. From the measurement of $S_{phase}$, the optical distance of the value is:

$$(n_{775nm}L)_{measured} = \frac{\lambda_{cw}}{4}(a + 0.111), \tag{9}$$

where α is an integer. Given the value of $S_{fringe}$, the possible values of $(n_{775\,nm}L)_{measured}$ can be limited to the following 3 values:

$$\frac{\lambda_{cw}}{4}(25.111),\ \frac{\lambda_{cw}}{4}(26.111) \text{ and } \frac{\lambda_{cw}}{4}(27.111).$$

Given that the value of $$\frac{\lambda_{cw}}{4}(27.111)$$

is closest to $$\frac{\lambda_{cw}}{4}(S_{fringe}),$$

it is the correct estimate of $(n_{775\,nm}L)_{measured}$.

In preferred embodiments for interferometry measurements based on harmonically related light sources, the appropriately chosen pair of light sources and the method of extracting difference phase allows the minimization and preferably the elimination of the effect of jitter in the interferometer, which would otherwise make high precision optical distance measurement impossible. The elimination of jitter also allows the comparison of scans performed at different times.

To demonstrate the capability of a preferred embodiment of the method, the system is used to probe the optical distance between the top and bottom surface of a fused quartz cover slip having a physical thickness, L=237±3 μm. In this embodiment there is a π phase shift associated with reflection from the first interface, that marks a positive refractive index transition. Hence, there is a $e^{-i\pi}$ term associated with the factors $R_{LC,1}$ and $R_{cw,1}$ in Equations 1 and 2. This results in a correction factor of half on $S_{fringe}$ and $S_{phase}$. FIG. 4 shows the result of typical scans at the LC wavelengths of 773.0 nm and 777.0 nm. The results of four scans are summarized in Table 1 which represents measurements of $(n_{755\,nm}L)$ on a piece of quartz cover slip. The repeatability of the experimental data indicates that the light source are sufficiently stable in frequency.

TABLE 1

| | $\frac{\lambda_{cw}}{4}S_{fringe}(\mu m)$ | $\frac{\lambda_{cw}}{4}S_{phase}(\mu m)$ | $(n_{775nm}L)_{measured}(\mu m)$ |
|---|---|---|---|
| Set 1 | 350.86 ± 0.17 | 0.3496 ± 0.0004 | 351.0371 ± 0.0004 |
| Set 2 | 351.08 ± 0.17 | 0.3497 ± 0.0004 | 351.0372 ± 0.0004 |
| Set 3 | 351.15 ± 0.16 | 0.3502 ± 0.0004 | 351.0377 ± 0.0004 |
| Set 4 | 351.04 ± 0.18 | 0.3498 ± 0.0004 | 351.0373 ± 0.0004 |
| Average | | | 351.0373 ± 0.0004 |

The experimental data yields an optical absolute distance measurement with sub-nanometer precision. The optical distance found is associated with the low coherence light source. The CW heterodyne signal serves as an optical ruler. If L of the quartz cover slip is known precisely, $n_{775\,nm}$ for quartz at the wavelength 775.0 nm can be found to a very high degree of accuracy from $(n_{775\,nm}L)_{measured}$.

Alternatively, without knowing the exact value of L, the refractive index ratio at two different wavelengths can be determined by measuring the corresponding optical distances using low coherence light at these wavelengths and CW light at their respective harmonics. Using a range of low coherence wavelengths, the dispersion profile of a material can be determined accurately. The dispersion profile maps out the refractive index differences at various wavelengths. The experimental results in accordance with a preferred embodiment predict that a precision of approximately seven significant figures can be achieved with an approximately 1 mm thick sample.

In another preferred embodiment the light sources of the system are changed to a low coherence superluminescent diode (SLD) emitting at 1550.0 nm and a CW Ti:Sapphire laser emitting at 775.0 nm. By adjusting the operating current through the SLD the center wavelength is changed by about 2 nm; this is adequate to achieve phase crossing. Using this preferred embodiment of the present invention system, the optical distance can be measured at 1550.0 nm. Taking the ratio of the result of this measurement with the previous measurement, the ratio of the refractive indices $n_{775\,nm}/n_{1550\,nm}$ for quartz can be determined. It should be noted that the index ratios found are for harmonically related wavelengths due to the sources used in the preferred embodiments. Refraction index ratios for other wavelengths can be measured with other appropriate choices of light sources. For comparison, the corresponding data for glass and acrylic plastic are tabulated in Table 2 as measurements of $n_{775\,nm}/n_{1550\,nm}$ for different materials.

TABLE 2

|  | $n_{775\,nm}/n_{1550\,nm}$ |
| --- | --- |
| Quartz | 1.002742 ± 0.000003 |
| Glass (German borosilicate) | 1.008755 ± 0.000005 |
| Acrylic plastic | 1.061448 ± 0.000005 |

Note that some of the equations used when the low coherence wavelength is half that of the CW wavelength are slightly different from the equations previously presented herein. For example:

$$\psi_{LC}(x) = \mathrm{mod}_{2\pi}\left(\arg\left(R_{LC,1}e^{i2k_{LC}(x-x_1)}e^{-\left(\frac{2}{l_c}(x-x_1)\right)^2} + \right.\right. \tag{10}$$
$$\left.\left. R_{LC,2}e^{i2k_{LC}(x-x_2)}e^{-\left(\frac{2}{l_c}(x-x_2)\right)^2}\right)\right)$$
$$\approx h_c(x-x_1)\mathrm{mod}_{2\pi}(2k_{LC}(x-x_1)) +$$
$$h_c(x-x_2)\mathrm{mod}_{2\pi}(2k_{LC}(x-x_2)),$$

$$\psi_{cw}(x) = \mathrm{mod}_{2\pi}(\arg(R_{cw,1}e^{i2k_{cw}(x-x_1)} + \tag{11}$$
$$R_{cw,2}e^{i2k_{cw}(x-(x_1+n_{1550nm}L))}))$$
$$= \mathrm{mod}_{2\pi}(\arg(Re^{i2k_{cw}(x-x)}))$$
$$= \mathrm{mod}_{2\pi}(2k_{cw}(x-x)),$$

$$2k_{LC} - k_{cw} + \Delta, \tag{12}$$

$$\psi_D(x) = 2\psi_{LC}(x) - \psi_{cw}(x) \tag{13}$$
$$= h_c(x-x_1)\mathrm{mod}_{2\pi}(4k_{LC}(\bar{x}-x_1) + 2\Delta(x-x_1)) +$$
$$h_c(x-x_2)\mathrm{mod}_{2\pi}(4k_{LC}(\bar{x}-x_2) + 2\Delta(x-x_1))$$

$$S_{phase} = \frac{\mathrm{mod}_{2\pi}(\psi_D(x=x_1) - \psi_D(x=x_2))}{2\pi} \tag{14}$$
$$= \frac{\mathrm{mod}_{2\pi}(4k_{LC}(x_2-x_1))}{2\pi}.$$

$$(x_2 - x_1)_{measured} = (n_{775nm}L)_{measured} \tag{15}$$
$$= \frac{\lambda_{LC}}{4}\left(\left[\mathrm{int}(S_{fringe}) + U\left(\Delta S - \frac{1}{2}\right) - \right.\right.$$
$$\left.\left. U\left(-\Delta S - \frac{1}{2}\right)\right] + S_{phase}\right)$$

Preferred embodiments of the methods for overcoming $2\pi$ ambiguity is of significant use in applications such as high precision depth ranging and high precision refractive index determination of thin film solid state materials.

The use of the preferred methods can be illustrated through consideration of a slab of glass. There exist systems that can measure the distance from the systems to the averaged center of the glass slab very accurately. There are also systems that can measure the roughness of the glass surface very accurately. A preferred embodiment of the present invention system measures with nanometer sensitivity the thickness of the glass slab end-face.

Figure 6A:
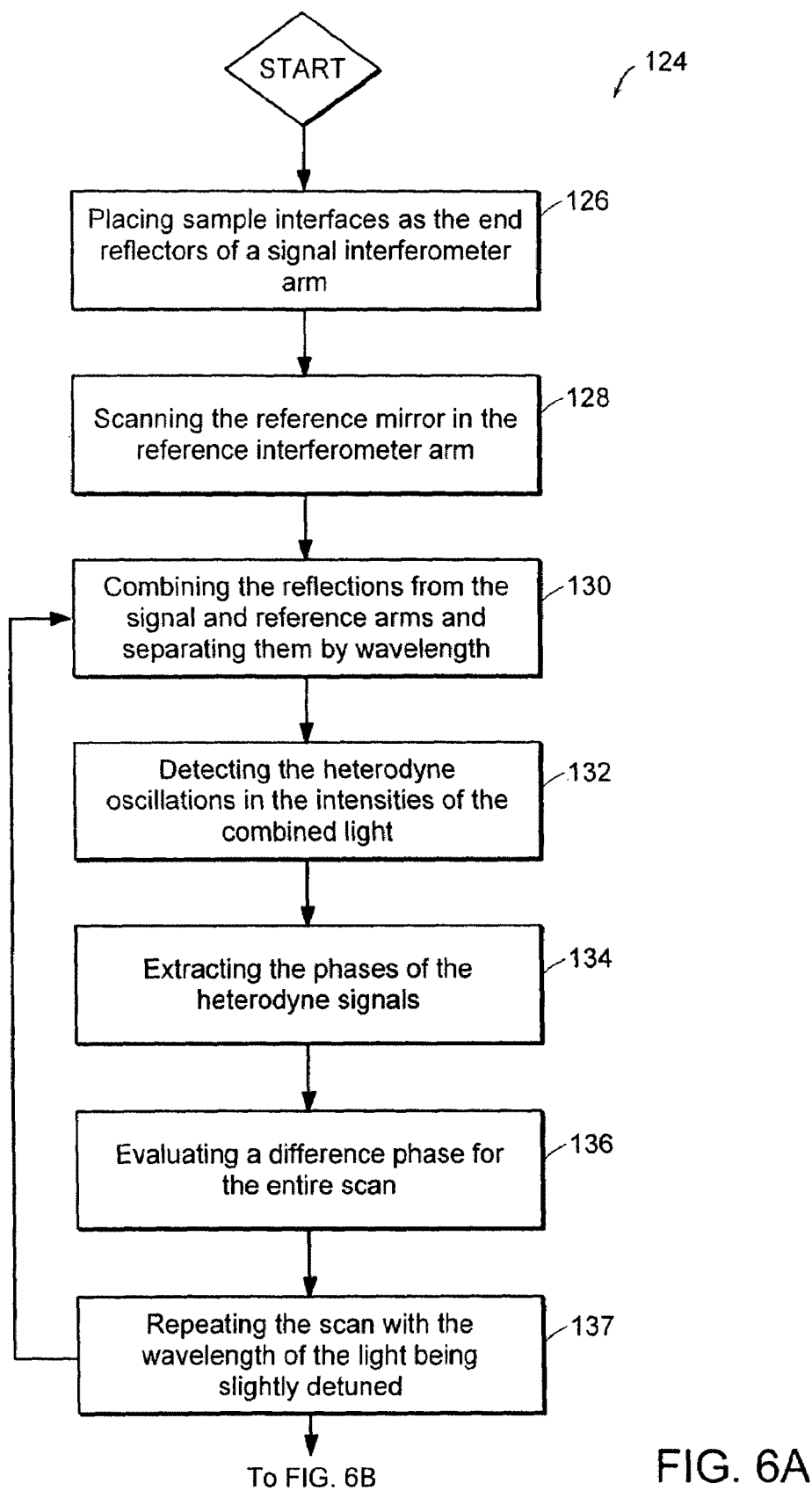
FIGS. 6A and 6B are a flow chart illustrating a method to measure an optical distance in accordance with a preferred embodiment of the present invention.
Figure 6B:
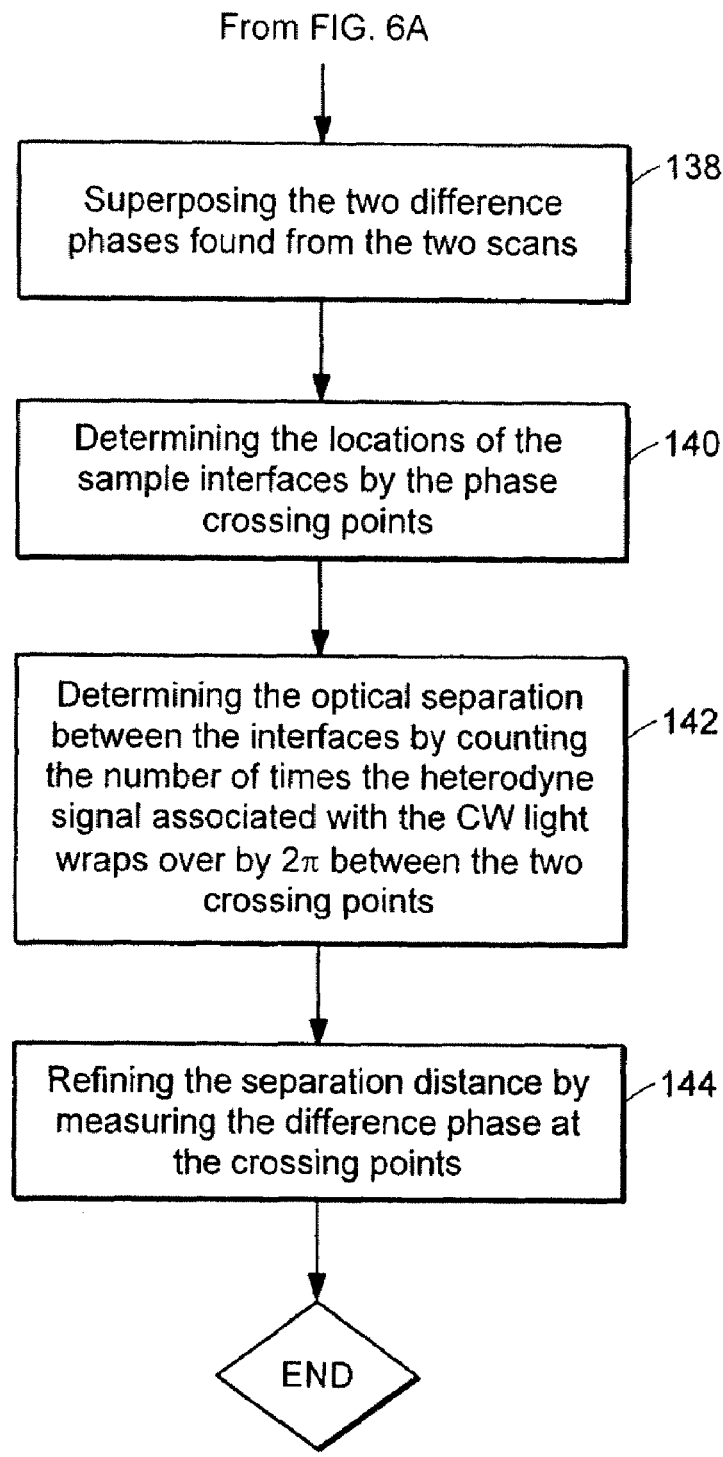

The steps in the implementation of a preferred embodiment of the method to determine the optical distance are illustrated in the flow chart 124 in FIGS. 6A and 6B. The method 124 includes the use of two harmonically related light sources in a Michelson interferometer, one of which is a CW source while the other is a low coherence source. The sample for which the optical distance needs to be measured between its interfaces is used as the end reflectors of the signal interferometer arm per step 126. The reference mirror in the reference interferometer arm is scanned per step 128. The method includes the step 130 in which the reflections from the signal and reference arms are combined and separated by wavelength. Further, per step 132 the heterodyne oscillations in the intensities of the combined light are detected. The phases of the heterodyne signals for both wavelengths are then found via, for example, a Hilbert transform or any alternate phase extraction method per step 134. A difference phase given by subtracting twice the phase of the longer wavelength from the shorter is evaluated for the whole scan per step 136. The scan is repeated with the wavelength of the light being slightly detuned per step 137. Steps 130-136 are then repeated.

The two difference phases found from the two scans are then superposed on each other on a graph with the x-axis representing the displacement of the reference mirror per step 138. It should be noted that the extraction of difference phases can also be done with the appropriate light sources or chromatic filters or software/hardware signal processing on a single scan.

The next step in method 124 includes determining the phase crossing points on a graph to mark the locations of the sample interfaces per step 140. By counting the number of times the heterodyne signal associated with the CW light wraps over by $2\pi$ between the two crossing points, the optical separation between the interfaces is determined per step 142 with accuracy to about a fraction of a wavelength, for example, of approximately 0.2. By measuring the difference phase at the crossing points, further localization and/or refining of the separation to a very small fraction of a wavelength, for example, approximately 0.001.

Figure 7:
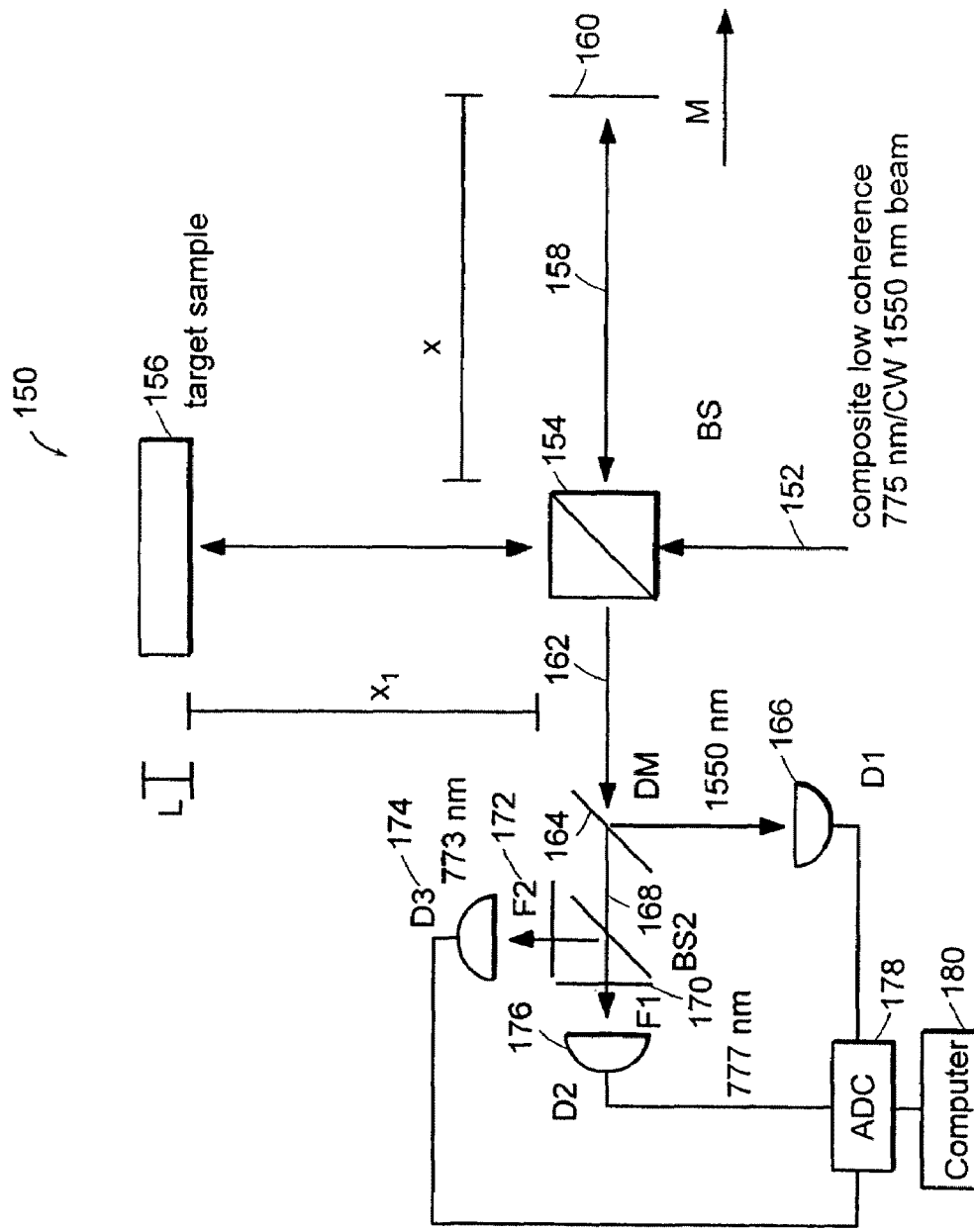
FIG. 7 is a schematic diagram of an alternate preferred embodiment of the system to measure an optical distance in accordance with the present invention.

In another preferred embodiment as illustrated in FIG. 7 which is a schematic diagram of the system to measure optical distance, the low coherence light source may be sufficiently broad in bandwidth, for example, more than 4 nm. On the detection end, a third detector 174 is added to the two detectors 166, 176. This results in the low coherence light signal 168 being further split into two. Prior to reaching the detectors, the two light beams are passed through different filters 170, 172. The filters transmit different parts of the spectrum. One passes the longer wavelength spectra component, while the second, the shorter wavelength spectral component. Preferably the two transmitted beams are separated in their spectrum by more than 2 nm.

The light beams are then incident on the detectors and their heterodyne signals are processed in the fashion discussed with respect to FIG. 1. The advantage of this method in accordance with alternate preferred embodiment is that the method eliminates the repetition of the process with an adjusted low coherence wavelength. The two signals are acquired in the same scan.

Figure 8A:
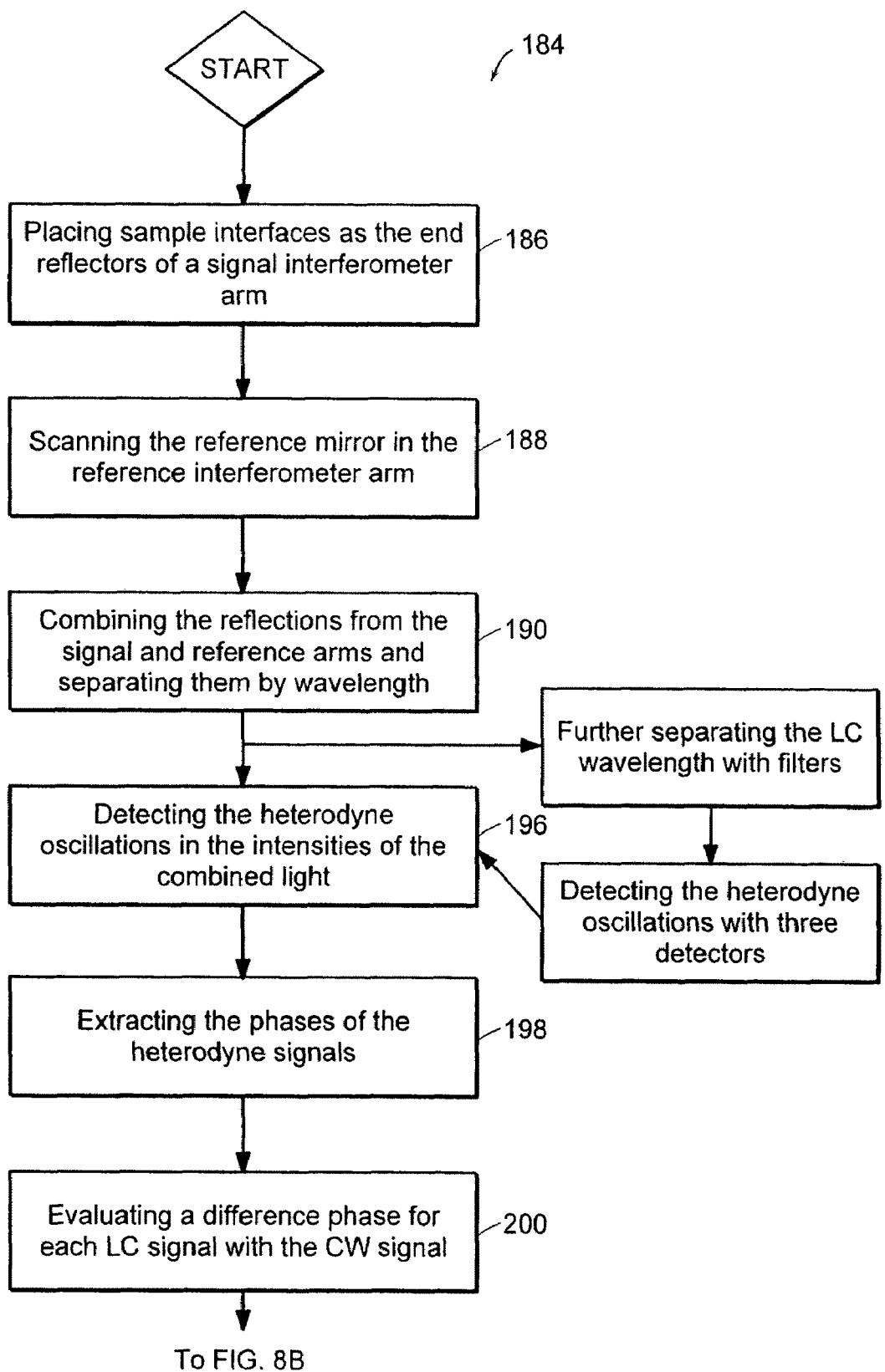
FIGS. 8A and 8B are a flow chart illustrating an alternate method to measure an optical distance in accordance with a preferred embodiment of the present invention.
Figure 8B:
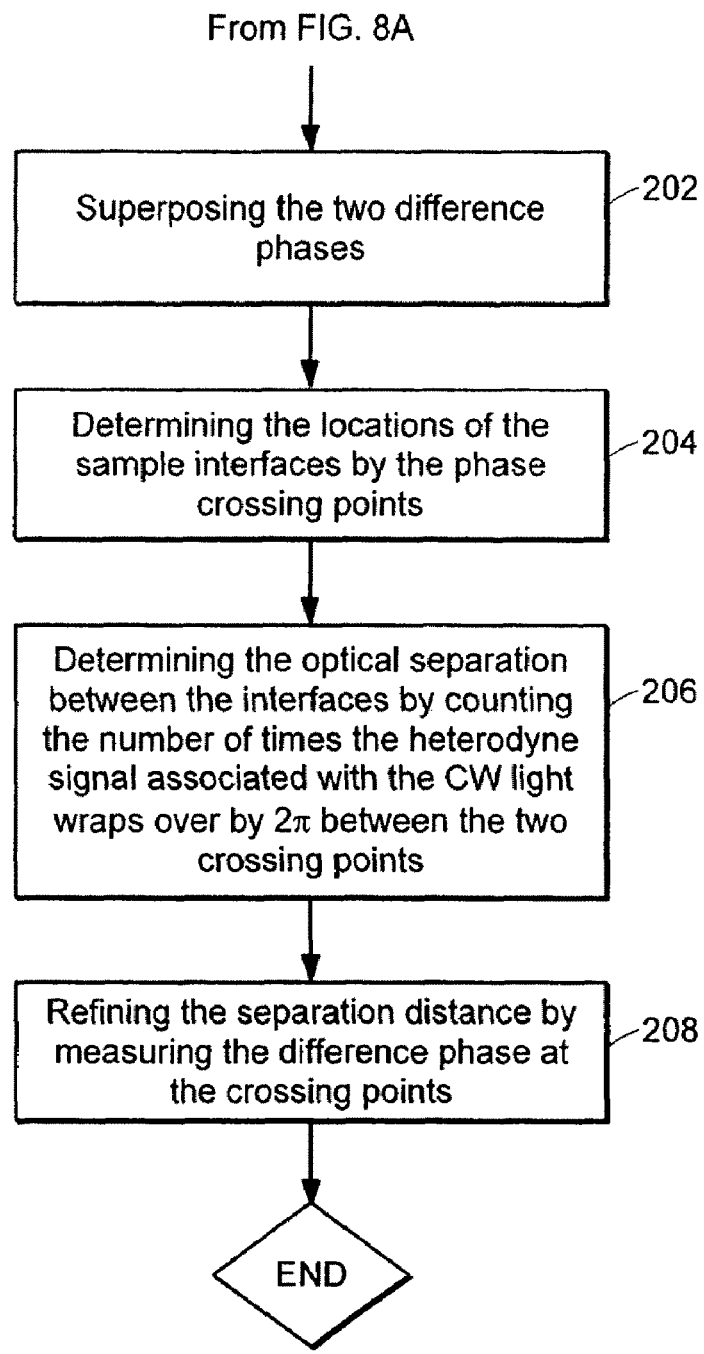

FIGS. 8A and 8B illustrate a flowchart 184 of an alternate method to measure an optical distance in accordance with a preferred embodiment of the present invention. The method 184 includes the use of two harmonically related light sources in an interferometer one of which is a CW source while the other is a low coherence source. The sample for which the optical distance needs to be measured is used as the end reflectors of the signal interferometer arm per step 186. The reference mirror in the reference interferometer arm is scanned per step 188. The method further includes the step 190 of combining the reflections from the signal and reference arms and separating them by wavelength. The low coherence wavelength is further separated using filters per step 192. The method 184 includes the step 194 of detecting the heterodyne oscillations with at least three detectors. The next step 196 includes detecting the heterodyne oscillations in the intensities of the combined light. The phases of the heterodyne signals for both wavelengths are then found via, for example, a Hilbert transform or any alternate phase extraction method per step 198. A difference phase for each low coherence signal with the CW signal is then evaluated per step 200.

The two difference phases are then superposed on each other on a graph with the x-axis representing the displacement of the reference mirror per step 202. The remaining steps 204, 206, 208 are similar to steps 140, 142, 144 as discussed with respect to FIG. 6B.

Figure 9:
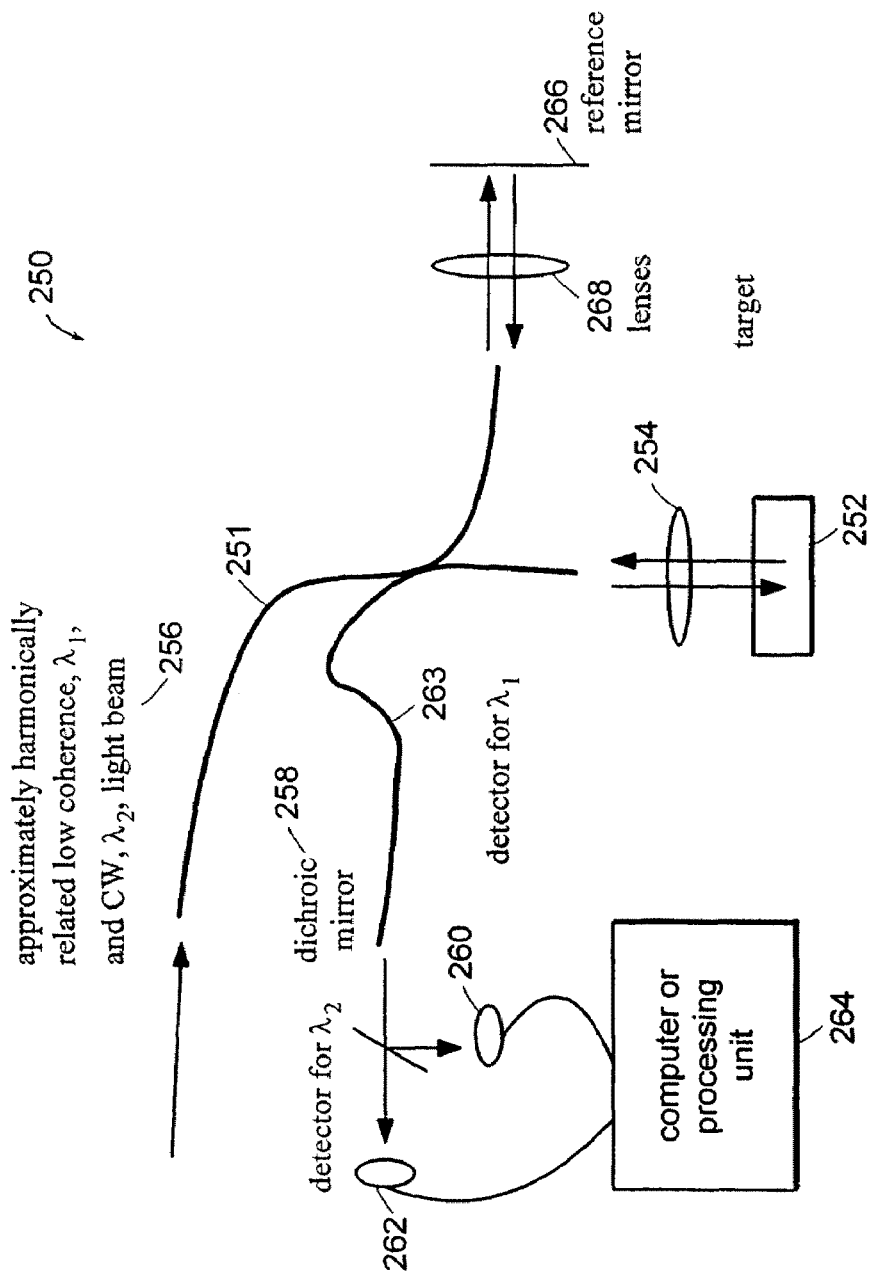
FIG. 9 schematically illustrates a preferred embodiment of a fiber based system to measure the thickness of an optically transmissive material such as a glass slab, tissue sample or layer.

The preferred embodiment of the method can be used to absolutely measure arbitrarily long optical distances with sub-nanometer precision. The preferred embodiment of the system can be free space based or fiber based. FIG. 9 illustrates a preferred embodiment of a fiber based system to measure an optical distance.

The input light 256 includes approximately harmonically related low coherence light having a wavelength $\lambda_1$ and a CW light beam having a wavelength $\lambda_2$ which travel in fiber 251. The composite beam is divided in two, one part of the signal is incident on the target lens 254 and sample 256 and travels in fiber 253 while the other is incident on the reference mirror 266 via a lens 268 and travels in fiber 251. The movement of the reference mirror introduces a Doppler shift on the reflected beam. The reflected beams are recombined and then separated into their component wavelength components by means of the dichroic mirror 258. These wavelength components are measured separately with photodetectors 260, 262. The resulting heterodyne signals at their respective Doppler-shifted frequencies are bandpassed around their respective center heterodyne frequencies and Hilbert transformed to extract the corresponding phases of the heterodyne signals, $\Psi_{CW}$ and $\Psi_{LC}$.

The preferred embodiment methods can be used to make precise optical distance measurements. From such measurements, optical properties of target objects can be accurately measured. By measuring the dispersion profile of the target, structural and/or chemical properties of the target can be evaluated. In the biomedical context, preferred embodiments of the present invention can be used to accurately determine the dispersion property of biological tissues in a non-contact and non-invasive manner. Such dispersion determination can be used on the cornea or aqueous humor of the eye. The sensitivity achieved can be sufficient to detect glucose concentration dependent optical changes. In a preferred embodiment of the present invention method, the blood glucose level can be determined through non-invasive measurements of the dispersion profile of either the aqueous, vitreous humor or the cornea of the eye.

As discussed hereinbefore, phase based interferometry methods are able to measure optical distances very sensitively. However, they are typically limited in their applications by a problem that is widely known in the field as the $2\pi$ ambiguity problem. The crux of this problem is that it is impossible to differentiate a length of 10.1 wavelengths from the length of 11.1 wavelengths. The preferred embodiments of the present invention overcome this limitation and allow absolute optical distance measurements with sub-nanometer accuracy.

There are numerous phase based methods that measure changes in optical distances with a sensitivity of approximately the nm range. As long as the change is small and gradual, the change can be continuously tracked. There are low coherence methods that measure absolute optical distance by tracking the delay in arrival at the detector of light reflected from different interfaces of the reflector sensitivity in approximately microns. As discussed hereinbefore, the simultaneous use of a CW and a low coherence light sources in an interferometer provides for the methods to measure optical distance. The heterodyne phases of the signals associated with the two wavelengths are intrinsically related. By processing the phase per the preferred embodiments, motional noise is minimized and preferably eliminated from our measurements.

An application of a preferred embodiment is the glucose level determination using the measurement of the refractive index of the vitreous and/or aqueous humor of the eye. The sensitivity of this technique affords the ability to measure chemical concentrations with a sensitivity that is clinically relevant. One of the more obvious applications of the method of a preferred embodiment is the determination of blood glucose level through measurements performed on the eye. The glucose level of the fluid in the eye mirrors that of the blood with clinically insignificant time delay.

Figure 10:
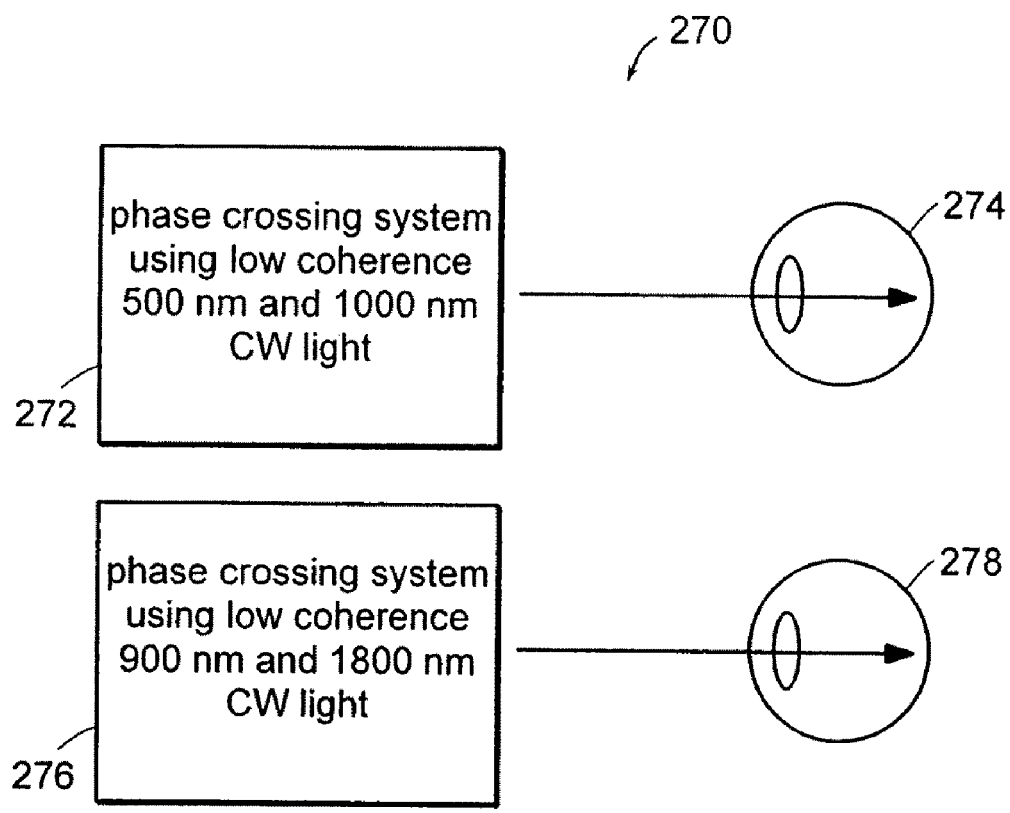
FIG. 10 illustrates a preferred embodiment of a system of the present invention used in a vitreous and/or aqueous humor glucose measurement system in accordance with the present invention.

The method of a preferred embodiment measures the optical path lengths of the vitreous and/or aqueous humor layer in the eye using at least two separate sets of wavelengths as illustrated in FIG. 10. The method measures the product of the refractive index at the low coherence wavelength and the physical separation between two interfaces. By changing the wavelength of the low coherence light source (and appropriately changing the CW wavelength to match), the refractive index difference at different wavelengths is measured. For example, one set of measurements is performed with a tunable 500 nm low coherence light source and a one micron CW light source to extract $n_{500\,nm}L$ where L is the physical thickness of the vitreous and/or aqueous humor at the point of measurement. Another set of measurements is performed with a tunable 1000 nm low coherence light source and a 1800 nm CW light source to extract $n_{900\,nm}L$. By taking the ratio of these two measurements, the refractive index ratio, $n_{500\,nm}/n_{900\,nm}$, of the vitreous and/or aqueous humor is extracted. With the existing sensitivity, for example, 0.5 nm optical path sensitivity, a preferred embodiment of the system, the ratio $n_{500\,nm}/n_{900\,nm}$ with $10^{-8}$ sensitivity can be measured for a material of thickness equal to that of the human vitreous and/or aqueous humor. This provides the sensitivity to changes in the glucose level of about 0.25 mg/dl. Given that the typical blood glucose level is about 100 mg/dl, a preferred embodiment of the present invention is well suited for blood glucose assessment. The choice of optical wavelengths is flexible, the wavelength used hereinabove is simply for illustrative purposes. For maximal sensitivity, the wavelength separation is preferably as large as possible. Preferred embodiments include a separation of greater than 500 nm.

In the event that such a refractive index ratio is insufficient for absolute blood glucose level determination due to the presence of other chemicals that are changing in the vitreous and/or aqueous humor, a more complete range of optical path length measurements can be made at a range of other wavelengths. This set of more complete measurements allows the determination of glucose level and other chemical concentrations by fitting the measurements to known dispersion profiles of glucose and other chemicals.

A preferred embodiment of the present invention can be applied as a measurement technique in semiconductor fabrication. As the preferred embodiment of the method is non-contact and non-destructive, it can be used to monitor the thickness of semiconductor structures as they are being fabricated. In addition, the composition of the semiconductor structures can be assessed in much the same manner as that discussed with respect to the characterization of the vitreous and/or aqueous humor measurements.

Phase Measurement and Imaging Systems:

Alternate preferred embodiments of the present invention are directed to imaging small biological objects or features with light. These embodiments can be applied to the fields of, for example, cellular physiology and neuroscience. These preferred embodiments are based on principles of phase measurements and imaging technologies. The scientific motivation for using phase measurements and imaging technologies is derived from, for example, cellular biology at the sub-micron level which can include, without limitation, imaging origins of dysplasia, cellular communication, neuronal transmission and implementation of the genetic code. The structure and dynamics of sub-cellular constituents cannot be currently studied in their native state using the existing methods and technologies including, for example, x-ray and neutron scattering. In contrast, light based techniques with nanometer resolution enable the cellular machinery to be studied in its native state. Thus, preferred embodiments of the present invention include systems based on principles of interferometry and/or phase measurements and are used to study cellular physiology. These systems include principles of low coherence interferometry (LCI) using optical interferometers to measure phase, or light scattering spectroscopy (LSS) wherein interference within the cellular components themselves is used, or in the alternative the principles of LCI and LSS can be combined in systems of the present invention.

The preferred embodiments for phase measurement and imaging systems include actively stabilized interferometers, isolation interferometers, common path interferometers and interferometers that provide differential measurements. The embodiments directed to differential measurement systems include two-point heterodyne interferometers and dual beam interferometers. Embodiments using common path interferometers can include phase contrast microscopy using spatial light modulation.

Optical low coherence interferometry (LCI) has found many applications in the study of biological media. The most widely used LCI technique is optical coherence tomography (OCT), which images the 2D or 3D backscattering profile of a biological sample. The LCI technique has been described by Drexler, W. et al, in "In vivo ultrahigh-resolution optical coherence tomography," Optics Letters Volume 24, No. 17 pages 1221-1223, the entire teachings of which are incorporated herein by reference. OCT has a depth sensitivity limited by the coherence length of the light source used. Ultra-broadband sources have resolved feature of size on the order of 1 micron.

Phase-sensitive low coherence interferometry is sensitive to sub-wavelength optical path changes in a sample. The primary difficulty in phase-sensitive LCI is phase noise due to optical path fluctuations in the arms of the interferometer. A laser beam of different wavelengths passing through a nearly identical optical path can be used to measure interferometer phase noise, which is then subtracted from a similarly noisy sample signal to extract real sample phase shifts. Other researchers have employed orthogonal laser polarizations along a common optical path to measure differential phase contrast or birefringence with high phase sensitivity. In both techniques, the reference arm path is scanned and computer calculations are required to extract the phase (via a Hilbert transform) from the resulting fringe data; in addition, a phase unwrapping algorithm must be used to eliminate the $2\pi$ ambiguity in the phase measurements. The fringe scanning and information processing procedures substantially reduce the speed of the measurement, and may increase noise.

Systems Including Actively Stabilized Inteferometers:

Preferred embodiments of the present invention use LCI methods in which active stabilization of an interferometer by a reference beam allows continuous detection of very small phase shifts with high bandwidths and minimal computer processing. Reference beam locking to an arbitrary phase angle gives a direct sample phase measurement without reference arm scanning. Preferred embodiments provide two-dimensional and three-dimensional phase imaging.

Figure 11:
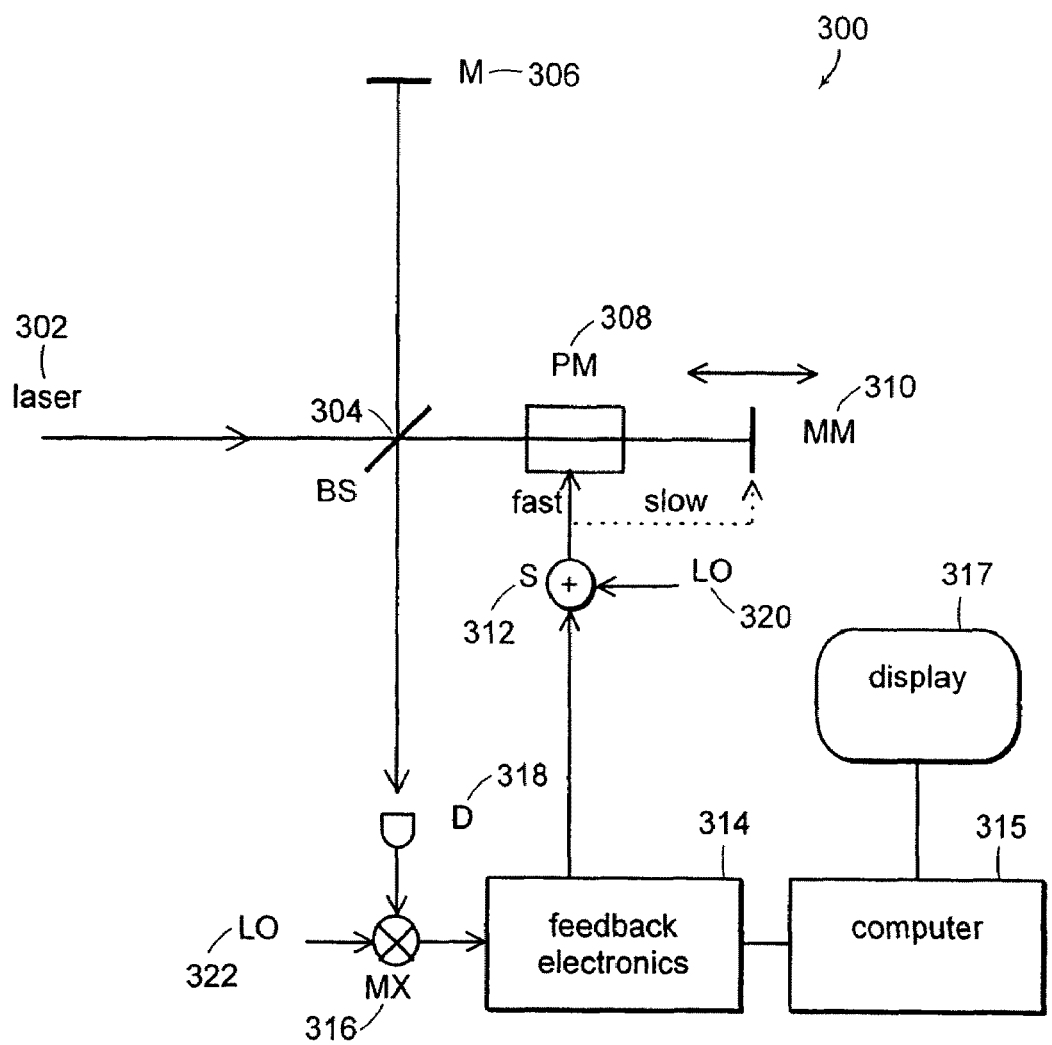
FIG. 11 illustrates an actively stabilized Michelson interferometer wherein M is a mirror, MM is a moving mirror, BS is a beamsplitter, PM is a phase modulator, D is a detector, LO is a local oscillator source, MX is a mixer and S is a summing amplifier in accordance with a preferred embodiment of the present invention.

Preferred embodiments rely on active stabilization of a Michelson interferometer by a reference laser beam. A schematic of a preferred embodiment of an actively stabilized interferometer 300 is shown in FIG. 11. The actively stabilized Michelson interferometer system 300 includes a mirror 306, a moving mirror 310, a beamsplitter 304, a phase modulator 308, a detector 318, local oscillator sources 320, 322, a mixer 316 and a summing amplifier 312. A continuous-wave laser beam divided by a beamsplitter 304 traverses two interferometer arms and is recombined at the detector 318. One of the interferometer arms contains a phase modulating element 308, such as an electro-optic modulator or a mirror mounted on a piezoelectric transducer. Large adjustments to the optical path difference may be performed by a translating mirror 310 or any other variable optical delay line. A processing device such as a computer 315 is in communication with the electronics used to provide feedback, and process phase shift measurements. An electronic image display 317 is used to display the phase shift and related images.

The phase difference between the two interferometer arms is modulated sinusoidally:

$$\Phi = \Psi + \Psi_d \sin(\Omega t) \tag{16}$$

where $\Psi = k(L_1 - L_2) = k\,\Delta L$ is the phase difference between the two arms, $\Psi_d < 2\pi$ is the modulation depth, and $\Omega$ is the modulation frequency. The detected interferometer signal is given by a coherent addition of beams from the two interferometer arms:

$$I = I_1 + I_2 + 2(I_1 I_2)^{1/2} \cos \phi \tag{17}$$

The nonlinear relation between I and $\phi$ results in a detected signal with frequency components at many harmonics of modulation frequency $\Omega$. The first ($I^\Omega$) and second ($I^{2\Omega}$) harmonic terms are given by $$I^\Omega = 4J_1(\Psi_d)(I_1 I_2)^{1/2} \sin\Psi \sin(\Omega t) \tag{18}$$

$$I^{2\Omega} = 4J_2(\Psi_d)(I_1 I_2)^{1/2} \cos\Psi \cos(2\Omega t) \tag{19}$$

Demodulation of $I^\Omega$ and $I^{2\Omega}$ at $\Omega$ and $2\Omega$, respectively, is performed via a mixer 316 or lock-in amplifier, and the two signals are amplified to give equal amplitudes as a function of $\Psi$:

$$V_1 = V_0 \sin\Psi \tag{20}$$

$$V_2 = V_0 \cos\Psi \tag{21}$$

Using analog or digital circuits, the linear combination $V_\theta$ is calculated with $\theta$ as a time varying parameter:

$$V_\theta = \cos\theta * V_1 - \sin\theta * V_2 = V_0 \sin(\Psi - \theta) \tag{22}$$

This signal is used as an error signal to lock the interferometer to any zero crossing with positive slope. $V_\theta(t)$ is integrated, filtered, and amplified before being fed back to the phase modulator (high frequency) and path length modulator (low frequency) to actively cancel interferometer noise. The linear combination $V_\theta(t)$ is used as the error signal in order to allow locking to an arbitrary phase $\theta$.

The stabilized interferometer may be combined with phase-sensitive low coherence interferometry as described herein. All of the system setups described herein may be implemented via free space optics or fiber optics. For clarity, the illustrations show free space optics implementations.

Figure 12:
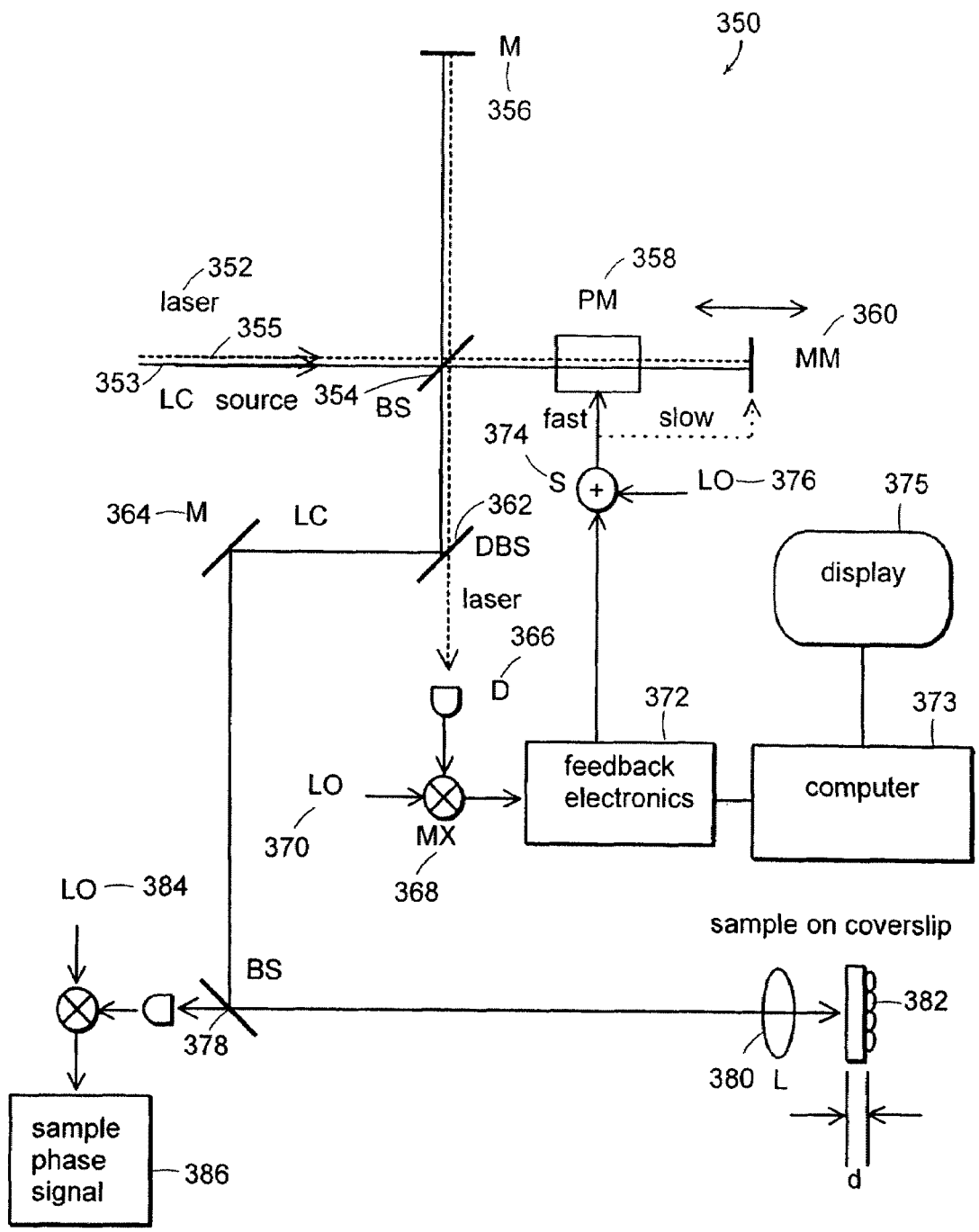
FIG. 12 illustrates a stabilized interferometer for optical delay phase-sensitive low coherence interferometry (LCI)

The schematic for a reference-beam stabilized interferometer for optical delay phase-sensitive LCI is shown in FIG. 12. A beam 353 from a low coherence source passes through the same path as the locking beam 355 in a stabilized interferometer. By varying the (stabilized) path length difference between the two arms of the interferometer, an output beam is prepared which is composed of the sum of two "copies" of the LC beam with a highly stable, continuously variable optical path delay between them, modulated at the interferometer lock modulation frequency.

The sample 382 is placed on a cover glass which has been anti-reflection-coated at the LC wavelength on the side in contact with the sample. The LC beam is focused by a microscope objective 380 through the glass and sample. Backscattered light is collected by the same optics and focused onto the detector 366. The detected signal is an autocorrelation of the backscattered field with time delay $\Delta L/c$. It can be shown to display interference fringes at zero delay and at delays corresponding to twice the optical path lengths between pairs of scattering or reflective surfaces in the sample arm illustrated in FIG. 13. In particular, the uncoated side of the cover glass is located approximately one coverslip thickness d away from the sample; an interference signal from the sample is seen at optical path delay nd, with n the refractive index of glass.

With $\Delta L = \sim 2nd$, the sample signal is demodulated by a mixer or lock-in amplifier at the modulation frequency to give a continuous measurement of sample phase. The interferometer lock phase $\theta$ may, in turn, be electronically varied in order to lock to a zero crossing in the demodulated low coherence signal. In this manner the time evolution of the interferometer lock phase is used as a direct measurement of the sample phase. This lock scheme has the advantage of being independent of the amplitude of the sample signal.

This system, in accordance with a preferred embodiment resembles a dual-beam optical computed tomography (OCT) technique in that an optical delay is prepared before the low coherence light enters the sample, and the detected signals are insensitive to changes in distance between sample and interferometer. In an alternative preferred embodiment, a Mach-Zender interferometer configuration to prepare the low coherence beam may also be used.

By introducing a variable attenuator into one or both of the interferometer arms, the relative amplitudes of the two time-delayed fields can be adjusted to optimize the interference signal.

A reference-beam stabilized phase-sensitive LCI schematic is shown in FIG. 14A. The system setup is similar to that of FIG. 11, but with the sample on cover glass 430 in place of one of the interferometer mirrors. Two beams 422, 424 from two low coherence sources (LC1 and LC2) are incident on the input of the interferometer. The reference beam has a coherence length comparable to or somewhat larger than the thickness of the cover glass, for example, about 150 microns. The cover glass reflection is used to lock the interferometer. The short coherence length of the reference beam prevents the interferometer lock from being influenced by spurious reflections from the microscope objective and other surfaces.

The signal beam has a coherence length several times smaller than the cover glass thickness, in order to distinguish between sample and back surface reflections. The reference arm length is adjusted to give interference fringes from the sample, and as previously described the signal is demodulated to give the sample phase as illustrated in FIGS. 15A and 15B. The lock of the interferometer with respect to the uncoated side of the cover glass results in a sample phase measurement relative to this interface, and excludes nearly all external interferometer noise.

Compared with the optical delay method described with respect to FIG. 11, this preferred embodiment has the disadvantage of having both the signal and reference beams incident onto the sample. For biological materials, especially living cells, this may limit the reference beam power that may be used, resulting in a reduced quality of lock. On the other hand, the scanning of the reference mirror allows a more straightforward identification of reflections from the sample. A processing device such as computer 453 is in communication with the electronics used to provide feedback, and process phase shift measurements. An electronic image display 455 is used to display the phase shift and related images.

Preferred embodiments can image sample phase over an area using two methods. In a preferred first method, the incident beam may be scanned in the X-Y direction on the sample, as in most implementations of OCT. In the embodiment including the reference-beam stabilized LCI, care must be taken to maintain the reference beam interferometer lock as the beam is scanned. In accordance to a second method, a charge-coupled device (CCD) or photodiode array may be used to detect the signals without scanning. FIG. 16 illustrates an imaging system 500 for stabilized phase sensitive LCI. This optical system is used to illuminate an extended region and image the scattered light onto a detector. FIG. 17 illustrates a simplified, unfolded version of the system configuration to illustrate the optical design in accordance with a preferred embodiment of the present invention. The solid lines represent incident rays while dashed lines represent backscattered rays.

For CCD imaging, measurement of relative phase may be performed by analyzing a sequence of 4 images, each varying in phase from the previous by $\pi/2$. FIG. 14B illustrates an embodiment for imaging using a CCD in a system for actively stabilized phase-sensitive low coherence interferometry using a mirror with a piezoelectric transducer (PZT) 461 to generate the phase shift in accordance with the present invention. The circuit 469 are the electronics that are used to create the phase shift using the PZT and the electronics using for detecting phase shift. The CCD is an array of pixels integrated into a single compact electronic chip. A CCD controller 477 is in communication with the CCD which in turn is connected to a processing device such as, for example, computer 478. An image display 479 is used to display phase shift and related images.

For high bandwidth phase imaging the signals from a photodiode array may be individually demodulated at both the first and second harmonics; this allows phase at each pixel to be measured without ambiguity.

The higher sensitivity and bandwidth of the preferred embodiments of the present invention interferometric systems open new possibilities for the measurement of small optical phase shifts in biological or nonbiological media. For example, the preferred embodiments enable studies of cell membrane motions and fluctuations. Dual wavelength, phase-sensitive LCI has been used to observe cell volume regulation and membrane dynamics of a human colon cell culture. Recently, low-frequency oscillations in the cell membranes have been observed subsequent to the addition of sodium azide to the culture. The preferred LCI embodiments allow the study of membrane dynamics on smaller time scales, where thermally-driven fluctuations and mechanical vibrations may be more important. Two-dimensional imaging methods in accordance with a preferred embodiment of the present invention allow the study of membrane fluctuations in collections of interacting cells. Oscillations and correlations can provide information related to cell signaling.

Preferred embodiments of the present invention can be used for measurements of neuron action potentials. There is great interest in neuroscience for improved optical methods for noninvasively monitoring the electrical signals of neurons. Current methods rely on calcium-sensitive or voltage-sensitive dyes, which have a number of problems, including short lifetimes, phototoxicity, and slow response times.

It has been known for several decades that the action potential is accompanied by optical changes in nerve fibers and cell bodies. In addition, nerves have been shown to exhibit a transient increase in volume during excitation. These changes have been interpreted in terms of phase transitions in the cell membrane, and index shifts due to reorientation of dipoles in the cell membrane.

Phase-sensitive LCI methods in accordance with the preferred embodiments may be used to measure the optical and mechanical changes associated with the action potential. Increased bandwidths allow sensitive phase measurements on the ~1 ms time scale of the action potential. Preferred embodiments of the present invention can be used to provide noninvasive long-term measurements of neural signals and provide the ability to image many neurons simultaneously. The embodiments help with analyzing spatio-temporal patterning of neural activity is important to understanding the brain. Small ($\approx 10^{-4}$ rad) index shifts and membrane fluctuations that are known to accompany the action potential can be detected in preferred embodiments of the present invention that provide a high level of sensitivity speed and high bandwidth (>1 kHz). These embodiments use noise-cancelling methods such as isolation, which prevents noise from entering; stabilization methods, which use feedback elements to cancel noise; differential measurement that provides for noise cancellation without feedback and common path interferometry that minimizes noise influence.

The embodiments as described herein can be used in many medical applications. For example, cortex mapping can be performed during neurosurgery with an improvement in the speed and resolution compared with electrode methods of the prior art. Further, the preferred embodiments can be used to localize an epileptic foci during neurosurgery. The embodiments can also enable the monitoring of the retinal nerve activity in an eye. Additional applications of the preferred embodiments of the present invention include two-dimensional and three-dimensional scanning due to the high speed provided by the embodiments; high dynamic range and DC rejection provided by the photodiode detectors; nanometer-scale imaging in cell biology; characterization of epithelial tissue and detection of vibrations of membranes, for example, but not limited to, auditory cells and blood vessels.

Systems Including Dual-Beam Interferometers:

A preferred embodiment of the present invention includes a fiber-based optical delay phase-sensitive low coherence interferometer for integration into a conventional light microscope. Simultaneous electrical and optical measurements can be performed in cultures of hippocampal neurons. A preferred embodiment includes an imaging system containing a photodiode array or a rapidly scanning beam. A method for optical excitation of neurons in combination with LCI measurements of action potentials can form an extremely useful new tool for investigating neural network dynamics, synaptic plasticity, and other fundamental problems in neuroscience.

Another embodiment applies phase-sensitive imaging techniques to brain slices and even neurons in vivo. Tracking and compensation for motions of the brain surface is a considerable challenge. Optical scattering limits the depth from which neuronal signals may be extracted, but a depth on the order of 100 microns may be possible.

Preferred embodiments of actively stabilized interferometers described herein before have included two wavelength systems wherein a first wavelength is used for stabilization and the second wavelength for phase measurement. FIG. 18A illustrates a schematic diagram of a two-point Mach-Zender heterodyne interferometer system wherein one wavelength is used. This point-stabilized/reference interferometer system measures phase differences of light passing through two points on a sample 586. An almost common-path geometry reduces interferometer phase noise.

A collimated laser beam or low coherence light source is split into sample 586 and reference paths by beamsplitter 584. The sample beam passes through the sample 586 and lenses $L_1$ (objective lens) 588 and $L_2$ (tube lens) 590 before the final beamsplitter 592. Lenses $L_1$ 588 and $L_2$ 590 have focal lengths $f_1$ and $f_2$ respectively and constitute a microscope with magnification $M=f_2/f_1$. The lenses are aligned such that the distance between sample 586 and $L_1$ 588 is $f_1$, the distance between $L_1$ and $L_2$ is $f_1+f_2$, and the image plane is located a distance $f_2$ from $L_2$.

The reference beam passes through two acousto-optic modulators 594 $AOM_1$ and $AOM_2$ which are driven by RF fields at frequencies $\omega_1$ and $\omega_2$, respectively. Irises are used to select the +1 order diffracted beam from $AOM_1$ and −1 order from $AOM_2$. Therefore, light at frequency $\omega_0$ incident on $AOM_1$ exits the second pinhole at frequency $\omega_R=\omega_0+\Omega$ where $\Omega=\omega_1-\omega_2$. This two AOM configuration is used in order to obtain a relatively low heterodyne frequency $\Omega$ on the order of 100 kHz. A low heterodyne frequency may be preferable for the use of high sensitivity photodetectors, and also facilitates optical alignment since $\Omega$ may be set equal to zero with only a very small change in beam direction. A single AOM may be used if a higher heterodyne frequency is desired. A processing device such as, for example, computer 609 and image display 611 are in communication with the system.

The frequency shifted reference beam is expanded by lenses $L_3$ 598 and $L_4$ 600 which are separated by a distance equal to the sum of their focal lengths. The signal and reference fields at the two image planes can be described in complex notation by $$E_S(x,y,t)=E_S^0(x,y)\exp[i(\phi_S(x,y,t)+\phi_{N,S}(x,y,t)-\omega t)] \quad (23)$$

$$E_R(x,y,t)=E_R^0(x,y)\exp[i\phi_{N,R}(x,y,t)-(\omega+\Omega)t] \quad (24)$$

Here x and y are the transverse coordinates along the optical path, $\phi_S(x,y,t)$ is the sample phase under investigation, $\phi_{N,S}(x,y,t)$ and $\phi_{N,R}(x,y,t)$ represent interferometer noise in the sample and reference arms, and $E_s^0(x,y)$, $E_R^0(x,y)$ are the field amplitude profiles which may be, for example, but not limited to, Gaussian.

The sample phase $\phi_S(x,y,t)$ may be expressed in terms of the time-dependent refractive index distribution of the sample $n_S(x,y,z,t)$:

$$\phi_S(x,y,t)=\int_{z1}^{z2} n_s(x/M, y/M,z,t)dz \quad (25)$$

where z is the axial coordinate and the integration is carried out over the depth of the sample. Note the magnification factor M.

The intensity at the two image planes is given by $$I_\pm=|E_S\pm E_R|^2=|E_S^0|^2+|E_R^0|^2\pm 2|E_S^0||E_R^0|\cos[\phi_S(x,y,t)+\phi_{N,S}(x,y,t)-\phi_{N,R}(x,y,t)+\Omega t] \quad (26)$$

This heterodyne signal is detected by two photodiodes PD1 604 and PD2 606 located at positions (x1, y1) and (x2, y2). The light may be collected through optical fibers or pinholes. The AC components of the detected intensities are given by $$I_1(t)=2|E_S^0||E_R^0|\cos[\phi_S(x_1,y_1,t)+\phi_{N,S}(x_1,y_1,t)-\phi_{N,R}(x_1,y_1,t)+\Omega t] \quad (27)$$

$$I_2(t)=-2|E_S^0||E_R^0|\cos[\phi_S(x_2,y_2,t)+\phi_{N,S}(x_2,y_2,t)-\phi_{N,R}(x_2,y_2,t)+\Omega t] \quad (28)$$

The phase difference between heterodyne signals $I_1$ and $-I_2$ is then measured by lock-in amplifiers or a phase detector circuit 608.

$$\Phi_{12}(t) = [\phi_S(x_1, y_1, t) + \phi_{N,S}(x_1, y_1, t) - \phi_{N,R}(x_1, y_1, t)] - \\ [\phi_S(x_2, y_2, t) + \phi_{N,S}(x_2, y_2, t) - \phi_{N,R}(x_2, y_2, t)] \\ = \phi_S(x_1, y_1, t) - \phi_2(x_2, y_2, t) + \phi_{N,S}(x_1, y_1 t) - \\ \phi_{N,S}(x_2, y_2, t) - \phi_{N,R}(x_1, y_1, t) + \phi_{N,R}(x_2, y_2, t) \quad (29)$$

If one now assumes that interferometer noise is independent of transverse position, that is $$\phi_{N,S}(x_1,y_1,t)=\phi_{N,S}(x_2,y_2,t) \quad (30a)$$

$$\phi_{N,R}(x_1,y_1,t)=\phi_{N,R}(x_2,y_2,t) \quad (30b)$$

then the measured phase difference is simply the difference in sample phase at the selected points:

$$\Phi_{12}(t)=\phi_S(x_1,y_1,t)-\phi_S(x_2,y_2,t) \quad (31)$$

This method in accordance with a preferred embodiment of the present invention may be implemented with any number of photodetectors at the image planes subject only to physical constraints. A photodiode array or photodiode-couple fiber bundle may be used to image the phase at many positions simultaneously. Any single detector may be chosen as a "reference" detector relative to which the phase differences at all other points are measured.

The schematic for the imaging Mach-Zender heterodyne interferometer is shown in FIG. 18B. This device 670 images the phase $\phi_S(x,y,t)=\int_{z1}^{z2} n_s(x/M,y/M,z,t)dz$ of light which has passed through a sample 673.

The optical layout is similar to the two-point Mach-Zender heterodyne interferometer, described with respect to FIG. 18A, except for two changes: (i) an imaging detector, for example, charged-coupled device (CCD) 682 is located at one of the imaging planes, and (ii) an electro-optic polarization modulator 672 and a polarizer 681 is used to perform stroboscopic detection. Quantitative phase images are obtained by phase shift interferometry.

The time-dependent intensity distribution at the CCD image plane is given by $$I_-(x,y,t)=|E_S \pm E_R|^2=|E_S^0|^2+|E_R^0|^2-2|E_S^0||E_R^0|\cos[\phi_S(x,y,t)+\phi_{N,S}(x,y,t)-\phi_{N,R}(x,y,t)+\Omega t] \quad (32a)$$

Stroboscopic phase shift interferometry is used to image this heterodyne fringe pattern in a phase sensitive manner. This requires "gating" of the detection at the CCD and can be performed in several ways. An intensified CCD can be gated by controlling the intensifier voltage. A large-aperture electro-optic cell in front of the CCD can be used as a fast shutter. In the system illustrated in FIG. 18B an electro-optic polarization switch is used to control the polarization of the input beam to the interferometer. The two polarizations can be labeled as "in-plane" and "out-of-plane", corresponding to the FIG. 18B. A linear polarizer 681 is placed in front of the CCD imaging device 682 so that only in-plane polarized light is detected; out-of-plane polarized light is absorbed or reflected by the polarizer.

A photodiode aligned (via fiber optic if necessary) to the first image plane is used to obtain the following signal as in the two-point heterodyne interferometer $$I_1(t)=2|E_S^0||E_R^0|\cos[\phi_S(x_1,y_1,t)+\phi_{N,S}(x_1,y_1,t)-\phi_{N,R}(x_1,y_1,t)+\Omega t] \quad (32b)$$

Gating signals are then derived from heterodyne signal $I_1$ as follows. An electronic comparator outputs "high" when the heterodyne signal is positive with positive slope. This corresponds to gate signal with phase 0. Similar signals at phase shifts of pi/2, pi, and 3pi/2 can be generated by triggering at heterodyne signal positive with negative slope, negative with negative slope, and negative with positive slope, respectively. The heterodyne 687 and gate 688-691 signals are shown in FIG. 18C in accordance with a preferred embodiment of the present invention.

The gate signals are then used in succession to gate the CCD detector. The sequence is controlled by a computer 685. Light is allowed to fall onto the CCD only when the gate signal is "high". Four exposures are captured by the CCD, corresponding to the four gate signals but equal numbers of heterodyne periods, so as to achieve corresponding intensities on the four exposures. The four measured fringe images are called $I_0(x,y)$, $I_{\pi/2}(x,y)$, $I_\pi(x,y)$, $I_{3\pi/2}(x,y)$. Then the relative sample phase can be calculated by $$\phi_S(x, y) = \tan^{-1}\left(\frac{I_{3\pi/2}(x, y) - I_{\pi/2}(x, y)}{I_0(x, y) - I_\pi(x, y)}\right) \quad (32c)$$

due to the phase shifts between each of the four frames. Other methods for phase shifting and calculating the phase can also be used, for example, those described by Creath, K., "Phase-Measurement Interferometry Techniques," in Progress in Optics. Vol. XXVI, E. Wolf, Ed., Elsevier Science Publishers, Amsterdam, 1988, pp, 349-393, the entire teachings of which are incorporated herein by reference. Furthermore, the interferometer noise, insofar as it is constant over the image plane; is cancelled via reference to the correlated noise heterodyne signal $I_1(t)$. Stroboscopic phase imaging can be considered a form of "bucket" integration, wherein the integration is performed over time with reference to a common heterodyne reference signal.

Stroboscopic phase imaging can also be performed with a dual-beam heterodyne interferometer in accordance with a preferred embodiment of the present invention. This requires a low coherence wavelength such as 850 nm capable of being detected by a CCD. It also requires a modification of the sample beam delivery system to an imaging system as shown in FIG. 18D as compared to FIG. 19 described hereinafter. In this embodiment the reference heterodyne signal used to generate the four gate signals is provided by the optical reference signal. The shuttering of the detected signal may be performed by a fiber optic switch or polarization modulator with polarizer.

Preferred embodiments of the present invention include a dual-beam reflection interferometer. A preferred embodiment of the dual-beam reflection interferometry includes an isolated dual-beam heterodyne LCI. The heterodyne dual beam interferometer 620 is shown in FIG. 19. This interferometer is used to measure phase changes of reflected light from a sample, relative to a partially reflective surface located in front of the sample. For example, one may measure the phase of light reflected from a sample on a thin piece of glass. As another example, measurements may be made relative to a reflection from the tip of a fiber optic probe placed near the sample under study.

A low coherence source 622 such as a superluminescent diode (SLD) or multimode laser diode is coupled into a single mode optical fiber which enters a vacuum chamber 640 through a vacuum feedthrough. Enclosed within the chamber is a vibration-isolated free space heterodyne Michelson interferometer. The low coherence beam is launched from the fiber via a collimating lens and split by a beamsplitter 626. The arms of the interferometer (called 1 (656) and 2 (658)) contain acousto-optic modulators (AOM1 628 and AOM2 634) driven by RF fields at frequencies $\omega_1$ and $\omega_2$. In each arm the positive-shift 1st order diffracted beams is selected by a pinhole. The light is focused by the lenses 630 and 636 and then reflected by the mirrors M1 632 and M2 638 back to the AOMs. The lenses are placed at a distance of one focal length away from both the AOMs and the mirrors. This design allows the AOM retroreflection alignment to be maintained across the spectrum of the low coherence (broad spectrum) light.

Since the AOMs are operated in double-pass configuration, the incident light at frequency $\omega_0$ is shifted to $\omega_0+2\omega_1$ and $\omega_0+2\omega_2$ after passing through arms 1 (656) and 2 (658), respectively. The frequency difference between two beams having passed through arms 1 and 2 is $\Omega=2(\omega_1-\omega_2)$.

One of the mirrors, M1 632, is attached to a translation stage to adjust the optical path length difference $\Delta l = l_1 - l_2$ between the two arms. The combined beam after passing through the two arms can be considered as a beam with two pulses separated by a time delay $\Delta l/c$. The reflections from the two interferometer arms is focused back into the fiber by the collimator 660 and exits the chamber 640.

An optical circulator is used to separate the backreflected beam from the incident beam. The light is launched as a free space beam by another collimator 662 and focused on the sample 642, passing first through a partially reflective surface 664. The backscattered light is collected by the same collimator and detected by a photodiode 650 after passing through another optical circulator. The optical delay in the Michelson interferometer is adjusted to match the optical path difference $\Delta s$ between the reflection from the sample S and the reflection from the reference surface. When this condition $\Delta L = \Delta s$ holds to within the coherence length $l_c$ of the source, a heterodyne signal at frequency $\Omega$ is detected due to interference between light reflected from surfaces S 642 and R 664. The phase of the heterodyne signal, measured relative to the local oscillator provided by mixing and doubling the two AOM driving fields, represents a measure of the phase of the sample reflection relative to the reference reflection.

The length $\Delta s$ must be substantially longer than the coherence length $l_c$, in order to keep a heterodyne signal from being created by a single surface reflection. It is also assumed that the sample thickness is smaller than the glass thickness $\Delta s$, so that signals are referenced to the glass surface, not scattering from the sample.

A quantitative description of the interferometer follows. Consider first a monochromatic source with wave number $k_0$. The electric field amplitude at the input of the Michelson interferometer can be described by $$E_i = A_i \cos(k_0 z - \omega_0 t) \tag{33}$$

The electric field returning from the beamsplitter after passing through the AOMs is given by a sum of fields from the two arms of the interferometer:

$$E_m = E_1 + E_2 = A_i \cos(2k_1 l_1 - (\omega_0 + 2\omega_1)t) + A_i \cos(2k_2 l_2 - (\omega_0 + 2\omega_2)t) \tag{34}$$

where $k_1 = k_0 + 2\omega_1/c$ and $k_2 = k_0 + 2\omega_2/c$

This dual beam is now incident on the sample. Let $s_1$ be the optical distance to the reference reflection and $S_2$ the optical distance to the sample reflection. If the reflectivities of the reference and sample reflections are $R_1$ and $R_2$ respectively, and multiple reflections are ignored, the field reflected from the sample is:

$$E_s = A_i \sqrt{R_1} \cos[2k_1(l_1+s_1)-(\omega_0+2\omega_1)t] + A_1 \sqrt{R_1} \cos[2k_2(l_2+s_1)-(\omega_0+2\omega_2)t] + A_i \sqrt{R_2} \cos[2k_1(l_1+s_1)-(\omega_0+2\omega_1)t] + A_1 \sqrt{R_2} \cos[2k_2(l_2+s_2)-(\omega_0+2\omega_2)t] \tag{35}$$

The detected intensity $i_D$ is proportional to the field amplitude squared:

$$i_D \propto \langle |E_s|^2 \rangle = (R_1+R_2)(1+\cos(2k_0\Delta l - \Omega t) + 2\sqrt{R_1 R_2}[2\cos(2k_0\Delta s) + \cos(2k_0(\Delta l + \Delta s - \Omega t)) + \cos(2k_0(\Delta l - \Delta s - \Omega t))] \tag{36}$$

where optical frequency oscillation terms have been ignored and the wavenumber shift $\Omega/c$ due to the frequency shift is assumed to be negligible compared with the inverse of the path length differences $\Delta s$ and $\Delta l$.

To model a low coherence (broadband) source, it is assumed that it has a Gaussian power spectral density with center wavenumber $k_0$ and full wavelength at half maximum (FWHM) spectral bandwidth $\Delta k$.

$$S(k) = \frac{2\sqrt{\ln 2}}{\Delta k \sqrt{\pi}} \exp\left[-\left(\frac{k-k_0}{\Delta k / (2\sqrt{\ln 2})}\right)^2\right] \tag{37}$$

The detected intensity for low coherence radiation is found by integrating the monochromatic result over the spectral distribution:

$$\begin{aligned}\tilde{i}_D &= \int i_D(k) S(k) dk \\ &= (R_1+R_2)(1 + F(\Delta l)\cos(2k_0\Delta l - \Omega t) + \\ &\quad 2\sqrt{R_1 R_2}\,[2F(\Delta s)\cos(2k_0\Delta t) + F(\Delta l + \Delta s)\cos(2k_0(\Delta l + \Delta s - \Omega t)) + F(\Delta l - \Delta s)\cos(2k_0(\Delta l - \Delta s - \Omega t))]\end{aligned} \tag{38}$$

where $$F(x) = \exp\left[-\left(\frac{x}{l_c/(2\ln 2)}\right)^2\right] \tag{39}$$

is the source coherence function for the chosen spectral density. Here $l_c$ is the coherence length $$l_c = \frac{4(\ln 2)}{\Delta k} = \frac{2(\ln 2)\lambda_0^2}{\pi \Delta \lambda} \tag{40}$$

If the path length difference is chosen such that $\Delta l = \Delta s$ to within the coherence length, and $\Delta l \gg l_c$ then the dominant time-dependent signal is of the form $$\tilde{i}_D(AC) = 2\sqrt{R_1 R_2}[F(\Delta l - \Delta s)\cos(2k_0(\Delta l - \Delta s - \Omega t))] \tag{41}$$

By measuring the phase of this signal relative to the local oscillator 652 LO=$\cos(\Omega t)$, changes in $\Delta s$ can be measured.

Note that isolation of the Michelson interferometer is required to keep phase noise from influencing the measurement through changes in $\Delta l$.

FIG. 20 illustrates an isolated dual-reference heterodyne low coherence interferometer in accordance with a preferred embodiment of the present invention. This interferometer is used to measure the phases of light reflected from a chosen depth in a sample, relative to scattering from a different depth in the sample. This setup has an advantage over the simpler dual-beam interferometer in that no glass reflective surface is required. This system is ideal for in vivo measurements. The dual-reference Michelson interferometer can be used for imaging neural activity over three-dimensional volumes in sufficiently thin or transparent samples. This system can be used to study the development of neural networks.

Light from a low coherence source 702 is split into upper and lower paths by a fiber optic coupler 706. The upper path is similar to the dual-beam interferometer described hereinabove with respect to FIG. 19, with a double-pass AOM with frequency shift $\omega_1$ taking the place of the sample, which is now located in the lower path of this interferometer. The two fields recombine at another fiber coupler 742. The photodiodes 746, 748 are arranged in double balanced mode.

A quantitative description of the interferometer with the case of a monochromatic source follows. The upper path field can be written as:

$$E_1 = A_i \cos(2k_0 l_1 - (\omega_0 + 2\omega_1 - 2\omega_3)t) + A_i \cos(2k_0 l_2 - (\omega_0 + 2\omega_2 - 2\omega_3)t) \quad (42)$$

and the lower path is (again assuming the sample contains two reflections at positions $s_1$ and $s_2$):

$$E_2 = A_i \sqrt{R_1} \cos[2k_0 s_1 - \omega_0 t] + A_i \sqrt{R_2} \cos[2k_0 s_2 \omega_0 t] \quad (43)$$

The path lengths of the fiber optic cables has been assumed to be equal between the two arms. The mirror 740 associated with the AOM 736 with frequency $\omega_3$ may be translated to equalize the path lengths.

The AC component of the photodetector signal is given by $$i_D \propto \langle |E_1 + E_2|^2 \rangle_{AC} = \sqrt{R_1}[\cos(2k_0(l_1-s_1)-\Omega_{13}t) + \cos(2k_0(l_2-s_1)-\Omega_{23}t)] + \sqrt{R_2}[\cos(2k_0(l_1-s_2)-\Omega_{13}t) + \cos(2k_0(l_2-s_2)-\Omega_{23}t)] \quad (44)$$

where $\Omega_{13} = 2(\omega_1 - \omega_3)$ and $\Omega_{23} = 2(\omega_2 - \omega_3)$. The polychromatic case for Gaussian spectral distribution gives:

$$\tilde{i}_D = \int i_D(k) S(k) dk \propto \sqrt{R_1} [F(l_1-s_1)\cos(2k_0(l_1-s_1) - \Omega_{13}t) + F(l_2-s_1)\cos(2k_0(l_2-s_1) - \Omega_{23}t)] + \sqrt{R_2} [F(l_1-s_2)\cos(2k_0(l_1-s_2) - \Omega_{13}t) + F(l_2-s_2)\cos(2k_0(l_2-s_2) - \Omega_{23}t)] \quad (45)$$

Suppose that to within the coherence length, $l_1 \approx s_1$ and $l_2 \approx s_2$, and furthermore $\Delta l, \Delta s \ll l_c$. Then the dominant terms are $$\tilde{i}_D \propto \sqrt{R_1} F(l_1-s_1)\cos(2k_0(l_1-s_1)-\Omega_{13}t) + F(l_2-s_2)\cos(2k_0(l_2-s_2)-\Omega_{23}t) \quad (46)$$

Next, these two frequency components are combined in a mixer and a bandpass filter selects the difference frequency $\Omega_{12} = \Omega_{13} - \Omega_{23} = \omega_1 - \omega_2$:

$$X = \sqrt{R_1 R_2} F(l_1-s_1) F(l_2-s_2) \cos(2k_0(l_1-l_2-(s_1-s_2))-\Omega_{12}t) \quad (47)$$

A phase-sensitive detector then measures the phase of this signal relative to a local oscillator at $\Omega_{12}$ generated by mixing and doubling the AOM drive fields. The measured phase is $\phi = 2k_0(\Delta l - \Delta s)$.

The phase shifter is used to compensate interferometer noise which may have some effect on the phase measurement despite its differential nature. The phase of the photodiode signal component $$\sqrt{R_1} F(l_1-s_1) \cos(2k_0(l_1-s_1)-\Omega_{13}t) \quad (48)$$

is measured and used as an error signal to lock the reflection from $s_1$, via the phase shifter, to a constant phase.

In an embodiment using an actual sample there will be not two reflections but a distribution of scattering. By setting the reference arm positions this interferometer measures the phase difference between light scattered from two different depths.

The embodiment described with respect to FIG. 19 measures phase of the optical heterodyne signal relative to the electrical signal created by mixing the acousto-optic modulator (AOM) RF fields. There are a plurality of sources of noise associated with this embodiment. They include a slow drift, probably due to AOM heating from the RF field, in the order of approximately one wavelength ($1\lambda$) over minutes and phase noise at 60 Hz and 120 Hz. Further, an amplitude is present and is probably due to line noise in the AOM turning voltage. An additional source of broadband amplitude and phase noise which changes when fiber optics outside the chamber are moved is most likely due to polarization mode dispersion (PMD) in the optical circulator.

Preferred embodiments of the present invention minimize and preferably eliminate the noise and include an optical-referenced measurement to reduce drifts and noise, or use an AOM tuning voltage provided by a precision voltage source or alternatively use polarization-maintaining fiber optic components.

FIG. 21 illustrates a preferred embodiment of an optical-referenced interferometer that minimizes noise. This embodiment addresses drift and noise issues experienced by the system described with respect to FIG. 19. The embodiment illustrated with respect to FIG. 21 is a heterodyne dual beam interferometer. This interferometer is used to measure phase changes of reflected light from a sample using a reference that may be a different transverse point on the sample object or a separate element. The low coherence source 762 such as a SLD is coupled into the single mode optical fiber which enters the vacuum chamber 782 through a vacuum feedthrough. The heterodyne Michelson interferometer operates as described with respect to FIG. 19. The reflections from the two interferometer arms are focused back into two fibers by collimators 766, 792 and exit the chamber. The additional optical path provides for the reference being a different transverse point on a separate element. The backscattered light is collected by two collimators 788, 790 and detected by two photodiodes 796, 800 after passing through optical circulators 794 and 798, respectively.

In this dual-referenced interferometry embodiment, combines the transverse reference point and reflection-referenced phase measurement. Ideally, the reference point and the sample object are located on the same glass. This has the additional benefit of canceling any tilt, vibration and/or expansion effects in the cover glass. As illustrated in FIG. 22, the measured phase is:

$$\phi(t) = (\phi_1 - \phi_1') - (\phi_2 - \phi_2') \quad (49)$$

A preferred embodiment of the dual-referenced interferometer includes photodetectors that have similar gains and frequency responses to cancel the noise. Further, polarization maintaining components and fibers can be used to address polarization effects in the fiber. In particular, polarization mode dispersion in optical circulator creates variable delay between two orthogonal polarizations which leads to noise in amplitude and phase which can be mitigated by using the polarization maintaining components. In a preferred embodiment, a digital bandpass filter is used to address harmonics found in optical signals.

FIG. 23A graphically illustrates the voltage of a piezoelectric transducer (PZT) which is used to calibrate the system described with respect to FIG. 21. The PZT calibration setup is illustrated in FIG. 25A.

The phase change corresponding to the displacement of the mirror 888 is graphically illustrated in FIG. 23B. This phase change corresponds to a calibrated distance change of 27 nm.

FIG. 24 graphically illustrates noise performance in radians over a total time period of 50 ms, associated with the interferometer illustrated in FIG. 21 wherein the two arms of the interferometer are made equal.

FIGS. 25A and 25B are schematic representations of the calibration setup for the sample and the reference signals in accordance with a preferred embodiment of the present invention. The spacing between mirrors and beamsplitter is varied with PZT. The PZT motion is calibrated by monitoring the source (He—Ne or Ti; Sapphire) transmission.

Preferred embodiments of the present invention are directed to a system including a dual-beam low coherence interferometer used to perform non-contact measurements of small motions of weakly reflecting surfaces such as nerve displacement motions during an action potential. Nerve fibers exhibit rapid outward lateral surface displacements during the action potential. This "swelling" phenomenon, which is generally attributed to water influx into axons, was first observed in crab nerve and later in a number of other invertebrate and vertebrate preparations. All observations of nerve swelling to date have relied on optical or piezoelectric sensors placed in physical contact with the nerve. An optical non-contact method for measuring nerve displacements can eliminate contact-related artifacts and permit the imaging of activity of multiple nerves simultaneously in their native state.

A preferred embodiment of the present invention includes a dual-beam heterodyne low coherence interferometer and its application to measuring the swelling effect in a lobster nerve bundle. Prior art methods of interferometric observation of nerve swelling have been unsuccessful because of low sensitivity and the failure to detect any movement associated with the action potential in frog or lobster nerves. More recently, the refractive index changes in a nerve during the action potential have been successfully measured using a transmitted light interferometer.

Measurement of nerve displacements, of the order of nanometers over millisecond time scales, requires a fast and stable interferometric measurement system capable of recording from surfaces of low reflectivity. In accordance with a preferred embodiment, a dual-beam system, composed of both single-mode fiber and free space elements, is shown in FIG. 26. Light from a fiber-coupled superluminescent diode 922 (Optospeed SLD, center wavelength 1550 nm, bandwidth 40 nm (FWHM) is collimated and enters a Michelson interferometer containing acousto-optic modulators 946, 952 (AOMs) aligned in a double-pass configuration and driven by RF fields at frequencies $\omega_1$=110.1 MHz and $\Phi_2$=110 MHz. A mirror mounted on a translation stage allows control of the round-trip optical path difference $\Delta L$ between the two interferometer arms. Light enters and exits the Michelson interferometer through fiber collimators.

The output from each of the two ports of the Michelson interferometer is a dual beam composed of two low coherence fields with different frequency shifts and a variable delay. One of the dual beams is incident on the nerve chamber setup (detailed in FIG. 27) and the other onto a reference gap. The nerve setup and reference gap each contain two reflective surfaces separated by an adjustable distance and are aligned to reflect the incident light back to its respective fiber. All but one of these surfaces are interfaces between air and uncoated glass. In the sample the second reflection comes from the interface between air and the nerve surface.

$\Delta L_S$ and $\Delta L_R$ are the round trip optical path differences between reflections from surfaces 1 and 2 of the sample and reference gaps, respectively. The various components are adjusted so that the three path lengths $\Delta L$, $\Delta L_S$ and $\Delta L_R$ are all equal to within the source coherence length. When this condition is satisfied the photodetectors 932, 962 (New Focus 2011) record heterodyne signals at frequency $\Omega = 2(\omega_1 - \omega_2) = 200$ kHz due to interference between: (1) light which traverses arm 1 of the Michelson interferometer and reflects from surface 2 of the sample (or reference gap) and (2) light which traverses arm 2 of the Michelson interferometer and reflects from surface 1 of the sample (or reference gap). The phase difference between the two heterodyne signals (up to a multiple of $2\pi$ is $\phi(t) = k_0[(\Delta L_S - \Delta L) - (\Delta L_R - \Delta L)] = k_0(\Delta L_S - \Delta L_R)$, where $k_0$ is the central wave number of the source. The quantity most susceptible to phase noise, the Michelson path delay $\Delta L$, is cancelled in this differential measurement method. Polarization independent optical circulators 926, 930, 960 are used to maximize detected power and keep the reflected light from re-entering the Michelson interferometer. A polarization controller (not shown) is used to minimize the effects of polarization-mode dispersion in the fiber optical components.

To measure the phase difference $\phi(t)$ the outputs of the photodetectors are digitized by a 12-bit A/D card (National Instruments PCI-6110) at 5M samples/s. A sequence of instructions in a computer calculates the phase difference between the two signals via a Hilbert transform, and expresses the phase shift as a relative surface displacement $d(t) = \phi(t)/2 k_0$.

To verify that the interferometer performs a displacement measurement, the nerve setup was replaced with a planar Fabry-Perot cavity with cavity spacing sinusoidally modulated at 300 Hz frequency and 27 nm amplitude using a piezo transducer. Dual-beam interferometer measurements of amplitude and frequency were in good agreement with values determined by monitoring the transmission of a 632.8 nm helium-neon laser beam as the cavity was scanned over several microns.

In accordance with a preferred embodiment, the walking leg nerve (~1 mm diameter, ~50 mm long) from an American lobster (*Homarus americanus*) was dissected and placed on a nerve chamber machined from acrylic as illustrated in FIG. 27. The chamber contains five wells filled with a lobster saline solution and between wells the nerve is surrounded by an insulating layer of petroleum jelly to maximize inter-well resistance. A stimulus isolator delivers a current pulse of variable amplitude 0-10 mA and duration 1 ms to excite the nerve through stimulation electrodes. The current delivered by the stimulus isolator is probably much greater than the actual current passing through the nerve, due to parallel conductance through the saline. The compound action potential generated in the nerve is detected by a pair of recording electrodes 998a, 998b and amplified with gain 104. In the central well the nerve rests on a small glass platform such that it is not submerged in the saline solution. The nerve is kept moist with saline during dissection and data collection.

FIGS. 28A and 28B illustrate the electrical potential and optically measured displacement of a nerve for one trial in accordance with a preferred embodiment of the present invention. The spike at time zero in the electrical signal is due to stimulus artifact. It is followed by a series of peaks describing the action potentials of multiple axons in the nerve bundle. The optical signal shows a peak of height approximately 5 nm and FWHM duration approximately 10 ms, with a direction corresponding to an upward surface displacement. The optical signal shows a single peak rather than multiple spikes as in the electrical signal; this may be due to the monophasic (single-sign) nature of the displacement signal. The rms noise of the displacement measurement was approximately 0.25 nm for 1 kHz bandwidth.

The displacements were observed in about half of the nerve preparations and varied in amplitude from 0 to 8 nm for 5 mA stimulation. The large variability may reflect differences in the nerves themselves or in the preparation procedure. Similar displacement amplitudes have also been reported using nerves of crab and crayfish. In a recent study of lobster nerve swelling using an optical lever about ~10 times smaller displacements were observed, which may reflect artifacts of the technique.

In order to control for artifacts such as thermal expansion from ohmic heating heating of the nerve due to stimulus current, the peak electrical and displacement signals of a single nerve were measured as the stimulus current was varied (as illustrated in FIG. 29). The electrical and displacement signals exhibit nearly identical threshold currents (approximately 1.5 mA) and saturation currents (approximately 5 mA), suggesting that the observed displacements are associated with the action potentials. By contrast, an ohmic effect would be characterized by a quadratic dependence on current and no saturation. Thus, preferred embodiments in accordance with the present invention provide the study of nerve displacements to control for stimulus artifacts. Preferred embodiments include a heterodyne low coherence interferometer to perform the first non-contact and first interferometric measurements of nerve swelling. The biophysical mechanisms of nerve swelling can be imaged and analyzed individual axons in accordance with a preferred embodiment of the present invention. The dual-beam low coherence interferometer may have many other applications in measuring nanometer-scale motions of living cells. Other embodiments can include a microscope based on the interferometer to detect mechanical changes in single neurons associated with action potentials. A related interferometric method is also used to measure cell volume changes in cultured cell monolayers.

FIG. 30 illustrates the optical layout of a scanning system for a dual-beam interferometer in accordance with a preferred embodiment of the present invention. Mirrors mounted on motorized galvanometers 1024, 1030 are placed at the Fourier planes of the imaging system and allow the beam to be scanned across the sample without changes in angle. The mirrors scan at approximately 30 Hz, amplitude 1-2 degrees (50-100 μm on sample). The galvanometers may be rastered or scanned in a Lissajous pattern 1052.

FIG. 31 illustrates galvanometer position and phase data collected from an empty coverglass using Lissajous scanning in accordance with a preferred embodiment of the present invention. The total field of view is approximately 100 microns. The vertical axis is the measured phase. The noise profile is approximately 25 mrad over 1 kHz.

FIGS. 32A and 32B illustrate the color maps of phase image and intensity (amplitude) image of backreflection in accordance with a preferred embodiment of the present invention. The beam scanning data is collected from a blank coverglass. The noise profile is approximately 25 mrad over 1 kHz. Power is highest at the center due to misalignment and clipping that occurs when the beam is moved away from the optical axis. The black dots in the images correspond to pixels which were not visited by the Lissajous pattern.

FIG. 33 illustrates schematically the focusing problem addressed by embodiments of the present invention. A cell 2002 rests on a glass coverslip 2004 in the dual-beam microscope. The solid line represents the beam focused on the upper glass surface and cell. The dotted line represents the beam reflecting from the bottom surface of the glass. The phase-reference interferometry system is dual-beam interferometry in accordance with a preferred embodiment of the present invention and requires collection of not only the light scattered from the samrple of interest, but also the reflection from a fixed referenced surface located in front of the sample. The different axial positions of the sample and reference challenge the efficient simultaneous collection of both reference and sample scattering, especially for a high numerical aperture optical system. Two solutions to the focus problem are provided by systems of the preferred embodiments, both of which allow efficient sample and reference light collection with a numerical aperture of 0.50. First, a bifocal lens system brings both the sample and reference surfaces simultaneously into focus by dividing the numerical aperture into marginal and axial rays, which pass through differently curved portions of a bifocal optical element. The bifocal element can be constructed by polishing flat a central region in the convex side of a plano-convex lens. Positioning the bifocal lens near the Fourier plane of the microscope allows beam scanning via mirror galvanometers for sample imaging.

FIG. 34 illustrates a design for a bifocal lens in accordance with a preferred embodiment of the present invention. It is easier to place the bifocal lens before rather than after the objective. This embodiment provides ease of translation.

FIG. 35 illustrates another design for a bifocal lens system in accordance with a preferred embodiment of the present invention. The bifocal lens system 2050 allows beam scanning by placing the bifocal lens at or near a Fourier plane of the imaging system. The beam 2068 is the axial beam while beam 2070 is the marginal beam. The optical properties are invariant to first order with tilted beams.

FIG. 36 illustrates the calculation of the optimal distance between lenses f3 (bifocal) and f2 such that the separation between the two foci after the objective is equal to delta=100 microns in accordance with a preferred embodiment of the present invention. The optical design is provided by ray tracing.

FIG. 37 illustrates the manufacturing of a bifocal lens in accordance with a preferred embodiment of the present invention. The bifocal lens can be made by polishing flat a central portion of a plano-convex lens. A very small thickness of glass is removed (approximately 2-10 μm). A small change in path length difference between signal and reference results.

FIG. 38 illustrates the backreflected intensity measured through an optical circulator, as the objective is scanned toward a glass coverslip in accordance with a preferred embodiment of the present invention. The reflections from the back and front surfaces are separated by about 100 microns. There is no overlap and thus no interference.

FIG. 39 illustrates the backreflected intensity versus the objective focus position for a bifocal lens with a single reflection from a mirror in accordance with a preferred embodiment of the present invention. Using a bifocal lens f3, a single peak from a mirror (as the objective position is scanned) is split into two, corresponding to the axial and marginal beams being focused at the mirror at different objective focus positions. The separation between peaks depends on the distance between lenses f2 and f3. In this embodiment, the separation is about 100 microns.

FIG. 40 illustrates the backreflected intensity versus the objective focus position using a bifocal lens with both coverglass reflections in accordance with a preferred embodiment of the present invention. This figure puts the two previous figures together, and provides four major peaks and several smaller ones.

FIG. 41 illustrates the backreflected intensity versus the objective focus position in accordance with a preferred embodiment of the present invention when the distance between f2 and f3 is adjusted to match the separation between the front and back glass surfaces. The marginal rays are focused on the back surface at the same positions where the axial rays are focused on the front surface. This provides the large peak seen in the center.

FIG. 42 illustrates the extra smaller peaks that result due to the coupling of the axial and marginal beams in accordance with a preferred embodiment of the present invention. These extra peaks can be explained by coupling from the axial to the marginal beam, which occurs exactly halfway between the two peaks. Amplitudes of the extra peaks are highly dependent on the optical alignment and can be minimized and preferably eliminated with fine adjustment of the optical system.

FIG. 43A illustrates a dual-beam probe having the reference surface as an integral element in accordance with a preferred embodiment of the present invention. The probe consists of a fiber collimator 2382 and a graded index (GRIN) lens 2390. The uncoated back surface of the GRIN lens provides the reference reflection. Since no separate reference surface is required the probe is well-suited for in vivo applications. The probe may be mounted on a fast scanning piezo translator in order to perform two-dimensional phase imaging or three-dimensional confocal phase imaging. This embodiment provides an easy to use prealigned fiber probe for displacement measurements. The probe has a high numerical aperture (NA), in a range of approximately 0.4-0.5, which provides efficient light gathering from scattering surfaces. The integral reference surface solves issues due to depth of focus. This preferred embodiment probe replaces a collection of complex optics and is suitable for in-vivo use.

Illustrated in FIG. 43B is another preferred embodiment of a fiber optic dual-beam interferometer probe 2381. In this embodiment, the reference reflection is provided by the cleaved end 2385 of the optical fiber. In this example, the end 2385 is polished to a right angle to the fiber axis. The fiber 2383 is mounted in a glass ferrule 2389 inserted into housing 2387. The light emitted by the fiber end 2385 is focused by a graded index (GRIN) lens, which in this example has a pitch of about 0.29 or 0.3. The fiber is aligned with a magnification M approximately equal to 3.5 to match the numerical apertures of the fiber (NA=0.13) and GRIN lens (NA=0.50). The beam comes to a focus at the sample, which is this example, is approximately 300 microns from the distal face of the probe.

FIG. 43C is a brightfield microscope image of two nerve fibers (axons or dendrites) from a rat hippocampal culture.

FIG. 44 is a schematic illustration 2400 of the dual-beam probe being applied to investigate the geometry of the displacement effect observed in nerves during an action potential in accordance with a preferred embodiment of the present invention. By varying the angle of the probe, displacements in different directions can be measured.

FIG. 45 illustrates a dual-beam probe system that can be used for imaging by scanning either the probe or the sample in accordance with a preferred embodiment of the present invention. Scanning the probe is preferable to avoid the introduction of artifacts due to sample motion. The probe can be scanned very quickly (approximately 1 kHz) due to its light weight (about 2-3 grams). As the reference surface is integral to the probe, three-dimensional confocal imaging (of both intensity and phase) is possible. The illustrated dual beam probe system can measure transmission or reflection. A preferred embodiment includes a scanning dual-beam probe microscope such that the objective-to-sample distance is highly stable.

FIGS. 46A-46C illustrate the intensity image, the measured phase image of backscattered light and brightfield image, respectively, from a dessicated human cheek epithelial cell (or two overlapping cells) placed on an anti-reflection coated glass coverslip using the bifocal dual-beam microscope in accordance with a preferred embodiment of the present invention. The images are generated by scanning the microscope stage with motorized translators. FIGS. 46A and 46B images (field of view 130 microns horizon×110 microns vertical, scan is 100×100 pixels) display the amplitude and phase, respectively, of the heterodyne signal. FIG. 46C is a brightfield image of the same cheek cell (field of view approximately 60 microns×40 microns). The phase image displays less than one wave of contrast. This may reflect the topography of the lower surface of the cell, which is nearly flat due to contact with the glass substrate.

FIGS. 46D-46G illustrate the profilometry capability of the dual-beam microscope illustrated in FIG. 43, the concave side of a 25 mm focal length plano-convex lens is placed onto a coverslip, the top of which is antireflection coated at 1.5 micron wavelength as shown in FIG. 46E. FIG. 46D illustrates the intensity image of the central portion of the lens. FIG. 46F is the phase map of the reflected light. FIG. 46G illustrates a cross section of the phase image, phase unwrapped, with a quadratic fit. The coefficient of the second-order term corresponds to a radius of curvature of 11.7 mm, consistent with the known curvature of the lens surface. The outlying points in the intensity and phase images may be due to dust particles or pits on the lens.

FIGS. 47A-47E illustrate principles of phase shifting interferometry including a schematic diagram of an interferogram and different methods to collect frames such as phase stepping (FIGS. 47B and 47C) and bucket integration (FIGS. 47D and 47E) in accordance with a preferred embodiment of the present invention. The method includes modulating phase, recording a minimum of three frames and calculating the optical phase displacement.

FIGS. 48A-48C illustrates principles of a stroboscopic heterodyne interferometry system in accordance with a preferred embodiment of the present invention. This system includes acousto-optic modulation that results in continuous phase ramping which is similar to bucket integration except bucket switching is referenced to a correlated-noise reference heterodyne signal to give very low phase noise. In contrast, a stroboscopic heterodyne interferometer provides continuous measurements as there is no stopping due to mechanical mirror displacements.

FIG. 49 illustrates a schematic of a stroboscopic dual-beam heterodyne interferometer 2570 in accordance with a preferred embodiment of the present invention. The light from a dual-beam interferometer is collimated and enters an electro-optic polarization modulator 2594. Light reflects from a beamsplitter 2582, passes through two lenses 2580, 2576 (f1 and f0, the objective) in a telescope configuration, and illuminates the sample as a collimated beam. The backreflected light from the sample, for example, a cell 2573 and from the rear surface of the coverslip is collected by the objective and f1 onto the CCD 2586. The lens f1 is aligned to be one focal length away from the CCD and one focal length away from the Fourier plane (FP) 2578. The objective f0 2576 is similarly one focal length from the Fourier plane and one focal length from the sample. The electro-optic polarization modulator in combination with the polarizer 2584 in front of the CCD acts as a fast optical switch. The electro-optic polarization modulator is gated according to some phase of the reference signal, which is a heterodyne signal from a reference gap, as in the dual-beam interferometer. An 820 nm SLD is used in a preferred embodiment. The light on the sample 2573 is collimated thus precluding any focus problem.

FIGS. 49B and 49C illustrate data showing the phase noise for the dual-beam probe illustrated in FIG. 43 focused on a stationary glass surface in accordance with a preferred embodiment of the present invention.

The system shown and described in connection with FIG. 26 presents the challenge of trying to focus light on a reflective surface and the sample, which are separated axially by about 100 microns in a typical example. Where the numerical aperature >0.1, this is much greater than the depth of field. It is possible to alter either the bifocal optical system or the probe design to address this issue, however, the bifocal system typically has a low collection efficiency that is worse with high numerical aperture objective and diffraction from off axis portion of the lens can create fringing effects. The probe design is limited by the fact that the reference surface is separated from the sample and the NA is limited to 0.5 with the GRIN lens.

Illustrated in FIG. 50A is a system 2700 in which the light from two paths is combined along a common path before the light is directed onto the sample. The light from path 1 is focused on surface 1 and the light from path 2 is focused on surface 2. An interferometer incorporating this feature is shown in the dual-beam system 2800 of FIG. 50B. The system 2800 has a source 2801, two moving reflectors 2803, 2805 and a polarizing beam splitter 2811 that directs light from both paths onto the sample 2807 surfaces and the reference 2809 surfaces. The direction of the polarization components is shown clearly in FIG. 50C. Each arm of the interferometer is directed onto one surface. The light is consequently used more efficiently. The beams are focused separately without edge effects from a bifocal lens. There is no resulting tradeoff in numerical aperture and the system can be configured in free space without the need for fiber optic coupling except optionally from the light source. This can improve light collection efficiency.

Quantitative Phase Microscopy Using Spatial Light Modulation:

In another aspect, the present invention provides microscopy systems and methods that combine phase contrast microscopy and phase shifting interferometry. The systems and methods of the present invention can be applied in a transmission geometry and reflection geometry. In various embodiments, the methods and systems utilize a common optical path for waves of different spatial frequency and shift the phase between waves of different spatial frequency that originate from the same point on a sample.

The phase of optical fields has been used for many years to provide the sub-wavelength accuracy needed in many applications. For example, biological systems, which are inherently weak scatterers, have been rendered visible using principles of phase contrast microscopy. Interferometry is one way to access the phase information and, therefore, various interferometric techniques have been developed over the past years with the purpose of retrieving the phase associated with a specimen. Techniques such as phase contrast and Nomarski microscopy, although very useful and popular methods use the optical phase just as a contrast agent and do not provide quantitative information about its magnitude.

Phase shifting techniques, on the other hand, are able to determine the phase information in a quantitative manner, and various interferometric schemes have been proposed over the past decades. Differential phase contrast techniques based on polarization optics have been interfaced with common optical coherence tomography. The bucket integration technique, as a particular case of phase shifting interferometry, has also been used for two-dimensional phase imaging. Most of these interferometers, however, require creating two physically separated beams, which makes them susceptible to uncorrelated environmental noise. This problem often requires specific measures to actively cancel the noise. Phase lock loops have been used for this purpose. What is needed is a microscopy system and method that reduces or eliminates uncorrelated noise from the interferometric signal.

The systems and methods of the present invention interfere different spatial frequencies of the light originating from a sample using a common optical path. In various embodiments, the present invention provides systems and methods that provide a phase image of a sample that is substantially free of uncorrelated environmental phase noise. In addition, in preferred embodiments, the methods of the present invention can obtain a phase image even in the presence of phase singularities when a low coherence illumination source is used.

In various preferred embodiments, the present invention provides an instrument that is not sensitive to environmental phase noise and that can provide highly accurate and stable phase information over an arbitrary exposure time. In various embodiments, the invention is based on the description of an image as an interference pattern. One example of such a description is Abbe's imaging theory. Each point in the image plane is considered a superposition (interference) of waves propagating at different angles with respect to the optical axis. If we consider the zero-order scattering from the sample, as the reference of an interferometer, the image can be viewed as an interference between the zero-order field and the fields traveling off the optical axis.

Figure 51A:
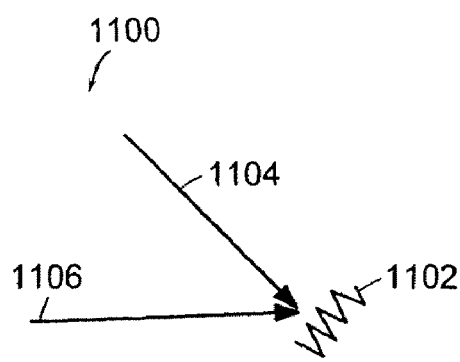
Figure 51B:
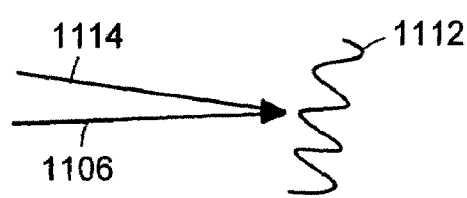
Figure 51C:
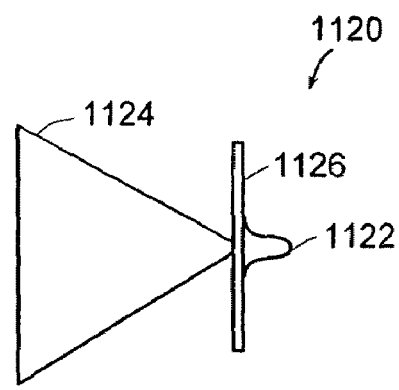
Figure 51D:
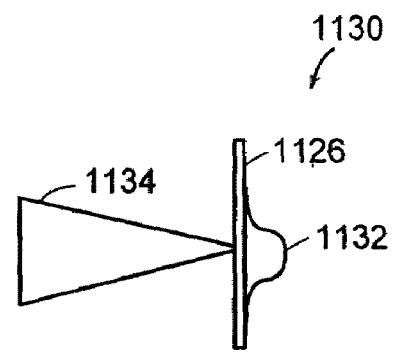

FIGS. 51A-51D are schematic representations of various features of such a description of an image. FIG. 51A is a schematic representation 1100 of an interference pattern 1102 created by a high spatial frequency component 1104 and the zero-order component 1106. FIG. 51B is a schematic representation 1110 of an interference pattern 1112 created by a low-frequency component 1114 and the zero-order component 1106. FIG. 51C is a schematic representation 1120 of a diffraction spot 1122 created by a superposition of a broad spatial frequency beam 1124 at an image plane 1126. FIG. 51D is a schematic representation 1130 of a wider diffraction spot 1132 generated by a narrower spatial spectrum 1134 at an image plane 1126. In addition, for example, the zero-order and higher order components can be thought of as a DC component and an AC component.

The amplitude of the electronic field in the imaging plane and the intensity in the image plane can be represented as:

$$E_{image} = e^{i \cdot \phi_0} + e^{i \cdot \phi_1} \tag{50}$$

$$I_{image} \propto \cos(\phi_1 - \phi_0) \tag{51}$$

where $E_{image}$ represents the amplitude of the electrical field of the light at a point on the imaging plane, $\phi$ represents the phase of the light, and $I_{image}$ represents the intensity of the light at a point on the imaging plane, and where the subscripts 0 and 1 represent, respectively, for the zero-order component and higher order components in Equations 50-56, for example, and unitary amplitudes have been considered. Equation 51 illustrates that for variations of phase, $\Delta\phi=\phi_1-\phi_0$, which are small compared to $\pi$ across the sample, the intensity in the image plane varies slowly, which is equivalent to saying that the image lacks contrast. However, by shifting the phase of the zero-order $\phi_0$ by $\pi/2$, the image intensity distribution can be represented as:

$$I_{image} \propto \sin(\phi_1-\phi_0) \quad (52)$$

Equation 52 illustrates that now the intensity in the image plane is very sensitive around the value $\Delta\phi=0$, which is equivalent to saying the image presents significant contrast even for purely phase objects.

In addition to improving intensity contrast, shifting the phase of the zero-order light component can also provide quantitative information about the phase distribution of the object. For example, consider shifting phase of the zero-frequency component by an amount $\delta$ that can be changed controllably. The total electric field $E(x,y)_{image}$ and the intensity, $I_{image}(x,y;\delta)$ at any point (x,y) in the image plane, keeping in mind that the zero-order field is constant over the image plane, can be represented by:

$$E(x,y)_{image}=E_0 e^{i\cdot(\phi_0+\delta)}+E_1(x,y)e^{i\cdot\phi_1(x,y)} \quad (53)$$

$$I_{image}(x,y;\delta) \propto I_0+I_1(x,y)+2\cdot\sqrt{I_0 \cdot I_1(x,y)}\cdot\cos[\phi_1(x,y)-\phi_0+\delta] \quad (54)$$

where $I_0$ is the intensity associated with the low frequency components and $I_1$ is the intensity associated with the high frequency components.

Herein, we generally refer to the order of the light coming from the sample. However, when a SLM is used, in practice, it is very difficult to controllably shift only the phase of the zero-order component of the light from the sample. Accordingly, in preferred embodiments, we shift the phase of the low frequency spatial components, which contain all the zero-order light. Accordingly, it is to be understood that the systems and methods of the present invention can be practiced by shifting the phase of only the zero-order component and that shifting the phase of other orders is not required.

By varying $\delta$, one can obtain $\Delta\phi(x,y)=\phi_1(x,y)-\phi_0$, and the expression:

$$\tan[\Delta\varphi(x,y)] = \frac{I_{image}(x,y;3\pi/2)-I_{image}(x,y;\pi/2)}{I_{image}(x,y;0)-I_{image}(x,y;\pi)} \quad (55)$$

The phase associated with the sample $\phi$ can be obtained using Equations 53 and 54, using, for example, a phasor representation of the total electric field E(x,y). The phase associated with the object can be represented by:

$$\varphi(x,y) = \arctan\left[\frac{\sqrt{\beta}\cdot\sin[\Delta\varphi(x,y)]}{1+\sqrt{\beta}\cdot\cos[\Delta\varphi(x,y)]}\right] \quad (56)$$

In Equation 56, $\beta=I_1/I_0$ and represents the ratio between the intensities associated with the high and low spatial frequency components, respectively. Values of $\beta$ can be obtained, for example, from $I_{image}(x,y;\delta)$ at four values of $\delta$.

In various embodiments, the systems and methods of the invention are based on a transmission geometry for the microscopy system. FIG. 52 schematically illustrates one embodiment of a microscopy system 1200 in accordance with the present invention based on a transmission geometry. Referring to FIG. 52, a pair of lenses, an objective lens 1204 and a tube lens 1206 image the sample 1210 at the image plane $P_2$ 1212 in a transmission geometry. The lens $L_3$ 1214 can be used to form a Fourier transform of the image onto a spatial light modulator (SLM) 1216. A central region 1217 on the SLM 1216 can apply, relative to the remainder of the SLM, a controllable phase shift $\delta$ to the central zone 1218 of the incident beam 1220 and reflects the entire incident beam 1220. The central zone of the incident beam 1220 corresponds to the low spatial frequency waves, depicted by the inner boundary 1222 of the beam. The outer boundary illustrates 1224 the path of the high frequency beam component, the divergences of both the low-frequency and high frequency beam components are exaggerated for visualization purposes. The lens $L_3$ 1214 can also serve as the second lens of a 4-f system, creating a final image on a detector 1230, such as, for example, a charge coupled device (CCD), using a beam splitter BS 1232.

A wide variety of devices can be used to control the SLM and acquire images of the sample. For example, in various embodiments, a computer 1250 controls the modulation of the SLM 1216, incrementing $\delta$ by $\pi/2$ and also preferably synchronizes the image acquisition of the detector 1230. The operation of Equation 55 can be performed in real time; thus the speed of the displayed phase images are limited in preferred embodiments only by the acquisition time of the detector 1230 and refresh rate of the SLM 1216.

A wide variety of illumination modes and illumination sources can be used to provide illumination 1260 for a transmission geometry of the present invention. The illumination can be performed in either bright or dark field mode. In addition, there are no specific requirements on the coherence properties of the source used. The system and methods of the present invention can use laser light, partially coherent radiation, or "white" light such as, for example, from a discharge lamp. The illumination source should, however, have good spatial coherence.

As illustrated in FIG. 52, the interfering low frequency and high frequency fields are components of the same beam; and thus, share a common optical path. The low frequency and high frequency components are thus affected in a similar fashion by phase noise and various embodiments of the systems of the present invention can be considered as an optically noise-free quantitative phase microscope. For example, in various embodiments, phase sensitivity of $\lambda/1,000$ is possible over arbitrary time scales of acquisition.

In various embodiments, the systems and methods of the invention are based on a reflection geometry for the microscopy system. The difference between the transmission and the reflection geometry is in the illumination geometry. The transmission geometry can be transformed into a reflection geometry.

FIG. 53 schematically illustrates one embodiment of a microscopy system 1300 in accordance with the present invention based on a reflection geometry. The outer boundaries of the paths of the low frequency and high frequency components are not illustrated in FIG. 53 for the sake of clarity. In addition, the divergences of the optical beams in FIG. 53 are exaggerated for visualization purposes. In various embodiments, a beam splitter $BS_1$, 1301 allows a second illumination source 1302 to be coupled into the system and provide illumination 1303. In one embodiment, the second illumination source includes a superluminescent diode (SLD). A low coherence source such as, for example, a SLD, is desirable to avoid interference due to reflections at various interfaces in the optical path.

Referring to FIG. 53, a pair of lenses, an objective lens 1304 and a tube lens 1306 image the sample 1310 at the image plane $P_2$ 1312. The lens $L_3$ 1314 can be used to form a Fourier transform of the image onto a spatial light modulator (SLM) 1316. A central region 1317 on the SLM 1316 can apply, relative to the remainder of the SLM, a controllable phase shift δ to the central zone 1318 of the incident beam 1320 and reflects the entire incident beam 1320. The central zone 1318 of the incident beam 1320 corresponds to the low spatial frequency waves. The lens $L_3$ 1314 can also serve as the second lens of a 4-f system, creating a final image on a detector 1330, such as, for example, a CCD, using a beam splitter BS 1332.

A wide variety of devices can be used to control the SLM and acquire images of the sample. For example, in various embodiments a computer 1350 controls the modulation of the SLM 1316 incrementing δ by π/2 and also preferably synchronizes the image acquisition of the detector 1330. The operation of Equation 55 can be performed in real time; thus the speed of the displayed phase images in preferred embodiment are limited only by the acquisition time of the detector 1330 and refreshing rate of the SLM 1316.

A reflection geometry in accordance with a preferred embodiment of the present invention can also include illumination 1360 such as used, for example, in a transmission geometry. Suitable transmission illumination modes include, but are not limited to, bright field and dark field modes. As in a transmission geometry in accordance with the present invention, there are no specific requirements on the coherence properties of the illumination source used. The system and methods of the present invention can use laser light, partially coherent radiation, or "white" light such as, for example, from a discharge lamp. The illumination source, however, should have good spatial coherence.

In a reflection geometry in accordance with the present invention, the interfering low frequency and high frequency fields are also components of the same beam; and thus, share a common optical path. The low frequency and high frequency components are thus affected in a similar fashion by phase noise and various embodiments of the systems of the present invention can be considered as an optically noise-free quantitative phase microscope. For example, in various embodiments, phase sensitivity of λ/1,000 are possible over arbitrary time scales of acquisition.

In various embodiments, the present invention provides a phase contrast microscopy system utilizing spatial light modulation that comprises an imaging module and a phase imaging module. The imaging and phase imaging modules can, for example, be built independently, facilitating their use in existing optical microscopes.

FIGS. 54A and 54B, referred to as FIG. 54 collectively, schematically illustrate one embodiment 1400 of integrating the present invention with an optical microscope. The outer boundaries of the paths of the low frequency and high frequency components are not illustrated in FIG. 54 for the sake of clarity. In addition, the divergences of the optical beams in FIG. 54 are exaggerated for visualization purposes. A phase imaging head 1450 can be interfaced with an optical microscope 1410 using, for example, the video output of the microscope. The optical microscope 1410 comprises a pair of lenses $L_1$ 1412 and $L_2$ 1414 and a mirror 1416 that can be steer the light from the sample 1420 to a video output of the microscope. Typically, a portion of the light is directed by a beam splitter 1424 to an ocular lens 1426, which focuses light for viewing by the human eye 1430.

The phase imaging head 1450 comprises a lens $L_3$ 1454 used to form the Fourier transform of the image onto a spatial light modulator (SLM) 1456. A central region of the SLM 1456 can apply, relative to the remainder of the SLM, a controllable phase shift δ to the central zone of the incident beam 1460 and reflects the entire incident beam 1460. The central zone of the incident beam 1460 corresponds to the low spatial frequency waves. The lens $L_3$ 1454 can also serve as the second lens of a 4-f system, creating a final image on a detector 1470, such as, for example, a CCD, using a beam splitter BS 1472.

Control of the SLM and the acquisition of images of the sample can be accomplished, for example, using a computer 1480 which controls the modulation of the SLM 1456 incrementing δ by π/2 and also preferably synchronizes the image acquisition of the detector 1470. The computer can be a stand alone computer, for example, provided with the phase imaging head or the "computer" can comprise instructions, in accordance with the present invention, that are resident on a computer associated with the microscope. The operation of Equation 55 can be performed in real time; thus the speed of the displayed phase images are limited in preferred embodiments only by the acquisition time of the detector 1470 and refreshing rate of the SLM 1456.

In various embodiments, the transverse resolution of the systems of the invention can be improved by the addition of a 4-f system. A 4-f system can be used in both transmission geometries and reflection geometries. In addition, a 4-f system can be used in systems including a calibration system. A 4-f system facilitates taking advantage of other Fourier operations performed to the image.

FIG. 55 schematically illustrates one embodiment of a system 1500 and method of the present invention utilizing a 4-f system. The 4-f system comprises a pair of lens $L_4$ 1504 and $L_5$ 1506, and can include a spatial filter, F, 1508. The spatial filter, F, 1508 provides control of the amplitude of individual spatial frequencies. In combination with the phase control provided by a SLM in accordance with the present invention, such amplitude control facilitates, for example, investigating small organelles inside a cell, as an enhancement of the high frequency component can improve contrast. Other applications are envisioned, where the spatial filter F can attenuate preferentially certain spatial frequencies.

A 4-f system can be added to both the various transmission geometry embodiments of the present invention and the reflection geometry embodiments of the present invention. A reflection source (such as, for example, the second illumination source 1302 at FIG. 53) can readily be added to the embodiment of FIG. 55 in accordance with the present invention by one of ordinary skill in the art using the disclosure of the invention provided.

The systems and methods for phase contrast microscopy utilizing spatial light modulation have a wide variety of applications. These systems and methods can, for example, be used to image micrometer and nanometer scale structures. Important classes of applications lie in the investigation of inter-cellular and intra-cellular organization, dynamics and behavior. The stability provided by using a common optical path for both low and high frequency components and the ability to perform measurements in transmission and back-scattering modes, makes various preferred embodiments of the present invention suitable for investigating single cells and ensembles of cells over extended periods of time, from a few hours to days. Thus, in various embodiments, the phase imaging provided by preferred embodiments of the present invention are used to provide information about slow dynamical processes of cells, such as, for example, the transformations in size and shape of a living cell during a life cycle, from mitosis to cell death.

In various preferred embodiments, the methods and systems of the present invention are used to investigate with nanometer precision the process of cell separation after division, and provide information about the dimensions, properties or both of the cell membrane. A phenomenon that has received particular attention lately is programmed cell death—apoptosis. Given that apoptosis can be controlled in the laboratory, in various preferred embodiments, the methods and systems of the present invention are used to investigate the transformation induced in the cell during this process. In various preferred embodiments, the methods and systems of the present invention are used to investigate and detect differences in the life cycles of various types of cells (e.g., cancerous vs. normal).

It is expected that confluent layers of cells have to a certain extent mutual interactions that can lead to a collective mechanical behavior. In various preferred embodiments, the methods and systems of the present invention are used to investigate this mutual interaction by, for example, performing cross correlations between different points of a phase image obtained in accordance with the present invention.

The phase imaging provided by preferred embodiments of the present invention can also be used to provide information about fast dynamical processes of cells, such as, for example, responses to stimuli. For example, processes such as cell volume regulation are responses of the living cell to a biochemical stimulus. The time scale for this response may be anywhere from milliseconds to minutes and should be measurable with high accuracy using preferred embodiments of the systems and methods of the present invention. In various preferred embodiments, the methods and systems of the present invention are used to investigate the response of cells to biochemical stimulus and measure the mechanical properties of the cell structure (for example, cytoskeleton).

In various preferred embodiments, the methods and systems of the present invention are used to investigate cell structure information which has important implications, for example, in understanding the phenomenon of organelle transport inside the cell, as well as in creating artificial biomaterials. In various preferred embodiments, the methods and systems of the present invention are used to investigate cell structure by, for example, using mechanical vibrations to excite the cell membrane and measuring the amplitude of the cell membrane oscillations to, for example, relate them with the mechanical properties of the cell and cellular matter. Traditionally, magnetic or trapped beads are used to excite this motion. In various preferred embodiments, the methods and systems of the present invention are used to investigate cell structure using magnetic or trapped beads to excite mechanical vibrations, the photon pressure of a femtosecond laser pulse to cause mechanical excitation, or both.

One important class of applications is the investigation of intra-cellular organization and dynamics of cell organelles. In various preferred embodiments, the methods and systems of the present invention are used to investigate the transport of various particles inside a cell.

In addition to the diversity of biological investigations, preferred embodiments of the present invention are suitable for industrial applications, such as, for example, the investigation of semiconductor nano-structures. The semiconductor industry lacks a fast and reliable assessment of wafer quality during the nano-fabrication process. In various embodiments, the methods and systems of the present invention are used to provide nanometer scale information about semiconductor structures in, for example, a quantitative manner. In preferred embodiments, nanometer scale information is provided with a measurement on the order of a second.

FIG. 56 schematically illustrates one embodiment of a phase contrast microscopy system 1600 utilizing spatial light modulation (SLM) in accordance with the present invention. The system illustrated in 1600 can use both a reflection geometry and a transmission geometry. In addition, the system is provided with a calibration subsystem.

Referring to FIG. 56, a pair of lenses, an objective lens $L_1$ 1607 and a tube lens $L_2$ 1606 image a sample 1610 at a plane P 1612 using a mirror 1613. The imaging can be performed using a transmission geometry by, for example, coupling through a fiber optic coupler (FC) 1614 and first fiber optic 1616 light from a first illumination source 1620 (here illustrated as a helium neon (HeNe) laser source) to the sample 1610. The imaging can also be performed using a reflection geometry by, for example, coupling through the FC 1614 and second fiber optic 1622 light from a second illumination source 1624 (here illustrated as a SLD) and using a first beam splitter 1626 to direct light from the second illumination source 1624 onto the sample 1610.

A lens $L_3$ 1630 is used to form a Fourier transform of the image onto a first spatial light modulator (SLM) 1632. The SLM 1632 is used to apply a controllable phase shift δ to the central zone of the incident beam 1634. In one embodiment, the lens $L_3$ 1630 serves as a second lens of a 4-f system creating a final image on a first detector 1636 (here illustrated as a CCD) using a second beam splitter 1638. In one embodiment, the system illustrated in FIG. 56 further includes a second 4-f system, such as, for example, schematically illustrated in FIG. 49. The system of FIG. 50 also includes a calibration subsystem for calibration of the SLM. The path of calibration light is schematically illustrated by the dashed line 1640 whereas the path of illumination light and imaged light is schematically illustrated by the solid line 1642. The calibration subsystem collects a portion of light from the first beam splitter 1626 using a pair of lenses $L_4$ 1652 and $L_5$ 1654 (which form a beam expander) and passes the light through a polarizer $P_C$ 1656 that can be used to switch the SLM operation between phase mode and amplitude mode. For calibration, the SLM 1658 is scanned in amplitude mode through phase shifts from 0 to $2\pi$ or and the resulting phase shifted light is attenuated as it goes back through the polarizer. This light is then collected through lens $L_6$ 1660 and focused on the detector 1664.

A variety of devices and schemes can be used to control the system of FIG. 50 and calibrate phase images. In one embodiment, a first control unit PC1 1670 is used in image acquisition by the first detector 1636 and a second control unit PC2 1672 is used to control the first and second SLMs 1632, 1658 and collect data from the detector 1664 through an oscilloscope 1674. The control units PC1, PC2 can be separate units or a single unit. For example, PC1 and PC2 can be separate computers or the same computer, the control units can comprise an analog and/or digital circuit adapted to perform the functions of the control unit.

In various embodiments, the systems and methods of the present include dynamic focus using, for example, a microlens. In various embodiments, the systems and methods of the present invention include parallel focus to, for example, image two or more points on a sample at the same time. In various embodiments, the systems and methods of the present include coherence function shaping to, for example, access in depth several points at the same time.

The phase contrast microscopy systems of the present invention utilizing spatial light modulation can be operated in two modes. In the first mode, referred to hereafter as the "amplitude mode" Fourier filtering can be obtained and calibration performed. In the second mode, referred to hereafter as the "phase mode" wavefronts of the light can be reconstructed and phase imaging performed.

In the "phase mode," in various embodiments, there is no polarizer before the SLM, and the light is aligned with the fast axis of the SLM. The incident light is phase shifted, for example, according to the addressed values on the SLM.

In the "amplitude mode" a polarizer is placed in front of the SLM. The incident light on the SLM is phase shifted (as, for example, in the "phase mode") and the polarization is rotated. As the light reflects from the SLM, it returns through the polarizer and the signal is attenuated. Therefore, there is a calibrated decrease in amplitude based on the SLM phase shift.

FIGS. 57A and 57B schematically illustrate an electro-optic effect on a pixel of an image in amplitude mode 1700 and phase mode 1750, where $E_i$ 1702, 1752 is the projection of the electric field of the incident wavefront, the s axis 1704, 1754 is the slow axis of the SLM, and the f axis 1706, 1756, is the fast axis of the SLM.

FIGS. 58A-58C are block diagrams 1800, 1850, 1855 of various embodiments of SLM modes of operation. FIG. 58A illustrates a normal operational mode of the set up for phase imaging and depicts the SLM operation. RGB 1802 is a gray scale value obtained by a control unit, for example a computer, which controls the SLM (RGB to φ was determined in the calibration.) RGB is converted to voltage and used to address the pixels on the SLM 1804. The voltage is applied to, for example a liquid crystal on the SLM, to give a phase shift to the incident light 1806. Calibration can be obtained in amplitude mode. FIG. 58B illustrates the conversion that occurs in calibration. Intensity is acquired as a function of the gray scale image using a detector 1852, such as, for example, a photodetector. The intensity as a function of gray scale image is then converted into phase as a function of gray scale 1854. FIG. 58C illustrates control-phase mode and illustrates how, in various embodiments, the calibration φ (grayscale) is made into the relationship between SLM control and physical phase shifts induced by the SLM. From this, for example, one can create a look up calibration table for the instrument. The phase as a function of gray scale is then used to generate a gray scale image 1856 (for example, for display on a computer) and is associated with a phase shift 1858 caused by the SLM.

FIG. 59 is an example of a calibration curve 1900 obtained for an instrument operated in amplitude mode. The calibration curve 1900 plots phase shift 1902 in units of radians versus gray scale 1904 in units of the RGB values. The resultant curve obtained 1906 shows the relationship between the computer control of the SLM and the physical phase shift induced by the SLM in the format of a calibration look-up table. FIG. 59 can serve as the calibration look-up table. The cut-off 1908 in the curve 1906 is the wrapping of the phase.

EXAMPLES

Examples are provided in which a transmission geometry in accordance with the present invention has been used and examples are provided in which a reflection geometry in accordance with the present invention has been used. The rotation unwrapped notation which appears, for example, in FIGS. 62-66B indicates that $2\pi$ ambiguity has been removed.

Example 1

Phase Imaging of a Calibrated Sample

In this example, a well calibrated sample has been investigated and illustrates that the present invention can provide quantitative information at the nanometer (nm) scale. The sample consisted of metal deposition on a glass substrate, followed by etching. The metal deposit pattern was in the shape of the numeral eight and the thickness of the metal layer was about 140 nm, as measured with a nano-profilometer.

Figures 60C, 60D:
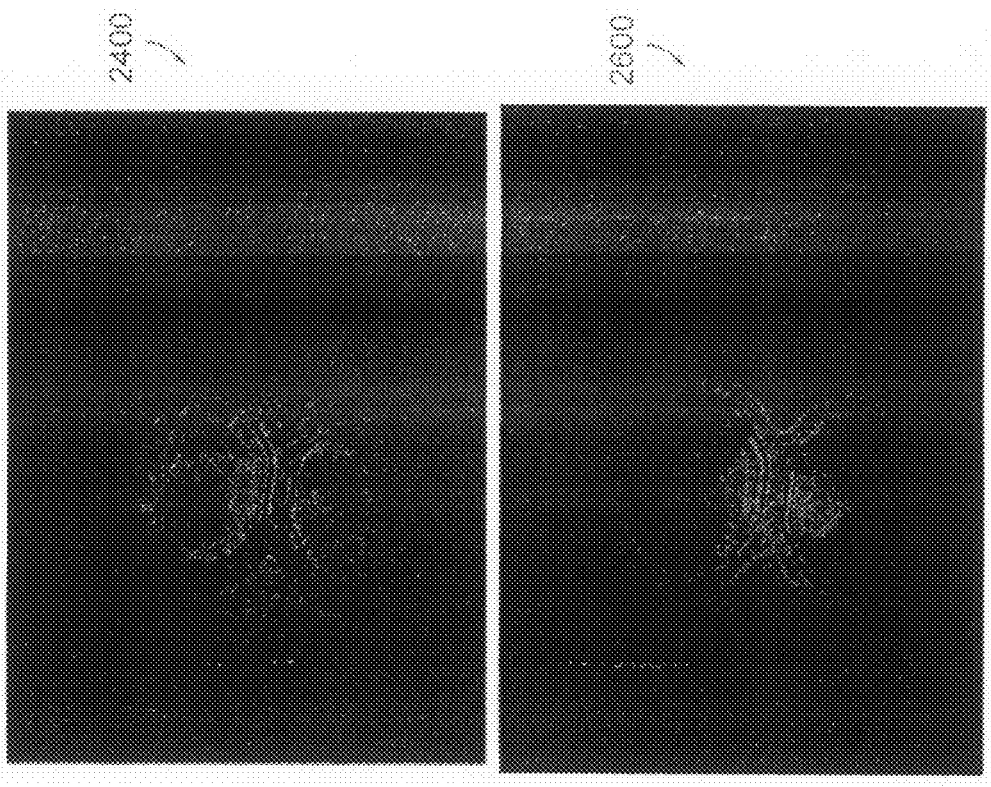
Figures 60A, 60B:
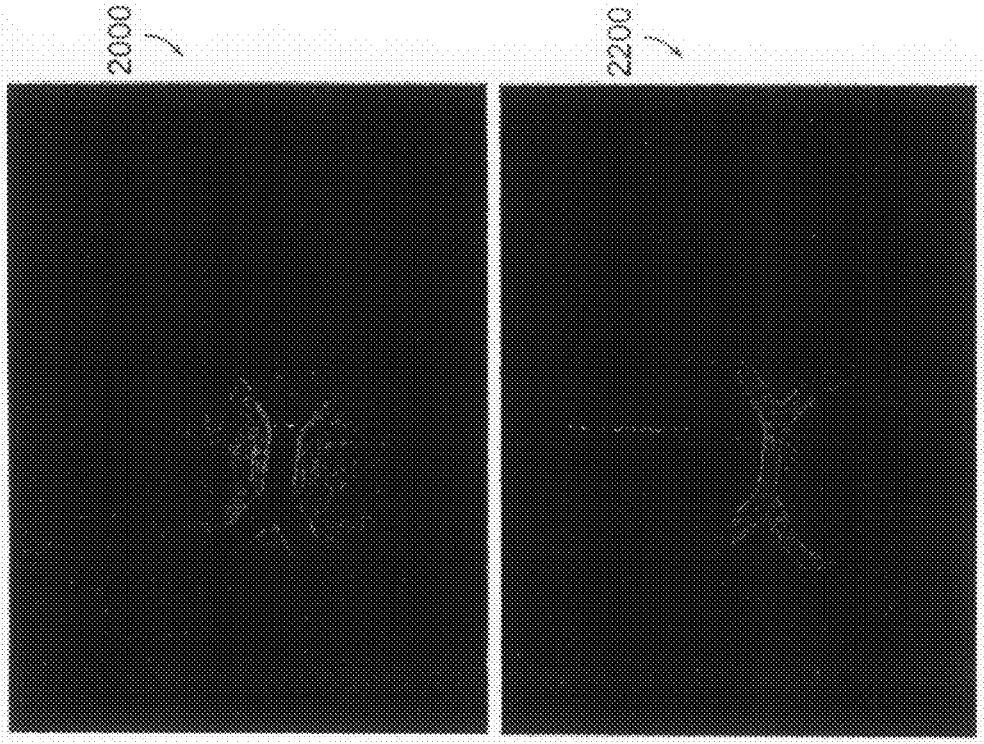

FIGS. 60A-60D show images obtained at four different phase shifts δ for a system using a reflection geometry. FIG. 60A is an image 2000 for δ=0; FIG. 60B is an image 2200 for δ=π; FIG. 60C is an image 2400 for δ=π/2; and FIG. 60D is an image 2600 for δ=3π/2.

FIG. 61 schematically illustrates a relationship 2100 between the electric field E vector 2102 and the high frequency wave vector component of the field, $E_H$, and the low frequency wave vector component of the field, $E_L$. As illustrated in FIG. 61, the y-axis 2110 and the x-axis 2112 represent CCD pixel dimensions. The phase φ is the "real" phase of the object.

FIG. 62 is a Δφ image of the calibrated sample 2200 generated using, for example, data such as illustrated in FIGS. 60A-60D and Equation 55. In FIG. 62 both the y-axis 2202 and the x-axis 2204 are in units of pixels on the CCD. The scale bar 2206 on the right of FIG. 62 represents Δφ in radians.

FIG. 63 is a phase image of the calibrated sample 2300 using a system and method in accordance with the present invention. FIG. 63 was generated using Equation 56 and data such as illustrated in FIG. 62. FIG. 63 can also be generated using Equations 55 and 56 and data such as illustrated in FIGS. 60A-60D. The y-axis 2302 and x-axis 2304, are in units of CCD pixels and the vertical scale bar 2306 is in units of nm.

As illustrated by FIG. 63, it can be seen that the height of the deposited metal pattern 2310 has been correctly recovered, which illustrates an ability of a system and method of the present invention to provide quantitative feature information. The noise present in the phase image 2300 is mostly due to the low-quality (8 bit) camera used for recording.

Example 2

Phase Imaging of a Phase Grating

FIG. 64 shows a phase image 2400 of a phase grating with grooves nominally 10 microns wide and nominally 266 nm deep that was obtained using a transmission geometry. In FIG. 64 the z-axis 2402 is in units of nm and the y-axis 2404 and x-axis 2406 are in the units of CCD pixels. The vertical scale bar 2408 is also in units of nm and is provided to further facilitate determining depth (z-axis dimension) from the phase image 2400.

Example 3

Phase Imaging of Onion Cells

In this example, onion cells were phase imaged using a transmission geometry in accordance with the present invention. An intensity image 2500 of the onion cells is shown in FIG. 65 for comparison to a phase image 2550 shown in FIG.

65. In both FIGS. 65 and 66 the y-axes 2502, 2552 and x-axes 2504, 2554 are in units of CCD pixels. The scale bar 2556 in FIG. 66 is in units of nm.

The intensity image, FIG. 65, represents the first acquired frame where there is no phase shift between the low and high frequency components δ=0. As shown by a comparison of FIGS. 65 and 66, a regular microscope (intensity) image has a very low contrast relative to the phase image obtained in accordance with the present invention. As seen in FIG. 66, the contrast is greatly enhanced in the phase image, where much finer structure of the cell can be distinguished. In addition, the information in the phase image is quantitative to a nanometer level precision and can be transformed in terms of optical path-length of the field passing through the cell. This type of information represents a great improvement not only with respect to the regular optical microscopy, but also to traditional phase contrast and Nomarski microscopy.

Preferred embodiments of the present invention include the use of the coherent decomposition of a low-coherence optical image field into two different spatial components that can be controllably shifted in phase with respect to each other to develop a phase imaging instrument. The technique transforms a typical optical microscope into a quantitative phase microscope, characterized by high accuracy and a sensitivity of λ/5,500. The results obtained on live biological cells suggest that the instrument in accordance with a preferred embodiment of the present invention has a great potential for quantitative investigation of biological structure and dynamics.

Phase contrast and differential interference contrast (DIC) microscopy are capable of providing high-contrast intensity images of transparent biological structures, without sample preparation. The structural information encoded in the phase of light is retrieved through an interference process. However, while both techniques reveal the structure of the sample in the transversal (x-y) plane, the information provided on the longitudinal (z) axis is largely qualitative.

As described herein before, phase shifting interferometry has been used for quite some time in quantitative metrology of phase samples and various interferometric techniques have been proposed. The phase noise due to air fluctuations and mechanical vibrations inherently present in any interferometer makes the quantitative retrieval of the phase associated with an optical field particularly challenging in practice. Preferred embodiments include related wavelengths to overcome this obstacle.

Further, a non-interferometric technique based on the irradiance transport equation has been proposed for full-field phase imaging, at the expense of time-consuming numerical computations. Using spatial light modulation with laser radiation, phase images of λ/30 sensitivity have been also obtained. Digitally recorded interference microscopy with automatic phase shifting (DRIMAPS) is a method that makes use of conventional interference microscopes and provides phase images of biological samples. Although in DRIMAPS no precautions are taken against the phase noise, which ultimately limits the sensitivity of nay phase measurement technique, the potential of this instrument for applications in cell biology has been demonstrated.

A preferred embodiment of the present invention includes a low-coherence phase microscope (LCPM) as a new instrument for biological investigation. The technique transforms a traditional optical microscope into a quantitative phase microscope characterized by very good accuracy and extremely low noise. The principle of the technique relies on the coherent decomposition of the field associated with an optical image into its spatial average and a spatially varying field, which can be controllably shifted in phase with respect to each other. Let E(x,y) be the complex image field, assumed to be stationary over the spatial domain of interest. This field can be expressed as $$E(x,y)=E_0+E_1(x,y) \qquad (57)$$

where $E_0$ is the spatial average and $E_1$ the spatially varying component of E. Thus an arbitrary image can be regarded as the result of an interference phenomenon between a plane wave (the average field) and a spatially varying field. It should be noted that, as a result of the central ordinate theorem, $E_0$ and $E_1$ can be assimilated in each point of the image with the zero- and high-spatial frequency components of the filed E. Consequently, these two spatial components ca be easily separated and independently phase modulated by performing a Fourier decomposition.

The experimental setup is depicted in FIG. 67. An inverted microscope (Axiovert 35, Zeiss Co.) is used to image the sample at the image plane IP. The low coherence field (with a central wavelength in a range 800-850, for example at $\lambda_0$=824 nm and bandwidth $\Delta\lambda$=21 nm or alternatively $\lambda_0$=809 nm and $\Delta\lambda$=20 nm) emitted by a superluminescent diode is used for transillumination. To ensure full spatial coherence of the illuminating field, the light is coupled into a single mode fiber and subsequently collimated by a fiber collimator. The ray traces emerging from the image show the undeflected light and the high spatial frequency component in dotted and continuous lines, corresponding to the fields $E_0$ and $E_1$, respectively. In order to decompose the image field into its components described in Equation 57, a Fourier lens FL (50 cm focal distance) is placed a focal distance away from the image plane IP. It can be seen in FIG. 67 that the microscope image formed at IP appears to be illuminated by a virtual point source (VPS), which is merely the microscope image of the end of the optical fiber used for illumination. Therefore, in order to obtain an exact (phase and amplitude) Fourier transform of the image field at the back focal plane of FL, a corrective lens CL was placed at the plane IP. The focal distance of CL is such that the VSP is imaged at infinity; thus the new image of the sample preserves its position and magnification, while it appears to be illuminated by a plane wave. In the Fourier plane of FL, the zero spatial frequency component $E_0$ is focused on the optical axis, while the high frequency component $E_1$ is distributed off-axis. In order to control the phase delay between $E_0$ and $E_1$, a programmable phase modulator (PPM) (Hamamatsu Co.) is placed in the Fourier plane. The PPM consists of an optically-addressed, two-dimensional liquid crystal array which, due to the properties of birefringence, offers precise control over the phase of the light reflected by its surface. The smallest addressable area on the PPM surface is 20×20 $\mu m^2$ or alternatively 26×26 $\mu m^2$, while the dynamic range of the phase control is 8 bit over one wavelength or $2\pi$. Depending on the orientation of the polarizer P with respect to the principle axis of the liquid crystal, the PPM can modify the phase (phase mode of operation) or the amplitude (amplitude mode) of the incident field, in a spatially resolved manner. The light reflected by the PPM travels back through FL and, upon reflection on the beam splitter BS, is collected by the CCD, which is placed at the conjugate position of IP. Thus, in the absence of PPM modulation, an exact phase and amplitude replica of the image at IP is recorded by the CCD. The phase of the high spatial frequency component is successively incremented in four steps of $\pi/2$ and the resulting irradiance distributions can be recorded by the CCD. The phase modulation on the PPM and the CCD acquisition rate are synchronized by the computer PC, using, for example, LabVIEW (National Instruments). Using the standard 4-frame phase shifting interferometry, the phase difference $\Delta\phi$ between $E_1$ and $E_0$ can be measured. It can be shown that the spatial phase distribution associated with the image field, which is the quantity of interest, has the following expression.

$$\phi(x, y) = \tan^{-1}\left[\frac{\beta(x, y)\sin[\Delta\phi(x, y)]}{1 + \beta(x, y)\cos[\Delta\phi(x, y)]}\right] \quad (58)$$

In Equation 58, the factor $\beta$ represents the amplitude ratio of the two field components, $\beta(x,y)=|E_1(x,y)|/|E_2|$. The parameter $\beta$ is measured operating the PPM as a $\lambda/2$ wave plane (amplitude mode) that selectively filters the two spatial frequency components. Thus, using Equation 58, the spatial phase distribution of a given transparent sample can be uniquely retrieved. The optimal value of the on-axis modulated area in the Fourier plane was found to be 160×160 $\mu m^2$, while the FWHM intensity-based diffraction spot associated with the optical system at the same plane had a diameter of approximately 100 $\mu m$. Since the numerical computations of Equation 58 are virtually instantaneous, the speed of the phase image retrieval is limited only by the refreshing rate of the PPM, which in one embodiment is 8 Hz. However, the overall speed of technique can be potentially increased by using other spatial modulators, such as ferroelectric liquid crystals.

In order to demonstrate its potential for quantitative phase imaging, the LCPM technique was applied for investigating various standard samples. FIGS. 68A and 68B show an example of such measurements, obtained from imaging polystyrene microspheres. The diameter of the particles were 3±0.045 $\mu m$, as provided by the manufacturer (Duke Scientific). To better simulate a transparent biological sample, the spheres were immersed in 100% glycerol and sandwiched between two cover slips. The refractive index contrast achieved between the particles and the surrounding medium was $\Delta n=0.12$. With no modulation on the PPM, a typical transmission intensity image was obtained, which is shown in FIG. 68A. It can be seen that the contrast of this image is highly unsatisfactory, due to the transparency of the sample. FIG. 68B shows the LCPM image obtained with the procedure outline above. Here, the contrast obtained is substantially higher, while the third dimension (z-axis) provides quantitative information about the thickness of the sample. Using the profiles through the centers of the spheres shown in FIG. 68B, the value obtained from the corresponding diameters was 2.97±7.7%, which agrees well with the values indicated by the manufacturer. The existing error might be due to imperfections of the beam quality and potential impurities present in the solution.

The LCPM instrument was further used to phase image live biological cells. FIG. 69A shows the quantitative phase image of a Hela cancer cell during the final stage of mitosis. It should be noted that the cell was surrounded by culture medium, living in typical culture conditions without any additional preparation prior to imaging. It has been previously shown that the phase delay accumulated by a field that propagates through a biological cell is proportional to the non-aqueous mass of the cell. Thus, quantitative phase images, should find important applications in automatic cell kinetic analysis during various stages of cell physiology, such as mitosis, cell growth, and death.

The phase image of a whole blood smear is shown in FIG. 69B. The sample was prepared by simply sandwiching between two cover slips a small drop of fresh whole blood from a healthy volunteer. It can be seen that the well known discoid shape of the red blood cells (RBC) is recovered. Simple analysis that takes into account the refractive index of hemoglobin with respect to plasma can easily provide quantitative information about the volume of cells. This level of detail in the RBC analysis is currently accessible only to electron and atomic force microscopy. The optical, non-invasive technique can potentially provide a fast procedure for pathological screening, since it is well known that the RBC shape is often a good indicator of the cell health. In addition, this technique in accordance with a preferred embodiment of the present invention can monitor the complex dynamic properties of the RBC membrane and surrounding proteins, responsible for blood coagulation.

In order to assess the stability of the instrument against the phase noise and, ultimately, quantify its sensitivity, a cell well containing culture medium only (no cells) was imaged over a period of 100 minutes, at intervals of 15 s. FIG. 69C shows an example of temporal phase fluctuations associated with a point contained in the field of view. The phase values were average over an area of 0.6×0.6 $\mu m^2$, which represents the transversal resolution limit of the microscope. The standard deviation of these fluctuations had a value of 0.15 nm, which is equivalent to $\lambda/5,500$. This result proves the remarkable sensitivity of the LCPM instrument. The extremely low noise characterizing our instrument can be explained by the fact that the two interfering fields travel over optical paths that overlap spatially and are affected by similar phase noise, which eventually cancels out in the interference term. The use of a low-coherence field, as opposed to laser radiation, contributes to the sensitivity of the method, as the possible fringes created by multiple reflections on various components are eliminated.

Thus, preferred embodiments of the present invention include a low-coherence phase microscope, which is characterized by high accuracy and a $\lambda/5,500$ level of sensitivity. The preliminary results on live cancer and red blood cells suggest that the apparatus and methods have the potential to become a valuable tool for structure and dynamics investigation of biological systems. By incorporating a traditional optical microscope in the system setup, the instrument in accordance with a preferred embodiment of the present invention is characterized by high versatility and particular ease of use.

The claims should not be read as limited to the described order or elements unless stated to that effect. Therefore, all embodiments that come within the scope and spirit of the following claims and equivalents thereto are claimed as the invention.

What is claimed:

1. A system for measuring phase of light passing through a portion of a sample, comprising:
   a first light source that generates a first signal at a first wavelength;
   an interferometer that receives the first signal and generates a second signal including a first pulse and a second pulse separated by a time delay to form a pulse pair;
   a first optical path that optically couples the pulse pair from the interferometer with the sample and a second optical path that optically couples the pulse pair from the interferometer with a reference; and
   a detector system that measures a first heterodyne signal from a reflected light pulse pair from the sample and a reflected light pulse pair from the reference resulting from interference between the reflected light from the sample and reflected light from the reference, a phase of the first heterodyne signal indicative of a phase of light from the sample relative to a phase of light from the reference.

2. The system of claim 1 wherein the first signal is a low coherence signal.

3. The system of claim 1 wherein the first light source is one of a superluminescent diode and multimode laser diode.

4. The system of claim 1 wherein the interferometer further comprises a first path and a second path, the second path having an acousto-optic modulator.

5. The system of claim 1 further comprising an optical pathway including an optical fiber.

6. The system of claim 1 further comprising a low coherence signal having a bandwidth of at least 5 nm.

7. The system of claim 1 wherein the system comprises a vibration-isolated heterodyne Michelson interferometer operating at a second wavelength.

8. The system of claim 1 wherein the interferometer further comprises a mirror attached to a translation stage to controllably adjust an optical path length difference.

9. The system of claim 1 wherein the detector system comprises a first detector that detects a signal reflected from the sample and a second detector that detects a signal reflected from the reference.

10. The system of claim 1 wherein the reference comprises a reflective optical surface.

11. The system of claim 1 further comprising a dual beam probe that delivers light onto tissue.

12. The system of claim 1 wherein the interferometer has an optical delay that matches an optical path difference between the first optical path and the second optical path.

13. A method for noncontact optical measurement of a sample having reflecting surfaces, comprising the steps of:
generating a first light signal at a first wavelength with a first light source;
generating a second signal including a first pulse and a second pulse separated by a time delay to form a light pulse pair using the first light signal and a dual-beam interferometer;
the first light signal and optically coupling the light pulse pair to a first optical path from the interferometer in communication with the sample and a second optical path from the interferometer in communication with a reference; and
measuring a first heterodyne signal from a first reflected light pulse pair from the sample and a second reflected light pulse pair from the reference; and
detecting a phase of the heterodyne signal indicative of a phase of reflected light from the sample relative to reflected light from the reference reflection.

14. The method of claim 13 wherein the first signal is a low coherence signal that is reflected by the sample.

15. The method of claim 13 wherein the first light source is one of a superluminescent diode and multimode laser diode.

16. The method of claim 13 wherein the interferometer further comprises a first path and a second path, the second path having acousto-optic modulators.

17. The method of claim 13 further comprising an optical pathway including an optical fiber.

18. The method of claim 13 wherein the sample is a portion of a nerve cell.

19. The method of claim 13 wherein the interferometer comprises a vibration-isolated heterodyne Michelson interferometer operating at a second wavelength.

20. The method of claim 13 wherein the interferometer further comprises a mirror attached to a translation stage to controllably adjust an optical path length difference.

21. The method of claim 13 wherein the step of measuring comprises a detector system having a first detector that detects a signal reflected from the sample and a second detector that detects a signal reflected from the reference.

22. The method of claim 13 wherein the sample comprises biological tissue.

23. The method of claim 13 further comprising providing a microscope to detect mechanical changes in the sample.

24. The method of claim 23 wherein the sample comprises at least one of a single neuron and cell mono layers.

25. The method of claim 23 wherein the microscope comprises a bifocal microscope.

* * * * *

UNITED STATES PATENT AND TRADEMARK OFFICE
CERTIFICATE OF CORRECTION

| | | |
|---|---|---|
| PATENT NO. | : 7,557,929 B2 | |
| APPLICATION NO. | : 10/871610 | |
| DATED | : July 7, 2009 | |
| INVENTOR(S) | : Christopher M. Fang-Yen et al. | |

It is certified that error appears in the above-identified patent and that said Letters Patent is hereby corrected as shown below:

Column 1, following "GOVERNMENT SUPPORT" please delete lines 18-20 and insert the new paragraph as follows:

--This invention was made with government support under Grant No. P41 RR002594, awarded by the National Institutes of Health. The government has certain rights in this invention.--

Signed and Sealed this
Seventeenth Day of May, 2011

David J. Kappos
*Director of the United States Patent and Trademark Office*